(12) United States Patent
Lim et al.

(10) Patent No.: US 11,401,332 B2
(45) Date of Patent: Aug. 2, 2022

(54) PROTEOLYTICALLY CLEAVABLE CHIMERIC POLYPEPTIDES AND METHODS OF USE THEREOF

(71) Applicant: The Regents of the University of California, Oakland, CA (US)

(72) Inventors: Wendell A. Lim, San Francisco, CA (US); Kole T. Roybal, San Francisco, CA (US); Jasper Z. Williams, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 192 days.

(21) Appl. No.: 16/325,657

(22) PCT Filed: Aug. 22, 2017

(86) PCT No.: PCT/US2017/048040
§ 371 (c)(1),
(2) Date: Feb. 14, 2019

(87) PCT Pub. No.: WO2018/039247
PCT Pub. Date: Mar. 1, 2018

(65) Prior Publication Data
US 2019/0202918 A1    Jul. 4, 2019

Related U.S. Application Data

(60) Provisional application No. 62/378,614, filed on Aug. 23, 2016.

(51) Int. Cl.
| | | |
|---|---|---|
| C07K 14/705 | (2006.01) | |
| C07K 14/71 | (2006.01) | |
| C07K 16/28 | (2006.01) | |
| C07K 16/30 | (2006.01) | |
| C07K 19/00 | (2006.01) | |
| C12N 5/10 | (2006.01) | |
| C12N 15/63 | (2006.01) | |
| C07K 14/74 | (2006.01) | |
| C07K 14/725 | (2006.01) | |
| A61P 35/00 | (2006.01) | |
| A61K 35/17 | (2015.01) | |

(Continued)

(52) U.S. Cl.
CPC .......... *C07K 16/2833* (2013.01); *A61K 35/17* (2013.01); *A61K 39/39558* (2013.01); *A61P 35/00* (2018.01); *C07K 14/705* (2013.01); *C07K 14/7051* (2013.01); *C07K 14/70539* (2013.01); *C07K 16/2803* (2013.01); *C07K 16/2809* (2013.01); *C07K 16/30* (2013.01); *C12N 15/63* (2013.01); *A61K 2039/505* (2013.01); *C07K 2317/14* (2013.01); *C07K 2317/31* (2013.01); *C07K 2317/32* (2013.01); *C07K 2317/622* (2013.01); *C07K 2319/00* (2013.01); *C07K 2319/50* (2013.01); *C07K 2319/60* (2013.01); *C07K 2319/715* (2013.01); *C07K 2319/80* (2013.01)

(58) Field of Classification Search
CPC ............ C07K 14/7051; C07K 2319/03; C07K 2317/622; C07K 14/70517; C07K 2319/02; C07K 14/70521; C07K 14/705; C07K 2319/00; C07K 16/00; C07K 16/2866; C07K 16/28; C07K 16/2809; C07K 14/70596; C07K 16/2818; C07K 16/2863; C07K 16/2869; C07K 16/2878; C07K 16/2896; C07K 2319/50; C07K 2319/30; A61K 38/00; A61K 39/39558; A61K 38/17; A61K 38/177; A61K 39/001112; A61K 39/001129; A61K 35/14; C12N 15/63; C12N 15/62; C12N 5/0635; C12N 5/0634; C12N 5/0636
See application file for complete search history.

(56) References Cited

U.S. PATENT DOCUMENTS

8,226,943 B2    7/2012    Gurney et al.
9,670,281 B2    6/2017    Lim et al.
(Continued)

FOREIGN PATENT DOCUMENTS

JP    2014158469 A    9/2014
JP    2016517848 A    6/2016
(Continued)

OTHER PUBLICATIONS

Bork, A. Powers and pitfalls in sequence analysis: the 70% hurdle. Genome Res 10: 398-400, 2000.*
(Continued)

*Primary Examiner* — Bridget E Bunner
(74) *Attorney, Agent, or Firm* — James S. Keddie; Bozicevic, Field & Francis LLP

(57) ABSTRACT

The instant disclosure provides chimeric polypeptides which modulate various cellular processes following a cleavage event induced upon binding of a specific binding member of the polypeptide with its binding partner. Methods of using chimeric polypeptides to modulate cellular functions, including e.g., induction of gene expression, are also provided. Nucleic acids encoding the subject chimeric polypeptides and associated expression cassettes and vectors as well as cells that contain such nucleic acids and/or expression cassettes and vectors are provided. Also provided, are methods of treating a subject using the described components and methods as well as kits for practicing the subject methods.

11 Claims, 30 Drawing Sheets
Specification includes a Sequence Listing.

(51) Int. Cl.
A61K 39/395 (2006.01)
A61K 39/00 (2006.01)

(56) References Cited

U.S. PATENT DOCUMENTS

| | | | |
|---|---|---|---|
| 9,834,608 | B2 | 12/2017 | Lim et al. |
| 10,590,182 | B2* | 3/2020 | Lim ..................... C07K 16/28 |
| 10,822,387 | B2* | 11/2020 | Lim ..................... C07K 14/715 |
| 10,836,808 | B2* | 11/2020 | Lim ..................... C07K 14/715 |
| 2004/0058443 | A1 | 3/2004 | Artavanis-Tsakonas et al. |
| 2004/0203099 | A1 | 10/2004 | Solari et al. |
| 2006/0140943 | A1 | 6/2006 | Champion et al. |
| 2010/0304410 | A1 | 12/2010 | Kijanka et al. |
| 2014/0099309 | A1 | 4/2014 | Powell et al. |
| 2014/0308746 | A1 | 10/2014 | Rossi et al. |
| 2015/0164896 | A1 | 6/2015 | Lu et al. |
| 2016/0081314 | A1 | 3/2016 | Thurston et al. |
| 2016/0250258 | A1 | 9/2016 | Delaney et al. |
| 2016/0264665 | A1* | 9/2016 | Lim ..................... C07K 16/30 |
| 2018/0079812 | A1 | 3/2018 | Lim et al. |
| 2018/0208636 | A1 | 7/2018 | Lim et al. |
| 2018/0355011 | A1 | 12/2018 | Lim et al. |

FOREIGN PATENT DOCUMENTS

| | | |
|---|---|---|
| WO | WO 2014/055668 | 4/2014 |
| WO | WO 2015/123642 | 8/2015 |
| WO | WO 2015/124715 | 8/2015 |
| WO | WO 2016/033331 | 8/2015 |
| WO | WO 2015/105995 | 11/2015 |
| WO | WO 2016/019300 A1 | 2/2016 |
| WO | WO2016/0093243 A1 | 6/2016 |
| WO | WO-2016138034 A1 * | 9/2016 |

OTHER PUBLICATIONS

Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects or mutations and protein evolvability. Curr Opin Structural Biol 19: 596-604, 2009.*
Wells. J.A. Additivity of mutational effects in proteins. Biochemistry 29 (37): 8509-8517, 1990.*
Heyman, et al.; Chimeric antigen receptor T cell therapy for solid tumors: current status, obstacles, and future strategies. Cancers 11:191, 2019 (21 total pages).
Lanitis et al.; Chimeric antigen receptor T cells with dissociated signaling domains exhibit focused antitumor activity with reduced potential for toxicity in vivo. Cancer Immunol Res 1(1): 1-11, 2013.
Sanz et al.; Antibodies and gene therapy: teaching old "magic bullets" new tricks. Trends Immunol 25(2): 85-91, 2004.
Abate-Daga, et a.; "CAR models: next-generation CAR modifications for enhanced T-cell function"; Molecular Therapy-Oncolytics; vol. 3, 7 pages (2016).
Baitsch, et al.; "Extended Co-Expression of Inhibitory Receptors by Human CD8 T-Cells Depending on Differentiation, Antigen-Specificity and Anatomical Localization"; PLoS One; vol. 7, No. 2, 10 pages (Feb. 2012).
Barnea, et al.; "The genetic design of signaling cascades to record receptor activation"; PNAS; vol. 105, No. 1, pp. 64-69 (Jan. 8, 2008).
Barrett, et al.; "Chimeric Antigen Receptor Therapy for Cancer"; Annu Rev Med; vol. 65, pp. 333-347 (2014).

Brooks, et al.; "IL-10 and PD-L1 operate through distinct pathways to suppress T-cell activity during persistent viral infection"; PNAS; vol. 105, No. 51, pp. 20428-20433 (Dec. 23, 2008).
Cao, et al.; "Design of Switchable Chimeric Antigen Receptor T Cells Targeting Breast Cancer"; Angew. Chem. Int. Ed.; vol. 55, 6 pages (2016).
Chillakuri, et al.; "Notch receptor-ligand binding and activation: Insights from molecular studies"; Seminars in Cell & Developmental Biology; vol. 23, pp. 421-428 (2012).
Cohen, et al.; "T-Cell Receptor-Like Antibodies: Targeting the Intracellular Proteome Therapeutic Potential and Clinical Applications"; Antibodies; vol. 2, pp. 517-534 (2013).
Dahan, et al.; "T-cell-receptor-like antibodies—generation, function and applications"; Expert Reviews in Molecular Medicine; vol. 14, 17 pages (Feb. 2012).
Daringer, et al.; "Modular Extracellular Sensor Architecture for Engineering Mammalian Cell-based Devices"; ACS Synthetic Biology; vol. 3, pp. 892-902 (2014).
Dhanik, et al.; "In-silico discovery of cancer-specific peptide-HLA complexes for targeted therapy"; BMC Bioinformatics; vol. 17, No. 286, 14 pages (2016).
Dotti, et al.; "Design and development of therapies using chimeric antigen receptor-expressing T cells"; Immunological Reviews; vol. 257, pp. 107-126 (2014).
Fridy, et al.; "A robust pipeline for rapid production of versatile nanobody repertoires"; Nat. Methods; vol. 11, No. 12, pp. 1253-1260 (Dec. 2014)—Supplemental Materials.
Fridy, et al.; "A robust pipeline for rapid production of versatile nanobody repertoires"; Nat. Methods; vol. 11, No. 12, pp. 1253-1260 (Dec. 2014).
Gooz; "ADAM-17: The Enzyme That Does It All"; Crit. Rev. Biochem. Mol. Biol.; vol. 45, No. 2, pp. 146-169, 146-169 (Apr. 2010).
Gordon, et al.; Mechanical Allostery: Evidence for a Force Requirement in the Proteolytic Activation of Notch; Cell; vol. 33, pp. 729-736 (2015).
Gordon, et al.; "Effects of S1 cleavage on the structure, surface export, and signaling activity of human Notch1 and Notch2"; PLoS One; vol. 4, No. 8, 12 pages (Aug. 2009).
Inaguma, et al.; "Construction and molecular characterization of a T-cell receptor-like antibody and CAR-T cells specific for minor histocompatibility antigen HA-1H"; Gene Therapy; vol. 21, pp. 575-584 (2014).
Jain, et al.; "Antitumor Activity of a Monoclonal Antibody Targeting Major Histocompatibility Complex Class I-Her2 Peptide Complexes"; JNCI; 17 pages (Nov. 5, 2012).
Kimchi-Sarfaty, et al.; "A 'Silent' Polymorphism in the MDR1 Gene Changes Substrate Specificity"; Science; vol. 315, pp. 525-528 (Jan. 26, 2007).
Kopan, et al.; "The Canonical Notch Signaling Pathway: Unfolding the Activation Mechanism"; Cell; vol. 137, pp. 216-233 (Apr. 17, 2009).
Lecourtois, et al.; "Indirect evidence for Delta-dependent intracellular processing of notch in *Drosophila* embryos"; Curr. Biol.; vol. 8, No. 13, pp. 771-774 (Jun. 1998).
Lim; "Designing customized cell signalling circuits"; Nature Reviews Molecular Cell Biology; vol. 11, No. 6, pp. 393-403 (Jun. 2010).
Ma, et al.; "A novel TCR-like CAR with specificity for PR1/HLA-A2 effectively targets myeloid leukemia in vitro when expressed in human adult peripheral blood and cord blood T cells"; Cytotherapy; vol. 18, pp. 985-994 (2016).
Ma, et al.; "Versatile strategy for controlling the specificity and activity of engineered T cells"; PNAS; 31 pages (Jan. 12, 2016).
Mahmud, et al.; "Antibody immunosuppressive therapy in solid-organ transplant"; Mabs; vol. 2, No. 2, pp. 148-156 (2010).
Matsuda, et al.; "Synthetic Signal Propagation Through Direct Cell-Cell Interaction"; Sci. Signal; vol. 5, No. 220, 9 pages (Apr. 17, 2012).
Morsut, et al.; "Engineering Customized Cell Sensing and Response Behaviors Using Synthetic Notch Receptors"; Cell; vol. 164, No. 4, pp. 1-12 (Feb. 11, 2016).

(56) References Cited

OTHER PUBLICATIONS

Mumm, et al.; "A ligand-induced extracellular cleavage regulates gamma-secretase-like proteolytic activation of Notch1"; Mol. Cell; vol. 5, No. 2, pp. 197-206 (Feb. 2000).
Musse, et al.; "Notch ligand endocytosis: Mechanistic basis of signaling activity"; Seminars in Cell & Developmental Biology; vol. 23, pp. 429-436 (2012).
Ngo, et al.; "Computational Complexity, Protein Structure Prediction, and the Levinthal Paradox"; The Protein Folding Problem and Tertiary Structure Prediction; pp. 433 and 492-495 (1994).
Odorizzi, et al.; "Inhibitory Receptors on Lymphocytes: Insights from Infections"; J. Immunol.; vol. 188, No. 7, pp. 2957-2965 (Apr. 1, 2012).
PDB-2004: Structure of LNR-HD (Negative Regulatory Region) from human Notch 2 [online] Apr. 3, 2007 [retrieved May 11, 2016]. Available on the internet: <URL: http://www.rcsb.org/pdb/explore/explore.do?structureId=2004>.
Pratt, et al.; "The cell giveth and the cell taketh away: An overview of Notch pathway activation by endocytic trafficking of ligands and receptors"; acta histochemica; vol. 113, pp. 248-255 (2011).
Roybal, et al.; "Engineering T Cells with Customized Therapeutic Response Programs Using Synthetic Notch Receptors"; Cell; vol. 167, pp. 419-432 (2016).
Roybal, et al.; "Precision Tumor Recognition by T Cells With Combinatorial Antigen-Sensing Circuits"; Cell; vol. 164, No. 4, pp. 770-779 (Feb. 11, 2016).
Sanchez-Irizarry, et al.; "Notch Subunit Heterodimerization and Prevention of Ligand-Independent Proteolytic Activation Depend, Respectively, on a Novel Domain and the LNR Repeats"; Molecular and Cellular Biology; vol. 24, No. 21, 9265-9273 (Nov. 2004).
Sastry, et al.; "Targeting Hepatitis B Virus-Infected Cells with a T-Cell Receptor-Like Antibody"; Journal of Virology; vol. 85, No. 5, pp. 1935-1942 (Mar. 2011).
Sergeeva, et al.; "Activity of 8F4, a T-cell receptor-like anti-PR1/HLA-A2 antibody, against primary human AML in vivo"; Leukemia; vol. 30, pp. 1475-1484 (2016).
Sergeeva, et al.; "An anti-PR1/HLA-A2 T-cell receptor-like antibody mediates complement-dependent cytotoxicity against acute myeloid leukemia progenitor cells"; Immunobiology; vol. 117, No. 16, pp. 4262-4272 (Apr. 2011).
Stewart-Jones; "Rational development of high-affinity T-cell receptor-like antibodies"; PNAS; vol. 106, No. 14, pp. 5784-5788 (Apr. 7, 2009).
Struhl, et al.; "Nuclear access and action of notch in vivo"; Cell; vol. 93, No. 4, pp. 649-660 (May 15, 1998).
Voet, et al.; Biochemistry; pp. 126-128 (1990).
Vooijs, et al.; "Mapping the consequence of Notch1 proteolysis in vivo with NIP-CRE"; Development; vol. 132, No. 3, pp. 535-544 (Feb. 2007).
Weissman, et al.; "Molecular cloning and chromosomal localization of the human T-cell receptor zeta chain: distinction from the molecular CD3 complex"; PNAS; vol. 85, No. 24, pp. 9709-9713 (Dec. 1988).
Willemsen, et al.; "A phage display selected Fab fragment with MHC class I-restricted specificity for MAGE-A1 allows for retargeting of primary human T lymphocytes"; Gene Therapy; vol. 8, pp. 1601-1608 (2001).
Wittman, et al.; "Antibody Targeting to a Class I MHC-Peptide Epitope Promotes Tumor Cell Death"; The Journal of Immunology; vol. 177, pp. 4187-4195 (2006).
WONG; "Altor Bioscience Corporation; Company Profile"; Biomarkers Med.; vol. 4, No. 4, pp. 499-504 (2010).
Wu, et al.; "Remote control of therapeutic T cells through a small molecule-gated chimeric receptor"; Science; vol. 350, No. 6258, 12 pages (Oct. 16, 2015).
Wu, et al.; "Synthetic Approaches to Engineer T cells"; Curr. Opin. Immunol.; vol. 35, pp. 123-130 (Aug. 2015).
Co-pending U.S. Appl. No. 16/096,248, filed Oct. 24, 2018.
Stieglmaier et al., "Utilizing the BiTE (bispecific T-cell engager) platform for immunotherapy of cancer", Expert Opin. Biol. Ther., 2015, 15(8): 1093-1099.
Tassev et al., "Retargeting NK92 cells using an HLA-A2-restricted, EBNA3C-specific chimeric antigen receptor", Cancer Gene Therapy, 2012, 19: 84-100.

\* cited by examiner

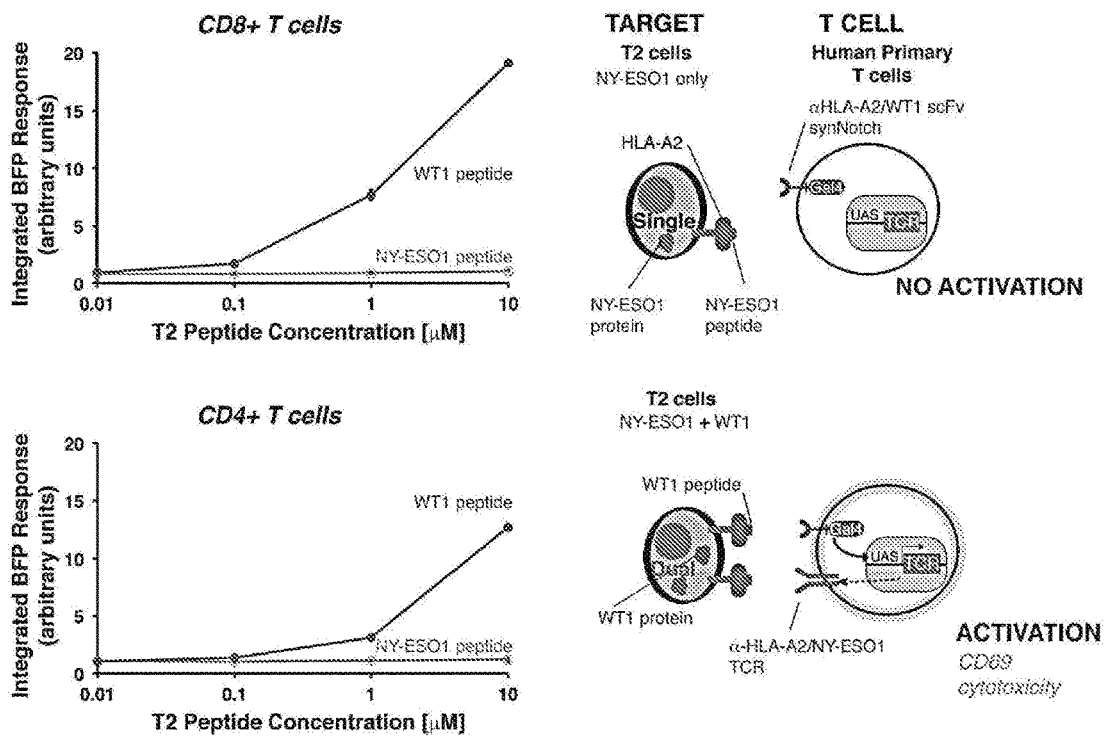
FIG. 5
FIG. 6
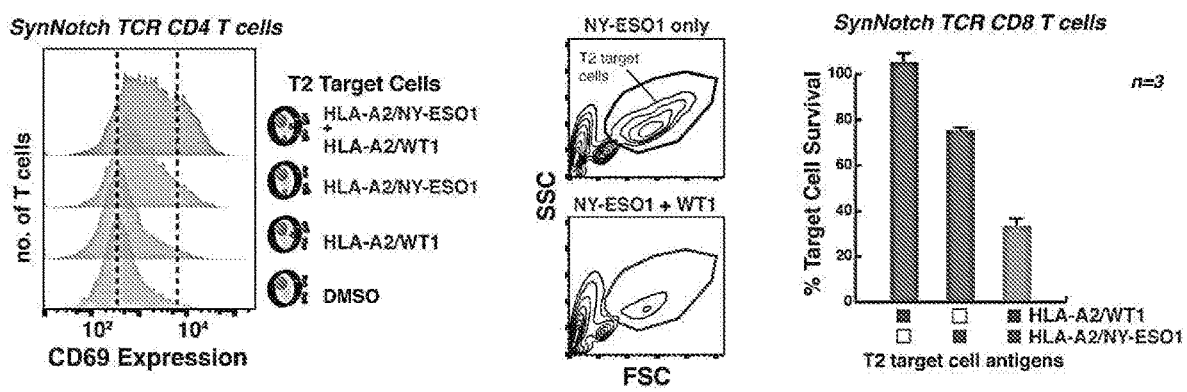
FIG. 7
FIG. 8

CD4 T cell Activation (CD69)

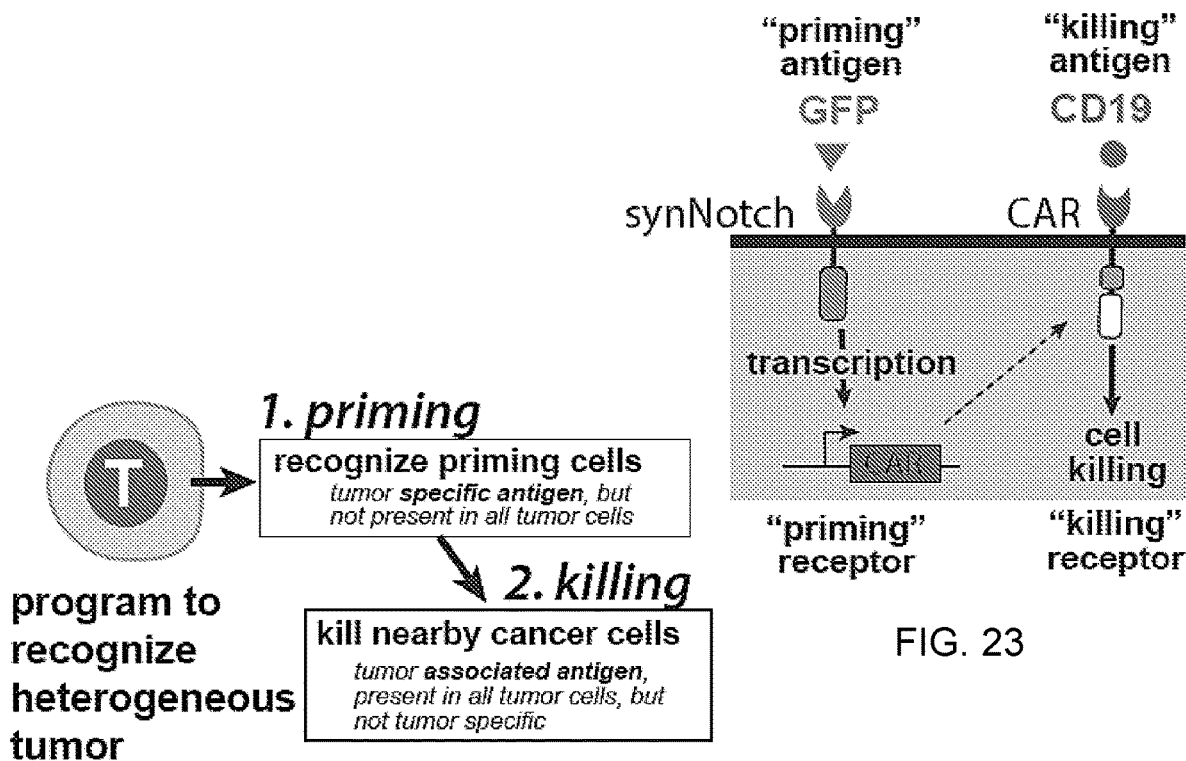
FIG. 22
FIG. 23
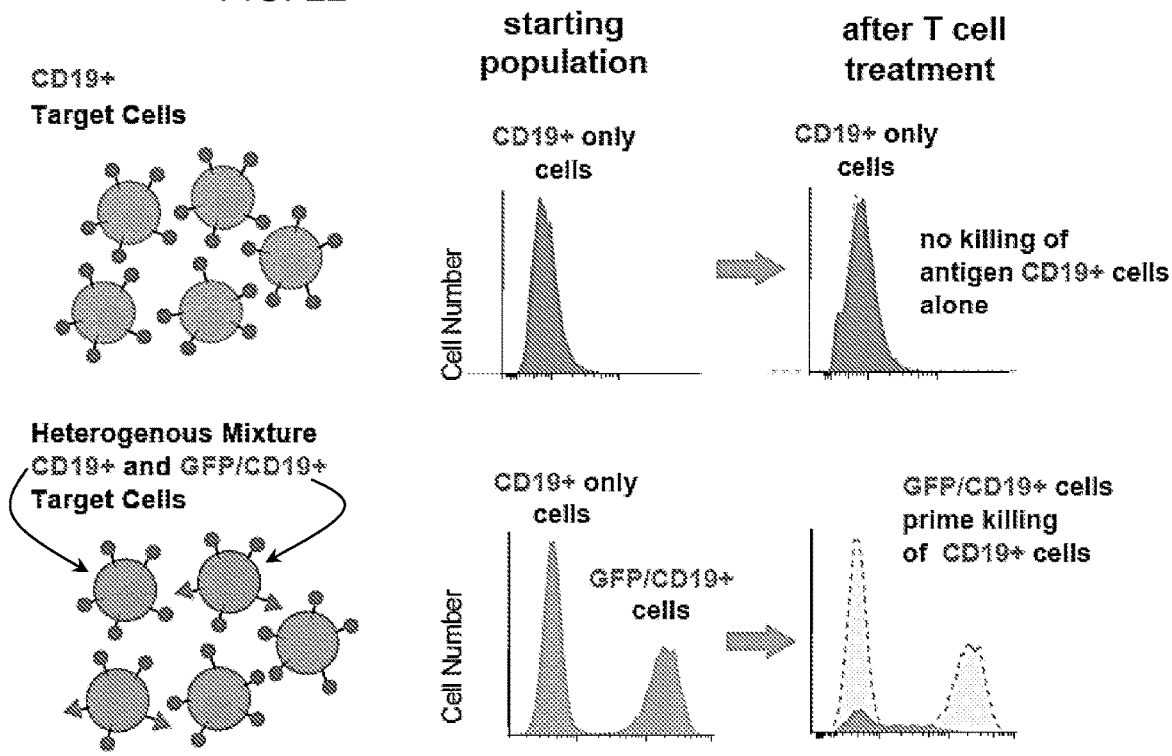
FIG. 24

FIG. 31A

*Homo sapiens* Notch-1
GenBank NP_060087
2555 aa

Grey Background Text – EGF Repeat
Boxed Text – LNR A B and C
Dashed Box Text – S1 cleavage
Dotted Box Text – S2 cleavage
Outlined & Boxed Text – S3 cleavage

```
   1 mppllapllc lallpalaar gprcsqpget clnggkceaa ngteacvcgg afvgprcqdp
  61 npclstpckn agtchvvdrr gvadyacsca igfsgplclt pldnacltnp crnggtcdll
 121 tlteykcrcp pgwsgkscqq adpcasnpca nggclpfea syichcppsf hgptcrqdvn
 181 ecgqkpglcr hggtchnevg syrcvcrath tgpncerpyv pcspspcqng gtcrptgdvt
 241 hecaclpgft gqnceenidd cpgnnckngg acvdgvntyn crcppewtgq yctedvdecq
 301 lmpnacqngg tchnthggyn cvcvngwtge dcseniddca saacfhgatc hdrvasfyce
 361 cphgrtglic hindacisnp pvngkaictc pvngkaictc psgytgpacs qdvdecsiga
 421 npcehagkci ntlgsfecqc lqgytgprce idvnecvsnp cqndatcldq igefqcicmp
 481 gyegvhcevn tdecasspcl hngrcldkin efqceceptgf tghlcqydvd ecastpckng
 541 akcldgpnty tcvctegytg thceevdidec dpdpchygsc kdgvatftcl crpgytghhc
 601 etninecssq pcrhggtcqd rdnaylcfcl kgttgpncei nlddcasspc dsgtcldkid
 661 gyecacepgy tgsmcniniid ecagnpchng gtcedgingf tcrcpegyhd ptclsevnec
 721 nsnpcvhgac rdslngykcd cdpgwsgtnc dinnecesn pcvnggtckd mtsgyvctcr
 781 egfsgpncqt ninecasnpc lnqgtciddv agykcnclip ytgatcevvi apcapspcrn
 841 ggecrqsedy esfscvcptg wqggtcevdi necvispcrh gascqnthgg yrchcqagys
 901 grncetdidd crpnpchngg sctdgintaf cdclpgfrgt fceedineca sdpcrnganc
 961 tdcvdsytct cpagfsgihc enntpdctes scfnggtcvd ginsftclcp pgftgsycqh
1021 dvnecdsqpc lhggtcqdgc gsyrctcpgg ytgpncqnlv hwcdsspckn ggkcwqthtq
1081 yrccepsgwt glycdvpsvs cevaaqrqgv dvaricqhgg lcvdagnthh crcqagytgs
1141 ycedlvdecs pspcqngatc tdylggysck cvagyhgvnc seeidecish pcqnggtcld
1201 lpntykcscp rgtggvhcei nvddcnppvd pvsrspkcfn ngtcvdqvgg ysctcppgfv
1261 gercegdvne clsnpcdarg tqncvqrvnd fhcecraght grrcesving ckgkpckngg
```

FIG. 31B

```
1321 tcavasntar gfickcpagf egatcendar tcgslrclng gtcisgprsp tciclgpftg
1381 pecqfpassp clgpncyng gtcptsesp fyrctcpakf ngtchildy sfgggagrdi
1441 pppiieeace lpecqedagn kvcslqcnnh acgwdggdcs lnfndpwknc tqslqcwkyf
1501 sdghcdsgcn sagclfdgfd cqraegqcnp lydqyckdhf sdghcdggcn saecewdgid
1561 cahvperla agtlvvvim ppeqlrnssf hflreisrvl htnvvfkrda hgqmifpyy
1621 greeelrkhp ikraaegwaa pdailgqvka slipggsegg rrrreldpmd vrgsivylei
1681 dnrqcvqass qcfqsatdva aflgalaslg slnipykiea vqsetveppp paqlhfmyva
1741 aaafvllffv gcMlisrkr rrqhgqlwfp egfkvseask kkrrepiged svglkpikna
1801 sdgalmddnq newgdediet kkfrfeepvv lpdiddqtdh rqwtqqhida adirmsamap
1861 tppqgevdad cmdvnvrgpd gftplmiasc sggqietgns eeeedapavi sdfiyqgasl
1921 hnqtdrtget alhiaarysr sdaakrilea sadaniqdnm grtplhaavs adaqgvfqil
1981 irnnratdlda rmhdgttpli laarlavegm iedllinshad vnavddlgks alhwaaavnn
2041 vdaavvllkn gankdmqnnr eetplfliaar egsyetakvl ldhfanrdit dhmdrlprdi
2101 aqermhhdiv rildeynlvr spqlhgaplg gtptlsppic spngylgsik pgvqgkkvrk
2161 psskglacgs keakdlkarr kksqdgkgcl ldssgmlspv dslesphgyl sdvassppllp
2221 spfqqspsvp lnhipgmpdt higighinva akpemaalgg ggrlafetgp prishlpvas
2281 gtstvlgsss ggainftvgg stslnggcew lsrlqsgmvp nqynplrgsv apgplstqap
2341 slqhgmvgpi hsslaasais qmmsyqglps trlatqphlv qtqqvqpqni qmqqqnlqpa
2401 niqqqslqp ppppqphig vssaasghlg rsflsgepsq advqplgpss lavhtilpqe
2461 spalptslps slvppvtaaq fltppsqhsy sspvdntpsh qlqvpehpfl tpspespdqw
2521 ssssphsnvs dwsegvsspp tsmqsqiari peafk
```

FIG. 31C

*Mus musculus* Notch-1
GenBank NP_032740
2531 aa

Grey Background Text :- EGF Repeat
Boxed Text :- LNR A B and C
Dashed Box Text :- S1 cleavage
Dotted Box Text :- S2 cleavage
Outlined & Boxed Text :- S3 cleavage

```
   1 mprlitpllc itllpalaar glrcsqpsgt clnggrceva ngteacvcsg afvggrcqds
  61 npclstpckn agtchvvdhg gtvdyacscp lgfsgpiclt pldnaclanp crnggtcdil
 121 titeykcrcp pgwsgkscqq adpcasnpca nggqcipfes syicrcppgf hgptcrqdvn
 181 ecsqnpglcr hggtchnneig syrcacrath tgphcelpyv pcspspcqng gtcrptgdtt
 241 hecacipgfa gqnceenvdd cpgnnckngg acvdgvntyn crcppewtgq yctedvdecq
 301 lmpnacqngg tchnthggyn cvcvngwtge dcseniddca saacfggatc hdrvasfyce
 361 cphgrtgllc hindacisnp cvngkaictc pvngkaictc psgytgpacs qdvdecalga
 421 npcehagkcl ntlgsfecqc lqgytgprce idvnecisnp cqndatcldq igefqcicmp
 481 gyegvycein tdecassscpl hnghcmdkin efqcqcpkgf nghlcqydvd ecastpckng
 541 akcldgpnty tcvctegytg thceevdidec dpdpchygsc kdgvatftcl cqpgytghhc
 601 etninechsq pcrhgtcqd rdnsyliclcl kgttgpncei niddcasnpc dsgtcldkid
 661 gyecacepgy tgsmcnvnid ecagspchng gtcedgiagf tcrcpegyhd ptclsevnec
 721 nsnpcihgac rdgingykcd capgwsgtnc dinnnecesn pcvnggtckd mtsgyvctcr
 781 egfsgpncqt ninecasnpc lnggtciddv agykcncpip ytgatcevvi apcatspckn
 841 sgvckesedy esfscvcptg wqggtcevdi necvkspcrh gascqntngs yrclcqagyt
 901 grncesdidd crpnpchngg sctdgintaf cdclpgfqga fceedineca snpcqnganc
 961 tdcvdsytct cpvgfngihc enntpdctes scfnggtcvd ginsftcicp pgftgsycqy
1021 dvnecdsrpc lhggtcqdsy gtykctcpgg ytglncqnlv rwcdsapckn ggrcwqtntq
1081 yhcecrsgwt gvncdvlsvs cevaaqkrgi dvtllcqhgg lcvdegdkhy chcqagytgs
1141 ycedevdecs pnpcqngatc tdylggfisck cvagyhgsnc seeineclsq pcqnggtcid
1201 ltnsykcscp rgtqgvhcei nvddchppld pasrspkcfn ngtcvdqvgg ytctcppgfv
1261 gercegdvne cisnpcdprg tqncvqrvnd fhcecraght grrceesving crgkpckngg
```

FIG. 31D

```
1321 vcavasntar gficrcpagf egatcendar tcgslrcing gtcisgprsp tciclgsftg
1381 pecqfpassg cvasnfvnd gtcelsenp tvrc cbakf nal childy sftggagrdi
1441 ppqieeace lpecqvdagn kvcniqcnnh acgwdggdcs lnfndpwknc tqsiqcwkyf
1501 sdghcdsqcn sagclfdqfd cqlteggcnp lydqvckdhf sdghcdqgcn saecewdqid
1561 cahvperia agtlvlvvll ppdqirnnsf hflrelshvl htnvvfkrda qggqmifpyy
1621 gheeelrkhp ikrstvgwat sslipgtsgg rqrreldpmd irgsivylei dnrqcvqsss
1681 qcfqsatdva aflgalaslg slnipykiea vksepveppi psqihlmyva aaafvliffv
1741 gdvlisrkr rrqhgqlwfp egfkvseask kkrrepiged svgikplkna sdgalmddnq
1801 newgdedlet kkfrfeepvv ipdlsdqtdh rqwtqqhlda adirmsamap tppqgevdad
1861 cmdvnvrgpd gftplmiasc sgggietgns eeeedapavi sdfiyggasl hnqtdrtget
1921 aihlaarysr sdaakrliea sadaniqdnm grtplhaavs adaqgvfqil lrnnratdida
1981 rmhdgttpli laarlavegm iedlinshad vnavddlgks alhwaaavnn vdaavvllkn
2041 gankdmqnnk eetplfliaar egsyetakvl idhfanrdit dhmdrlprdi agermhhdiv
2101 rildeynlvr spqlhgtalg gtptisptlc spngylgnik satqgkkark pstkglacgs
2161 keakdikarr kksqdgkgcl idsssmispv dslesphgyi sdvaspplip spfqqspsmp
2221 lshlpgmpdt higishinva akpemaalag gsrlafeppp prlshipvas sastvlstng
2281 tgamnftvga paslnggcew iprlqngmvp sqynplrpgv tpgtistqaa glqhsmmgpi
2341 hssistntis piiygglipnt rlatqphlvq tqqvqpqnlq iqpqnlqpps qphlsvssaa
2401 nghlgrsfls gepsqadvqp lgpsslpvht ilpqesqaip tslpssmvpp mttqfitpp
2461 sqhsyssspv dntpshqlqv pehpffitpsp espdqwssss phsnisdwse gisspttmp
2521 sqithipeaf k
```

FIG. 31E

*Caenorhabditis elegans* Lin-12
GenBank NP_499007.1
1429 aa

Grey Background Text – EGF Repeat
Boxed Text – LNR A B and C
Dashed Box Text – S1 cleavage
Dotted Box Text – S2 cleavage
Outlined & Boxed Text – S3 cleavage

```
   1 mripticflif llisiskslh igscigliicg rnghchagpv ngtqtsywcr cdegfggeyc
  61 eqgcdvskcg adekcvfdkd yrmetcvckd cdingnsilk pscpsgyggd dcktggwcyp
 121 svcmnggqci gagnrakcac pdgfkgerce idvneceenk nacgnrstcm ntlgtyicvc
 181 pqgflppdci kpgntstvef kqpvcfleis adhpdgrsmy cqnggficdka sskcqcppgy
 241 hgstcelliek edscasnpcs hgvcisfsgg fqcicddgys gsycqegkdn cvnnkceags
 301 kcingvnsyf cdcppertgp ycekmdcsai pdicnhgtci dspisekafe cqcepgyegi
 361 lceqdknecl senmclnngt cvnlpgsfrc dcargfggkw cdeplnmcqd fhcendgtcm
 421 htsdhspvcq ckngfigkrc ekecpigfgg vrcdirleig icsrqggkcf nggkcisgfc
 481 vcppdftgng cevnrkngks sisenlclsd pcmnnatcid vdahigyaci ckqgfegdic
 541 erhkdiclen pcsngqvchg hresfscdcp pgfyqngceq ekmficcdqvfq ncdadcnyaa
 601 skgkkcs yrsqate kinltgftek dsllrsvcek rkcseranddg ncdadcnyaa
 661 ckfdggdcsg krepfiskcry gnmcadffan qvcngacnne eclydqmdcl pavvrcpvki
 721 rehcasrfan qicdpecntn gcqfdggdcd netnatiitn iritvgmdpk efqvtggqsl
 781 meissalrvt vriqrdeegp lvfqwngese mdrvkmnerq iteqhvlsts isrkikrsat
 841 nigvvvylev qencdtgkcl ykdaqsvvds isarlakkgi dsfgipisea lvaeprksgn
 901 ntgfiswnal liligagcliv mvvlmigalp gnrtrkrrmi nasvwmppme neeknrknhq
 961 sitssqhsil easydgyikr qrnelqhysl ypnpggygng ndfigdfnht niqiptepep
1021 espikihtea agsyaitepi tresvniidp rhnrtvlhwi asnssaekse dlivheakec
1081 iaagadvnam dcdentplml aviarrrrlv aylmkagadp tiynksersa ihqaaanrdf
1141 gmmvymlnst kikgdieeld rngmtalmiv ahnegrdqva sakllvekga kvdydgaark
1201 dsekykgrta ihyaaqvsnm pivkylvgek gsnkdkqded gktpimlaaq egrievvmyi
1261 iqggasveav datdhtarqi aqannhhniv difdrcrper eysmdihigh thqpqpsrkv
1321 trapkkqtsr skkesasnsr dsthltppps dgststpspq hfmntthttp tslnylspey
1381 qteagsseaf qpqcgafgng emwytrasts ytqmqnepmt rysepahyf
```

FIG. 31F

*Drosophila melanogaster* Notch
GenBank NP_476859.2
2703 aa

Grey Background Text – EGF Repeat
Boxed Text – LNR A B and C
Dashed Box Text – S1 cleavage
Dotted Box Text – S2 cleavage
Outlined & Boxed Text – S3 cleavage

```
   1 mqsqrsrrrs rapntwicfw inkmhavasl paslplilt lafanlpntv rgtdtalvaa
  61 sctsvgcqng gtcvtqlngk tycacddshyv gdycehrnpc nsmrcqnggt cqvtfrngrp
 121 gisckcplgf desiceiavp nacdhvtcin ggtcqlktle eytcacangy tgercetkni
 181 casspcrnga tctalagsss ftcscppgft gdtcsydiee cqsnpckygg tcvnthgsyq
 241 cmcptgytgk dcdtkykpcs pspcqnggic rsnglsyeck cpkgfegknc eqnyddclgh
 301 lcqnggtcid gisdytcrcp pnftgrfcqd dvdecaqrdh pvcqngatct nthgsyscic
 361 vngwaglcds nntddckqaa cfygatcidg vgsfycqctk gktglichld dactsnpcha
 421 daicdtspin gsyacscatg ykgvdcsedi decdgspce hngicvntpg syrcncsqgf
 481 tgprcetnin eceshpcqne gsciddpgtf rcvcmpgftg tqceididec qsnpcindgt
 541 chdkingfkc scalgftgar cqiniddcqs qpcrnrgich dsiagyscec ppgytgtsce
 601 inindcdsnp chrgkciddv nsfkclcdpg ytgyicqkqi necesnpcqf dghcqdrvgs
 661 yycqcqagts gkncevnvne chsnpcnnga tcidginsyk cqcvpgftgq hceeknvdeci
 721 sspcanngvc idqvngykce cprgfydahc lsdvdecasn pcvnegrced ginefichcp
 781 pgytgkrcel didecssnpc qhggtcydkl nafscqcmpg ytgqkcetni ddcvtnpcgn
 841 ggtcidkvng ykcvckvpft grdcesknmdp casnrcknea kctpssnfld fsctcklgyt
 901 grycdedide cslsspcrng asclnvpgsy rcictkgyeg rdcaintddc asfpcqnggt
 961 cldgigdysc lcvdgfdgkh cetdinecis qpcqngatcs qyvnsytctc plgfsgincq
1021 tndedctess clnggscidg ingynccia gysgancqyk lnkcdsnpcl ngatcheqnn
1081 eytchcpsgf tgkqcseyvd wcgqspceng atcsqmkhqf sckcsagwtg kicdvqtisc
1141 qdaadrkgls lrqlcnngtc kdygnshvcy csqgyagsyc qkeidecqsq pcqnggtcrd
```

FIG. 31G

```
1201 ligayecqcr qgfqqqncel niddcapnpc qnggtchdrv mnfscscppg tmgiiceink
1261 ddckpgachn ngscidrvgg fecvcqpgfv garcegdine clsnpcsnag tldcvqlvnn
1321 yhcncrpghm grhcehkvdf caqspcqngg ncnirqsghh cicnngfygk nceisgq
1381 snpcxgncy vateqyes scretigeh ceidtidecs pnpcaggaac edligdveci
1441 cpskwkgkrc diydanypgw nggsg

FIG. 31H

Bos taurus
Notch receptor
GenBank DAA24217

```
   1 mtpvctptrp gpcahpalpr stphsitdss raepiesfiv ispalelrll lavvgqdtpl
  61 gdvwaggkas gggdtegpls egskegeaat gpqapgaewh apprstclss tprpeavpps
 121 lpcrspgwga cggrrpgpal epahmgsvps qqrppgidrs redngpppqi psphggasla
 181 papppacrgw qpplrwpgaa aarvpghrrt cspaalcpcc rcliywarfs shcnsrslpg
 241 qdalgpqiwv psatqagtrq pvtgstlsgg hatfpriqgm alpepegegp pttsaggcgp
 301 svraafpgrc qlgavgafhp rgsaagkrea wlvpepiigf pssslrgdp gghvpprikk
 361 prqqvakggp gaqvagaepf pvgsagdqaw gwaggkappt pgspatvaar epaqgipdcg
 421 gafagqgcga pnpclsapck nggtchtter eglvdyvcgc rlgfsgplci tprdhacias
 481 pcinggtcdl itlteykclc tpgwsgktcq qadpcaasnpc anggqclpfe asyichcppg
 541 fhgptcrqdv necsqspglc hhggtclnev gsyrcvcrpt htgphcelpy vpcspspcqn
 601 ggtcrptgdt thecacipgf tgqnceenid dcpgnsckng gacvdgvnty ncrcppewtg
 661 gytcedvdec qlmpnacqng gtchnthggy ncvcvngwtg edcseniddc asascfggat
 721 chdrvasfyc ecphgrtgli chindacisn pcnegsncdt npvngkaict cpsgytgpac
 781 sqdvdecsig anpcehagkc intlgsfecq clqggytgprc eidvnecvsn pcqndatcld
 841 qigefqcicm pgyeglhcev ntdecasspc lqngrcidki nefvceceptg ftghlcqydv
 901 decastpckn gakcldgpnt ytcvctegyt gphceevdide cdpdpchygs ckdgvatftc
 961 lcqpgytghh cesninechs qpcrhggtcq drdnayicfc lkgttgpnce iniddcasnp
1021 cdsgtcldki dgyecacepg ytgsmcnini decadspchn ggtcedging ftcrcpegyh
1081 dptcisevne cssnpcihga crdslngykc dcdpgwsgan cdvnndeces npcinggtck
1141 dmtsgyvcac regfsgpncq tninecasnp clnggtcidd vagykcncli pytgatcevv
1201 lapcapgpcr nggeceresed yesfscacpa gwgggtceid inecvkspcr agascqntng
1261 syrchcqagy tgrncetdid dcrpnpchng gsctdginta fcdclpgfqg afceedinec
1321 asspcrngan ctdcvdsytc tcptgfsgih cenntpdcte sscfnggtcv dginsftclc
1381 ppgftgsycq hdvnecdsrp clhggtchds ygtytctcpq gytglncqti vrwcdsspck
1441 ndgrcwqtna lyrccechsgw tglycdvpsv sceevaarqgq vnvthlcrng gicmnagnth
1501 rchcqagytg syceeqvdec spspcqngat ctdypggysc ecvagyhgvn cseevnecis
1561 qpcinggtci dlintykcsc prgtggvhce invddcnppi dpvsrgpkcf nngtcvdqvg
1621 gyscscppgf vgercegdvn ecisnpcdar gtqncvghvn afhcecragh tgrrcesvin
1681 gckdrpckng gscavasnta rgfickcpag fegatcenda rscgslrcln ggtclagprs
1741 ptclclqpft gpecqfpass pcvggnpcyn qgvceptaes pfyrcrcpak fngllchild
1801 ysfgggvgid ippqieetc elpgcreeag nkvcslgcns hacgwdggdc sldiddpwqn
```

FIG. 31

```
1861  ctqslqcwky fsngrcdsgc nsagclfdgf dcqraegqcn plydqyckdh frdghcdqgc
1921  nsaecewdgl dcaehvperl aagtlvlvvl mppeqlrnrs lhflreisrl lhtnvvfkrd
1981  asgqmifpy ygraplpage rseecrcehh acpagaggge psgpictsrs ivyleidnrg
2041  cvqsssqcfq satdvaaflg aiaslgsini pykieavqse tveppppppl hfmyvavvaf
2101  vliffvgcgv iisrkrrqh gqiwfpegfk vseaskkkrr eplgedsvgl kplknssdga
2161  lmddnqnewg degleakkfr feepvvipdl ddqtdhrqwt qqhldaadlr vsamaptppq
2221  geadadcmdv nvrgpdgftp lmiascsggg letgnseeee dapavisdfi yqgaslhnqt
2281  drtgetaihl aarysrsdaa krlleasada niqdnmgrtp ihaavsadaq gvfqilirnr
2341  atdldarmhd gttplilaar lavegmiedl inshadvnav ddlgksalhw aaavnnveaa
2401  vvilkngank dmqnnkeetp lfliaaregsy etakvllidhf anrditdhmd riprdiaqer
2461  mhhdivrild eyslvrsppl hgatlggtpt isppicspng yignikppmq gkkarkpstk
2521  giacggkepk dikarrkksq dqkgclidsg svmspvdsle sphgyisdva spplipspfq
2581  pspsvpinhl pgmpethigv shisvaakpe mavlsggsrl afeagpprls hipvassstst
2641  iigsggsggs gavnftvgga aginqqcewl sriqnglvpn qynpirggvt pgtlstqaag
2701  lqhgtvgplh apalsqvmty qalpstrlas qphlvqpqqn iqmqppsmpp qpnlqphlgv
2761  ssaasghigr sfiggeisqa dmqplgpgnl aahtvlpqdg qvlptslpst lapptmappm
2821  ttaqfltpps qhsyssspvd ntpshqliqvp ehpfltpspe spdqwssssp hsnisdwseg
2881  isspptsvps qiahvpeafk
```

FIG. 31J

*Gallus gallus*
Notch receptor
Genbank NP_001025466

```
   1 mgrcsaahpr ggvhcpgica vpdalilfpg vrctqlaesc lnggkcetfl ngtevcqcss
  61 ahmgercqlp npclsspckn agtcipllrg stadytcvcr lgftdelclt pldnacisnp
 121 crnggtcdlv tlseykcrcp pgwsgktcqq adpcaasnpca nggqcvpfea hyicrctagf
 181 hganckqdvn ecnisppvck nggsctnevg tyqcsckpay tgqncehlyv pcnpspcqng
 241 gtcrqtgdtt ydctclpgft gqnceenidd cpgnncrngg tcvdgvntyn cqppewtgq
 301 yctedvdecq lmpnacqngg tchnnhggyn cvcvngwtge dcseniddca maacfqgatc
 361 hdrvasfyce cphgrtgllc hiddacisnp pvngkaictc psgymgpacn
 421 qdvdecslga npcehagkci ntqgsfgcqc lqgysgprce idvneclsnp cqndatcidq
 481 igefqcicmp gyegvycein tdecasspci hngncldkin efhceeptgf nghicqfdid
 541 ecastpckng akcvdgpnty sceetegfsg vhceididec npdpchygtc kdsiaaftci
 601 cqpgytghrc dininecsgq pcrnggtcqd rdnaynclcl kgttgpncei nlddcasnpc
 661 dygkcidkin gyectcepgy tgrmcninid ecasnpchng gtckdgingf tclcpegfhd
 721 pkclsevnec nsnpcihgrc hdgingyrcd cdpgwsgtnc dinnneecesn pcmnggtckd
 781 mtsgyictcr egfsgpncqt ninecasnpc lnggtciddv agytcncllp ytgatcedvi
 841 apcaggpckn ggecresedy krfscscppg wqgqtceidi necvkspcrn gatcqntngs
 901 yrclcrvgfa grncdtdidd cqpnpchngg scsdgigtff ceclagfrgi kceedineca
 961 snpckngnc tdcvnsytct cpsgfsgihc enntpdctes scfnggtcvd qintftcicp
1021 sgftgsyceh ninecdskpc inggtcqdsy gtykctcpgg ytglncqnlv rwcdsspckn
1081 ggkcwqtnnl yrcecnsgwt glvcdvpsvs cevaakqggi dvahlcrnsg lcvdsgnthf
1141 crcqagytgs yceeqvdecs pnpcqngatc tdylggysce cvagyhgvnc seeinecish
1201 pcqnggtcid lintykcscp rgtgvhcei nvddcspffd pvtlgpkcfn ngkctdrvgg
1261 yscicppgfv gercegdvne cisnpcdarg tqncvqrvnd ykcecrpgya grrcdtvvdg
1321 ckgkpcrngg tcavasntgr gfickcppgf vgatcendsh tcgtlhclng gtcismhkss
1381 kcvcaaaftg pecqypassp cisnpcyngg tceflsdasp yyhcncpanf nginchildf
1441 dfqggfgqdi ippkieekce iavcasyagn kicdgkcnnh acgwdggdcs lnfndpwknc
1501 sqslqcwkyf ndgkcdsqcn nagclydgfd cqkyeggcnp lydqyckdhf sdghcdqgcn
1561 nfecewdgld cannmpekia dgtlvvvli tpeniknnsf nflrelsrvl htnvvfkkna
1621 kgeymifpyy gneeelkkhy ikrstedwad mssavinkvk sslysragrr qkreldqmdi
1681 rgsivyleid nrqcigsssq cfqsatdvaa flgalasign lnipykieav ksetaeparn
```

FIG. 31K

```
1741  sqlypmyvvv  aalvliafig  vgvlvsrkrr  rehgqiwfpe  gfkvtesskk  krrepigeds
1801  vgikpiknas  dgtlmddnqn  ewgdeetidt  kkfrfeeqam  ipdtddqtdh  rqwtqqhlda
1861  adirissmap  tppqgeidad  cmdvnvrgpd  gftplmiasc  sgggletgns  eeeddapavi
1921  sdfiyqgasl  hnqtdrtget  aihlaarysr  sdaakriiea  sadaniqdnm  grtpihaavs
1981  adaqgvfqil  irnratdida  rmhdgttpli  iaarlavegm  iedlinchad  vnavddigks
2041  aihwaaavnn  veaavvlikn  gankdmqnnk  eetplfiaar  egsyetakvi  idhfanrdit
2101  dhmdriprdi  aqermhhdiv  riideynivr  spplhsgplg  aptispplcs  pssyignlkp
2161  avqgkkarkp  stkglscngk  dskdlkarrk  ksqdgkgcll  dnssvispvd  slesphgyls
2221  dvasppimts  pfqqspsmpl  nhipgmpdah  msinhinmag  kqemaiggsg  rmafeavppr
2281  ishlpvssps  tamsnapmnf  svggaagisg  qcdwlsriqs  gmvqnqygam  rggmqpgthq
2341  qaqnlqhgmn  ssihngipst  sisqnmsyqa  mpstriasqp  hllqnqmqq  mqqpgmqpqp
2401  gmqpqpgmqq  pqqpqgqpq  pqqhhnpgsn  asghmgqnfl  gtelsqpdmq  pvssamavh
2461  tiipqdsqll  ptslpssiaq  pmttqfiitp  psqhsysspl  dntpshqlqv  pdhpfitpsp
2521  espdqwssss  phsnvsdwse  gisspptsmq  sqmghipeaf  k
```

FIG. 31L

Rattus norvegicus Notch receptor
GenBank CAA40667

```
   1 mprilaplic itlipalaar glrcsqpsgt clnggrceva ngteacvcsg afvggrcqdp
  61 spcistpckn agtcyvvdhg givdyacscp igfsgplcit planacianp crnggtcdll
 121 tlteykcrcp pgwsgkscqq adpcasnpca nggqcipfes syicgcppgf hgptcrqdvn
 181 ecsqnpglcr hggtchneig syrcacrath tgphcelpyv pcspspcqng gtcrptgdtt
 241 hecacipgfa ggnceenvdd cpgnnckngg acvdgvntyn crcppewtgq yctedvdecq
 301 impnacqnag tchnshggyn cvcvngwtge dcsdniddca saacfqgatc hdrvasfyce
 361 cphgrtgllc hindacisnp pvngkaictc prgytgpacs qdvdecaiga
 421 npcehagkcl ntlgsfecqc iqgytgprce idvneclsnp cqndatcldq igefqcicmp
 481 gyegvycein tdecasspcl hngrcvdkin eflcqcpkgf sghicqydvd ecastpckng
 541 akcldgpnty tcvctegytg thcevdidec dpdpchigic kdgvatftci cqpgytghhc
 601 etninechsq pcrhgqtcqd rdnyiclcl kgttgpncei nlddcasnpc dsgtcldkid
 661 gyecacepgy tgsmcnvnid ecagspchng gtcedgiagf tcrcpegyhd ptclsevnec
 721 nsnpcihgac rdgingykcd capgwsgtnc dinnnecesn pcvnggtckd mtsgvvctcr
 781 egfsgpncqt nineecasnpc inggtciddv agykcncpip ytgatceevi apcatspckn
 841 sgvckesedy esfscvcptg wggqtceidi necvksperh gascqntngs yrclcqagyt
 901 grncesdidd crpnpchngg sctdgvnaaf cdcipgfqga fceedineca tnpcqnganc
 961 tdcvdsytct cptgfngihc enntpdctes scfnggtcvd ginsftclcp pgftgsycqy
1021 dvnecdsrpc lhggtcqdsy gtykctcpgg ytgincqnlv rwcdsapckn ggkcwqtntq
1081 yhcecrsgwt gfncdvlsvs cevaaqkrgi dvtllcqhgg icvdeedkhy chcqagytgs
1141 ycedevdecs pnpcqngatc tdyiggfisck cvagyhgsnc seeineclsq pcqnggtcid
1201 itntykcscp rgtqgvhcei nvddchppid pasrspkcfn ngtcvdqvgg ytctcppgfv
1261 gercegdvne clsnpcdprg tqncvqrvnd fhcecraght grrcesving crgkpcrngg
1321 vcavasntar gflcrcparf egatcendar tcgsircing gtcisgprsp tciclgsftg
1381 pecqfpassp cvgsnpcyng gtceptsesp fyrclcpakf ngllchildy sftgaagrdi
1441 pppqleeace ipecqedagn kvcnlqcnnh acgwdgqdcs infndpwknc tqslqcwkyf
1501 sdghcdsqcn sagclfdgfd cqltegqcnp lydqyckdhf sdghcdqgcn saecewdgld
1561 caehvperla agtlvlvvll ppdqlrnnsf hflrdvshvl htnvvfkrda qgqmifpyy
1621 greeeirkhp lkrsavgwat tslipgtngg rqrreldpmd ihgsivylei dnrqcvqsss
1681 qcfqsatdva afigalasig slnipykiea vksetveppl psqlhlmyva aaafvlffv
1741 gcgvllsrkr rrqhgqlwfp egfkvseask kkrrepiged svglkplkna sdgaimddnq
```

FIG. 31M

```
1801 newgdediet kkfrfeepvv ipdlddqtdh rqwtqqhida adlrvsamap tppqgevdad
1861 cmdvnvrgpd gftplmiasc sgggletgns eeeedapavi sdfiyqgasl hnqtdrtget
1921 aihlaarysr sdaakriiea sadaniqdnm grtplhaavs adaqgvfqil irnratdlda
1981 rmhdgttpli laarlavegm iedlinshad vnavddigks aihwaaavnn vdaavvilkn
2041 gankdmqnnk eetplfiaar egsyetakvl idhfanrdit dhmdriprdi aqermhhdiv
2101 riideynivr spqlhgtalg gtptlsptlc spngylgnlk satqgkkark pstkglacss
2161 keakdlkarr kksqdgkgcl ldsssmispv dsiesphgyl sdvasppllp spfqqspsmp
2221 ishlpgmpdt higishinva akpenaaiag gsrlafeppp prlshipvas sastvlstng
2281 tgamnftvga pasinggcew iprlqngmvp sqynplrpgv tpgtlstqaa giqhgmmgpi
2341 hsslstntls piiyqgipnt riatqphivq tqqvqpqnlq iqpqniqpps qphlsvssaa
2401 nghlgrsfls gepsqadvqp lgpsslpvht iipqesqalp tslpssmvpp mttqfltpp
2461 sqhsyssspv dntpshqiqv pehpfltpsp espdqwssss rhsnisdwse gisspptsmp
2521 sqithipeaf k
```

FIG. 32A

Notch receptor polypeptide ("Notch regulatory region")

Outlined Text - Lin Notch Repeats (A-C)
Bold Text - Heterodimerization Domains (N and C)
Outlined & Underlined Text - S1 Cleavage
Outlined & Dot Underlined Text - S2 Cleavage
Bold & Underlined Text - S3 Cleavage
Boxed Text - Transmembrane ILDYSFTGGAGRDIPPPQIEEACELPECQVDAGNKVCNLQCNNHACGWDGGDCSLNF
NDPWKNCTQSLQCWKYFSDGHCDSQCNSAGCLFDGFDCQLTEGQCNPLYDQYCKD
HFSDGHCDQGCNSAECEWDGLDCAEHVPERLAAGTLVLVVLLPPDQLRNNSFHFLRE
LSHVLHTNVVFKRDAQGQQMIFPYYGHEEELRKHPIKRSTVGWATSSLLPGTSGGRQR
RELDPMDIRGSIVYLEIDNRQCVQSSSQCFQSATDVAAFLGALASLGSLNIPYKIEAVKS
EPVEPPLPSQLHLMYVAAAAFVLLFFVGCGVLLSRKRRRQLCIQKL

FIG. 32B

Notch receptor polypeptide ("Notch regulatory region") with EGF Repeat

PCVGSNPCYNQGTCEPTSENPFYRCLCPAKFNGLLCHILDYSFTGGAGRDIPPPQIEEA
CELPECQVDAGNKVCNLQCNNHACGWDGGDCSLNFNDPWKNCTQSLQCWKYFSDG
HCDSQCNSAGCLFDGFDCQLTEGQCNPLYDQYCKDHFSDGHCDQGCNSAECEWDG
LDCAEHVPERLAAGTLVLVVLLPPDQLRNNSFHFLRELSHVLHTNVVFKRDAQGQQMIF
PYYGHEEELRKHPIKRSTVGWATSSLLPGTSGGRQRRELDPMDIRGSIVYLEIDNRQCV
QSSSQCFQSATDVAAFLGALASLGSLNIPYKIEAVKSEPVEPPLPSQLHLMYVAAAAFVL
LFFVGCGVLLSRKRRRQLCIQKL

PROTEOLYTICALLY CLEAVABLE CHIMERIC POLYPEPTIDES AND METHODS OF USE THEREOF

CROSS-REFERENCE

This application claims the benefit of U.S. Provisional Patent Application No. 62/378,614, filed Aug. 23, 2016, which application is incorporated herein by reference in its entirety.

STATEMENT REGARDING FEDERALLY SPONSORED RESEARCH

This invention was made with government support under grant no. RO1 CA196277, awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCSF-544WO_SeqList_ST25.txt" created on Aug. 22, 2017 and having a size of 365 KB. The contents of the text file are incorporated by reference herein in their entirety.

INTRODUCTION

Conventionally, control of cellular behaviors and activities has been achieved through the use of inducible expression constructs driving expression of a protein that, when expressed, alters cellular behavior and/or activity. In the research setting, inducible expression systems have greatly advanced our understanding of many areas of the life sciences, including cell biology, molecular biology, genetics, biochemistry and others. Well-studied inducible cell systems (e.g., chemically inducible, optically inducible, etc.) generally affect cell behaviors and activities globally and/or require a user-provided input to restrict a change in activity to particular cells of a population or control the system, e.g., toggling the system "on" or "off". Cellular engineering has recently provided the ability to attempt to reprogram cells to detect signals in their environments, e.g., as provided by neighboring cells, and autonomously transduce such signaling inputs into desired behavioral or activity outputs.

SUMMARY

The instant disclosure provides chimeric polypeptides which modulate various cellular processes following a cleavage event induced upon binding of a specific binding member of the polypeptide with its binding partner. Methods of using chimeric polypeptides to modulate cellular functions, including e.g., induction of gene expression, are also provided. Nucleic acids encoding the subject chimeric polypeptides and associated expression cassettes and vectors as well as cells that contain such nucleic acids and/or expression cassettes and vectors are provided. Also provided, are methods of treating a subject using the described components and methods as well as kits for practicing the subject methods.

Aspects of the instant disclosure include a chimeric polypeptide comprising, from N-terminal to C-terminal and in covalent linkage: a) an extracellular domain comprising a specific binding member that specifically binds to a peptide-major histocompatibility complex (peptide-MHC); b) a proteolytically cleavable Notch receptor polypeptide comprising one or more proteolytic cleavage sites; and c) an intracellular domain comprising a transcriptional activator or repressor, wherein binding of the specific binding member to the peptide-MHC induces cleavage of the Notch receptor polypeptide at the one or more proteolytic cleavage sites, thereby releasing the intracellular domain.

In some embodiments, the specific binding member comprises an antibody. In some embodiments, the antibody is a nanobody, a diabody, a triabody, or a minibody, a F(ab')$_2$ fragment, a Fab fragment, a single chain variable fragment (scFv) or a single domain antibody (sdAb).

In some embodiments, the specific binding member specifically binds a peptide-MHC comprising an intracellular cancer antigen peptide. In some embodiments, the intracellular cancer antigen peptide is a WT1 peptide or a NY-ESO peptide.

In some embodiments, the Notch receptor polypeptide comprises, at its N-terminus, one or more epidermal growth factor (EGF) repeats. In some embodiments, the Notch receptor polypeptide comprises, at its N-terminus, 2 to 11 EGF repeats. In some embodiments, the Notch receptor polypeptide comprises a synthetic linker. In some embodiments, the Notch receptor polypeptide comprises a synthetic linker between the one or more EGF repeats and the one or more proteolytic cleavage sites. In some embodiments, the Notch receptor polypeptide has a length from 50 amino acids to 1000 amino acids. In some embodiments, the Notch receptor polypeptide has a length from 300 amino acids to 400 amino acids. In some embodiments, the one or more proteolytic cleavage sites comprises an S2 proteolytic cleavage site, an S3 proteolytic cleavage site or a combination thereof. In some embodiments, the one or more proteolytic cleavage sites comprises an S2 proteolytic cleavage site that is an ADAM family type protease cleavage site, such as e.g., an ADAM-17-type protease cleavage site comprising an Ala-Val dipeptide sequence. In some embodiments, the one or more proteolytic cleavage sites comprises an S3 proteolytic cleavage site that is a gamma-secretase (γ-secretase) cleavage site comprising a Gly-Val dipeptide sequence. In some embodiments, the one or more proteolytic cleavage sites further comprises an S1 proteolytic cleavage site. In some embodiments, the S1 proteolytic cleavage site is a furin-like protease cleavage site comprising the amino acid sequence Arg-X-(Arg/Lys)-Arg (SEQ ID NO:130), where X is any amino acid. In some embodiments, the Notch receptor polypeptide lacks an S1 proteolytic cleavage site. In some embodiments, the Notch receptor polypeptide has at least 85% amino acid sequence identity to a sequence provided in FIG. 31A-32B. In some embodiments, the Notch receptor polypeptide has at least 85% amino acid sequence identity to the sequence provided in FIGS. 31A-31B or the sequence provided in FIG. 31C-31D.

Aspects of the instant disclosure include a nucleic acid encoding any of the above described chimeric polypeptides.

In some embodiments, the nucleic acid further comprises a transcriptional control element responsive to the transcriptional activator or repressor operably linked to a nucleic acid sequence encoding a polypeptide of interest (POI). In some embodiments, the POI is a heterologous polypeptide selected from the group consisting of: a reporter protein, a chimeric antigen receptor (CAR), an antibody, a chimeric bispecific binding member, an engineered T cell receptor (TCR) and an innate-immune response inducer.

Aspects of the instant disclosure include a recombinant expression vector comprising any of the above described nucleic acids.

Aspects of the instant disclosure include a method of inducing expression of a heterologous polypeptide in a cell, the method comprising: contacting a cell with a peptide-major histocompatibility complex (peptide-MHC), wherein the cell expresses any of the chimeric polypeptides described above and comprises a sequence encoding the heterologous polypeptide operably linked to a transcriptional control element responsive to a transcriptional activator of the chimeric polypeptide, thereby releasing the intracellular domain of the chimeric polypeptide and inducing expression of the heterologous polypeptide.

In some embodiments, the heterologous polypeptide is a reporter protein, a chimeric antigen receptor (CAR), an antibody, a chimeric bispecific binding member, an engineered T cell receptor (TCR) and an innate-immune response inducer.

Aspects of the instant disclosure include a host cell comprising: a) a nucleic acid encoding any of the chimeric polypeptides described above that specifically binds to a first peptide-major histocompatibility complex (peptide-MHC); and b) a transcriptional control element responsive to a transcriptional activator of the chimeric polypeptide operably linked to a nucleic acid encoding a polypeptide of interest (POI).

In some embodiments, the host cell is genetically modified and the nucleic acid and the transcriptional control element are present within the genome of the host cell. In some embodiments, the nucleic acid and the transcriptional control element are present extrachromosomally within the host cell. In some embodiments, the POI is a heterologous polypeptide. In some embodiments, the heterologous polypeptide is selected from the group consisting of: a reporter protein, a chimeric antigen receptor (CAR), an antibody, a chimeric bispecific binding member, an engineered T cell receptor (TCR) and an innate-immune response inducer. In some embodiments, the heterologous polypeptide is a CAR that specifically binds to a second peptide-MHC. In some embodiments, the specific binding member of the chimeric polypeptide specifically binds to a first peptide-MHC comprising a first intracellular cancer antigen peptide and the CAR specifically binds to a second peptide-MHC comprising a second intracellular cancer antigen peptide. In some embodiments, first intracellular cancer antigen peptide is a WT1 peptide and the second intracellular cancer antigen peptide is a NY-ESO peptide. In some embodiments, the first intracellular cancer antigen peptide is a NY-ESO peptide and the second intracellular cancer antigen peptide is a WT1 peptide. In some embodiments, the heterologous polypeptide is an engineered TCR that specifically binds to a second peptide-MHC. In some embodiments, the specific binding member of the chimeric polypeptide specifically binds to a first peptide-MHC comprising a first intracellular cancer antigen peptide and the engineered TCR specifically binds to a second peptide-MHC comprising a second intracellular cancer antigen peptide. In some embodiments, the first intracellular cancer antigen peptide is a WT1 peptide and the second intracellular cancer antigen peptide is a NY-ESO peptide. In some embodiments, the first intracellular cancer antigen peptide is a NY-ESO peptide and the second intracellular cancer antigen peptide is a WT1 peptide.

Aspects of the instant disclosure include a host cell comprising: a) a nucleic acid encoding a chimeric polypeptide comprising, from N-terminal to C-terminal and in covalent linkage: i) an extracellular domain comprising a specific binding member that specifically binds to a target molecule present on the surface of a cancer cell; ii) a proteolytically cleavable Notch receptor polypeptide comprising one or more proteolytic cleavage sites; and iii) an intracellular domain comprising a transcriptional activator; b) a nucleic acid encoding a chimeric bispecific binding member operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the chimeric bispecific binding member to be expressed.

In some embodiments, the chimeric bispecific binding member comprises a binding domain specific for a cancer antigen and a binding domain specific for a protein expressed on the surface of an immune cell. In some embodiments, the chimeric bispecific binding member comprises at least one antibody derived antigen-binding domains. In some embodiments, the chimeric bispecific binding member is a bispecific antibody or a fragment thereof. In some embodiments, the chimeric bispecific binding member comprises at least one receptor or ligand binding domain of a ligand-receptor binding pair. In some embodiments, the chimeric bispecific binding member comprises at least one antibody derived antigen-binding domain and at least one receptor or ligand binding domain of a ligand-receptor binding pair. In some embodiments, the protein expressed on the surface of an immune cell is CD3. In some embodiments, the protein expressed on the surface of an immune cell is Natural Killer Group 2D (NKG2D) receptor. In some embodiments, the target molecule is a cancer antigen. In some embodiments, the target molecule is a tissue specific molecule. In some embodiments, the target molecule is an organ specific molecule. In some embodiments, the target molecule is a cell type specific molecule.

Aspects of the instant disclosure include a method of treating a subject for a neoplasia comprising administering to the subject an effective amount of host cells according to any of those described above, wherein the neoplasia expresses the target molecule and the cancer antigen.

Aspects of the instant disclosure include a host cell comprising: a) a nucleic acid encoding a chimeric polypeptide comprising, from N-terminal to C-terminal and in covalent linkage: i) an extracellular domain comprising a specific binding member that specifically binds to a target molecule present on the surface of a cancer cell; ii) a proteolytically cleavable Notch receptor polypeptide comprising one or more proteolytic cleavage sites; and iii) an intracellular domain comprising a transcriptional activator; b) a nucleic acid encoding an anti-Fc chimeric antigen receptor (CAR) operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the anti-Fc CAR to be expressed.

In some embodiments, the target molecule is a cancer antigen. In some embodiments, the target molecule is a tissue specific molecule. In some embodiments, the target molecule is an organ specific molecule. In some embodiments, the target molecule is a cell type specific molecule. In some embodiments, the host cell further comprises a nucleic acid encoding an antibody specific for a cancer antigen present on the surface of a cancer cell and comprising an Fc region that is bound by the anti-Fc CAR. In some embodiments, the nucleic acid encoding the antibody is operably linked to the transcriptional control element.

Aspects of the instant disclosure include, a method of treating a subject for a neoplasia comprising administering to the subject an effective amount of any of the host cells described above, wherein the neoplasia expresses the target molecule.

In some embodiments, the method further comprises administering to the subject an antibody specific for a cancer antigen present on the surface of a cancer cell and comprising an Fc region that is bound by the anti-Fc CAR.

Aspects of the instant disclosure include a host cell comprising: a) a nucleic acid encoding a chimeric polypeptide comprising, from N-terminal to C-terminal and in covalent linkage: i) an extracellular domain comprising a specific binding member that specifically binds to a target molecule present on the surface of a cancer cell; ii) a proteolytically cleavable Notch receptor polypeptide comprising one or more proteolytic cleavage sites; and iii) an intracellular domain comprising a transcriptional activator; b) a nucleic acid encoding an innate-immune response inducer operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the innate-immune response inducer to be expressed.

In some embodiments, the target molecule is a tissue specific molecule. In some embodiments, the target molecule is an organ specific molecule. In some embodiments, the target molecule is a cell type specific molecule. In some embodiments, the target molecule is a cancer antigen. In some embodiments, the innate-immune response inducer is bacterial protein or fragment thereof. In some embodiments, the innate-immune response inducer is viral protein or fragment thereof. In some embodiments, the innate-immune response inducer is fungal protein or fragment thereof. In some embodiments, the innate-immune response inducer is a protein or fragment thereof expressed by a mammalian parasite. In some embodiments, the mammalian parasite is a human parasite.

Aspects of the instant disclosure include a method of inducing a local innate immune response in an area of a subject, the method comprising administering to the subject an effective amount of those host cells described above, wherein the area expresses the target molecule. In some embodiments, the area of the subject comprises a neoplasia.

Aspects of the instant disclosure include a host cell comprising: a) a nucleic acid encoding a chimeric polypeptide comprising, from N-terminal to C-terminal and in covalent linkage: i) an extracellular domain comprising a specific binding member that specifically binds to a target molecule present on the surface of a cancer cell; ii) a proteolytically cleavable Notch receptor polypeptide comprising one or more proteolytic cleavage sites; and iii) an intracellular domain comprising a transcriptional activator; b) a nucleic acid encoding an immune suppression factor operably linked to a transcriptional control element responsive to the transcriptional activator, wherein binding of the specific binding member to the target molecule induces cleavage of the Notch receptor polypeptide at the one or more proteolytic cleavage sites, thereby releasing the intra- cellular domain, activating the transcriptional control element and causing the immune suppression factor to be expressed.

In some embodiments, the target molecule is a tissue specific molecule. In some embodiments, the target molecule is an organ specific molecule. In some embodiments, the target molecule is a cell type specific molecule. In some embodiments, the target molecule is an autoantigen. In some embodiments, the immune suppression factor is an immunosuppressive cytokine. In some embodiments, the immunosuppressive cytokine is IL-10. In some embodiments, the immune suppression factor is a cell-to-cell signaling immunosuppressive ligand. In some embodiments, the cell-to-cell signaling immunosuppressive ligand is PD-L1.

Aspects of the instant disclosure include a method of suppressing an immune response in a subject, the method comprising administering to the subject an effective amount of any of the host cells described above, wherein the subject expresses the target molecule. In some embodiments, the subject has an autoimmune disease.

Aspects of the instant disclosure include a method of killing a heterogeneous tumor, the method comprising: contacting a heterogeneous tumor comprising a first cell expressing a killing antigen and a second cell expressing the killing antigen and a priming antigen with an engineered immune cell comprising: a proteolytically cleavable chimeric polypeptide that specifically binds the priming antigen; a nucleic acid sequence encoding a therapeutic polypeptide that specifically binds the killing antigen; and a transcriptional control element operably linked to the nucleic acid that is responsive to the proteolytically cleavable chimeric polypeptide, wherein binding of the proteolytically cleavable chimeric polypeptide to the priming antigen activates the transcriptional control element to induce expression of the therapeutic polypeptide which, when bound to the killing antigen, kills the first and second cells of the heterogeneous tumor.

In some embodiments, the therapeutic polypeptide is a chimeric antigen receptor (CAR). In some embodiments, the therapeutic polypeptide is a T cell Receptor (TCR). In some embodiments, the therapeutic polypeptide is a therapeutic antibody. In some embodiments, the therapeutic polypeptide is a chimeric bispecific binding member. In some embodiments, at least one of the priming antigen or the killing antigen is an intracellular antigen presented in the context of MHC. In some embodiments, both the priming antigen and the killing antigen are intracellular antigens presented in the context of MHC.

BRIEF DESCRIPTION OF THE DRAWINGS

FIG. 5 demonstrates the sensitivity and antigen concentration dependent reporter activation of an anti-MHC-presented WT1 proteolytically cleavable chimeric polypeptide in CD8+ T cells and CD4+ T cells according to one embodiment.

FIG. 6 schematically depicts a proteolytically cleavable chimeric polypeptide-gated circuit utilizing an MHC-presented WT1 specific chimeric polypeptide driving expression of a T cell receptor (TCR) specific for MHC-presented NY-ESO1 antigen. In the depicted embodiment, the T cell becomes activated only when contacted with a target cell expressing both WT1 and NY-ESO1 intracellular antigens.

FIG. 7 depicts proteolytically cleavable chimeric polypeptide-gated T cell activation (as shown by CD69 activation marker expression), according to the system depicted in FIG. 6, only when contacted with target cells expressing both WT1 and NY-ESO1 intracellular antigens.

FIG. 8 depicts significant proteolytically cleavable chimeric polypeptide-gated target cell killing, according to the system depicted in FIG. 6, only when the engineered T cell is contacted with target cells expressing both WT1 and NY-ESO1 intracellular antigens.

FIG. 22 schematically depicts programming a T cell to recognize and treat a heterogeneous tumor according to an embodiment described herein.

FIG. 23 schematically depicts a model system designed to demonstrate programming a T cell to recognize and treat a heterogeneous tumor expressing a GFP "priming" antigen and a CD19 "killing" antigen according to an embodiment described herein.

FIG. 24 demonstrates the effective targeting and killing of an in vitro modeled dual-antigen heterogeneous tumor ("heterogeneous mixture") according to FIG. 23.

FIG. 31A-31M provide amino acid sequences of Notch receptor polypeptides of various species (SEQ ID NOs:1-7).

FIG. 32A-32B depict examples of Notch receptor polypeptide Notch regulatory regions and the components therein (SEQ ID NOs:16-17).

DEFINITIONS

Figure 1:
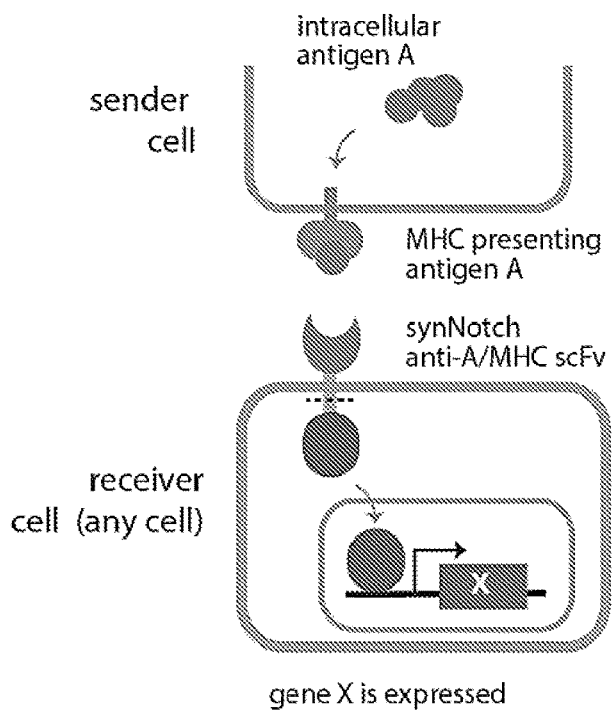
FIG. 1 schematically depicts specific binding of an embodiment of a proteolytically cleavable chimeric polypeptide (synNotch) expressed on a receiver cell with a major histocompatibility complex (MHC)-presented antigen of a sender cell to induce expression of a gene or coding sequence ("X") in the receiver cell.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

"Operably linked" refers to a juxtaposition wherein the components so described are in a relationship permitting them to function in their intended manner. For instance, a promoter is operably linked to a coding sequence if the promoter affects its transcription or expression. Operably linked nucleic acid sequences may but need not necessarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

A "vector" or "expression vector" is a replicon, such as plasmid, phage, virus, or cosmid, to which another DNA segment, i.e. an "insert", may be attached so as to bring about the replication of the attached segment in a cell.

"Heterologous," as used herein, means a nucleotide or polypeptide sequence that is not found in the native (e.g., naturally-occurring) nucleic acid or protein, respectively. Heterologous nucleic acids or polypeptide may be derived from a different species as the organism or cell within which the nucleic acid or polypeptide is present or is expressed. Accordingly, a heterologous nucleic acids or polypeptide is generally of unlike evolutionary origin as compared to the cell or organism in which it resides.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a complementarity-determining region (CDR) derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. In some cases, a specific binding member present in the extracellular domain of a chimeric polypeptide of the present disclosure binds specifically to a peptide-major histocompatibility complex (peptide-MHC). "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel, Switzerland).

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "individual," "subject," "host," and "patient," used interchangeably herein, refer to a mammal, including, but not limited to, murines (e.g., rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells ($CD4^+$ cells), cytotoxic T-cells ($CD8^+$ cells), T-regulatory cells (Treg) and gamma-delta T cells.

A "cytotoxic cell" includes $CD8^+$ T cells, natural-killer (NK) cells, and neutrophils, which cells are capable of mediating cytotoxicity responses.

The term "synthetic" as used herein generally refers to an artificially derived polypeptide or polypeptide encoding nucleic acid that is not naturally occurring. Such synthetic polypeptides and/or nucleic acids may be assembled de novo from basic subunits including, e.g., single amino acids, single nucleotides, etc., or may be derived from pre-existing polypeptides or polynucleotides, whether naturally or artificially derived, e.g., as through recombinant methods.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The instant disclosure provides chimeric polypeptides which modulate various cellular processes following a cleavage event induced upon binding of a specific binding member of the chimeric polypeptide with its binding partner. Methods of using chimeric polypeptides to modulate cellular functions, including e.g., induction of gene expression, are also provided. Nucleic acids encoding the subject chimeric polypeptides and associated expression cassettes and vectors as well as cells that contain such nucleic acids and/or expression cassettes and vectors are provided. Also provided, are methods of treating a subject using the described components and methods as well as kits for practicing the subject methods.

Methods

Methods are provided for modulating one or more cellular processes and/or activities and/or functions using chimeric polypeptides that undergo a binding-induced cleavage event to release an intracellular domain from the chimeric polypeptide. As described in more detail below, chimeric polypeptides of the instant disclosure may generally include: a) an extracellular domain comprising a specific binding member; b) a proteolytically cleavable Notch receptor polypeptide comprising one or more proteolytic cleavage sites; and c) an intracellular domain. Methods of the instant disclosure include using such chimeric polypeptides to modulate one or more cellular processes and/or activities and/or functions upon binding of the specific binding member to its binding partner.

According to the methods described herein, in some instances, chimeric polypeptides are expressed from a nucleic acid, within or introduced into a cell, which encodes the chimeric polypeptide. As such, in some instances, the instant methods may include contacting a cell with a nucleic acid encoding a chimeric polypeptide wherein such contacting is sufficient to introduce the nucleic acid into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like.

Introduced nucleic acids may be maintained within the cell or transiently present. As such, in some instance, an introduced nucleic acid may be maintained within the cell, e.g., integrated into the genome. Any convenient method of nucleic acid integration may find use in the subject methods, including but not limited to e.g., viral-based integration, transposon-based integration, homologous recombination-based integration, and the like. In some instance, an introduced nucleic acid may be transiently present, e.g., extrachromosomally present within the cell. Transiently present nucleic acids may persist, e.g., as part of any convenient transiently transfected vector.

An introduced nucleic acid encoding a chimeric polypeptide of the instant disclosure may be introduced in such a manner as to be operably linked to a promoter that drives the expression of the chimeric polypeptide. The source of such promoters may vary and may include e.g., where the promoter is introduced with the nucleic acid, e.g., as part of an expression construct or where the promoter is present in the cell prior to introducing the nucleic acid or introduced after the nucleic acid. As described in more detail herein, useful promoters can include endogenous promoters and heterologous promoters. For example, in some instances, a nucleic acid may be introduced as part of an expression construct containing a heterologous promoter operably linked to the nucleic acid. In some instances, a nucleic acid may be introduced as part of an expression construct containing a copy of a promoter that is endogenous to the cell into which the nucleic acid is introduced. In some instances, a nucleic acid may be introduced without a promoter and, upon integration into the genome of the cell, the nucleic acid may be operably linked to an endogenous promoter already present in the cell. Depending on the confirmation and/or the promoter utilized, expression of the chimeric polypeptide from the nucleic acid may be configured to be constitutive, inducible, tissue-specific, cell-type specific, etc., including combinations thereof.

Chimeric polypeptides of the instant disclosure within a cell, regardless of the method of introduction, generally will reside in the plasma membrane and remain inactive when the specific binding member of such a chimeric polypeptide is not bound by its binding partner. As used herein, in relationship to chimeric polypeptides of the instant disclosure, by "inactive" is meant the intracellular domain of the chimeric polypeptide remains linked to the cleavable polypeptide (e.g., cleavable Notch polypeptide) such that the intracellular domain is sequestered and unable to modulate intracellular functions and/or cellular activities. Upon binding of the specific binding member to its binding partner the chimeric polypeptide may be said to become active, wherein the term "active" generally refers to the release of the intracellular domain from the chimeric polypeptide by a cleavage event triggered by the binding, such that the intracellular domain is freed and may influence intracellular functions and/or cellular activities.

Cellular processes and/or activities and/or functions that may be modulated according to the instant methods will vary any may include but are not limited to modulating expression of a gene or other coding sequence, e.g., inducing expression of a gene or coding sequence, repressing expression of a gene or coding sequence, etc. Accordingly, in some instances, the intracellular domain of a chimeric polypeptide used in the subject methods may include a transcriptional modulator, including e.g., a transcriptional activator or a transcriptional repressor.

In some instances, cellular processes and/or activities and/or functions that may be modulated include but are not limited to e.g., expression of a gene product of the cell, proliferation of the cell, apoptosis of the cell, non-apoptotic death of the cell, differentiation of the cell, dedifferentiation of the cell, migration of the cell, secretion of a molecule from the cell (e.g., secretion of a therapeutic polypeptide, secretion of a cytokine, etc.), cellular adhesion of the cell, immune cell activation (e.g., T cell activation, etc.), production of effector molecules (e.g., cytokines, antibodies, growth factors, etc.), transcription of a target nucleic acid, translation of a target mRNA, organelle activity, intracellular trafficking, and the like.

In some instances, the expression and/or secretion of a cytokine may be modulated. Non-limiting examples of cytokines, the expression/secretion of which may be modulated, include but are not limited to e.g., Interleukins and related (e.g., IL-1-like, IL-1$\alpha$, IL-1$\beta$, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.), Interferons (e.g., IFN-$\alpha$, IFN-$\beta$, IFN-$\gamma$, etc.), TNF family (e.g., CD154, LT-$\beta$, TNF-$\alpha$, TNF-$\beta$, 4-1BBL, APRIL, CD70, CD153, CD178, GITRL, LIGHT, OX40L, TALL-1, TRAIL, TWEAK, TRANCE, etc.), TGF-$\beta$ family (e.g., TGF-$\beta$1, TGF-$\beta$2, TGF-$\beta$3, etc.) and the like. In some instances, activation of a cell through a chimeric polypeptide of the present disclosure, or a plurality thereof, may induce an increase in cytokine expression and/or secretion relative to that of a comparable cell where the chimeric polypeptide is not present or otherwise inactive. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

In some instances, where dual-antigen recognition is employed, described in more detail below, a cell activated by binding of both antigens of a target cell may display an increase in cellular activation or expression/secretion of a cytokine as compared to a corresponding cell bound to only one antigen. In some instance, such an increase may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

In some instances, the methods described herein include methods of inducing expression of a polypeptide in a cell expressing a chimeric polypeptide of the instant disclosure by contacting the cell with a binding partner of the specific binding member of the chimeric polypeptide. Depending on the particular configuration, such methods may include inducing expression of an endogenous gene or coding sequence or a heterologous gene or coding sequence. In some instances, the binding partner of the specific binding member may be present on the surface of a cell. In some instances, the binding partner of the specific binding member may not be present on the surface of a cell and may be e.g., bound to a substrate (e.g., a solid support such as the surface of a plate or bead), unbound or freely diffusible, etc. Accordingly, where methods described herein include contacting a cell with a binding partner of a specific binding member of a chimeric polypeptide, such contacting may include but is not limited to e.g., contacting with medium containing freely diffusible binding partner, contacting with cells expressing the binding partner on their surface, contacting with a substrate with attached binding partner, etc. Unbound or freely diffusible specific binding members may, in some instances, function as a soluble adapter molecule, e.g., facilitating binding between an anchor cell and a receiver cell to generate the force necessary to activate a subject cleavable chimeric polypeptide, e.g., as described in PCT Application No. US2016/019188 (Pub. No. WO 2016/138034); the disclosure of which is incorporated herein by reference in its entirety. In some instances, an unbound or freely diffusible binding partner may be subsequently captured or anchored by any other convenient means, including but not limited to e.g., the introduction of an additional binding partner that specifically binds the unbound or freely diffusible binding partner and is bound to or otherwise associated with a substrate or the surface of a cell.

In the subject methods, any convenient pair of specific binding member and binding partner may be utilized, provided the pair specifically binds to one another sufficiently to activate the chimeric polypeptide. In some instances, a useful pair of specific binding member and binding partner may include an antigen-antibody pair, where e.g., the antibody is utilized as the specific binding member and the antigen as the binding partner or the antigen is utilized as the specific binding member and the antibody as the binding partner.

In some instances, the methods described herein include methods of modulating a cellular activity of a cell expressing a chimeric polypeptide by contacting the cell with a peptide-major histocompatibility complex (peptide-MHC) under conditions sufficient for the peptide-MHC to bind the specific binding member of the chimeric polypeptide. In some instances, the binding of the peptide-MHC to the chimeric polypeptide activates the chimeric polypeptide releasing the intracellular domain and inducing expression of a polypeptide within the cell.

Where methods of the instant disclosure include contacting a cell expressing a chimeric polypeptide with a binding partner to induce expression of a gene or coding sequence, essentially any polypeptide, natural or recombinant, may be induced to be expressed. In some instances, an expressed polypeptide may be referred to as a polypeptide of interest (POI). A POI may be essentially any polypeptide and may include but is not limited to polypeptides of research interest (e.g., reporter polypeptides, mutated polypeptides, novel synthetic polypeptides, etc.), polypeptides of therapeutic interest (e.g., naturally occurring therapeutic proteins, recombinant therapeutic polypeptides, etc.), polypeptides of industrial interest (e.g., polypeptides used in industrial applications such as e.g., manufacturing), and the like.

In some instances, polypeptides induced to be expressed may include but are not limited to e.g., reporter proteins, chimeric antigen receptors (CAR), antibodies, chimeric bispecific binding members, engineered T cell receptors (TCR), innate-immune response inducers, etc.

"Contacting" of the instant methods may vary depending on the context and may include in vitro contacting, ex vivo contacting, and in vivo contacting. For example, in some instances, e.g., where a cell expressing a chimeric polypeptide is cultured in vitro, the contacting may include adding the binding partner or a cell expressing the binding partner or a substrate, with the binding partner attached, to the in vitro culture. In some instances, e.g., where the binding partner is present in an individual in vivo, including e.g., present on a cell present in the individual in vivo, the contacting may include administering a cell expressing the chimeric polypeptide to the individual. In some instances, e.g., where the cell expressing the chimeric polypeptide is present in an individual in vivo the contacting may include administering the binding partner to the individual, removing the cell from the individual and contacting the cell with the binding partner ex vivo, causing or allowing both the chimeric polypeptide and the binding partner to be simultaneously expressed in vivo, etc.

Methods of the present disclosure for modulating the activity of a cell can be carried out in a single cell, or in a multicellular environment (e.g., a naturally-occurring tissue; an artificial tissue; etc.). Methods of the present disclosure for modulating the activity of a cell can be carried out in parallel or in series.

Methods of the instant disclosure may further include culturing a cell expressing a chimeric polypeptide of the instant disclosure including but not limited to e.g., culturing the cell prior to contacting the cell with the binding partner, culturing the cell while contacting the cell with the binding partner, culturing the cell following contacting the cell with the binding partner. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Methods of Treatment

Methods of the present disclosure include methods of treating a subject using one or more proteolytically cleavable chimeric polypeptides as described herein. Any convenient method of delivering the chimeric polypeptide may find use in the subject methods. In some instances, the subject chimeric polypeptides may be delivered by administering to the subject a cell expressing the chimeric polypeptide. In some instances, the subject chimeric polypeptides may be delivered by administering to the subject a nucleic acid comprising a nucleotide sequence encoding the chimeric polypeptide. Administering to a subject a nucleic acid encoding the chimeric polypeptide may include administering to the subject a cell containing the nucleic acid where the nucleic acid may or may not yet be expressed. In some instances, administering to a subject a nucleic acid encoding the chimeric polypeptide may include administering to the subject a vector designed to deliver the nucleic acid to a cell.

Accordingly, in the subject methods of treatment, nucleic acids encoding chimeric polypeptides may be administered in vitro, ex vivo or in vivo. In some instances, cells may be collected from a subject and transfected with nucleic acid and the transfected cells may be administered to the subject, with or without further manipulation including but not limited to e.g., in vitro expansion. In some instances, the nucleic acid, e.g., with or without a delivery vector, may be administered directly to the subject.

Given the diversity of cellular activities that may be modulated through the use of the subject proteolytically cleavable chimeric polypeptides, the instant methods of treatment may be utilized for a variety of applications. As non-limiting examples, the instant methods may find use in a treatment directed to a variety of diseases including but not limited to e.g., Acanthamoeba infection, *Acinetobacter* infection, Adenovirus infection, ADHD (Attention Deficit/Hyperactivity Disorder), AIDS (Acquired Immune Deficiency Syndrome), ALS (Amyotrophic Lateral Sclerosis), Alzheimer's Disease, Amebiasis, Intestinal (*Entamoeba histolytica* infection), Anaplasmosis, Human, Anemia, *Angiostrongylus* Infection, Animal-Related Diseases, *Anisakis* Infection (Anisakiasis), Anthrax, Aortic Aneurysm, Aortic Dissection, Arenavirus Infection, Arthritis (e.g., Childhood Arthritis, Fibromyalgia, Gout, Lupus (SLE) (Systemic lupus erythematosus), Osteoarthritis, Rheumatoid Arthritis, etc.), *Ascaris* Infection (Ascariasis), *Aspergillus* Infection (Aspergillosis), Asthma, Attention Deficit/Hyperactivity Disorder, Autism, Avian Influenza, B virus Infection (Herpes B virus), *B. cepacia* infection (*Burkholderia cepacia* Infection), Babesiosis (*Babesia* Infection), Bacterial Meningitis, Bacterial Vaginosis (BV), *Balamuthia* infection (*Balamuthia mandrillaris* infection), *Balamuthia mandrillaris* infection, Balantidiasis, *Balantidium* Infection (Balantidiasis), *Baylisascaris* Infection, *Bilharzia*, Birth Defects, Black Lung (Coal Workers' Pneumoconioses), *Blastocystis hominis* Infection, *Blastocystis* Infection, Blastomycosis, Bleeding Disorders, Blood Disorders, Body Lice (*Pediculus humanus corporis*), *Borrelia burgdorferi* Infection, Botulism (*Clostridium botulinim*), Bovine Spongiform Encephalopathy (BSE), Brainerd Diarrhea, Breast Cancer, Bronchiolitis, Bronchitis, *Brucella* Infection (Brucellosis), Brucellosis, *Burkholderia cepacia* Infection (*B. cepacia* infection), *Burkholderia mallei*, *Burkholderia pseudomallei* Infection, *Campylobacter* Infection (Campylobacteriosis), Campylobacteriosis, Cancer (e.g., Colorectal (Colon) Cancer, Gynecologic Cancers, Lung Cancer, Prostate Cancer, Skin Cancer, etc.), *Candida* Infection (Candidiasis), Candidiasis, Canine Flu, Capillaria Infection (Capillariasis), Capillariasis, Carbapenem resistant *Klebsiella pneumonia* (CRKP), Cat Flea Tapeworm, Cercarial Dermatitis, Cerebral Palsy, Cervical Cancer, Chagas Disease (*Trypanosoma cruzi* Infection), Chickenpox (Varicella Disease), Chikungunya Fever (CHIKV), Childhood Arthritis, German Measles (Rubella Virus), Measles, Mumps, Rotavirus Infection, *Chlamydia* (*Chlamydia trachomatis* Disease), *Chlamydia pneumoniae* Infection, *Chlamydia trachomatis* Disease, Cholera (*Vibrio cholerae* Infection), Chronic Fatigue Syndrome (CFS), Chronic Obstructive Pulmonary Disease (COPD), Ciguatera Fish Poisoning, Ciguatoxin, Classic Creutzfeldt-Jakob Disease, Clonorchiasis, *Clonorchis* Infection (Clonorchiasis), *Clostridium* botulinim, *Clostridium difficile* Infection, *Clostridium perfringens* infection, *Clostridium tetani* Infection, Clotting Disorders, CMV (Cytomegalovirus Infection), Coal Workers' Pneumoconioses, Coccidioidomycosis, Colorectal (Colon) Cancer, Common Cold, Conjunctivitis, Cooleys Anemia, COPD (Chronic Obstructive Pulmonary Disease), *Corynebacterium diphtheriae* Infection, *Coxiella burnetii* Infection, Creutzfeldt-Jakob Disease, CRKP (Carbapenem resistant *Klebsiella pneumonia*), Crohn's Disease, Cryptococcosis, Cryptosporidiosis, *Cryptosporidium* Infection (Cryptosporidiosis), *Cyclospora* Infection (Cyclosporiasis), Cyclosporiasis, Cysticercosis, Cystoisospora Infection (Cystoisosporaiasis), Cystoisosporaiasis, Cytomegalovirus Infection (CMV), Dengue Fever (DF), Dengue Hemorrhagic Fever (DHF), Dermatophytes, Dermopathy, Diabetes, Diamond Blackfan Anemia (DBA), *Dientamoeba fragilis* Infection, Diphtheria (*Corynebacterium diphtheriae* Infection), Diphyllobothriasis, *Diphyllobothrium* Infection (Diphyllobothriasis), *Dipylidium* Infection, Dog Flea Tapeworm, Down Syndrome (Trisomy 21), Dracunculiasis, Dwarf Tapeworm (*Hymenolepis* Infection), *E. coli* Infection (*Escherichia coli* Infection), Ear Infection (Otitis Media), Eastern Equine Encephalitis (EEE), Ebola Hemorrhagic Fever, Echinococcosis, Ehrlichiosis, Elephantiasis, Encephalitis (Mosquito-Borne and Tick-Borne), *Entamoeba histolytica* infection, *Enterobius vermicularis* Infection, Enterovirus Infections (Non-Polio), Epidemic Typhus, Epilepsy, Epstein-Barr Virus Infection (EBV Infection), *Escherichia coli* Infection, Extensively Drug-Resistant TB (XDR TB), *Fasciola* Infection (Fascioliasis), *Fasciolopsis* Infection (Fasciolopsiasis), Fibromyalgia, Fifth Disease (Parvovirus B19 Infection), Flavorings-Related Lung Disease, Folliculitis, Food-Related Diseases, *Clostridium perfringens* infection, Fragile X Syndrome, *Francisella tularensis* Infection, Genital Candidiasis (Vulvovaginal Candidiasis (VVC)), Genital Herpes (Herpes Simplex Virus Infection), Genital Warts, German Measles (Rubella Virus), Giardia Infection (Giardiasis), Glanders (*Burkholderia mallei*), *Gnathostoma* Infection, Gnathostomiasis (*Gnathostoma* Infection), Gonorrhea (*Neisseria gonorrhoeae* Infection), Gout, Granulomatous amebic encephalitis (GAE), Group A Strep Infection (GAS) (Group A Streptococcal Infection), Group B Strep Infection (GBS) (Group B Streptococcal Infection), Guinea Worm Disease (Dracunculiasis), Gynecologic Cancers (e.g., Cervical Cancer, Ovarian Cancer, Uterine Cancer, Vaginal and Vulvar Cancers, etc.), H1N1 Flu, *Haemophilus influenzae* Infection (Hib Infection), Hand, Foot, and Mouth Disease (HFMD), Hansen's Disease, Hantavirus Pulmonary Syndrome (HPS), Head Lice (*Pediculus humanus capitis*), Heart Disease (Cardiovascular Health), Heat Stress, Hemochromatosis, Hemophilia, Hendra Virus Infection, Herpes B virus, Herpes Simplex Virus Infection, Heterophyes Infection (Heterophyiasis), Hib Infection (*Haemophilus influenzae* Infection), High Blood Pressure, *Histoplasma capsulatum* Disease, Histoplasmosis (*Histoplasma capsulatum* Disease), Hot Tub Rash (*Pseudomonas* dermatitis Infection), HPV Infection (Human Papillomavirus Infection), Human Ehrlichiosis, Human Immunodeficiency Virus, Human Papillomavirus Infection (HPV Infection), *Hymenolepis* Infection, Hypertension, Hyperthermia, Hypothermia, Impetigo, Infectious Mononucleosis, Inflammatory Bowel Disease (IBD), Influenza, Avian Influenza, H1N1 Flu, Pandemic Flu, Seasonal Flu, Swine Influenza, Invasive Candidiasis, Iron Overload (Hemochromatosis), *Isospora* Infection (Isosporiasis), Japanese Encephalitis, Jaundice, *K. pneumoniae* (*Klebsiella pneumoniae*), Kala-Azar, Kawasaki Syndrome (KS), Kernicterus, *Klebsiella pneumoniae* (*K. pneumoniae*), La Crosse Encephalitis (LAC), La Crosse Encephalitis virus (LACV), Lassa Fever, Latex Allergies, Lead Poisoning, Legionnaires' Disease (Legionellosis), *Leishmania* Infection (Leishmaniasis), Leprosy, Leptospira Infection (Leptospirosis), Leptospirosis, Leukemia, Lice, *Listeria* Infection (Listeriosis), Listeriosis, Liver Disease and Hepatitis, *Loa loa* Infection, Lockjaw, Lou Gehrig's Disease, Lung Cancer, Lupus (SLE) (Systemic lupus erythematosus), Lyme Disease (*Borrelia burgdorferi* Infection), Lymphatic Filariasis, Lymphedema, Lymphocytic Choriomeningitis (LCMV), Lymphogranuloma venereum Infection (LGV), Malaria, Marburg Hemorrhagic Fever, Measles, Melioidosis (*Burkholderia pseudomallei* Infection), Meningitis (Meningococcal Disease), Meningococcal Disease, Methicillin Resistant *Staphylococcus aureus* (MRSA), Micronutrient Malnutrition, Microsporidia Infection, Molluscum Contagiosum, Monkey B virus, Monkeypox, Morgellons, Mosquito-Borne Diseases, Mucormycosis, Multidrug-Resistant TB (MDR TB), Mumps, *Mycobacterium abscessus* Infection, *Mycobacterium avium* Complex (MAC), *Mycoplasma pneumoniae* Infection, Myiasis, *Naegleria* Infection (Primary Amebic Meningoencephalitis (PAM)), Necrotizing Fasciitis, Neglected Tropical Diseases (NTD), *Neisseria gonorrhoeae* Infection, Neurocysticercosis, New Variant Creutzfeldt-Jakob Disease, Newborn Jaundice (Kernicterus), Nipah Virus Encephalitis, Nocardiosis, Non-Polio Enterovirus Infections, Nonpathogenic (Harmless) Intestinal Protozoa, Norovirus Infection, Norwalk-like Viruses (NLV), Novel H1N1 Flu, Onchocerciasis, *Opisthorchis* Infection, Oral Cancer, Orf Virus, Oropharyngeal Candidiasis (OPC), Osteoarthritis (OA), Osteoporosis, Otitis Media, Ovarian Cancer, Pandemic Flu, Paragonimiasis, *Paragonimus* Infection (Paragonimiasis), Parasitic Diseases, Parvovirus B19 Infection, *Pediculus humanus* capitis, *Pediculus humanus* corporis, Pelvic Inflammatory Disease (PID), Peripheral Arterial Disease (PAD), Pertussis, Phthiriasis, Pink Eye (Conjunctivitis), Pinworm Infection (*Enterobius vermicularis* Infection), Plague (*Yersinia pestis* Infection), *Pneumocystis jirovecii* Pneumonia, Pneumonia, Polio Infection (Poliomyelitis Infection), Pontiac Fever, Prion Diseases (Transmissible spongiform encephalopathies (TSEs)), Prostate Cancer, *Pseudomonas* dermatitis Infection, Psittacosis, Pubic Lice (Phthiriasis), Pulmonary Hypertension, Q Fever (*Coxiella burnetii* Infection), Rabies, Raccoon Roundworm Infection (*Baylisascaris* Infection), Rat-Bite Fever (RBF) (*Streptobacillus moniliformis* Infection), Recreational Water Illness (RWI), Relapsing Fever, Respiratory Syncytial Virus Infection (RSV), Rheumatoid Arthritis (RA), *Rickettsia rickettsii* Infection, Rift Valley Fever (RVF), Ringworm (Dermatophytes), Ringworm in Animals, River Blindness (Onchocerciasis), Rocky Mountain Spotted Fever (RMSF) (*Rickettsia rickettsii* Infection), Rotavirus Infection, RVF (Rift Valley Fever), RWI (Recreational Water Illness), *Salmonella* Infection (*Salmonellosis*), Scabies, Scarlet Fever, Schistosomiasis (*Schistosoma* Infection), Seasonal Flu, Severe Acute Respiratory Syndrome, Sexually Transmitted Diseases (STDs) (e.g., Bacterial Vaginosis (BV), *Chlamydia*, Genital Herpes, Gonorrhea, Human Papillomavirus Infection, Pelvic Inflammatory Disease, Syphilis, Trichomoniasis, HIV/AIDS, etc.), *Shigella* Infection (Shigellosis), Shingles (Varicella Zoster Virus (VZV)), Sickle Cell Disease, Single Gene Disorders, Sinus Infection (Sinusitis), Skin Cancer, Sleeping Sickness (African Trypanosomiasis), Smallpox (Variola Major and Variola Minor), Sore Mouth Infection (Orf Virus), Southern Tick-Associated Rash Illness (STARI), Spina *Bifida* (Myelomeningocele), Sporotrichosis, Spotted Fever Group *Rickettsia* (SFGR), St. Louis Encephalitis, *Staphylococcus aureus* Infection, *Streptobacillus moniliformis* Infection, Streptococcal Diseases, *Streptococcus pneumoniae* Infection, Stroke, *Strongyloides* Infection (Strongyloidiasis), Sudden Infant Death Syndrome (SIDS), Swimmer's Itch (Cercarial Dermatitis), Swine Influenza, Syphilis (*Treponema pallidum* Infection), Systemic lupus erythematosus, Tapeworm Infection (*Taenia* Infection), Testicular Cancer, Tetanus Disease (*Clostridium tetani* Infection), Thrush (Oropharyngeal Candidiasis (OPC)), Tick-borne Relapsing Fever, Tickborne Diseases (e.g., Anaplasmosis, Babesiosis, Ehrlichiosis, Lyme Disease, Tourette Syndrome (TS), Toxic Shock Syndrome (TSS), Toxocariasis (*Toxocara* Infection), Toxoplasmosis (*Toxoplasma* Infection), Trachoma Infection, Transmissible spongiform encephalopathies (TSEs), Traumatic Brain Injury (TBI), Trichinellosis (Trichinosis), Trichomoniasis (*Trichomonas* Infection), Tuberculosis (TB) (*Mycobacterium tuberculosis* Infection), Tularemia (*Francisella tularensis* Infection), Typhoid Fever (*Salmonella typhi* Infection), Uterine Cancer, Vaginal and Vulvar Cancers, Vancomycin-Intermediate/Resistant *Staphylococcus aureus* Infections (VISA/VRSA), Vancomycin-resistant Enterococci Infection (VRE), Variant Creutzfeldt-Jakob Disease (vCJD), Varicella-Zoster Virus Infection, Variola Major and Variola Minor, *Vibrio cholerae* Infection, *Vibrio parahaemolyticus* Infection, *Vibrio vulnificus* Infection, Viral Gastroenteritis, Viral Hemorrhagic Fevers (VHF), Viral Hepatitis, Viral Meningitis (Aseptic Meningitis), Von Willebrand Disease, Vulvovaginal Candidiasis (VVC), West Nile Virus Infection, Western Equine Encephalitis Infection, Whipworm Infection (Trichuriasis), Whitmore's Disease, Whooping Cough, Xenotropic Murine Leukemia Virus-related Virus Infection, Yellow Fever, *Yersinia pestis* Infection, Yersiniosis (*Yersinia enterocolitica* Infection), Zoonotic Hookworm, Zygomycosis, and the like.

In some instances, methods of treatment utilizing one or more proteolytically cleavable polypeptides of the instant disclosure may find use in treating a cancer. Cancers, the treatment of which may include the use of one or more proteolytically cleavable polypeptides of the instant disclosure, will vary and may include but are not limited to e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

In some instances, a method of the instant disclosure will include treating a neoplasia by administering to a subject having the neoplasia a cell expressing a chimeric polypeptide of the instant disclosure or a nucleic acid encoding a chimeric polypeptide of the instant disclosure. In some instances, such a method may further include administering to the subject a nucleic acid operably linked to a transcriptional control element that is regulated by the intracellular domain of the chimeric polypeptide. As used herein, the term "neoplasia" generally refers to an abnormal growth of tissue or an abnormally proliferating cell or population of cells, including but not limited to solid tumors, blood cancers, etc., including e.g., those of any cancer, including e.g., those cancers listed herein. A neoplasia may be benign or malignant.

In some instances, the instant methods may be applied to the treatment of heterogeneous tumors. As used herein, the term "heterogeneous tumors" generally refers to a tumor having at least two different types of tumor cells differentially expressing at least one antigen. For example, a heterogeneous tumor may include one type of tumor cell expressing a first antigen and a second type of tumor cell that does not express the antigen. In some instances, a heterogeneous tumor may include one type of tumor cell highly expressing a first antigen and a second type of tumor cell having low expression of the antigen. By "low expression" is meant that the antigen is expressed at a level that makes directly targeting the antigen with a therapeutic impractical. Methods of targeting a heterogeneous tumor as described herein will generally include therapeutically targeting at least two different cell types of the tumor, including e.g., two cell types that differentially express an antigen. Accordingly, the herein described method of targeting a heterogeneous tumor may allow for a therapeutic effect on a cell type of the tumor that does not express or shows low expression of an antigen of a cell type targeted in the method.

Differentially expressed antigens useful in the described methods of treating a heterogeneous tumor may essentially include any antigen that may be targeted with a specific binding member as described herein, including but not limited to e.g., cancer cell antigens (e.g., surface expressed cancer antigens, intracellular cancer antigens, etc.), tissue specific antigens, cell type specific antigens, and the like. In some instances, antigens are endogenously expressed by the cell. In some instances, an antigen may be heterologous to the cell from which it is expressed, including e.g., where an expressed heterologous protein serves as an antigen.

In some instances, a method of treating a heterogeneous tumor may include contacting the tumor with an immune cell engineered to express a proteolytically cleavable chimeric polypeptide specific for a priming antigen. As used herein, the term "priming antigen" generally refers to an antigen sufficient to activate the chimeric polypeptide in the proximity of the heterogeneous tumor. In some instances, a priming antigen may be an antigen present in a subset of cells of the heterogeneous tumor, e.g., present on some cells of the heterogeneous tumor but not present in all cells of the heterogeneous tumor. In some instances, upon activation of a chimeric polypeptide by a priming antigen the freed intracellular domain of the chimeric polypeptide may induce expression of a second antigen-specific polypeptide. In some instances, the antigen of the second antigen-specific polypeptide may be referred to herein as a "therapeutic antigen" or a "killing antigen". As used herein, the term "therapeutic antigen" may generally refer to the antigen to which a therapeutic construct is directed, e.g., an antigen that is directly targeted by a therapeutic construct including but not limited to e.g., an antibody, a CAR, a TCR, a chimeric bispecific binding member, and the like. As used herein, the term "killing antigen" may generally refer to the antigen to which a construct designed to target a cell for killing is directed, e.g., an antigen that is targeted by a construct that results in killing of the cell expressing the killing antigen by an immune cell including but not limited to e.g., an antibody, a CAR, a TCR, a chimeric bispecific binding member, and the like. In some instances, the second antigen-specific polypeptide may be directed to a therapeutic antigen that is present in all or nearly all or most cells of the heterogeneous tumor.

In some instances, the methods described herein include inducing an innate immune response in a subject. In some instances, a chimeric polypeptide of the instant disclosure may induce the expression of a polypeptide that, when expressed, induces an innate immune response in a subject. As the specific binding member of a chimeric polypeptide of the instant disclosure may be engineered to activate the chimeric polypeptide in response to binding a specific antigen, in some instances, an innate immune response may be induced in response to the presence of a particular antigen. A chimeric polypeptide may be engineered to be activated by any convenient and appropriate antigen including but not limited to e.g., a cancer antigen, a cell type specific antigen, a tissue specific antigen, an infectious disease antigen (e.g., a bacterial antigen, a viral antigen, a fungal antigen, a pathogenic antigen, etc.), and the like. In some instances, the innate immune response may be locally activated e.g., based on the local presence of the antigen, e.g., an antigen locally present in a tumor, an antigen locally present in the tumor microenvironment, an antigen locally present in an infected area or tissue, etc.

In some instances, the methods described herein include controlling expression of one or more immune suppression factors in a subject. In some instances, a chimeric polypeptide of the instant disclosure may induce the expression of a polypeptide that, when expressed, induces immune suppression in a subject. As the specific binding member of a chimeric polypeptide of the instant disclosure may be engineered to activate the chimeric polypeptide in response to binding a specific antigen, in some instances, an immunosuppressive response may be induced in response to the presence of a particular antigen. A chimeric polypeptide may be engineered to be activated by any convenient and appropriate antigen including but not limited to e.g., an autoantigen (e.g., a self-antigen that induces an autoimmune response), a cell type specific antigen, a tissue specific antigen, and the like. In some instances, the immunosuppression may be locally activated e.g., based on the local presence of the antigen, e.g., an antigen locally present in a tissue, an antigen locally present in an organ, etc. In some instances, immunosuppression may be performed globally e.g., by using an antigen present globally to activate a chimeric polypeptide of the instant disclosure. In some instances, a subject in need of immunosuppression according to the herein described method may be a subject with an autoimmune disease.

As will be readily understood, the methods of treating described herein may, in some instances, be combined with one or more conventional treatments. For example, in the case of oncology, the methods described herein may, in some instances, be combined with a conventional cancer therapy including but not limited to e.g., conventional chemotherapy, conventional radiation therapy, conventional immunotherapy, surgery, etc. In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRβ, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer); Dabrafenib (Tafinlar) targeting BRAF (approved for use in Melanoma, Non-small cell lung cancer); Daratumumab (Darzalex) targeting CD38 (approved for use in Multiple myeloma); Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3Kδ (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRα (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRβ, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2-)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/ hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma, Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/ neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like.

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a cancer.

Chimeric Polypeptides

The present disclosure provides proteolytically cleavable chimeric polypeptides. The chimeric polypeptides of the instant disclosure may generally include: a) an extracellular domain comprising a specific binding member; b) a proteolytically cleavable Notch receptor polypeptide comprising one or more proteolytic cleavage sites; and c) an intracellular domain. Binding of the specific binding member by its binding partner generally induces cleavage of the proteolytically cleavable Notch receptor at the one or more proteolytic cleavage sites, thereby releasing the intracellular domain. Release of the intracellular domain may modulate an activity of a cell or generally trigger the production of a payload that is contained within the cell, expressed on the cell surface or secreted. The chimeric polypeptides of the instant disclosure will generally include at least one sequence that is heterologous to the Notch receptor polypeptide (i.e., is not derived from a Notch receptor), including e.g., where the extracellular domain is heterologous to the Notch receptor polypeptide, where the intracellular domain is heterologous to the Notch receptor polypeptide, where both the extracellular domain and the intracellular domain are heterologous to the Notch receptor polypeptide, etc.

Domains, e.g., the extracellular domain, the Notch receptor polypeptide regulatory domain, the intracellular domain, etc., may be joined directly, i.e., with no intervening amino acid residues or may include a peptide linker that joins two domains. Peptide linkers may be synthetic or naturally derived including e.g., a fragment of a naturally occurring polypeptide.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa. A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

Extracellular Domains

Proteolytically cleavable chimeric polypeptides of the instant disclosure will generally include an extracellular domain that includes a specific binding member that specifically binds to a specific binding partner. Binding of the specific binding member to its specific binding partner triggers proteolytic cleavage of the Notch receptor polypeptide, releasing the intracellular domain which modulates an activity of the cell expressing the chimeric polypeptide.

The specific binding member of the extracellular domain generally determines the specificity of the chimeric polypeptide. In some instances, a chimeric polypeptide may be referred according to its specificity as determined based on its specific binding member. For example, a specific binding member having binding partner "X" may be referred to as an X chimeric polypeptide or an anti-X chimeric polypeptide.

Any convenient specific binding pair, i.e., specific binding member and specific binding partner pair, may find use in the chimeric polypeptides of the instant disclosure including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a scaffold protein and its binding partner may be a protein to which the scaffold protein specifically binds.

In some cases, the specific binding member of the chimeric polypeptide is an antibody. The antibody can be any antigen-binding antibody-based polypeptide, a wide variety of which are known in the art. In some instances, the specific binding member is or includes a monoclonal antibody, a single chain Fv (scFv), a Fab, etc. Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

Where the specific binding member of a chimeric polypeptide of the present disclosure is an antibody-based binding member, the chimeric polypeptide can be activated in the presence of a binding partner to the antibody-based binding member, including e.g., an antigen specifically bound by the antibody-based binding member. In some instances, antibody-based binding member may be defined, as is commonly done in the relevant art, based on the antigen bound by the antibody-based binding member, including e.g., where the antibody-based binding member is described as an "anti-" antigen antibody, e.g., an anti-CD19 antibody. Accordingly, antibody-based binding members suitable for inclusion in a chimeric polypeptide of the present disclosure can have a variety of antigen-binding specificities.

In some cases, the antigen-binding domain is specific for a cancer antigen, i.e., an antigen expressed by (synthesized by) a neoplasia or cancer cell, i.e., a cancer cell associated antigen or a cancer (or tumor) specific antigen.

A cancer cell associated antigen can be an antigen associated with, e.g., a breast cancer cell, a B cell lymphoma, a pancreatic cancer, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

A cancer cell specific antigen can be an antigen specific for cancer and/or a particular type of cancer or cancer cell including e.g., a breast cancer cell, a B cell lymphoma, a pancreatic cancer, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer (or tumor) specific antigen is generally not expressed by non-cancerous cells (or non-tumor cells). In some instances, a cancer (or tumor) specific antigen may be minimally expressed by one or more non-cancerous cell types (or non-tumor cell types). By "minimally expressed" is meant that the level of expression, in terms of either the per-cell expression level or the number of cells expressing, minimally, insignificantly or undetectably results in binding of the specific binding member to non-cancerous cells expressing the antigen.

In some instances, a specific binding member of a chimeric polypeptide may specifically bind a target comprising a fragment of a protein (e.g., a peptide) in conjunction with a major histocompatibility complex (MHC) molecule. As MHC molecules present peptide fragments of both intracellularly expressed and extracellularly expressed proteins, specific binding members directed to MHC-peptide complexes allows for the targeting of intracellular antigens as well as extracellularly expressed antigens.

Intracellularly expressed target proteins (e.g., cytoplasmically expressed (i.e., cytoplasmic proteins), nuclearly expressed (i.e., nuclear proteins), etc.) may be referred to as intracellular antigens (e.g., cytoplasmic antigens, nuclear antigens, etc.). Accordingly, specific binding members of the subject disclosure may be specific for intracellular antigen fragments complexed with MHC, e.g., a peptide-MHC complex, also, in some instances, described as a human leukocyte antigen (HLA)-peptide complex.

All endogenous cellular proteins (host or pathogen) are processed into short peptides for display at the cell surface in association with HLA molecules. Peptide-HLA class I complexes displayed on the cell surface play an important role in the T-cell mediated immune response. The approximately 9-residue long peptides originate from proteins that are digested by the proteasome inside the cell. Depending on whether the T-cell receptor recognizes a peptide as self or non-self, an immune response may be initiated. Peptide-HLA complexes displayed specifically on the surface of cancer cells provide an excellent opportunity to develop targeted cancer therapeutics, including engineered T-cells or "TCR-like" antibodies. The advent of various technologies, including e.g., MHC based tetramer technology, have advanced the ability to develop TCR-like anti-HLA/peptide specific antibodies.

In some instances, the binding partner of a specific binding member of the subject chimeric polypeptides may include peptide-MHC or HLA/peptide complexes. In some instances, the specific binding member of the subject chimeric polypeptides is specific for a MHC class I MHC-peptide complex including e.g., a HLA-A/peptide complex, a HLA-B/peptide complex or a HLA-C/peptide complex. In some instances, the specific binding member of the subject chimeric polypeptides is specific for a MHC class II MHC-peptide complex including e.g., a HLA-DPA1/peptide complex, a HLA-DPB1/peptide complex, a HLA-DQA1/peptide complex, a HLA-DQB1/peptide complex, a HLA-DRA/peptide complex or a HLA-DRB1/peptide complex. In some instances, the specific binding member of the subject chimeric polypeptides is specific for a MHC class III MHC-peptide complex.

Peptide-MHC Binding partners will generally include a target protein fragment peptide presented in the context of MHC. Such peptides vary in size depending on numerous factors including e.g., the class of MHC molecule to which they are bound. For example, class I MHC associated peptides are generally 9 aa in length but may vary in size including less than about 9 aa or more than about 9 aa including but not limited to e.g., 8 aa or 10 aa. Whereas, class II MHC associated peptides may also vary in size from about 13 aa to about 25 aa, including but not limited to e.g., 13 aa, 14 aa, 15 aa, 16 aa, 17 aa, 18 aa, 19 aa, 20 aa, 21 aa, 22 aa, 23 aa, 24 aa or 25 aa.

Exemplary protein targets to which a specific binding member targeting a peptide-MHC complex may be directed as well as exemplary peptides in the context of MHC for each protein target are provided in Table 1 below.

TABLE 1 anti-peptide-MHC targets

| Target | Exemplary Peptides | HLA | References |
|---|---|---|---|
| WT1 | RMFPNAPYL (SEQ ID NO: 18) | HLA-A2 | Leukemia. (2015) 29(11):2238-47 |
| KRAS and KRAS mutants (e.g., G12V & G12C) | KLVVVGAGGV (SEQ ID NO: 19); KLVVVGAVGV (SEQ ID NO: 20); KLVVVGACGV (SEQ ID NO: 21); KLVVVGADGV (SEQ ID NO: 22); VVGAVGVGK (SEQ ID NO: 23); VVGACGVGK (SEQ ID NO: 24); VVGAGGVGK (SEQ ID NO: 25) | HLA-A2; HLA-A3 | Proc Natl Acad Sci U.S.A. (2015) 112(32) |
| EGFP and EGFP mutants (e.g., L858R) | KITDFGLAK (SEQ ID NO: 26); KITDFGRAK (SEQ ID NO: 27); | HLA-A3 | Proc Natl Acad Sci U.S.A. (2015) 112(32) |
| PR1/ Proteinase 3 | VLQELNVTV (SEQ ID NO: 28) | HLA-A2 | Cytotherapy. (2016) 18(8):985-94 |
| MAGE-A1 | EADPTGHSY (SEQ ID NO: 29) | HLA-A1 | Blood. (2011) 117(16):4262-4272 |
| MAGE3 | FLWGPRALV (SEQ ID NO: 30) | HLA-A2 | Eur J Immunol (2005) 35:2864-2875 |
| P53 | LLGRNSFEV (SEQ ID NO: 31); STTPPPGTRV (SEQ ID NO: 32) RMPEAAPPV (SEQ ID NO: 33) GLAPPQHLIRV (SEQ ID NO: 34) | HLA-A2 | Gene Ther. (2001) 8(21):1601-8 PLoS One (2017) 12:1-16 |
| MART-1 | ELAGIGILTV (SEQ ID NO: 35) EAAGIGILTV (SEQ ID NO: 36) | HLA-A2 | Biomark Med. (2010) 4(4):496-7 Eur J Immunol (2007) 37:2008-2017 |
| gp100 | IMDQVPFSV (SEQ ID NO: 37) KTWGQYWQV (SEQ ID NO: 38) YLEPGPVTV (SEQ ID NO: 39) YLEPGPVTA (SEQ ID NO: 40) ITDQVPFSV (SEQ ID NO: 41) | HLA-A2 | Biomark Med. (2010) 4(4):496-7 J Immunol (2002) 169:4399-407 U.S. Patent Pub. No. US20030223994 J Immunol (2003) 171:2197-2207 |
| CMV pp65 | NLVPMVATV (SEQ ID NO: 42) | HLA-A2 | Biomark Med. (2010) 4(4):496-7 |
| HIV Vpr | AIIRILQQL (SEQ ID NO: 43) | HLA-A2 | Biomark Med. (2010) 4(4):496-7 |
| HA-1H | VLHDDLLEA (SEQ ID NO: 44); VLRDDLLEA (SEQ ID NO: 45) | HLA-A2 | Biomark Med. (2010) 4(4):496-7 |
| NY-ESO-1 | SLLMWITQV (SEQ ID NO: 46) | HLA-A2 | Gene Ther. (2014) 21(6):575-84 |
| EBNA3C | LLDFVRFMGV (SEQ ID NO: 47) | HLA-A2 | Proc Natl Acad Sci U.S.A. (2009) 106(14):5784-8 |
| AFP | FMNKFIYEI (SEQ ID NO: 48) | HLA-A2 | Cancer Gene Ther. (2012) 19(2):84-100 |

TABLE 1 -continued anti-peptide-MHC targets

| Target | Exemplary Peptides | HLA | References |
|---|---|---|---|
| Her2 | KIFGSLAFL (SEQ ID NO: 49) | HLA-A2 | Clin Cancer Res. (2016) pii: clincanres 1203.2016 |
| hCG-beta | GVLPALPQV (SEQ ID NO: 50)<br>TMTRVLQGV (SEQ ID NO: 51) | HLA-A2 | J Natl Cancer Inst. (2013) 105(3):202-18<br>Vaccine (2008) 26:3092-3102 |
| HBV Env183-91 | FLLTRILTI (SEQ ID NO: 52) | HLA-A2 | J Immunol. (2006) 177(6):4187-95 |
| hTERT | ILAKFLHWL (SEQ ID NO: 53)<br>RLVDDFLLV (SEQ ID NO: 54) | HLA-A2 | Cancer Res (2002) 62:3184-3194 |
| MUC1 | LLLTVLTVV (SEQ ID NO: 55) | HLA-A2 | Cancer Res (2002) 62:5835-5844 |
| TARP | FLRNFSLML (SEQ ID NO: 56) | HLA-A2 | Eur J Immunol (2008) 38:1706-1720 |
| Tyrosinase | YMDGTMSQV (SEQ ID NO: 57) | HLA-A2 | J Immunol (2009) 182:6328-41 |
| p68 | YLLPAIVHI (SEQ ID NO: 58) | HLA-A2 | Cancer Immunol Immunother (2010) 59:563-573 |
| MIF | FLSELTQQL (SEQ ID NO: 59) | HLA-A2 | J Immunol (2011) 186:6607 |
| PRAME | ALYVDSLFFL (SEQ ID NO: 60) | HLA-A2 | J Clin Invest (2017) 1-14 |

In some instances, the specific binding member of a proteolytically cleavable chimeric polypeptide of the instant disclosure specifically binds a peptide-MHC having an intracellular cancer antigen peptide of Table 1. In some instances, the specific binding member of a proteolytically cleavable chimeric polypeptide of the instant disclosure specifically binds a WT1 peptide-MHC. In some instances, the specific binding member of a proteolytically cleavable chimeric polypeptide of the instant disclosure specifically binds a NY-ESO-1 peptide-MHC.

In some instances, the specific binding member of a proteolytically cleavable chimeric polypeptide of the instant disclosure is an antibody (e.g., a scFv) that specifically binds a peptide-MHC having an intracellular cancer antigen peptide of Table 1. In some instances, the specific binding member of a proteolytically cleavable chimeric polypeptide of the instant disclosure is an antibody (e.g., a scFv) that specifically binds a WT1 peptide-MHC.

In some instances, an antibody that specifically binds to a WT1 peptide-MHC includes one or more or all of the following heavy-chain (VH) CDR sequences: SYAMS (SEQ ID NO:61), QIDPWGQETLYADSVKG (SEQ ID NO:62) and LTGRFDY (SEQ ID NO:63).

In some instances, an antibody that specifically binds to a WT1 peptide-MHC includes one or more or all of the following light-chain (VL) CDR sequences: RASQSIS-SYLN (SEQ ID NO:64), SASQLQS (SEQ ID NO:65) and QQGPGTPNT (SEQ ID NO:66).

In some instances, an antibody that specifically binds to a WT1 peptide-MHC is an scFv having the following amino acid sequence:

(SEQ ID NO: 67)
EVQLLESGGGLVQPGGSLRLSCAASGFTFSSYAMSWVRQAPGKGLEWVS

QIDPWGQETLYADSVKGRFTISRDNSKNTLYLQMNSLRAEDTAVYYCAK

LTGRFDYWGQGTLVTVSSGGGGSGGGGSGGGGSTDIQMTQSPSSLSASV

GDRVTITCRASQSISSYLNWYQQKPGKAPKLLIYSASQLQSGVPSRFSG

SGSGTDFTLTISSLQPEDFATYYCQQGPGTPNTFGQGTKVEIKRA.

In some instances, the specific binding member of a proteolytically cleavable chimeric polypeptide of the instant disclosure is an antibody (e.g., a scFv) that specifically binds a NY-ESO-1 peptide-MHC.

In some instances, the specific binding member of a proteolytically cleavable chimeric polypeptide of the instant disclosure is an antibody (e.g., a scFv) that specifically binds a KRAS-G12V peptide-MHC (e.g., anti-HLA-A2/KRAS-G12V scFv).

In some instances, an antibody that specifically binds to a KRAS-G12V peptide-MHC is an scFv having the following amino acid sequence:

(SEQ ID NO: 68)
DIQMTQSPSSLSASVGDRVTITCRASQDVNTAVAWYQQKPGKAPKLLIY

SASFLYSGVPSRFSGSRSGTDFTLTISSLQPEDFATYYCQQYYYYPPTF

GQGTKVEIKRTGGGSGGGGSGGGASEVQLVESGGGLVQPGGSLRLSCAA

SGFNINGSYIHWVRQAPGKGLEWVAYIDPETGYSRYADSVKGRFTISAD

TSKNTAYLQMNSLRAEDTAVYYCSRDSASDAMDVWGQGTLVTVSS.

In some instances, the specific binding member of a proteolytically cleavable chimeric polypeptide of the instant disclosure is an antibody (e.g., a scFv) that specifically binds a KRAS-G12V/C peptide-MHC (e.g., anti-HLA-A2/KRAS-G12V/C scFv).

In some instances, an antibody that specifically binds to a KRAS-G12V/C peptide-MHC is an scFv having the following amino acid sequence:

```
                                       (SEQ ID NO: 69)
DIQMTQSPSSLSASVGDRVTIACRASQDVNTAVAWYQQKPGKAPKLLIY

SASFLYSGVPSRFSGSRSGTDFTLTISSLQPEDFATYYCQQYYYPPTF

GQGTKVEIKRTGGGSGGGSGGGASEVQLVESGGGLVQPGGSLRLSCAA

SGFHINGSYIHWVRQAPGKGLKWVAYIDPETGYSRYADSVKGRFAISAD

MSKNTAYLQMNSLRAEDTAVYYCSRDSASDAMDVWGQGTLVTVSS.
```

In some instances, the specific binding member of a proteolytically cleavable chimeric polypeptide of the instant disclosure is an antibody (e.g., a scFv) that specifically binds an EGFR-L858R peptide-MHC (e.g., anti-HLA-A3/EGFR-L858R scFv).

In some instances, an antibody that specifically binds to an EGFR-L858R peptide-MHC is an scFv having the following amino acid sequence:

```
                                       (SEQ ID NO: 70)
DIQMTQSPSSLSASVGDRVTITCRASQDVNTAVAWYQQKPGKAPKLLIY

SASFLYSGVPSRFSGSRSGTDFTLTISSLQPEDFATYYCQQYYSYPPTF

GQGTKVEIKRTGGGSGGGSGGGASEVQLVESGGGLVQPGGSLRLSCAA

SGFNITSSYIHWVRQAPGKGLEWVAYISPEDGYARHADSVKGRFTISAD

TSKNTAYLQMNSLRAEDTAVYYCSRDDTYYYSAMDVWGQGTLVTVSS.
```

In some instances, the specific binding member (e.g., an antibody, scFv, etc.) of a proteolytically cleavable chimeric polypeptide of the instant disclosure specifically binds a peptide-MHC described in Dhanik et al. *BMC Bioinformatics* (2016) 17:286, the disclosure of which is incorporated herein by reference in its entirety, including but not limited to e.g., a NLRP4 peptide (e.g., HLSPIDCEV (SEQ ID NO:71))-MHC complex, a UMODL1 peptide (e.g., LTSMWSPAV (SEQ ID NO:72))-MHC complex, a NLRP4 peptide (e.g., HLDHPHPAV (SEQ ID NO:73))-MHC complex, a MAGEC2 peptide (e.g., SLSVMSSNV (SEQ ID NO:74))-MHC complex, a NLRP4 peptide (e.g., MMAWSDNKI (SEQ ID NO:75))-MHC complex, a COX7B2 peptide (e.g., TQIGIEWNL (SEQ ID NO:76))-MHC complex, a NLRP4 peptide (e.g., CLFEMQDPA (SEQ ID NO:77))-MHC complex, a UMODL1 peptide (e.g., YLSHPSCNV (SEQ ID NO:78))-MHC complex, a COX7B2 peptide (e.g., GIEWNLSPV (SEQ ID NO:79))-MHC complex, a MAGEA11 peptide (e.g., GLGCSPASI (SEQ ID NO:80))-MHC complex, a RPE65 peptide (e.g., RQAFEFPQI (SEQ ID NO:81))-MHC complex, a NLRP4 peptide (e.g., GMWTDTFEF (SEQ ID NO:82))-MHC complex, a TRIM51 peptide (e.g., YLNWQDTAV (SEQ ID NO:83))-MHC complex, a MAGEA11 peptide (e.g., VLWGPITQI (SEQ ID NO:84))-MHC complex, a NLRP4 peptide (e.g., TLDHTGVVV (SEQ ID NO:85))-MHC complex, a RPE65 peptide (e.g., TMGVWLHIA (SEQ ID NO:86))-MHC complex, a MAGEC2 peptide (e.g., KVWVQGHYL (SEQ ID NO:87))-MHC complex, a UMODL1 peptide (e.g., KINCNNFRL (SEQ ID NO:88))-MHC complex, etc.

Any suitable anti-peptide-MHC specific binding member (e.g., anti-peptide-MHC antibody) may find use as the specific binding member of an extracellular domain of a subject chimeric polypeptide as described herein, including but not limited to e.g., those suitable anti-peptide-MHC binding members and antibodies, as well as antibodies to those suitable epitopes, described in e.g.: U.S. Pat. Nos. 6,042,831; 6,252,052; 6,291,430; 6,602,510; 7,157,091; 7,622,569; 7,632,923; 7,638,124; 7,718,777; 8,119,139; 8,647,629; 8,815,528; 8,961,985; 9,023,348; 9,040,669; 9,074,000; 9,095,533; 9,334,317; U.S. Patent Application Pub. Nos: 20070092530; 20090042285; 20090226474; 20090304679; 20100062001; 20100111957; 20100158927; 20100158931; 20110020357; 20110033473; 20110293623; 20110318369; 20120141517; 20120294874; 20130101594; 20140024809; 20140065708; 20140271644; 20140294841; 20140296492; 20140363440; 20150125477; 20150125478; 20150259436; 20150320848; 20150322154; 20150368298; 20160017031; 20160168200; PCT Pub. Nos: WO2002014870; WO2003068201; WO2005120166; WO2007030451; WO2007143104; WO2008120202; WO2008120203; WO2009108372; WO2009125394; WO2009125395; WO2009138236; WO2010037514; WO2010106431; WO2011062560; WO2012007950; WO2012007951; WO2012017003; WO2012109659; WO2012135854; WO2014011489; WO2014143835; WO2015018805; WO2015063302; WO2015070061; WO2015070078; WO2015090229; WO2015130766; WO2015142675; WO2015169945; WO2015193359; WO2015199617; WO2016102272; and the like, the disclosures of which are incorporated herein by reference in their entirety.

In some instances, an anti-peptide-MHC specific binding member (e.g., an anti-peptide-MHC antibody) that may find use as the specific binding member of an extracellular domain of a subject chimeric polypeptide as described herein, may include but is not limited to e.g., those suitable anti-peptide-MHC binding members and antibodies, as well as antibodies to those suitable epitopes, described in e.g.: *T Cells Expressing Cars Directed Against HLA-0201 eRmf WT-1 Peptide Complex Can Effectively Eradicate WT1+ A0201+ Tumor Cells in-Vitro.* (2014) Biol Blood Marrow Transplant; *A novel TCR-like CAR with specificity for PR1/HLA-A2 effectively targets myeloid leukemia in vitro when expressed in human adult peripheral blood and cord blood T cells.* (2016) Cytotherapy; *Functional Comparison of Engineered T Cells Carrying a Native TCR versus TCR-like Antibody-Based Chimeric Antigen Receptors Indicates Affinity/Avidity Thresholds.* (2014) Journal of Immunology; *Affinity maturation of T-cell receptor-like antibodies for Wilms tumor 1 peptide greatly enhances therapeutic potential.* (2015) Leukemia; *Construction and molecular characterization of a T-cell receptor-like antibody and CAR-T cells specific for minor histocompatibility antigen HA-1H.* (2014) Gene Therapy; *Targeting the Intracellular WT1 Oncogene Product with a Therapeutic Human Antibody.* (2013) Science *Translational Medicine; A phage display selected Fab fragment with MHC class I-restricted specificity for MAGE-A1 allows for retargeting of primary human T lymphocytes.* (2001) Gene Therapy; *Therapeutic bispecific T-cell engager antibody targeting the intracellular oncoprotein WT1.* (2015) Nature Biotechnology; *Generation of MANAbodies specific to HLA-restricted epitopes encoded by somatically mutated genes.* (2015) PNAS; *Antitumor Activity of a Mono-* clonal Antibody targeting Major Histocompatibility complex class i-Her2 Peptide complexes. (2013) Journal of the National Cancer Institute; *Anti-melanoma activity of T cells redirected with a TCR-like chimeric antigen receptor.* (2014) Scientific Reports; and the like.

In some instances, a specific binding member of a chimeric polypeptide of the instant disclosure may include a T-cell receptor-like anti-peptide-MHC antibody including but not limited to e.g., those described in e.g., Dahan & Reiter. Expert Rev Mol Med. (2012) 14:e6 and/or Cohen & Reiter. Antibodies (2013), 2: 517-534, the disclosures of which are incorporated herein by reference in their entirety, including but not limited to e.g.: clone G2D12 targeting HLA-A2/gp100-154; clone 1A7 targeting HLA-A2/gp100-209; clone GI targeting HLA-A2/gp100-209; clone 2F1 targeting HLA-A2/gp100-280; clone TA2 targeting HLA-A2/Tyrosinase-369; clone CAG10, CLA12 targeting HLA-A2/MART-1-26; clone Fab-G8 targeting HLA-A1/MAGE-A1; clone Fab-Hyb3 targeting HLA-A1/MAGE-A1; clone 7D4 targeting HLA-A2/MAGE3-271; clone RL6A targeting HLA-A2/p68 RNA helicase-128; clone 3M4E5, 3M4F4 targeting HLA-A2/NYESO-1-157; clone T1 targeting HLA-A2/NYESO-1-157; clone D2 targeting HLA-A2/TARP-29; clone RL4B, 1B10 targeting HLA-A2/hCGβ-47; clone 3F9 targeting HLA-A2/hCGβ-40; clone 1B8 targeting HLA-A2/Her2-369; clone 8F4 targeting HLA-A2/PR1; clone F2 targeting HLA-A2/WT1-db126; clone M3A1, M3B8 targeting HLA-A2/MUC-1-D6-13; clone 4A9, 4G9 targeting HLA-A2/telomerase-540; clone 3G3, 3H2 targeting HLA-A2/telomerase-865; clone T3A4, T3D4, T3E3, T3F2, T3D3, T2H9 targeting HLA-A2/TAX-11; clone M1-D1, M1-G8, M1-D12, M1-A2 targeting HLA-A2/M1-58; the clone targeting HLA-A2/ENV-183; clone C3 targeting HLA-C7/Nef-105; clone 4F7 targeting HLA-A2/eIF4G-720; clone scFv #3, scFv #27 targeting HLA-A24/Nef-138; clone H9 targeting HLA-A2/pp65-495; and the like.

In addition to or in exchange of a peptide-MHC binding partner described herein, chimeric polypeptides of the instant disclosure may, in some cases, target a surface expressed antigen. As used herein the term "surface expressed antigen" generally refers to antigenic proteins that are expressed at least partially extracellularly such that at least a portion of the protein is exposed outside the cells and available for binding with a binding partner. Essentially any surface expressed protein may find use as a target of a chimeric polypeptide of the instant disclosure. Non-limiting examples of surface expressed antigens include but are not limited to e.g., CD19, CD20, CD30, CD38, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), IL-13R-a2, GD2, and the like. Surface expressed antigens that may be targeted also include but are not limited to e.g., those specifically targeted in conventional cancer therapies, including e.g., those targets of the targeted cancer therapeutics described herein.

In some instances, the specific binding member of a chimeric polypeptide of the instant disclosure may target a cancer-associated antigen. In some instances, a specific binding member of the instant disclosure may include an antibody specific for a cancer associated antigen. Non-limiting examples of cancer associated antigens include but are not limited to e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like. Cancer-associated antigens also include, e.g., 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

In some instances, the specific binding member of a chimeric polypeptide of the instant disclosure may target or may include all or a portion of an antibody targeting phosphatase of regenerating liver 3 (PRL-3, also known as PTP4A3), such as e.g., PRL3-zumab as described in Thura et al. (JCI Insight. 2016; 1(9):e87607); the disclosure of which is incorporated herein by reference in its entirety.

In some instances, the extracellular domain of a chimeric polypeptide may include only one specific binding member. In some instances, the extracellular domain of a chimeric polypeptide may by mono-specific.

In some instances, the extracellular domain of a chimeric polypeptide may by multi-specific, including e.g., bispecific. In some instances, a bispecific extracellular domain of a chimeric polypeptide may include a bispecific chimeric binding member, or portion thereof, including e.g., those described herein, including but not limited to e.g., a bispecific antibody. In some instances, a bispecific extracellular domain may include two specific binding domains that are linked, including e.g., directly linked to each other or linked via a linker.

In some instances, the extracellular domain of a chimeric polypeptide may include more than one specific binding member, including two or more specific binding members where the two or more specific binding members may be linked (either directly or indirectly, e.g., through the use of a linker) to each other or they may each be linked (either directly or indirectly, e.g., through the use of a linker) to another component of the chimeric polypeptide.

Multi-specific extracellular domains may recognize or bind to any combination of binding partners and thus may target any combination of targets, including but not limited to e.g., those binding partners and targets described herein. Accordingly, e.g., a bispecific extracellular domain may target two different antigens including but not limited to e.g., two different intracellular antigens, two different extracellular (e.g., surface expressed) antigens or an intracellular antigen and an extracellular (e.g., surface expressed) antigen. In some instances, a bispecific extracellular domain may include two specific binding members, including e.g., two specific binding members described herein, that each bind an antigen, including e.g., an antigen described herein.

The specific binding domains of a multi-specific extracellular domain may each activate the chimeric polypeptide of which they are a part. The specific binding domains of a bispecific extracellular domain may each activate the chimeric polypeptide of which they are a part. In some instances, multi-specific or bispecific binding domains may find use as part of a molecular circuit as described herein including e.g., as an OR-gate of a circuit described herein.

In some instances, the binding partner bound by a specific binding domain may be mutated as compared to the wild-type binding partner. In some instances, a specific binding domain that recognizes a mutated binding partner may not specifically bind the wild-type binding partner. In some instances, a specific binding domain that recognizes a mutated binding partner may bind the wild-type binding partner with lower affinity as compared to its binding affinity with the mutated binding partner.

Any binding partner, including e.g., those described herein, may be mutated or may be a mutated binding partner. Accordingly, a chimeric polypeptide of the instant disclosure may include a specific binding member that specifically binds a mutated (i.e., non-wild-type) binding partner. Non-limiting examples of mutated binding partners include but are not limited to e.g., mutated antigens, mutated cancer antigens, mutated auto-antigens, mutated extracellular antigens, mutated extracellular cancer antigens, mutated extracellular auto-antigens, mutated surface antigens, mutated surface cancer antigens, mutated surface auto-antigens, peptide-MHC complexes presenting a mutated antigen peptide, peptide-MHC complexes presenting a mutated cancer antigen peptide, peptide-MHC complexes presenting a mutated auto-antigen peptide, and the like.

Cancers commonly involve mutated proteins that are associated with the disease. Genes commonly mutated in cancers include e.g., ABI1, ABL1, ABL2, ACKR3, ACSL3, ACSL6, AFF1, AFF3, AFF4, AKAP9, AKT1, AKT2, ALDH2, ALK, AMER1, APC, ARHGAP26, ARHGEF12, ARID1A, ARID2, ARNT, ASPSCR1, ASXL1, ATF1, ATIC, ATM, ATP1A1, ATP2B3, ATRX, AXIN1, BAP1, BCL10, BCL11A, BCL11B, BCL2, BCL3, BCL6, BCL7A, BCL9, BCOR, BCR, BIRC3, BLM, BMPR1A, BRAF, BRCA1, BRCA2, BRD3, BRD4, BRIP1, BTG1, BUB1B, C15orf65, C2orf44, CACNA1D, CALR, CAMTA1, CANT1, CARD11, CARS, CASC5, CASP8, CBFA2T3, CBFB, CBL, CBLB, CBLC, CCDC6, CCNB1IP1, CCND1, CCND2, CCND3, CCNE1, CD274, CD74, CD79A, CD79B, CDC73, CDH1, CDH11, CDK12, CDK4, CDK6, CDKN2A, CDKN2C, CDX2, CEBPA, CEP89, CHCHD7, CHEK2, CHIC2, CHN1, CIC, CIITA, CLIP1, CLP1, CLTC, CLTCL1, CNBP, CNOT3, CNTRL, COL1A1, COL2A1, COX6C, CREB1, CREB3L1, CREB3L2, CREBBP, CRLF2, CRTC1, CRTC3, CSF3R, CTNNB1, CUX1, CYLD, DAXX, DCTN1, DDB2, DDIT3, DDX10, DDX5, DDX6, DEK, DICER1, DNM2, DNMT3A, EBF1, ECT2L, EGFR, EIF3E, EIF4A2, ELF4, ELK4, ELL, ELN, EML4, EP300, EPS15, ERBB2, ERC1, ERCC2, ERCC3, ERCC4, ERCC5, ERG, ETV1, ETV4, ETV5, ETV6, EWSR1, EXT1, EXT2, EZH2, EZR, FAM46C, FANCA, FANCC, FANCD2, FANCE, FANCF, FANCG, FAS, FBXO11, FBXW7, FCGR2B, FCRL4, FEV, FGFR1, FGFR1OP, FGFR2, FGFR3, FH, FHIT, FIP1L1, FLCN, FLI1, FLT3, FNBP1, FOXA1, FOXL2, FOXO1, FOXO3, FOXO4, FOXP1, FSTL3, FUBP1, FUS, GAS7, GATA1, GATA2, GATA3, GMPS, GNA11, GNAQ, GNAS, GOLGA5, GOPC, GPC3, GPHN, H3F3A, H3F3B, HERPUD1, HEY1, HIP1, HIST1H4I, HLA-A, HLF, HMGA1, HMGA2, HNF1A, HNRNPA2B1, HOOK3, HOXA11, HOXA13, HOXA9, HOXC11, HOXC13, HOXD11, HOXD13, HRAS, HSP90AA1, HSP90AB1, IDH1, IDH2, IKZF1, IL2, IL21R, IL6ST, IL7R, IRF4, ITK, JAK1, JAK2, JAK3, JAZF1, JUN, KAT6A, KAT6B, KCNJ5, KDM5A, KDM5C, KDM6A, KDR, KDSR, KIAA1549, KIAA1598, KIF5B, KIT, KLF4, KLF6, KLK2, KMT2A, KMT2C, KMT2D, KRAS, KTN1, LASP1, LCK, LCP1, LHFP, LIFR, LMNA, LMO1, LMO2, LPP, LRIG3, LSM14A, LYL1, MAF, MAFB, MALT1, MAML2, MAP2K1, MAP2K2, MAP2K4, MAX, MDM2, MDM4, MECOM, MED12, MEN1, MET, MITF, MKL1, MLF1, MLH1, MLLT1, MLLT10, MLLT11, MLLT3, MLLT4, MLLT6, MN1, MNX1, MPL, MSH2, MSH6, MSI2, MSN, MTCP1, MUC1, MUTYH, MYB, MYC, MYCL, MYCN, MYD88, MYH11, MYH9, MYO5A, NAB2, NACA, NBN, NCKIPSD, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM1, NUTM2A, NUTM2B, OLIG2, OMD, P2RY8, PAFAH1B2, PALB2, PATZ1, PAX3, PAX5, PAX7, PAX8, PBRM1, PBX1, PCM1, PCSK7, PDCD1LG2, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, POT1, POU2AF1, POU5F1, PPARG, PPFIBP1, PPP2R1A, PRCC, PRDM1, PRDM16, PRF1, PRKAR1A, PRRX1, PSIP1, PTCH1, PTEN, PTPN11, PTPRB, PTPRC, PTPRK, PWWP2A, RABEP1, RAC1, RAD21, RAD51B, RAF1, RALGDS, RANBP17, RAP1GDS1, RARA, RB1, RBM15, RECQL4, REL, RET, RHOH, RMI2, RNF213, RNF43, ROS1, RPL10, RPL22, RPL5, RPN1, RSPO2, RSPO3, RUNX1, RUNX1T1, SBDS, SDC4, SDHAF2, SDHB, SDHC, SDHD, SEPT5, SEPT6, SEPT9, SET, SETBP1, SETD2, SF3B1, SFPQ, SH2B3, SH3GL1, SLC34A2, SLC45A3, SMAD4, SMARCA4, SMARCB1, SMARCE1, SMO, SOCS1, SOX2, SPECC1, SRGAP3, SRSF2, SRSF3, SS18, SS18L1, SSX1, SSX2, SSX2B, SSX4, SSX4B, STAG2, STAT3, STAT5B, STAT6, STIL, STK11, SUFU, SUZ12, SYK, TAF15, TAL1, TAL2, TBL1XR1, TCEA1, TCF12, TCF3, TCF7L2, TCL1A, TERT, TET1, TET2, TFE3, TFEB, TFG, TFPT, TFRC, THRAP3, TLX1, TLX3, TMPRSS2, TNFAIP3, TNFRSF14, TNFRSF17, TOP1, TP53, TPM3, TPM4, TPR, TRAF7, TRIM24, TRIM27, TRIM33, TRIP11, TRRAP, TSC1, TSC2, TSHR, TTL, U2AF1, UBR5, USP6, VHL, VTI1A, WAS, WHSC1, WHSC1L1, WIF1, WRN, WT1, WWTR1, XPA, XPC, XPO1, YWHAE, ZBTB16, ZCCHC8, ZMYM2, ZNF331, ZNF384, ZNF521 and ZRSR2. In some instances, a specific binding member binds to the mutated version of a gene that is commonly mutated in cancer, including but not limited to e.g., those listed above. In some instances, a specific binding member binds to a peptide-MHC complex presenting a mutated cancer antigen peptide derived from the mutated version of a gene that is commonly mutated in cancer, including but not limited to e.g., those listed above. In some instances, a specific binding member binds to a peptide-MHC complex presenting a mutant KRAS peptide.

In some instances, a binding partner/specific binding member pair may be orthogonalized. As used herein, by "orthogonalized" is meant modified from their original or wild-type form such that the orthogonal pair specifically bind one another but do not specifically or substantially bind the non-modified or wild-type components of the pair. Any binding partner/specific binding pair may be orthogonalized, including but not limited to e.g., those binding partner/specific binding pairs described herein.

Certain extracellular domains and components thereof that may be adapted for use in chimeric polypeptides and the methods and circuits described herein include but are not limited to e.g., those described in PCT Application No. US2016/019188 (Pub. No. WO 2016/138034), the disclosure of which is incorporated herein by reference in its entirety.

Notch Receptor Polypeptides

As noted above, a chimeric polypeptide of the present disclosure includes a Notch receptor polypeptide. Notch receptor polypeptides of the subject chimeric polypeptides will vary and may range in length from about 50 amino acids or less to about 1000 amino acids or more and will generally include one or more ligand-inducible proteolytic cleavage sites. Notch receptor polypeptides include synthetic receptors containing a Notch regulatory region or a modified form thereof.

In some cases, the Notch receptor polypeptide present in a chimeric polypeptide of the present disclosure has a length of from 50 amino acids (aa) to 1000 aa, e.g., from 50 aa to 75 aa, from 75 aa to 100 aa, from 100 aa to 150 aa, from 150 aa to 200 aa, from 200 aa to 250 aa, from 250 a to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, from 750 aa to 800 aa, from 800 aa to 850 aa, from 850 aa to 900 aa, from 900 aa to 950 aa, or from 950 aa to 1000 aa. In some cases, the Notch receptor polypeptide present in a chimeric polypeptide of the present disclosure has a length of from 300 aa to 400 aa. In some cases, the Notch receptor polypeptide present in a chimeric polypeptide of the present disclosure has a length of from 300 aa to 350 aa. In some cases, the Notch receptor polypeptide present in a chimeric polypeptide of the present disclosure has a length of from 300 aa to 325 aa. In some cases, the Notch receptor polypeptide present in a chimeric polypeptide of the present disclosure has a length of from 350 aa to 400 aa. In some cases, the Notch receptor polypeptide present in a chimeric polypeptide of the present disclosure has a length of from 750 aa to 850 aa. In some cases, the Notch receptor polypeptide present in a chimeric polypeptide of the present disclosure has a length of from 50 aa to 75 aa. In some cases, the Notch receptor polypeptide present in a chimeric polypeptide of the present disclosure has a length of from 310 aa to 320 aa, e.g., 310 aa, 311 aa, 312 aa, 313 aa, 314 aa, 315 aa, 316 aa, 317 aa, 318 aa, 319 aa, or 320 aa. In some cases, the Notch receptor polypeptide present in a chimeric polypeptide of the present disclosure has a length of 315 aa. In some cases, the Notch receptor polypeptide present in a chimeric polypeptide of the present disclosure has a length of from 360 aa to 370 aa, e.g., 360 aa, 361 aa, 362 aa, 363 aa 364 aa, 365 aa, 366 aa, 367 aa, 368 aa, 369 aa, or 370 aa. In some cases, the Notch receptor polypeptide present in a chimeric polypeptide of the present disclosure has a length of 367 aa.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor including e.g., any of SEQ ID NOs: 1, 2 and 5-15. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence, including e.g., SEQ ID NOs: 1, 2 and 5-15.

Subject Notch regulatory regions may include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an S1 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta-binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

Notch Receptor Polypeptide Comprising a TM Domain

In some cases, the Notch receptor polypeptide present in a chimeric polypeptide of the present disclosure comprises an amino acid sequence having at least 75%, at least 80%, at least 85%, at least 90%, at least 95%, at least 98%, at least 99%, or 100%, amino acid sequence identity to the following amino acid sequence:

(SEQ ID NO: 89)
IPYKIEAVKSEPVEPPLPSQL<u>HLMYVAAAAFVLLFFVGCGVLLS</u>RKRRR

QLCIQKL;

where the TM domain is underlined; where the Notch receptor polypeptide comprises an S2 proteolytic cleavage site and an S3 proteolytic cleavage site; where the Notch receptor polypeptide has a length of from 50 amino acids (aa) to 65 aa, e.g., 50, 51, 52, 53, 54, 55, 56, 57, 58, 59, 60, 61, 62, 63, 64, or 65 aa. In some cases, the Notch receptor polypeptide present in a chimeric polypeptide of the present disclosure comprises an amino acid sequence having at least 75%, at least 80%, at least 85%, at least 90%, at least 95%, at least 98%, at least 99%, or 100%, amino acid sequence identity to the following amino acid sequence:

(SEQ ID NO: 89)
IPYKIEAVKSEPVEPPLPSQLHLMYVAAAAFVLLFFVGCGVLLSRKRRR

QLCIQKL;

where the TM domain is underlined; where the Notch receptor polypeptide comprises an S2 proteolytic cleavage site and an S3 proteolytic cleavage site; where the Notch receptor polypeptide has a length of 56 amino acids.

Figure 30A:
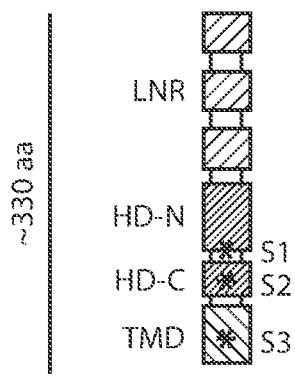
FIG. 30A-30G provide schematic depictions of exemplary Notch regulatory regions of Notch receptor polypeptides of the present disclosure.

Notch Receptor Polypeptide Comprising an LNR Segment, an HD-N Segment, an HD-C Segment, and a TM Domain In some cases, the Notch receptor polypeptide present in a chimeric polypeptide of the present disclosure comprises, in order from N-terminus to C-terminus: i) a LNR-A segment; ii) a LNR-B segment; iii) a LNR-C segment; iv) an HD-N segment, v) an HD-C segment; and vi) a TM domain. A LNR-A segment, LNR-B segment, and LNR-C segment can collectively be referred to as an "LNR segment." Such a Notch receptor polypeptide is depicted schematically in FIG. 30A.

An LNR segment can comprise an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and can have a length of from 90 amino acids to 150 amino acids, e.g., from 90 amino acids (aa) to 100 aa, from 100 aa to 110 aa, from 110 aa to 120 aa, from 120 aa to 130 aa, from 130 aa to 140 aa, or from 140 aa to 150 aa. In some cases, an LNR segment comprises an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and has a length of from 115 aa to 125 aa, e.g., 115, 116, 117, 118, 119, 120, 121, 122, 123, 124, or 125 aa.

An LNR segment can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 90)
PPQIEEACELPECQVDAGNKVCNLQCNNHACGWDGGDCSLNFNDPWKNC

TQSLQCWKYFSDGHCDSQCNSAGCLFDGFDCQLTEGQCNPLYDQYCKDH

FSDGHCDQGCNSAECEWDGLDC;

and can have a length of from 118 to 122 amino acids (e.g., 118, 119, 120, 121, or 122 amino acids).

An HD-N segment can comprise an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and can have a length of from 90 amino acids (aa) to 110 aa, e.g., 90 aa to 95 aa, 95 aa to 100 aa, 100 aa to 105 aa, or 105 aa to 110 aa. In some cases, an HD-N segment comprises an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and has a length of from 95 aa to 105 aa, e.g., 95, 96, 98, 98, 99, 100, 101, 102, 103, 104, or 105 aa.

An HD-C segment can comprise an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and can have a length of from 60 amino acids (aa) to 80 aa, e.g., from 60 aa to 65 aa, from 65 aa to 70 aa, from 70 aa to 75 aa, or from 75 aa to 80 aa. In some cases, an HD-C segment comprises an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and has a length of from 65 amino acids to 75 amino acids, e.g., 65, 66, 67, 68, 69, 70, 71, 72, 73, 74, or 75 amino acids.

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 91)
AAGTLVLVVLLPPDQLRNNSFHFLRELSHVLHTNVVFKRDAQGQQMIFP

YYGHEEELRKHPIKRSTVGWATSSLLPGTSGGRQRRELDPMDIRGSIVY

LEIDNRQCVQSSSQCFQSATDVAAFLGALASLGSLNIPYKIEAVKSEPV

EPPLP;

and can have a length of 150, 151, 152, 153, or 154 amino acids.

A transmembrane segment can comprise an amino acid sequence having at least 75%, at least 80%, at least 85%, at least 90%, at least 95%, at least 98%, at least 99%, or 100%, amino acid sequence identity to amino acids 1736 to 1756 of the amino acid sequence depicted in FIGS. 31A-31B, or a corresponding segment of another Notch receptor polypeptide, where examples of corresponding segments are depicted in FIG. 31C-31G; and can have a length of from 15 amino acids (aa) to 25 amino acids, e.g., 15, 16, 17, 18, 29, 20, 21, 22, 23, 24, or 25 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO:92); and can have a length of 21, 22, 23, 24, or 25 amino acids.

In some cases, a Notch receptor polypeptide has a length of from about 310 amino acids (aa) to about 320 aa (e.g., 310 aa, 311 aa, 312 aa, 313 aa, 314 aa, 315 aa, 316 aa, 317 aa, 318 aa, 319 aa, or 320 aa), and comprises an amino acid sequence having at least 75%, at least 80%, at least 85%, at least 90%, at least 95%, at least 98%, at least 99%, or 100%, amino acid sequence identity to amino acids 1442-1756 of the amino acid sequence depicted in FIG. 31A-31B, or a corresponding segment of another Notch receptor polypeptide, where examples of corresponding segments are depicted in FIG. 31C-31G.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 93)
PPQIEEACELPECQVDAGNKVCNLQCNNHACGWDGGDCSLNFNDPWKNC

TQSLQCWKYFSDGHCDSQCNSAGCLFDGFDCQLTEGQCNPLYDQYCKDH

FSDGHCDQGCNSAECEWDGLDCAEHVPERLAAGTLVLVVLLPPDQLRNN

SFHFLRELSHVLHTNVVFKRDAQGQQMIFPYYGHEEELRKHPIKRSTVG

WATSSLLPGTSGGRQRRELDPMDIRGSIVYLEIDNRQCVQSSSQCFQSA

TDVAAFLGALASLGSLNIPYKIEAVKSEPVEPPLPSQLHLMYVAAAAFV

LLFFVGCGVLLS;

and has a length of from 300 amino acids to 310 amino acids (e.g., 300, 301, 302, 303, 304, 305, 306, 307, 308, 309, or 310 amino acids).

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 94)
PCVGSNPCYNQGTCEPTSENPFYRCLCPAKFNGLLCHILDYSFTGGAGR

DIPPPQIEEACELPECQVDAGNKVCNLQCNNHACGWDGGDCSLNFNDPW

KNCTQSLQCWKYFSDGHCDSQCNSAGCLFDGFDCQLTEGQCNPLYDQYC

KDHFSDGHCDQGCNSAECEWDGLDCAEHVPERLAAGTLVLVVLLPPDQL

RNNSFHFLRELSHVLHTNVVFKRDAQGQQMIFPYYGHEEELRKHPIKRS

TVGWATSSLLPGTSGGRQRRELDPMDIRGSIVYLEIDNRQCVQSSSQCF

QSATDVAAFLGALASLGSLNIPYKIEAVKSEPVEPPLPSQLHLMYVAAA

AFVLLFFVGCGVLLS;

and has a length of from 350 amino acids to 370 amino acids (e.g., 350 351, 352, 353, 354, 355, 356, 357, 358, 359, 360, 361, 362, 363, 364, 365, 366, 367, 368, 369, or 370 amino acids).

Figure 30B:
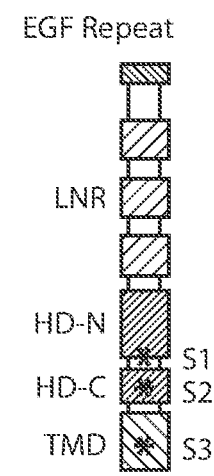

Notch Receptor Polypeptide Comprising a Single EGF Repeat, an LNR Segment, an HD-N Segment, an HD-C Segment, and a TM Domain In some cases, the Notch receptor polypeptide present in a chimeric polypeptide of the present disclosure comprises, in order from N-terminus to C-terminus: i) a single EGF repeat; ii) an LNR segment; iii) an HD-N segment, iv) an HD-C segment; and v) a TM domain. Such a Notch receptor polypeptide is depicted schematically in FIG. 30B.

An EGF repeat can comprises an amino acid sequence having at least 75%, at least 80%, at least 85%, at least 90%, at least 95%, at least 98%, at least 99%, or 100%, amino acid sequence identity to amino acids 1390 to 1430 of the amino acid sequence depicted in FIG. 31A-31B, or a corresponding segment of another Notch receptor polypeptide, where examples of corresponding segments are depicted in FIG. 31C-31G; and can have a length of from 35 amino acids (aa) to 45 aa (e.g., 35, 36, 37, 38, 39, 40, 41, 42, 43, 44, or 45 aa).

An EGF repeat can comprise an amino acid sequence having at least 75%, at least 80%, at least 85%, at least 90%, at least 95%, at least 98%, at least 99%, or 100%, amino acid sequence identity to the following sequence: PCVGSNPCYNQGTCEPTSENPFYRCLCPAKFNGLLCH (SEQ ID NO:95); and can have a length of 35 amino acids to 40 amino acids (e.g., 35, 36, 37, 38, 39, or 40 amino acids).

An LNR segment can comprise an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and can have a length of from 90 amino acids to 150 amino acids, e.g., from 90 amino acids (aa) to 100 aa, from 100 aa to 110 aa, from 110 aa to 120 aa, from 120 aa to 130 aa, from 130 aa to 140 aa, or from 140 aa to 150 aa. In some cases, an LNR segment comprises an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and has a length of from 115 aa to 125 aa, e.g., 115, 116, 117, 118, 119, 120, 121, 122, 123, 124, or 125 aa.

An LNR segment can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 90)
PPQIEEACELPECQVDAGNKVCNLQCNNHACGWDGGDCSLNFNDPWKNC

TQSLQCWKYFSDGHCDSQCNSAGCLFDGFDCQLTEGQCNPLYDQYCKDH

FSDGHCDQGCNSAECEWDGLDC;

and can have a length of from 118 to 122 amino acids (e.g., 118, 119, 120, 121, or 122 amino acids).

An HD-N segment can comprise an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and can have a length of from 90 amino acids (aa) to 110 aa, e.g., 90 aa to 95 aa, 95 aa to 100 aa, 100 aa to 105 aa, or 105 aa to 110 aa. In some cases, an HD-N segment comprises an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and has a length of from 95 aa to 105 aa, e.g., 95, 96, 98, 98, 99, 100, 101, 102, 103, 104, or 105 aa.

An HD-C segment can comprise an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and can have a length of from 60 amino acids (aa) to 80 aa, e.g., from 60 aa to 65 aa, from 65 aa to 70 aa, from 70 aa to 75 aa, or from 75 aa to 80 aa. In some cases, an HD-C segment comprises an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and has a length of from 65 amino acids to 75 amino acids, e.g., 65, 66, 67, 68, 69, 70, 71, 72, 73, 74, or 75 amino acids.

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 91)
AAGTLVLVVLLPPDQLRNNSFHFLRELSHVLHTNVVFKRDAQGQQMIFP

YYGHEEELRKHPIKRSTVGWATSSLLPGTSGGRQRRELDPMDIRGSIVY

LEIDNRQCVQSSSQCFQSATDVAAFLGALASLGSLNIPYKIEAVKSEPV

EPPLP;

and can have a length of 150, 151, 152, 153, or 154 amino acids.

A transmembrane segment can comprise an amino acid sequence having at least 75%, at least 80%, at least 85%, at least 90%, at least 95%, at least 98%, at least 99%, or 100%, amino acid sequence identity to amino acids 1736 to 1756 of the amino acid sequence depicted in FIG. 31A-31B, or a corresponding segment of another Notch receptor polypeptide, where examples of corresponding segments are depicted in FIG. 31C-31G; and can have a length of from 15 amino acids (aa) to 25 amino acids, e.g., 15, 16, 17, 18, 29, 20, 21, 22, 23, 24, or 25 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO:92); and can have a length of 21, 22, 23, 24, or 25 amino acids.

In some cases, a Notch receptor polypeptide has a length of from about 360 amino acids (aa) to about 375 aa (e.g., 360 aa, 361 aa, 362 aa, 363 aa, 364 aa, 365 aa, 366 aa, 367 aa, 368 aa, 369 aa, 370 aa, 371 aa, 372 aa, 373 aa, 374 aa, or 375 aa), and comprises an amino acid sequence having at least 75%, at least 80%, at least 85%, at least 90%, at least 95%, at least 98%, at least 99%, or 100%, amino acid sequence identity to amino acids 1390-1756 of the amino acid sequence depicted in FIG. 31A-31B, or a corresponding segment of another Notch receptor polypeptide, where examples of corresponding segments are depicted in FIG. 31C-31G.

Figure 30C:
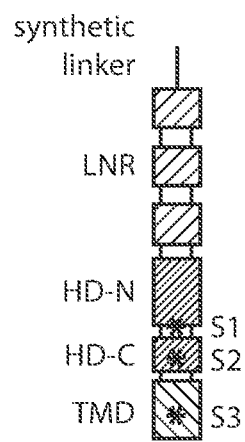

In some cases, a Notch receptor polypeptide comprises a synthetic linker. For example, in some cases, a Notch receptor polypeptide comprises, in order from N-terminus to C-terminus: i) a synthetic linker; ii) an EGF repeat; iii) an LNR segment; iv) an HD-N segment, v) an HD-C segment; and vi) a TM domain. Such a Notch receptor polypeptide is depicted schematically in FIG. 30C.

A synthetic linker can have a length of from about 10 amino acids (aa) to about 200 aa, e.g., from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A synthetic linker can have a length of from 10 aa to 30 aa, e.g., 10, 11, 12, 13, 14, 15, 16, 17, 18, 19, 20, 21, 22, 23, 24, 25, 26, 27, 28, 29, or 30 aa. A synthetic linker can have a length of from 30 aa to 50 aa, e.g., from 30 aa to 35 aa, from 35 aa to 40 aa, from 40 aa to 45 aa, or from 45 aa to 50 aa.

In some instances, a synthetic linker, as described herein, may include an extracellular protein structural domain or a portion thereof. Extracellular protein structural domains suitable for use as a synthetic linker include but are not limited to e.g., Ig-like extracellular structural domains, Fc extracellular structural domains, fibronectin extracellular structural domains and the like. In some instances, a synthetic linker may include a plurality of extracellular protein structural domains where the plurality may include a plurality of the same domain or a plurality of different domains.

Figure 30D:
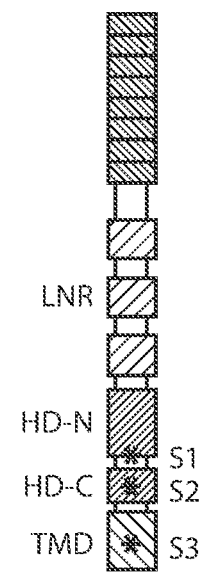

Notch Receptor Polypeptide Comprising 2-11 EGF Repeats, an LNR Segment, an HD-N Segment, an HD-C Segment, and a TM Domain In some cases, the Notch receptor polypeptide present in a chimeric polypeptide of the present disclosure comprises, in order from N-terminus to C-terminus: i) from two to eleven EGF repeats; ii) an LNR segment; iii) an HD-N segment, iv) an HD-C segment; and v) a TM domain. Such a Notch receptor polypeptide is depicted schematically in FIG. 30D.

In some cases, the Notch receptor polypeptide present in a chimeric polypeptide of the present disclosure comprises, in order from N-terminus to C-terminus: i) two EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) three EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) four EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) five EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) six EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) seven EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) eight EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) nine EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) ten EGF repeats; ii) an LNR segment; iii) an HD-N segment, iv) an HD-C segment; and v) a TM domain. In some cases, the Notch receptor polypeptide present in a chimeric polypeptide of the present disclosure comprises, in order from N-terminus to C-terminus: i) eleven EGF repeats; ii) an LNR segment; iii) an HD-N segment, iv) an HD-C segment; and v) a TM domain.

An EGF repeat can comprise an amino acid sequence having at least 75%, at least 80%, at least 85%, at least 90%, at least 95%, at least 98%, at least 99%, or 100%, amino acid sequence identity to amino acids 1390 to 1430 of the amino acid sequence depicted in FIG. 31A-31B, or a corresponding segment of another Notch receptor polypeptide, where examples of corresponding segments are depicted in FIG. 31C-31G; and can have a length of from 35 amino acids (aa) to 45 aa (e.g., 35, 36, 37, 38, 39, 40, 41, 42, 43, 44, or 45 aa).

An EGF repeat can comprise an amino acid sequence having at least 75%, at least 80%, at least 85%, at least 90%, at least 95%, at least 98%, at least 99%, or 100%, amino acid sequence identity to amino acids 869-905 (DINECVLSPCRHGASCQNTHGGYRCHCQAGYSGRNCE; SEQ ID NO:96) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 907-943 (DIDDCRPNPCHNGGSCTDGINTAFCDCLPG-FRGTFCE; SEQ ID NO:97) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 945-981 (DINECASDPCRNGANCTDCVDSYTCTCPAGFSGIHCE; (SEQ ID NO:98) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 988-1019 (TESSCFNGGTCVDGINSFTCLPPGFTGSYCQ; SEQ ID NO:99) of the amino acid sequence depicted in FIG. 31A-31B, or a corresponding segment of another Notch receptor polypeptide, where examples of corresponding segments are depicted in FIG. 31C-31G; and can have a length of from 30 amino acids (aa) to 35 aa (e.g., 30, 31, 32, 33, 34, or 35 aa).

An EGF repeat can comprise an amino acid sequence having at least 75%, at least 80%, at least 85%, at least 90%, at least 95%, at least 98%, at least 99%, or 100%, amino acid sequence identity to amino acids 1021-1057 (DVNECDSQPCLHGGTCQDGCGSYRCTCPQGYTGPNCQ; SEQ ID NO:100) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 1064-1090 (DSSPCKNGGKCWQTHTQYRCECPSGWT; SEQ ID NO:101) of the amino acid sequence depicted in FIG. 31A-31B, or a corresponding segment of another Notch receptor polypeptide, where examples of corresponding segments are depicted in FIG. 31C-31G; and can have a length of from 25 amino acids (aa) to 30 aa, e.g., 25, 26, 27, 28, 29, or 30 aa.

An EGF repeat can comprise an amino acid sequence having at least 75%, at least 80%, at least 85%, at least 90%, at least 95%, at least 98%, at least 99%, or 100%, amino acid sequence identity to amino acids 1146-1180 (LVDECSPSPCQNGATCTDYLGGYSCKCVAGYHGVNC; SEQ ID NO:102) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 1184-1219 (IDECLSHPCQNGGTCLDLPNTYKCSCPRGTQGVHCE; SEQ ID NO:103) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to amino acids 1238-1265 (CFNNGTCVDQVGGYSCTCPPGFVGERCE; SEQ ID NO:104) of the amino acid sequence depicted in FIG. 31A-31B, or a corresponding segment of another Notch receptor polypeptide, where examples of corresponding segments are depicted in FIG. 31C-31G; and can have a length of from 25 amino acids (aa) to 30 aa, e.g., 25, 26, 27, 28, 29, or 30 aa.

An EGF repeat can comprise an amino acid sequence having at least 75%, at least 80%, at least 85%, at least 90%, at least 95%, at least 98%, at least 99%, or 100%, amino acid sequence identity to amino acids 1267-1305 (DVNECLSNPCDARGTQNCVQRVNDFHCECRAGHTGRRCE; (SEQ ID NO: 105) of the amino acid sequence depicted in FIG. 31A-31B, or a corresponding segment of another Notch receptor polypeptide, where examples of corresponding segments are depicted in FIG. 31C-31G; and can have a length of from 35 amino acids to about 40 amino acids (aa) (e.g., 35, 36, 37, 38, 39, or 40 aa).

An EGF repeat can comprise an amino acid sequence having at least 75%, at least 80%, at least 85%, at least 90%, at least 95%, at least 98%, at least 99%, or 100%, amino acid sequence identity to the following sequence: PCVG-SNPCYNQGTCEPTSENPFYRCLCPAKFNGLLCH (SEQ ID NO:95); and can have a length of 35 amino acids to 40 amino acids (e.g., 35, 36, 37, 38, 39, or 40 amino acids.

An LNR segment can comprise an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and can have a length of from 90 amino acids to 150 amino acids, e.g., from 90 amino acids (aa) to 100 aa, from 100 aa to 110 aa, from 110 aa to 120 aa, from 120 aa to 130 aa, from 130 aa to 140 aa, or from 140 aa to 150 aa. In some cases, an LNR segment comprises an amino acid sequence having at least 75%, at least 80%, at least 85%, at least 90%, at least 95%, at least 98%, at least 99%, or 100%, amino acid sequence identity to amino acids 1442-1562 of the amino acid sequence depicted in FIG. 31A-31B, or a corresponding segment of another Notch receptor polypeptide, where examples of corresponding segments are depicted in FIG. 31C-31G; and has a length of from 115 aa to 125 aa, e.g., 115, 116, 117, 118, 119, 120, 121, 122, 123, 124, or 125 aa.

An LNR segment can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 90)
PPQIEEACELPECQVDAGNKVCNLQCNNHACGWDGGDCSLNFNDPWKNC

TQSLQCWKYFSDGHCDSQCNSAGCLFDGFDCQLTEGQCNPLYDQYCKDH

FSDGHCDQGCNSAECEWDGLDC;

and can have a length of from 118 to 122 amino acids (e.g., 118, 119, 120, 121, or 122 amino acids).

An HD-N segment can comprise an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and can have a length of from 90 amino acids (aa) to 110 aa, e.g., 90 aa to 95 aa, 95 aa to 100 aa, 100 aa to 105 aa, or 105 aa to 110 aa. In some cases, an HD-N segment comprises an amino acid sequence having at least 75%, at least 80%, at least 85%, at least 90%, at least 95%, at least 98%, at least 99%, or 100%, amino acid sequence identity to amino acids 1563-1664 of the amino acid sequence depicted in FIG. 31A-31B, or a corresponding segment of another Notch receptor polypeptide, where examples of corresponding segments are depicted in FIG. 31C-31G; and has a length of from 95 aa to 105 aa, e.g., 95, 96, 98, 98, 99, 100, 101, 102, 103, 104, or 105 aa.

An HD-C segment can comprise an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and can have a length of from 60 amino acids (aa) to 80 aa, e.g., from 60 aa to 65 aa, from 65 aa to 70 aa, from 70 aa to 75 aa, or from 75 aa to 80 aa. In some cases, an HD-C segment comprises an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and has a length of from 65 amino acids to 75 amino acids, e.g., 65, 66, 67, 68, 69, 70, 71, 72, 73, 74, or 75 amino acids.

An HD segment (HD-N plus HD-C) can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 91)
AAGTLVLVVLLPPDQLRNNSFHFLRELSHVLHTNVVFKRDAQGQQMIFP

YYGHEEELRKHPIKRSTVGWATSSLLPGTSGGRQRRELDPMDIRGSIVY

LEIDNRQCVQSSSQCFQSATDVAAFLGALASLGSLNIPYKIEAVKSEPV

EPPLP;

and can have a length of 150, 151, 152, 153, or 154 amino acids.

A transmembrane segment can comprise an amino acid sequence having at least 75%, at least 80%, at least 85%, at least 90%, at least 95%, at least 98%, at least 99%, or 100%, amino acid sequence identity to amino acids 1736 to 1756 of the amino acid sequence depicted in FIG. 31A-31B, or a corresponding segment of another Notch receptor polypeptide, where examples of corresponding segments are depicted in FIG. 31C-31G; and can have a length of from 15 amino acids (aa) to 25 amino acids, e.g., 15, 16, 17, 18, 29, 20, 21, 22, 23, 24, or 25 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO:92); and can have a length of 21, 22, 23, 24, or 25 amino acids.

In some cases, a Notch receptor polypeptide has a length of from about 490 amino acids (aa) to about 900 aa, and comprises an amino acid sequence having at least 75%, at least 80%, at least 85%, at least 90%, at least 95%, at least 98%, at least 99%, or 100%, amino acid sequence identity to: i) amino acids 1267-1756; ii) 1238-1756; iii) 1184-1756; iv) 1146-1756; v) 1064-1756; vi) 1021-1756; vii) 988-1756; viii) 945-1756; ix) 907-1756; or x) 869-1756, of the amino acid sequence depicted in FIG. 31A-31B, or a corresponding segment of another Notch receptor polypeptide, where examples of corresponding segments are depicted in FIG. 31C-31G.

Figure 30E:
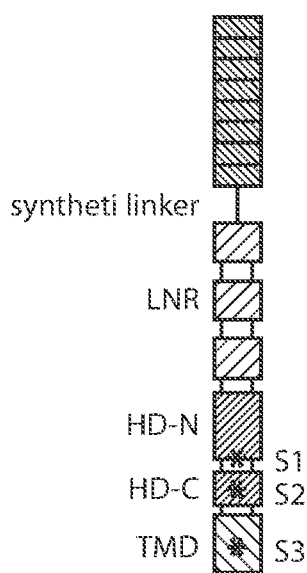

In some cases, a Notch receptor polypeptide comprises a synthetic linker. For example, in some cases, a Notch receptor polypeptide comprises, in order from N-terminus to C-terminus: i) two to eleven EGF repeats; ii) a synthetic linker; iii) an LNR segment; iv) an HD-N segment, v) an HD-C segment; and vi) a TM domain. Such a Notch receptor polypeptide is depicted schematically in FIG. 30E.

A synthetic linker can have a length of from about 10 amino acids (aa) to about 200 aa, e.g., from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A synthetic linker can have a length of from 10 aa to 30 aa, e.g., 10, 11, 12, 13, 14, 15, 16, 17, 18, 19, 20, 21, 22, 23, 24, 25, 26, 27, 28, 29, or 30 aa. A synthetic linker can have a length of from 30 aa to 50 aa, e.g., from 30 aa to 35 aa, from 35 aa to 40 aa, from 40 aa to 45 aa, or from 45 aa to 50 aa.

Notch Receptor Polypeptide Comprising an HD-C Segment and a TM Domain

Figure 30F:
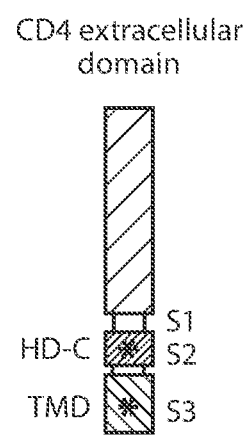

In some cases, a Notch receptor polypeptide comprises, in order from N-terminus to C-terminus: i) an HD-C segment; and ii) a TM domain, where the Notch receptor polypeptide does not include an LNR segment. In some cases, the LNR segment is replaced with a heterologous polypeptide. Such a Notch receptor polypeptide is depicted schematically in FIG. 30F.

An HD-C segment can comprise an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and can have a length of from 60 amino acids (aa) to 80 aa, e.g., from 60 aa to 65 aa, from 65 aa to 70 aa, from 70 aa to 75 aa, or from 75 aa to 80 aa. In some cases, an HD-C segment comprises an amino acid sequence having at least 75%, at least 80%, at least 85%, at least 90%, at least 95%, at least 98%, at least 99%, or 100%, amino acid sequence identity to amino acids 1665-1733 of the amino acid sequence depicted in FIG. 31A-31B, or a corresponding segment of another Notch receptor polypeptide, where examples of corresponding segments are depicted in FIG. 31C-31G; and has a length of from 65 amino acids to 75 amino acids, e.g., 65, 66, 67, 68, 69, 70, 71, 72, 73, 74, or 75 amino acids.

A transmembrane segment can comprise an amino acid sequence having at least 75%, at least 80%, at least 85%, at least 90%, at least 95%, at least 98%, at least 99%, or 100%, amino acid sequence identity to amino acids 1736 to 1756 of the amino acid sequence depicted in FIG. 31A-31B, or a corresponding segment of another Notch receptor polypeptide, where examples of corresponding segments are depicted in FIG. 31C-31G; and can have a length of from 15 amino acids (aa) to 25 amino acids, e.g., 15, 16, 17, 18, 29, 20, 21, 22, 23, 24, or 25 amino acids.

A transmembrane segment can comprise an amino acid sequence having at least 75%, at least 80%, at least 85%, at least 90%, at least 95%, at least 98%, at least 99%, or 100%, amino acid sequence identity to the following amino acid sequence: HLMYVAAAAFVLLFFVGCGVLLS (SEQ ID NO:92); and can have a length of 21, 22, 23, 24, or 25 amino acids.

In some cases, a Notch receptor polypeptide comprises an amino acid sequence having at least 75%, at least 80%, at least 85%, at least 90%, at least 95%, at least 98%, at least 99%, or 100%, amino acid sequence identity to amino acids 1665 to 1756 of the amino acid sequence depicted in FIG. 31A-31B, or a corresponding segment of another Notch receptor polypeptide, where examples of corresponding segments are depicted in FIG. 31C-31G; and has a length of from 85 amino acids (aa) to 95 aa (e.g., 85, 86, 87, 88, 89, 90, 91, 92, 93, 94, or 95 aa).

In some cases, a Notch receptor polypeptide comprises an amino acid sequence having at least 75%, at least 80%, at least 85%, at least 90%, at least 95%, at least 98%, at least 99%, or 100%, amino acid sequence identity to amino acids 1665 to 1756 of the amino acid sequence depicted in FIG. 31A-31B, or a corresponding segment of another Notch receptor polypeptide, where examples of corresponding segments are depicted in FIG. 31C-31G; and comprises a heterologous polypeptide fused in-frame at the N-terminus of the Notch receptor polypeptide.

Proteolytic Cleavage Sites

As noted above, a chimeric polypeptide of the present disclosure comprises a Notch receptor polypeptide, e.g., having a length of from 50 amino acids to 1000 amino acids, and having one or more proteolytic cleavage sites.

In some cases, the Notch receptor polypeptide includes only one proteolytic cleavage site. In some cases, the Notch receptor polypeptide includes two proteolytic cleavage sites. In some cases, the Notch receptor polypeptide includes three proteolytic cleavage sites. For simplicity, cleavage sites will be referred to herein as "S1," "S2," and "S3" proteolytic cleavage sites.

In some cases, the Notch receptor polypeptide includes an S1 proteolytic cleavage site. An S1 proteolytic cleavage site can be located between the HD-N segment and the HD-C segment. In some cases, the S1 proteolytic cleavage site is a furin-like protease cleavage site. A furin-like protease cleavage site can have the canonical sequence Arg-X-(Arg/Lys)-Arg (SEQ ID NO:130), where X is any amino acid; the protease cleaves immediately C-terminal to the canonical sequence. For example, in some cases, an amino acid sequence comprising an S1 proteolytic cleavage site can have the amino acid sequence GRRRRELDPM (SEQ ID NO:106), where cleavage occurs between the "RE" sequence. As another example, an amino acid sequence comprising an S1 proteolytic cleavage site can have the amino acid sequence RQRRELDPM (SEQ ID NO:107), where cleavage occurs between the "RE" sequence.

In some cases, the Notch receptor polypeptide includes an S2 proteolytic cleavage site. An S2 proteolytic cleavage site can be located within the HD-C segment. In some cases, the S2 proteolytic cleavage site is an ADAM family type protease cleavage site, such as e.g., an ADAM-17-type protease cleavage site. An ADAM-17-type protease cleavage site can comprise an Ala-Val dipeptide sequence, where the enzyme cleaves between the Ala and the Val. For example, in some cases, amino acid sequence comprising an S2 proteolytic cleavage site can have the amino acid sequence KIEAVKSE (SEQ ID NO:108), where cleavage occurs between the "AV" sequence. As another example, an amino acid sequence comprising an S2 proteolytic cleavage site can have the amino acid sequence KIEAVQSE (SEQ ID NO:109), where cleavage occurs between the "AV" sequence.

In some cases, the Notch receptor polypeptide includes an S3 proteolytic cleavage site. An S3 proteolytic cleavage site can be located within the TM domain. In some cases, the S3 proteolytic cleavage site is a gamma-secretase (γ-secretase) cleavage site. A γ-secretase cleavage site can comprise a Gly-Val dipeptide sequence, where the enzyme cleaves between the Gly and the Val. For example, in some cases, an S3 proteolytic cleavage site has the amino acid sequence VGCGVLLS (SEQ ID NO:110), where cleavage occurs between the "GV" sequence. In some cases, an S3 proteolytic cleavage site comprises the amino acid sequence GCGVLLS (SEQ ID NO:111).

Figure 30G:
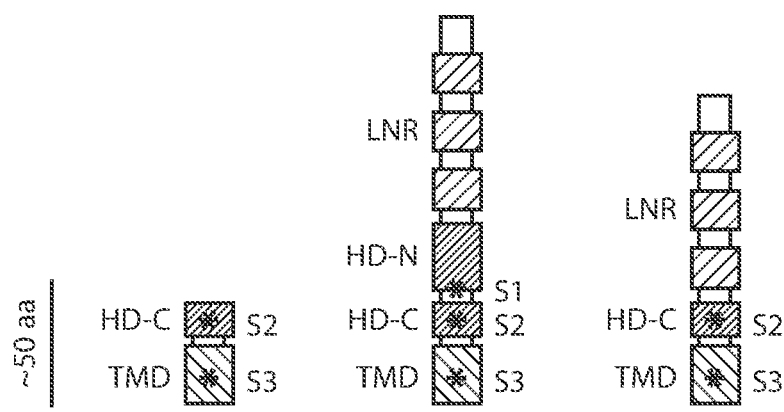

In some cases, the Notch receptor polypeptide lacks an S1 proteolytic cleavage site. In some cases, the Notch receptor polypeptide lacks an S2 proteolytic cleavage site. In some cases, the Notch receptor polypeptide lacks an S3 proteolytic cleavage site. In some cases, the Notch receptor polypeptide lacks both an S1 proteolytic cleavage site and an S2 proteolytic cleavage site. In some cases, the Notch receptor polypeptide includes an S3 proteolytic cleavage site; and lacks both an S1 proteolytic cleavage site and an S2 proteolytic cleavage site. Examples are depicted schematically in FIG. 30G.

In some instances, a Notch receptor polypeptide of a chimeric polypeptide of the present disclosure may be a Notch receptor polypeptide of FIG. 32A-32B or may include all or none or more parts of a Notch receptor polypeptide presented in FIG. 32A-32B.

Certain Notch receptor polypeptides and components thereof that may be adapted for use in the chimeric polypeptides and the methods and circuits described herein include but are not limited to e.g., those described in PCT Application No. US2016/019188 (Pub. No. WO 2016/138034), the disclosure of which is incorporated herein by reference in its entirety.

Intracellular Domains

As noted above, a chimeric polypeptide of the present disclosure comprises an intracellular domain that is released following binding of the chimeric polypeptide to the binding partner of the extracellular specific binding member, where such binding induces cleavage of an above-mentioned proteolytic cleavage site.

The intracellular domain comprises an amino acid sequence that is heterologous to the Notch receptor polypeptide. In other words, the intracellular domain comprises an amino acid sequence that is not naturally present in a Notch receptor polypeptide.

In some instances, the intracellular domain, when released from the chimeric polypeptide, induces a transcriptional response in the cell or otherwise modulates transcription. For example, in some instances, the intracellular domain activates transcription within the cell and thus serves as a transcriptional activator and may contain a transcription activation domain.

The intracellular domain may provide essentially any effector function attributable to an expressed peptide or protein, wherein such effector functions may include but are not limited to, e.g., increased production of one or more cytokines by the cell; reduced production of one or more cytokines by the cell; increased or decreased production of a hormone by the cell; production of an antibody by the cell; a change in organelle activity; a change in trafficking of a polypeptide within the cell; a change in transcription of a target gene; a change in activity of a protein; a change in cell activity, e.g., cell death; cellular proliferation; effects on cellular differentiation; effects on cell survival; modulation of cellular signaling responses; etc. In some cases, the intracellular domain, when released from the chimeric polypeptide, provides for a change in transcription of a target gene. In some cases, the intracellular domain, when released from the chimeric polypeptide, provides for an increase in the transcription of a target gene. In some cases, the intracellular domain, when released from the chimeric polypeptide, provides for a decrease in expression of a target gene.

In some instances, the intracellular domain of a proteolytically cleavable chimeric polypeptide of the instant disclosure includes a transcriptional activator. Any convenient transcriptional activator may find use in the intracellular domain of a chimeric polypeptide of the instant disclosure. Within a cell or system, a transcriptional activator may be paired with a transcriptional control element that is responsive to the transcriptional activator, e.g., to drive expression of a nucleic acid encoding a polypeptide of interest that is operably linked to the transcriptional control element. Useful transcriptional activators, transcriptional control elements, activator/control element pairs, and components of such systems may include but are not limited to e.g., those used in inducible expression systems including but not limited to e.g., those described in Goverdhana et al. Mol Ther. (2005) 12(2): 189-211; U.S. Patent Application Pub. Nos. 20160152701, 20150376627, 20130212722, 20070077642, 20050164237, 20050066376, 20040235169, 20040038249, 20030220286, 20030199022, 20020106720; the disclosures of which are incorporated herein by reference in their entirety.

In some instances, useful transcriptional activators may include mammalian transcription factors or engineered or mutated forms thereof. In some instances, useful transcriptional activators may include human transcription factors or engineered or mutated forms thereof. In some instances, useful transcriptional activators may include mouse transcription factors or engineered or mutated forms thereof. In some instances, useful transcriptional activators may include rat transcription factors or engineered or mutated forms thereof. In some instances, useful transcriptional activators may include cow transcription factors or engineered or mutated forms thereof. In some instances, useful transcriptional activators may include pig transcription factors or engineered or mutated forms thereof.

In some instances, use of a mammalian transcription factor may reduce the chance that the transcription factor induces an immune response in a mammal. In some instances, use of an engineered or mutated transcription factor, including e.g., mutated or engineered mammalian transcription factors, may reduce the chance that the transcription factor induces an immune response in a mammal. Useful mammalian transcription factors include but are not limited to e.g., zinc finger (ZnF) proteins.

In some instances, the intracellular domain is a transcriptional activator. In some cases, the intracellular domain comprises an amino acid sequence having at least 75%, at least 80%, at least 85%, at least 90%, at least 95%, at least 98%, at least 99%, or 100%, amino acid sequence identity to the following tetracycline-controlled transcriptional activator (tTA) amino acid sequence:

(SEQ ID NO: 112)
MSRLDKSKVINSALELLNEVGIEGLTTRKLAQKLGVEQPTLYWHVKNKR

ALLDALAIEMLDRHHTHFCPLEGESWQDFLRNNAKSFRCALLSHRDGAK

VHLGTRPTEKQYETLENQLAFLCQQGFSLENALYALSAVGHFTLGCVLE

DQEHQVAKEERETPTTDSMPPLLRQAIELFDHQGAEPAFLFGLELIICG

LEKQLKCESGGPADALDDFDLDMLPADALDDFDLDMLPADALDDFDLDM

LPG;

and has a length of from about 245 amino acids to 252 amino acids (e.g., 248, 249, 250, 251, or 252 amino acids).

In some embodiments, the intracellular domain comprises a transcriptional activator. In some cases, the transcriptional activator is GAL4-VP16. In some cases, the transcriptional activator is VP64 Zip(+). In some cases the transcriptional activator is an engineered protein, such as a zinc finger or TALE based DNA binding domain fused to an effector domain such as VP64. A variety of other transcriptional transactivators known in the art are suitable for use.

In some cases, the intracellular domain comprises an amino acid sequence having at least 75%, at least 80%, at least 85%, at least 90%, at least 95%, at least 98%, at least 99%, or 100%, amino acid sequence identity to the following GAL4-VP64 sequence:

```
                                        (SEQ ID NO: 113)
MKLLSSIEQACDICRLKKLKCSKEKPKCAKCLKNNWECRYSPKTKRSPL

TRAHLTEVESRLERLEQLFLLIFPREDLDMILKMDSLQDIKALLTGLFV

QDNVNKDAVTDRLASVETDMPLTLRQHRISATSSSEESSNKGQRQLTVS

AAAGGSGGSGGSDALDDFDLDMLGSDALDDFDLDMLGSDALDDFDLDML

GSDALDDFDLDMLGS;
``` and has a length of from 208 to 214 amino acids (e.g., 208, 209, 210, 211, 212, 213, or 214 amino acids).

In some cases, the intracellular domain comprises an amino acid sequence having at least 75%, at least 80%, at least 85%, at least 90%, at least 95%, at least 98%, at least 99%, or 100%, amino acid sequence identity to the following VP64 Zip(+) transcriptional activator sequence:

```
                                        (SEQ ID NO: 114)
PKKKRKVDALDDFDLDMLGSDALDDFDLDMLGSDALDDFDLDMLGSDAL

DDFDLDMLGSGGSGGSGGSLEIEAAFLERENTALETRVAELRQRVQRLR

NRVSQYRTRYGPLGGGK;
``` and has a length of from 105 to 115 amino acids (e.g., 105, 106, 107, 108, 109, 110, 111, 112, 113, 114 or 115 amino acids).

In some instances, the intracellular domain of a proteolytically cleavable chimeric polypeptide of the instant disclosure, upon activation of the chimeric polypeptide, induces expression of a POI. A POI may be essentially any polypeptide and may include but is not limited to polypeptides of research interest (e.g., reporter polypeptides, mutated polypeptides, novel synthetic polypeptides, etc.), polypeptides of therapeutic interest (e.g., naturally occurring therapeutic proteins, recombinant therapeutic polypeptides, etc.), polypeptides of industrial interest (e.g., polypeptides used in industrial applications such as e.g., manufacturing), and the like.

In some instances, a POI may be a therapeutic polypeptide including but not limited to a therapeutic polypeptide for treating a neoplasia such as e.g., a tumor, a cancer, etc. In some instances, a therapeutic POI for treating a neoplasia may be a POI used in immunotherapy for cancer. In some instances, a therapeutic POI may be a CAR. In some instances, a therapeutic POI may be a TCR. In some instances, a therapeutic POI may be an antibody. In some instances, a therapeutic POI may be a chimeric bispecific binding member. In some instances, a therapeutic POI may be an innate-immune response inducer. In some instances, a therapeutic POI may be an immune suppression factor.

POIs of the instant disclosure include orthogonalized POIs. Orthogonalized POIs include those POIs that have been modified from their original or wild-type form such that the orthogonal POI specifically reacts with or binds a specific orthogonalized partner but does not specifically or substantially react with of bind the unmodified or wild-type partner. Any POI may be orthogonalized, including but not limited to e.g., those POIs described herein.

In some instances, a therapeutic POI may be an anti-Fc CAR. An anti-Fc CAR generally includes the extracellular domain of an Fc receptor, an intracellular signaling domain and optionally a co-stimulatory domain. Depending on the therapeutic context, an anti-Fc CAR may include an extracellular domain of any Fc receptor including e.g., a Fc-gamma receptor (e.g., FcγRI (CD64), FcγRIIA (CD32), FcγRIIB (CD32), FcγRIIIA (CD16a), FcγRIIIB (CD16b)), a Fc-alpha receptor (e.g., FcαRI (CD89)) or a Fc-epsilon receptor (e.g., FcεRI, FcεRII (CD23)). For example, in some instances, an anti-Fc CAR may include the extracellular domain of the CD16 Fc receptor. In some instances, an anti-Fc CAR may include the extracellular domain of the CD16 Fc receptor, a CD3-zeta intracellular signaling domain and a 4-1BB co-stimulatory domain. In some instances, an anti-Fc CAR may be an Antibody-Coupled T-cell Receptor (ACTR), e.g., as available from (Unum Therapeutics Inc.; Cambridge, Mass.).

In some instances, one or more domains of the anti-Fc CAR may be a mutated domain including where the domain is mutated, e.g., to modulate affinity (e.g., increase affinity or decrease affinity) for a binding partner, to modulate intracellular signaling properties (e.g., increase signaling or decrease signaling), etc.

In some instances, a chimeric polypeptide of the present disclosure may be expressed on a cell such that, upon binding the specific binding partner of the chimeric polypeptide, the intracellular domain of the chimeric polypeptide induces transcription of an anti-Fc CAR from a nucleic acid sequence within the cell. In some instances, an antibody that binds the anti-Fc CAR and a tumor antigen may be administered to a subject also administered such a cell. In some instances, a chimeric polypeptide of the present disclosure may be expressed on a cell such that, upon binding the specific binding partner of the chimeric polypeptide, the intracellular domain of the chimeric polypeptide induces transcription of an anti-Fc CAR and an antibody that binds the anti-Fc CAR and a tumor antigen from one or more nucleic acid sequences within the cell.

In some instances, a therapeutic POI may be a chimeric bispecific binding member. As used herein, by "chimeric bispecific binding member" is meant a chimeric polypeptide having dual specificity to two different binding partners (e.g., two different antigens). Non-limiting examples of chimeric bispecific binding members include bispecific antibodies, bispecific conjugated monoclonal antibodies (mab)$_2$, bispecific antibody fragments (e.g., F(ab)$_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. *MAbs*. (2012) 4(2): 182-197; Stamova et al. *Antibodies* 2012, 1(2), 172-198; Farhadfar et al. *Leuk Res*. (2016) 49:13-21; Benjamin et al. *Ther Adv Hematol*. (2016) 7(3):142-56; Kiefer et al. *Immunol Rev*. (2016) 270(1):178-92; Fan et al. *J Hematol Oncol*. (2015) 8:130; May et al. *Am J Health Syst Pharm*. (2016) 73(1):e6-e13; the disclosures of which are incorporated herein by reference in their entirety.

In some instances, a chimeric bispecific binding member may be a bispecific antibody. In some instances, a bispecific antibody that may be expressed in response to activation of a chimeric polypeptide of the present disclosure may be a bispecific antibody targeting at least one cancer antigen (including e.g., two cancer antigens) including but not limited to e.g., at least one (including e.g., two) cancer antigens described herein. In some instances, a bispecific antibody that may be expressed in response to activation of a chimeric polypeptide of the present disclosure may be a bispecific antibody targeting at one cancer antigen and one immune cell antigen including but not limited to e.g., a cancer antigen described herein and an immune antigen described herein.

In some instances, a bispecific antibody that may be expressed in response to activation of a chimeric polypeptide of the present disclosure may be e.g., bsAb MDX-210 (targeting Her2 and CD64), MDX-H210 (targeting Her2 and CD64), MDX-447 (targeting EGFR and CD64), HRS-3/A9 (a bispecific F(ab')2 antibody targeting the CD30 antigen and receptor FcγRIII (CD16)), an anti-CD3×anti-EpCAM TriomAb/bsAb, Catumaxomab, Ertumaxomab, Bi20 (Lymphomun or fBTA05), an anti-CD19×CD3 diabody, an anti-CD19×CD16 diabody, an anti-EGFR×CD3 diabody, an anti-PSMA×CD3 diabody, a diabody targeting rM28 and NG2, an anti-CD28×CD20 bispecific tandem scFv, or the like.

In some instances, a chimeric bispecific binding member may be a bispecific T cell engager (BiTE). A BiTE is generally made by fusing a specific binding member (e.g., a scFv) that binds an immune cell antigen to a specific binding member (e.g., a scFv) that binds a cancer antigen (e.g., a tumor associated antigen, a tumor specific antigen, etc.). For example, an exemplary BiTE includes an anti-CD3 scFv fused to an anti-tumor associated antigen (e.g., EpCAM, CD19, etc.) scFv via a short peptide linker (e.g., a five amino acid linker, e.g., GGGGS (SEQ ID NO:115)).

In some instances, a BiTE that may be expressed in response to activation of a chimeric polypeptide of the present disclosure may be a BiTE targeting at least one cancer antigen including but not limited to e.g., a cancer antigen described herein. In some instances, a BiTE that may be expressed in response to activation of a chimeric polypeptide of the present disclosure may be a BiTE targeting one cancer antigen and one immune cell antigen including but not limited to e.g., a cancer antigen described herein and an immune antigen described herein.

In some instances, a chimeric polypeptide of the present disclosure may be expressed on a cell such that, upon binding the specific binding partner of the chimeric polypeptide, the intracellular domain of the chimeric polypeptide induces transcription of a BiTE from a nucleic acid sequence within the cell. In some instances, a chimeric polypeptide of the present disclosure may be expressed on a cell such that, upon binding a peptide-MHC specific binding partner, the intracellular domain of the chimeric polypeptide induces transcription of a BiTE. In some instances, a BiTE suitable for use as herein described includes e.g., an anti-CD3×anti-CD19 BiTE (e.g., Blinatumomab), an anti-EpCAM×anti-CD3 BiTE (e.g., MT110), an anti-CEA×anti-CD3 BiTE (e.g., MT111/MEDI-565), an anti-CD33×anti-CD3 BiTE, an anti-HER2 BiTE, an anti-EGFR BiTE, an anti-IgE BiTE, and the like.

In some instances, a chimeric bispecific binding member may be a Micabody or mutant thereof. A Micabody generally includes an antigen-specific binding portion linked to at least one domain that specifically binds a NKG2D receptor. In some instances, a Micabody or mutant thereof includes engineered MICA α1-α2 domains that specifically bind to NKG2D receptors.

In some instances, a Micabody or mutant thereof that may be expressed in response to activation of a chimeric polypeptide of the present disclosure may be a Micabody or mutant thereof targeting at least one cancer antigen including but not limited to e.g., a cancer antigen described herein.

In some instances, a Micabody or mutant thereof that may be expressed in response to activation of a chimeric polypeptide of the present disclosure may be a Micabody or mutant thereof targeting HER2 (e.g., an anti-HER2 Micabody or mutants thereof). Non-limiting examples of Micabodies and related components and operating principles are described in e.g., Cho et al., Cancer Res. (2010) 70(24): 10121-30; Bauer et al. Science. (1999) 285(5428):727-9; Morvan et al. Nat Rev Cancer. (2016) 16(1):7-19; the disclosures of which are incorporated herein by reference in their entirety.

In some instances, a chimeric polypeptide of the present disclosure may be expressed on a cell such that, upon binding the specific binding partner of the chimeric polypeptide, the intracellular domain of the chimeric polypeptide induces transcription of a Micabody or mutant thereof from a nucleic acid sequence within the cell. In some instances, a chimeric polypeptide of the present disclosure may be expressed on a cell such that, upon binding a peptide-MHC specific binding partner, the intracellular domain of the chimeric polypeptide induces transcription of a Micabody or mutant thereof. Micabodies and mutants thereof include those developed by AvidBiotics (South San Francisco, Calif.) and described online at (avidbiotics(dot)com).

In some instances, a chimeric bispecific binding member may be a CAR T cell adapter. As used herein, by "CAR T cell adapter" is meant an expressed bispecific polypeptide that binds the antigen recognition domain of a CAR and redirects the CAR to a second antigen. Generally, a CAR T cell adapter will have to binding regions, one specific for an epitope on the CAR to which it is directed and a second epitope directed to a binding partner which, when bound, transduces the binding signal activating the CAR. Useful CAR T cell adapters include but are not limited to e.g., those described in Kim et al. J Am Chem Soc. (2015) 137(8): 2832-5; Ma et al. Proc Natl Acad Sci USA. (2016) 113(4): E450-8 and Cao et al. Angew Chem Int Ed Engl. (2016) 55(26):7520-4; the disclosures of which are incorporated herein by reference in their entirety.

In some cases, a therapeutic POI that is induced by a chimeric polypeptide of the instant disclosure is an antibody. Suitable antibodies include, e.g., Natalizumab (Tysabri; Biogen Idec/Elan) targeting α4 subunit of α4β1 and α4β7 integrins (as used in the treatment of MS and Crohn's disease); Vedolizumab (MLN2; Millennium Pharmaceuticals/Takeda) targeting α4β7 integrin (as used in the treatment of UC and Crohn's disease); Belimumab (Benlysta; Human Genome Sciences/GlaxoSmithKline) targeting BAFF (as used in the treatment of SLE); Atacicept (TACI-Ig; Merck/Serono) targeting BAFF and APRIL (as used in the treatment of SLE); Alefacept (Amevive; Astellas) targeting CD2 (as used in the treatment of Plaque psoriasis, GVHD); Otelixizumab (TRX4; Tolerx/GlaxoSmithKline) targeting CD3 (as used in the treatment of T1D); Teplizumab (MGA031; MacroGenics/Eli Lilly) targeting CD3 (as used in the treatment of T1D); Rituximab (Rituxan/Mabthera; Genentech/Roche/Biogen Idec) targeting CD20 (as used in the treatment of Non-Hodgkin's lymphoma, RA (in patients with inadequate responses to TNF blockade) and CLL); Ofatumumab (Arzerra; Genmab/GlaxoSmithKline) targeting CD20 (as used in the treatment of CLL, RA); Ocrelizumab (2H7; Genentech/Roche/Biogen Idec) targeting CD20 (as used in the treatment of RA and SLE); Epratuzumab (hLL2; Immunomedics/UCB) targeting CD22 (as used in the treatment of SLE and non-Hodgkin's lymphoma); Alemtuzumab (Campath/MabCampath; Genzyme/Bayer) targeting CD52 (as used in the treatment of CLL, MS); Abatacept (Orencia; Bristol-Myers Squibb) targeting CD80 and CD86 (as used in the treatment of RA and JIA, UC and Crohn's disease, SLE); Eculizumab (Soliris; Alexion pharmaceuticals) targeting C5 complement protein (as used in the treatment of Paroxysmal nocturnal haemoglobinuria); Omalizumab (Xolair; Genentech/Roche/Novartis) targeting IgE (as used in the treatment of Moderate to severe persistent allergic asthma); Canakinumab (Ilaris; Novartis) targeting IL-10 (as used in the treatment of Cryopyrin-associated periodic syndromes, Systemic JIA, neonatal-onset multisystem inflammatory disease and acute gout); Mepolizumab (Bosatria; GlaxoSmithKline) targeting IL-5 (as used in the treatment of Hyper-eosinophilic syndrome); Reslizumab (SCH55700; Ception Therapeutics) targeting IL-5 (as used in the treatment of Eosinophilic oesophagitis); Tocilizumab (Actemra/RoActemra; Chugai/Roche) targeting IL-6R (as used in the treatment of RA, JIA); Ustekinumab (Stelara; Centocor) targeting IL-12 and IL-23 (as used in the treatment of Plaque psoriasis, Psoriatic arthritis, Crohn's disease); Briakinumab (ABT-874; Abbott) targeting IL-12 and IL-23 (as used in the treatment of Psoriasis and plaque psoriasis); Etanercept (Enbrel; Amgen/Pfizer) targeting TNF (as used in the treatment of RA, JIA, psoriatic arthritis, AS and plaque psoriasis); Infliximab (Remicade; Centocor/Merck) targeting TNF (as used in the treatment of Crohn's disease, RA, psoriatic arthritis, UC, AS and plaque psoriasis); Adalimumab (Humira/Trudexa; Abbott) targeting TNF (as used in the treatment of RA, JIA, psoriatic arthritis, Crohn's disease, AS and plaque psoriasis); Certolizumab pegol (Cimzia; UCB) targeting TNF (as used in the treatment of Crohn's disease and RA); Golimumab (Simponi; Centocor) targeting TNF (as used in the treatment of RA, psoriatic arthritis and AS); and the like.

In some cases, the antibody whose production is induced is a therapeutic antibody for the treatment of cancer. Such antibodies include, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-L1; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukaemia); Alemtuzumab targeting CD52 (as used in the treatment of Chronic lymphocytic leukaemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and haematological malignancies); Mapatumumab (HGS-ETR1) targeting TRAILR1 (as used in the treatment of Colon, lung and pancreas tumors and haematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 81C6 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

In some cases, useful antibodies, the expression of which can be induced by a chimeric polypeptide of the instant disclosure, include but are not limited to 8H9, Abagovomab, Abciximab, Abituzumab, Abrilumab, Actoxumab, Aducanumab, Afelimomab, Afutuzumab, Alacizumab pegol, ALD518, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab/tocilizumab, Atorolimumab, Bapineuzumab, Basiliximab, Bavituximab, Bectumomab, Begelomab, Benralizumab, Bertilimumab, Besilesomab, Bevacizumab/Ranibizumab, Bezlotoxumab, Biciromab, Bimagrumab, Bimekizumab, Bivatuzumab mertansine, Blosozumab, Bococizumab, Brentuximabvedotin, Brodalumab, Brolucizumab, Brontictuzumab, Cantuzumab mertansine, Cantuzumab ravtansine, Caplacizumab, Capromab pendetide, Carlumab, Catumaxomab, cBR96-doxorubicin immunoconjugate, Cedelizumab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Dacetuzumab, Daclizumab, Dalotuzumab, Dapirolizumab pegol, Daratumumab, Dectrekumab, Demcizumab, Denintuzumab mafodotin, Derlotuximab biotin, Detumomab, Dinutuximab, Diridavumab, Dorlimomab aritox, Drozitumab, Duligotumab, Dupilumab, Durvalumab, Dusigitumab, Ecromeximab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Erlizumab, Ertumaxomab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gevokizumab, Girentuximab, Glembatumumab vedotin, Gomiliximab, Guselkumab, Ibalizumab, Ibalizumab, Icrucumab, Idarucizumab, Igovomab, IMAB362, Imalumab, Imciromab, Imgatuzumab, Inclacumab, Indatuximab ravtansine, Indusatumab vedotin, Inolimomab, Inotuzumab ozogamicin, Intetumumab, Iratumumab, Isatuximab, Itolizumab, Ixekizumab, Keliximab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Margetuximab, Maslimomab, Matuzumab, Mavrilimumab, Metelimumab, Milatuzumab, Minretumomab, Mirvetuximab soravtansine, Mitumomab, Mogamulizumab, Morolimumab, Morolimumab immune, Motavizumab, Moxetumomab pasudotox, Muromonab-CD3, Nacolomab tafenatox, Namilumab, Naptumomab estafenatox, Narnatumab, Nebacumab, Necitumumab, Nemolizumab, Nerelimomab, Nesvacumab, Nofetumomab merpentan, Obiltoxaximab, Obinutuzumab, Ocaratuzumab, Odulimomab, Olaratumab, Olokizumab, Onartuzumab, Ontuxizumab, Opicinumab, Oportuzumab monatox, Orticumab, Otlertuzumab, Oxelumab, Ozanezumab, Ozoralizumab, Pagibaximab, Palivizumab, Pankomab, Panobacumab, Parsatuzumab, Pascolizumab, Pasotuxizumab, Pateclizumab, Patritumab, Perakizumab, Pexelizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Rilotumumab, Rinucumab, Robatumumab, Roledumab, Romosozumab, Rontalizumab, Rovelizumab, Ruplizumab, Sacituzumab govitecan, Samalizumab, Sarilumab, Satumomab pendetide, Secukinumab, Seribantumab, Setoxaximab, Sevirumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teprotumumab, Tesidolumab, Tetulomab, TGN1412, Ticilimumab/tremelimumab, Tigatuzumab, Tildrakizumab, TNX-650, Toralizumab, Tosatoxumab, Tovetumab, Tralokinumab, TRBSO7, Tregalizumab, Trevogrumab, Tucotuzumab celmoleukin, Tuvirumab, Ublituximab, Ulocuplumab, Urelumab, Urtoxazumab, Vandortuzumab vedotin, Vantictumab, Vanucizumab, Vapaliximab, Varlilumab, Vatelizumab, Veltuzumab, Vepalimomab, Vesencumab, Visilizumab, Vorsetuzumab mafodotin, Votumumab, Zalutumumab, Zanolimumab, Zatuximab, Ziralimumab, Zolimomab aritox, and the like.

In some instances, a proteolytically cleavable chimeric polypeptide of the instant disclosure may induce the expression of a T-cell receptor (TCR) in a cell. Any TCR can be induced by a chimeric polypeptide using a method of the present disclosure including e.g., TCRs that are specific for any of a variety of epitopes, including, e.g., an epitope expressed on the surface of a cancer cell, a peptide-MHC complex on the surface of cancer cell, and the like. A TCR generally includes an alpha chain and a beta chain; and recognizes antigen when presented by a major histocompatibility complex. In some cases, the TCR is an engineered TCR.

Any engineered TCR having immune cell activation function can be induced using a method of the present disclosure. Such TCRs include, e.g., antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID: 25483644); Gschweng et al. Immunol Rev. 2014; 257(1): 237-49 (PMID:24329801); Hinrichs et al. Immunol Rev. 2014; 257(1):56-71 (PMID:24329789); Zoete et al. Front Immunol. 2013; 4:268 (PMID:24062738); Marr et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Clin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2): e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety.

In some instances, a chimeric polypeptide of the instant disclosure induces expression of an engineered TCR targeting a cancer antigen, including e.g., an intracellular cancer antigen. In some instances, an engineered TCR induced to be expressed by a chimeric polypeptide of the instant disclosure is an engineered TCR targeting an antigen target listed in Table 2 below.

TABLE 2

Engineered TCR Targets

| Target | HLA | References |
| --- | --- | --- |
| NY-ESO-1 | HLA-A2 | J Immunol. (2008) 180(9): 6116-31 |
| MART-1 | HLA-A2 | J Immunol. (2008) 180(9): 6116-31; Blood. (2009) 114(3): 535-46 |
| MAGE-A3 | HLA-A2 | J Immunother. (2013) 36(2): 133-51 |
| MAGE-A3 | HLA-A1 | Blood. (2013) 122(6): 863-71 |
| CEA | HLA-A2 | Mol Ther. (2011) 19(3): 620-626 |
| gp100 | HLA-A2 | Blood. (2009) 114(3): 535-46 |
| WT1 | HLA-A2 | Blood. (2011) 118(6): 1495-503 |
| HBV | HLA-A2 | J Hepatol. (2011) 55(1): 103-10 |
| gag (WT and/or α/6) | HLA-A2 | Nat Med. (2008) 14(12): 1390-5 |

TABLE 2-continued

Engineered TCR Targets

| Target | HLA | References |
|---|---|---|
| P53 | HLA-A2 | Hum Gene Ther. (2008) 19(11): 1219-32 |
| TRAIL bound to DR4 | N/A | J Immunol. (2008) 181(6): 3769-76 |
| HPV-16 (E6 and/or E7) | HLA-A2 | Clin Cancer Res. (2015) 21(19): 4431-9 |
| Survivin | HLA-A2 | J Clin Invest. (2015) 125(1): 157-68 |
| KRAS mutants | HLA-A11 | Cancer Immunol Res. (2016) 4(3): 204-14 |
| SSX2 | HLA-A2 | PLoS One. (2014) 9(3): e93321 |
| MAGE-A10 | HLA-A2 | J ImmunoTherapy Cancer. (2015) 3(Suppl2): P14 |
| MAGE-A4 | HLA-A24 | Clin Cancer Res. (2015) 21(10): 2268-77 |
| AFP | HLA-A2 | J ImmunoTherapy Cancer. (2013) 1(Suppl1): P10 |

In some instances, an expressed TCR targeting a particular antigen may be described as an anti-[antigen] TCR. Accordingly, in some instances, exemplary TCRs that may be induced to be expressed by a chimeric polypeptide of the instant disclosure include but are not limited to e.g., an anti-NY-ESO-1 TCR; an anti-MART-1 TCR; an anti-MAGE-A3 TCR; an anti-MAGE-A3 TCR; an anti-CEA TCR; an anti-gp100 TCR; an anti-WT1 TCR; an anti-HBV TCR; an anti-gag (WT and/or α/6) TCR; an anti-P53 TCR; an anti-TRAIL bound to DR4 TCR; an anti-HPV-16 (E6 and/or E7) TCR; an anti-Survivin TCR; an anti-KRAS mutants TCR; an anti-SSX2 TCR; an anti-MAGE-A10 TCR; an anti-MAGE-A4 TCR; an anti-AFP TCR; and the like.

In some instances, the TCR is an anti-NY-ESO1 TCR (e.g., an anti-HLA-A2/NY-ESO1 scTv). In some instances, the anti-NY-ESO1 TCR has the following sequence:

```
(SEQ ID NO: 116)
METLLGLLILWLQLQWVSSKQEVTQIPAALSVPEGENLVLNCSFTDSAI

YNLQWFRQDPGKGLTSLLLIQSSQREQTSGRLNASLDKSSGRSTLYIAA

SQPGDSATYLCAVRPLLDGTYIPTFGRGTSLIVHPGSADDAKKDAAKKD

GKSMSIGLLCCAALSLLWAGPVNAGVTQTPKFQVLKTGQSMTLQCAQDM

NHEYMSWYRQDPGMGLRLIHYSVGAGTTDRGEVPNGYNVSRSTIEDFPL

RLLSAAPSQTSVYFCASSYVGDTGELFFGEGSRLTVL.
```

Useful TCRs include those having wild-type affinity for their respective antigen as well as those having enhanced affinity for their respective antigen. TCRs having enhanced affinity for their respective antigen may be referred to as "affinity enhanced" or "enhanced affinity" TCRs. The affinity of a TCR may enhanced by any convenient means, including but not limited to binding-site engineering (i.e., rational design), screening (e.g., TCR display), or the like. Non-limiting examples of affinity enhanced TCRs and methods of generating enhanced affinity TCRs include but are not limited to e.g., those described in PCT Pub. Nos. 20150118208, 2013256159, 20160083449; 20140349855, 20100113300, 20140371085, 20060127377, 20080292549, 20160280756, 20140065111, 20130058908, 20110038842, 20110014169, 2003276403 and the like; the disclosures of which are incorporated herein by reference in their entirety.

Useful TCRs may, in some instances, also include modified TCR chains that include one or more cysteine modifications. Such cysteine modifications may be paired between two modified TCR chains. When paired between two TCR chains, corresponding modifications may result in a recombinant disulfide bond between the paired chains.

In some embodiments, a TCR may include a first cysteine modification in an alpha chain and a second cysteine modification in a beta chain where the first and second cysteine modifications, when both chains are present in a cell, form a recombinant disulfide bond between the alpha chain and the beta chain. Such cysteine modifications that form a recombinant disulfide bond may be referred to as "corresponding cysteine modifications".

In some instances, a modified TCR alpha chain may include a substitution of a residue to a cysteine resulting in a cysteine modification sufficient to produce a recombinant disulfide bond. Any appropriate residue of a TCR alpha chain having a corresponding residue in a TCR beta chain that, when mutated to a cysteine results in a recombinant disulfide bond, may be employed in generating a cysteine modified alpha chain. In some instances, the substituted residue is a residue present in the TCR alpha constant region. In some instances, the substitution is a tyrosine to cysteine substitution. In some instances, the substitution is a T48C substitution, or corresponding mutation, such as the T48C substitution present in the following human TCR alpha chain constant region sequence:

```
(SEQ ID NO: 131)
PNIQNPDPAVYQLRDSKSSDKSVCLFTDFDSQTNVSQSKDSDVYITDKC

VLDMRSMDFKSNSAVAWSNKSDFACANAFNNSIIPEDTFFPSPESSCDV

KLVEKSFETDTNLNFQNLSVIGFRILLLKVAGFNLLMTLRLWSS.
```

In some instances, the substitution is a T84C substitution, or corresponding mutation, such as the T84C substitution present in the following mouse TCR alpha chain constant region sequence:

```
(SEQ ID NO: 132)
PYIQNPEPAVYQLKDPRSQDSTLCLFTDFDSQINVPKTMESGTFITDKT

VLDMKAMDSKSNGAIAWSNQTSFTCQDIFKETNACYPSSDVPCDATLTE

KSFETDMNLNFQNLSVMGLRILLLKVAGFNLLMTLRLWSS.
```

In some instances, a subject TCR alpha chain or corresponding domain thereof (e.g., an alpha variable domain, an alpha constant domain, an alpha transmembrane domain, an alpha connecting peptide domain, and the like), may have at least about 75%, at least about 80%, at least about 85%, at least about 90%, at least about 95%, at least about 98%, or 100% amino acid sequence identity to a cysteine modified alpha chain, such as e.g., the T48C or T84C containing TCR alpha sequences provided above.

In some instances, a modified TCR beta chain may include a substitution of a residue to a cysteine resulting in a cysteine modification sufficient to produce a recombinant disulfide bond. Any appropriate residue of a TCR beta chain having a corresponding residue in a TCR beta chain that, when mutated to a cysteine results in a recombinant disulfide bond, may be employed in generating a cysteine modified beta chain. In some instances, the substituted residue is a residue present in the TCR beta constant region. In some instances, the substitution is a serine to cysteine substitution. In some instances, the substitution is a S58C substitution, or corresponding mutation, such as the S58C substitution present in the following human TCR beta chain constant region sequence:

```
                                          (SEQ ID NO: 133)
EDLNKVFPPEVAVFEPSEAEISHTQKATLVCLATGFFPDHVELSWWVNG

KEVHSGVCTDPQPLKEQPALNDSRYCLSSRLRVSATFWQNPRNHFRCQV

QFYGLSENDEWTQDRAKPVTQIVSAEAWGRADCGFTSVSYQQGVLSATI

LYEILLGKATLYAVLVSALVLMAMVKRKDF.
```

In some instances, the substitution is a S79C substitution, or corresponding mutation, such as the S79C substitution present in the following mouse TCR beta chain constant region sequence:

```
                                          (SEQ ID NO: 134)
EDLRNVTPPKVSLFEPSKAEIANKQKATLVCLARGFFPDHVELSWWVNG

KEVHSGVSTDPQAYKESNYSYCLSSRLRVCATFWHNPRNHFRCQVQFHG

LSEEDKWPEGSPKPVTQNISAEAWGRADCGITSASYQQGVLSATILYEI

LLGKATLYAVLVSTLVVMAMVKRKNS.
```

In some instances, a subject TCR beta chain or corresponding domain thereof (e.g., a beta variable domain, a beta constant domain, a beta transmembrane domain, a beta connecting peptide domain, and the like), may have at least about 75%, at least about 80%, at least about 85%, at least about 90%, at least about 95%, at least about 98%, or 100% amino acid sequence identity to a cysteine modified beta chain, such as e.g., the S58C or S79C containing TCR beta sequences provided above.

In some instances, a therapeutic POI may be an innate-immune response inducer. As used herein, by "innate-immune response inducer" is meant any protein that when expressed within a mammal induces an innate immune response. Innate immune inducers include but are not limited to e.g., proteins or fragments thereof derived from bacteria, proteins or fragments thereof derived from virus, proteins or fragments thereof derived from fungus, proteins or fragments thereof derived from a mammalian parasite, including e.g., human parasites. Any protein that induces an innate immune response when expressed by a mammalian cell may find use as an innate-immune inducer of the instant disclosure. In some instances, an innate immune response inducer may be a flagellin protein.

In some instances, a chimeric polypeptide of the present disclosure may be expressed on a cell such that, upon binding the specific binding partner of the chimeric polypeptide, the intracellular domain of the chimeric polypeptide induces transcription of an innate-immune response inducer from a nucleic acid sequence within the cell. In some instances, a chimeric polypeptide of the present disclosure may be expressed on a cell such that, upon binding a peptide-MHC specific binding partner, the intracellular domain of the chimeric polypeptide induces transcription of an innate-immune response inducer.

In some instances, a therapeutic POI may be an immune suppression factor. As used herein, by "immune suppression factor" is meant any protein that when expressed within a mammal suppresses an immune response. Immune suppression factors include but are not limited to e.g., immunosuppressive cytokines (e.g., IL-10), immunosuppressive cell-to-cell signaling ligands (e.g., PD-L1), immunosuppressive secreted proteins (e.g., TGF-beta), immunosuppressive antibodies, anti-CD3 antibodies (e.g., Orthoclone OKT3 (also known as Muromonab-CD3), etc.), anti-CD25 antibodies, (e.g., Basiliximab, Daclizumab, etc.) anti-CD52 antibodies (e.g., Campath-1H (also known as alemtuzumab), etc.), and the like. Any protein that suppresses an immune response when expressed by a mammalian cell may find use as an immune suppression factor of the instant disclosure. In some instances, an immune suppression factor may be IL-10. In some instances, an immune suppression factor may be PD-L1. In some instances, an immune suppression factor may be TGF-beta. In some instances, an immune suppression factor may be an immunosuppressive antibody (e.g., (e.g., an anti-CD3 antibody (e.g., Orthoclone OKT3 (also known as Muromonab-CD3), etc.), an anti-CD25 antibody, (e.g., Basiliximab, Daclizumab, etc.) anti-CD52 antibody (e.g., Campath-1H (also known as alemtuzumab), etc.).

In some instances, a chimeric polypeptide may drive expression of two or more immune suppression factors including e.g., an immunosuppressive cytokine and an immunosuppressive cell-to-cell signaling ligand, two or more immunosuppressive cytokines, two or more immunosuppressive cell-to-cell signaling ligands, etc. In some instances, a chimeric polypeptide may drive expression of both IL-10 and PD-L1. In some instances, a chimeric polypeptide may drive expression of three or more immune suppression factors.

In some instances, a chimeric polypeptide of the present disclosure may be expressed on a cell such that, upon binding the specific binding partner of the chimeric polypeptide, the intracellular domain of the chimeric polypeptide induces transcription of an immune suppression factor from a nucleic acid sequence within the cell. In some instances, a chimeric polypeptide of the present disclosure may be expressed on a cell such that, upon binding a peptide-MHC specific binding partner, the intracellular domain of the chimeric polypeptide induces transcription of an immune suppression factor.

In some instances, a therapeutic POI may be chemokine. An expressed chemokine may affect one or more cellular behaviors including but not limited to cell migration. In some instances, the intracellular domain of a chimeric receptor polypeptide of the present disclosure may induce expression of a chemokine. Examples of suitable chemokines include, e.g., MIP-1, MIP-1β, MCP-1, RANTES, IP10, and the like. Additional examples of suitable chemokines include, but are not limited to, chemokine (C-C motif) ligand-2 (CCL2; also referred to as monocyte chemotactic protein-1 or MCP1); chemokine (C-C motif) ligand-3 (CCL3; also known as macrophage inflammatory protein-1A or MIP1A); chemokine (C-C motif) ligand-5 (CCL5; also known as RANTES); chemokine (C-C motif) ligand-17 (CCL17; also known as thymus and activation regulated chemokine or TARC); chemokine (C-C motif) ligand-19 (CCL19; also known as EBI1 ligand chemokine or ELC); chemokine (C-C motif) ligand-21 (CCL21; also known as 6Ckine); C-C chemokine receptor type 7 (CCR7); chemokine (C-X-C motif) ligand 9 (CXCL9; also known as monokine induced by gamma interferon or MIG); chemokine (C-X-C motif) ligand 10 (CXCL10; also known as interferon gamma-induced protein 10 or IP-10); chemokine (C-X-C motif) ligand 11 (CXCL11; also called interferon-inducible T-cell alpha chemoattractant or I-TAC); chemokine (C-X-C motif) ligand 16 (CXCL16; chemokine (C motif) ligand (XCL1; also known as lymphotactin); and macrophage colony-stimulating factor (MCSF).

Certain intracellular domains and components thereof that may be adapted for use in chimeric polypeptides and the methods and circuits described herein include but are not limited to e.g., those described in PCT Application No.

US2016/019188 (Pub. No. WO 2016/138034), the disclosure of which is incorporated herein by reference in its entirety.

Additional Polypeptides

A chimeric polypeptide of the present disclosure can further include one or more additional polypeptides, where suitable additional polypeptides include, but are not limited to, a signal sequence; an epitope tag; an affinity domain; a nuclear localization signal (NLS); and a polypeptide that produces a detectable signal. One or more additional sequences may be appended to the chimeric polypeptide at essentially any location where appropriate including e.g., at the N-terminus, at the C-terminus, between two domains (e.g., between the extracellular domain and the transmembrane domain, between the extracellular domain and the Notch receptor polypeptide, between the Notch receptor polypeptide and the intracellular signaling domain, etc.). Additional sequences may function with a chimeric polypeptide independently of other domains or may be associated with and function together with any domain of the chimeric polypeptide.

Signal sequences that are suitable for use in a chimeric polypeptide of the present disclosure include any eukaryotic signal sequence, including a naturally-occurring signal sequence, a synthetic (e.g., man-made) signal sequence, etc.

Suitable epitope tags include, but are not limited to, hemagglutinin (HA; e.g., YPYDVPDYA (SEQ ID NO:117); FLAG (e.g., DYKDDDDK (SEQ ID NO:118); c-myc (e.g., EQKLISEEDL; SEQ ID NO:119), and the like.

Affinity domains include peptide sequences that can interact with a binding partner, e.g., such as one immobilized on a solid support, useful for identification or purification. Multiple consecutive single amino acids, such as histidine, when fused to a chimeric polypeptide of the present disclosure, may be used for one-step purification of the recombinant chimeric polypeptide by high affinity binding to a resin column, such as nickel sepharose. Exemplary affinity domains include His5 (HHHHH) (SEQ ID NO:120), HisX6 (HHHHHH) (SEQ ID NO:121), C-myc (EQKLISEEDL) (SEQ ID NO:119), Flag (DYKDDDDK) (SEQ ID NO:118), StrepTag (WSHPQFEK) (SEQ ID NO:122), hemagglutinin, e.g., HA Tag (YPYDVPDYA) (SEQ ID NO:117), GST, thioredoxin, cellulose binding domain, RYIRS (SEQ ID NO:123), Phe-His-His-Thr (SEQ ID NO:124), chitin binding domain, S-peptide, T7 peptide, SH2 domain, C-end RNA tag, WEAAAREACCRECCARA (SEQ ID NO:125), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Suitable nuclear localization signals ("NLS"; also referred to herein as "nuclear localization sequences") include, e.g., PKKKRKV (SEQ ID NO:126); KRPAATKKAGQAKKKK (SEQ ID NO:127); MVPKKKRK (SEQ ID NO:128); MAPKKKRKVGIHGVPAA (SEQ ID NO:129); and the like. An NLS can be present at the N-terminus of a chimeric polypeptide of the present disclosure; near the N-terminus of a chimeric polypeptide of the present disclosure (e.g., within 5 amino acids, within 10 amino acids, or within 20 amino acids of the N-terminus); at the C-terminus of a chimeric polypeptide of the present disclosure; near the C-terminus of a chimeric polypeptide of the present disclosure (e.g., within 5 amino acids, within 10 amino acids, or within 20 amino acids of the C-terminus); or internally within a chimeric polypeptide of the present disclosure.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Certain additional polypeptides and components thereof that may be adapted for use in the chimeric polypeptides and the methods and circuits described herein include but are not limited to e.g., those described in PCT Application No. US2016/019188 (Pub. No. WO 2016/138034), the disclosure of which is incorporated herein by reference in its entirety.

Nucleic Acids

The present disclosure provides a nucleic acid comprising a nucleotide sequence encoding a proteolytically cleavable chimeric polypeptide of the present disclosure. In some cases, a nucleic acid comprising a nucleotide sequence encoding a chimeric polypeptide of the present disclosure is contained within an expression vector. Thus, the present disclosure provides a recombinant expression vector comprising a nucleic acid comprising a nucleotide sequence encoding a chimeric polypeptide of the present disclosure. In some cases, the nucleotide sequence encoding a chimeric polypeptide of the present disclosure is operably linked to a transcriptional control element (e.g., a promoter; an enhancer; etc.). In some cases, the transcriptional control element is inducible. In some cases, the transcriptional control element is constitutive. In some cases, the promoters are functional in eukaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90: 7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some cases, a nucleic acid comprising a nucleotide sequence encoding a chimeric polypeptide of the present disclosure is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a chimeric polypeptide of the present disclosure is a recombinant lentivirus vector. In some cases, a nucleic acid comprising a nucleotide sequence encoding a chimeric polypeptide of the present disclosure is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

Nucleic acids of the instant disclosure may include nucleic acid sequence encoding a polypeptide of interest (POI). A POI may be essentially any polypeptide and may include but is not limited to polypeptides of research interest (e.g., reporter polypeptides, mutated polypeptides, novel synthetic polypeptides, etc.), polypeptides of therapeutic interest (e.g., naturally occurring therapeutic proteins, recombinant therapeutic polypeptides, etc.), polypeptides of industrial interest (e.g., polypeptides used in industrial applications such as e.g., manufacturing), and the like.

In some instances, a POI may be a transcriptional activator. In some instances, a POI may be a CAR. In some instances, a POI may be a TCR. In some instances, a POI may be an antibody. In some instances, a POI may be a chimeric bispecific binding member. In some instances, a POI may be an innate-immune response inducer. In some instances, a POI may be an immune suppression factor. In some instances, a POI may be a proteolytically cleavable chimeric polypeptide as described herein, e.g., as used in a multi-component circuit as describe herein.

Certain nucleic acids and components thereof that may be adapted for use in the chimeric polypeptides and the methods and circuits described herein include but are not limited to e.g., those described in PCT Application No. US2016/019188 (Pub. No. WO 2016/138034), the disclosure of which is incorporated herein by reference in its entirety.

Cells

The present disclosure includes cells engineered to express a chimeric polypeptide as described herein. In some instances, cells of the instant disclosure will include a nucleic acid encoding a chimeric polypeptide as described herein. In some instances, cells of the instant disclosure will include a nucleic acid operably linked to a transcription control element, e.g., a transcriptional activator, that is responsive the freed intracellular domain of chimeric polypeptide of the instant disclosure thereby inducing expression of the nucleic acid upon activation of the chimeric polypeptide. Any polypeptide of interest may be encoded from a nucleic acid within a cell operably linked to a transcription control element responsive to a chimeric polypeptide of the instant disclosure.

A method of the present disclosure can be used to modulate an activity of any eukaryotic cell. In some cases, the cell is in vivo. In some cases, the cell is ex vivo. In some cases, the cell is in vitro. In some cases, the cell is a mammalian cell. In some cases, the cell is a human cell. In some cases, the cell is a non-human primate cell. In some cases, the cell is rodent cell. In some cases, the cell is mouse cell. In some cases, the cell is a rat cell.

Suitable cells include neural cells; liver cells; kidney cells; immune cells; cardiac cells; skeletal muscle cells; smooth muscle cells; lung cells; and the like.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. In some cases, the cell is an induced pluripotent stem cell. In some cases, the cell is a mesenchymal stem cell. In some cases, the cell is a hematopoietic stem cell. In some cases, the cell is an adult stem cell.

Suitable cells include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoetic stem cells (HSCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs)

In some cases, the stem cell is a hematopoietic stem cell (HSC), and the transcription factor induces differentiation of the HSC to differentiate into a red blood cell, a platelet, a lymphocyte, a monocyte, a neutrophil, a basophil, or an eosinophil. In some cases, the stem cell is a mesenchymal stem cell (MSC), and the transcription factor induces differentiation of the MSC into a connective tissue cell such as a cell of the bone, cartilage, smooth muscle, tendon, ligament, stroma, marrow, dermis, or fat.

Cells of the subject disclosure may be genetically modified host cells, e.g., modified with a nucleic acid of the present disclosure, i.e., host cells genetically modified with a nucleic acid comprising a nucleotide sequence encoding a chimeric polypeptide of the present disclosure. In one embodiment, the present disclosure provides a method of inducing expression of a heterologous polypeptide in a cell, e.g., a host cell genetically modified to contain a nucleic acid of the instant disclosure. The method generally involves contacting the cell with the binding partner of the specific binding member of a chimeric polypeptide of the present disclosure. Such binding induces cleavage of the Notch receptor polypeptide at the one or more proteolytic cleavage sites, thereby releasing the intracellular domain. Release of the intracellular domain may modulate an activity of the cell, e.g., induce expression of a heterologous gene or coding sequence.

In one embodiment, a method of the present disclosure generally involves contacting a cell with a peptide-MHC that binds the specific binding member of a chimeric polypeptide of the present disclosure. Such binding induces cleavage of the Notch receptor polypeptide at the one or more proteolytic cleavage sites, thereby releasing the intracellular domain. Release of the intracellular domain may modulate an activity of the cell, e.g., induce expression of a heterologous gene or coding sequence.

In some cases, the cell is a eukaryotic cell. In some cases, the cell is a mammalian cell, an amphibian cell, a reptile cell, an avian cell, or a plant cell. In some cases, the cell is a plant cell.

In some cases, the cell is a mammalian cell. In some cases, the cell is a human cell. In some cases, the cell is a mouse cell. In some cases, the cell is rat cell. In some cases, the cell is non-human primate cell. In some cases, the cell is lagomorph cell. In some cases, the cell is an ungulate cell.

In some cases, the cell is an immune cell, e.g., a T cell, a B cell, a macrophage, a dendritic cell, a natural killer cell, a monocyte, etc. In some cases, the cell is a T cell. In some cases, the cell is a cytotoxic T cell (e.g., a CD8$^+$ T cell). In some cases, the cell is a helper T cell (e.g., a CD4$^+$ T cell). In some cases, the cell is a regulatory T cell ("Treg"). In some cases, the cell is a B cell. In some cases, the cell is a macrophage. In some cases, the cell is a dendritic cell. In some cases, the cell is a peripheral blood mononuclear cell. In some cases, the cell is a monocyte. In some cases, the cell is a natural killer (NK) cell. In some cases, the cell is a CD4$^+$, FOXP3$^+$ Treg cell. In some cases, the cell is a CD4$^+$, FOXP3$^-$ Treg cell.

In some instances, the cell is obtained from an individual. For example, in some cases, the cell is a primary cell. As another example, the cell is a stem cell or progenitor cell obtained from an individual.

As one non-limiting example, in some cases, the cell is an immune cell obtained from an individual. As an example, the cell can be a T lymphocyte obtained from an individual. As another example, the cell is a cytotoxic cell (e.g., a cytotoxic T cell, a helper T cell, etc.) obtained from an individual. As another example, the cell can be a helper T cell obtained from an individual. As another example, the cell can be a regulatory T cell obtained from an individual. As another example, the cell can be an NK cell obtained from an individual. As another example, the cell can be a macrophage obtained from an individual. As another example, the cell can be a dendritic cell obtained from an individual. As another example, the cell can be a B cell obtained from an individual. As another example, the cell can be a peripheral blood mononuclear cell obtained from an individual.

In some cases, the host cell is a somatic cell, e.g. a fibroblast, a hematopoietic cell, a neuron, a pancreatic cell, a muscle cell, a bone cell, a hepatocyte, a pancreatic cell, an epithelial cell, an endothelial cell, a cardiomyocyte, a T cell, a B cell, an osteocyte, and the like.

In some cases, the cell is genetically modified to express two or more different chimeric polypeptides of the present disclosure, including but not limited to e.g., 2 different chimeric polypeptides of the present disclosure, 3 different chimeric polypeptides of the present disclosure, 4 different chimeric polypeptides of the present disclosure, 5 different chimeric polypeptides of the present disclosure, etc.

Certain cells and components and activities thereof that may be adapted for use in the chimeric polypeptides and/or be modulated in the methods and circuits described herein include but are not limited to e.g., those described in PCT Application No. US2016/019188 (Pub. No. WO 2016/138034), the disclosure of which is incorporated herein by reference in its entirety.

Circuits

The intracellular domain of a chimeric polypeptide of the present disclosure, when released upon binding of the binding partner to the specific binding member of the extracellular domain, may induce the expression of various polypeptides as described herein. In some instances, induced expression of two or more polypeptides may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates).

"AND" gates of the present disclosure include where two or more inputs are required for propagation of a signal. For example, in some instances, an AND gate allows signaling through a chimeric polypeptide of the instant disclosure and a second binding-dependent molecule. In an AND gate two inputs, e.g., two antigens, are required for signaling through the circuit.

"OR" gates of the present disclosure include where either of two or more inputs may allow for the propagation of a signal. For example, in some instances, an OR gate allows signaling through either of two different chimeric polypeptides of the instant disclosure. In an OR gate any one input, e.g., either of two antigens, may induce the signaling output of the circuit. In one embodiment, an OR gate may be achieved through the use of two separate molecules or constructs. In another embodiment, an OR gate may be achieved through the use of a single construct that recognizes two antigens, including e.g., a proteolytically cleavable chimeric polypeptide having two different specific binding members that each bind a different binding partner but either can activate the chimeric polypeptide. In some instances, an OR gate may be achieved through the use of a single construct that recognizes two antigens, including e.g., a proteolytically cleavable chimeric polypeptide having two different antibody specific binding members that each bind a different antigen but either antigen can activate the chimeric polypeptide.

"NOT" gates of the present disclosure include where an input is capable of preventing the propagation of a signal. For example, in some instances, a NOT gate inhibits signaling through a chimeric polypeptide of the instant disclosure. In one embodiment, a NOT gate may include the inhibition of a binding interaction. For example, a competitive inhibitor that prevents the binding of parts of a split chimeric polypeptide of the instant disclosure may serve as a NOT gate that prevents signaling through the circuit. In another embodiment, a NOT gate may include functional inhibition of an element of a circuit. For example, an inhibitor that functionally prevents signaling through a chimeric polypeptide of the instant disclosure or the outcome of signaling through a circuit may serve as a NOT gate.

In some instances, the production of immunosuppressive agents (e.g., an immune suppression factor) may provide NOT gate functionality in a multi-input circuit described herein.

Multi-input gates may make use of a NOT gate in various different ways to prevent signaling through some other component of a circuit or turn off a cellular response when and/or where a signal activating the NOT gate (e.g., a particular negative antigen) is present. For example, an AND+NOT gate may include a chimeric polypeptide of the instant disclosure that positively influences a particular cellular activity in the presence of a first antigen and a chimeric polypeptide of the instant disclosure that negatively influences the cellular activity in the presence of a second antigen.

In some instances, circuits of the present disclosure may make use of the recognition of intracellular antigens provided by specific binding members specific for peptide-MHC complexes displaying a peptide of an intracellular antigen. Circuits making use of intracellular antigen recognition may, in some instances, couple intracellular antigen recognition with recognition of a second antigen where the second antigen may also be an intracellular antigen or may be an extracellular (e.g., surface expressed) antigen. Accordingly, in some instances, a circuit may be an "inside-inside" circuit where the circuit relies upon the recognition of two intracellular antigens. In some instances, a circuit may be an "inside-outside" circuit where the circuit relies upon the first recognition of an intracellular antigen and the second recognition of an extracellular antigen. In some instances, a circuit may be an "outside-inside" circuit where the circuit relies upon the first recognition of an extracellular antigen and the second recognition of an intracellular antigen. In some instances, a circuit may be an "outside-outside" circuit where the circuit relies upon the recognition of two extracellular antigens. Such circuits are not limited to two antigens may, in some instances, include e.g., inside-inside-inside antigen circuits, inside-inside-outside antigen circuits, inside-outside-inside antigen circuits, outside-inside-inside antigen circuits, inside-outside-outside antigen circuits, etc.

In one embodiment, an "inside-inside" circuit may include a first chimeric polypeptide that, upon binding a first intracellular antigen in the context of a peptide-MHC, induces the expression of a therapeutic that recognizes a second intracellular antigen in the context of a peptide-MHC including, e.g., a TCR, a CAR, an antibody, a chimeric bispecific binding member, and the like. In one embodiment, an "inside-inside" circuit may include a first chimeric polypeptide that, upon binding a WT1 intracellular antigen in the context of MHC, induces the expression of a therapeutic that recognizes a second intracellular antigen in the context of a peptide-MHC including, e.g., a TCR, a CAR, an antibody, a chimeric bispecific binding member, and the like. In one embodiment, an "inside-inside" circuit may include a first chimeric polypeptide that, upon binding a NY-ESO1 intracellular antigen in the context of MHC, induces the expression of a therapeutic that recognizes a second intracellular antigen in the context of a peptide-MHC including, e.g., a TCR, a CAR, an antibody, a chimeric bispecific binding member, and the like.

In one embodiment, an "inside-outside" circuit may include a chimeric polypeptide that, upon binding an intracellular antigen in the context of a peptide-MHC, induces the expression of a therapeutic that recognizes an extracellular antigen including, e.g., a TCR, a CAR, an antibody, a chimeric bispecific binding member, and the like. In one embodiment, an "inside-outside" circuit may include a chimeric polypeptide that, upon binding a WT1 intracellular antigen in the context of MHC, induces the expression of a therapeutic that recognizes an extracellular antigen including, e.g., a TCR, a CAR, an antibody, a chimeric bispecific binding member, and the like. In one embodiment, an "inside-outside" circuit may include a chimeric polypeptide that, upon binding a NY-ESO1 intracellular antigen in the context of MHC, induces the expression of a therapeutic that recognizes an extracellular antigen including, e.g., a TCR, a CAR, an antibody, a chimeric bispecific binding member, and the like.

Multi-input circuits and logic gated systems of the instant disclosure are not limited to those specifically described and may include alternative configurations and/or higher order gates as compared to those described. For example, in some instances a logic gated system of the instant disclosure may be a two input gate, a three input gate, a four input gate, a five input gate, a six input gate, a seven input gate, an eight input gate, a nine input gate, a ten input gate or greater. Any construct described herein including e.g., a chimeric polypeptide, a CAR, a TCR, a chimeric bispecific binding member, and the may find use in a circuit in conjunction with any other construct described herein including e.g., a chimeric polypeptide, a CAR, a TCR, a chimeric bispecific binding member, a second chimeric polypeptide, a second CAR, a second TCR, a second chimeric bispecific binding member, and the like.

Certain circuits and components thereof that may be adapted for use with the chimeric polypeptides and the methods described herein include but are not limited to e.g., those described in PCT Application No. US2016/019188 (Pub. No. WO 2016/138034), the disclosure of which is incorporated herein by reference in its entirety.

Kits

The present disclosure provides a kit for carrying out a method as described herein and/or constructing one or more chimeric polypeptides, nucleic acids encoding chimeric polypeptides, components thereof, etc.

In some cases, a subject kit comprises an expression vector comprising a nucleotide sequence encoding a chimeric polypeptide of the present disclosure or one or more portions thereof. In some cases, a subject kit comprises a chimeric polypeptide of the present disclosure.

In some cases, a subject kit comprises a cell, e.g., a host cell or host cell line, that is or is to be genetically modified with a nucleic acid comprising a nucleotide sequence encoding a chimeric polypeptide of the present disclosure. In some cases, a subject kit comprises a cell, e.g., a host cell, that is or is to be genetically modified with a recombinant expression vector comprising a nucleotide sequence encoding a chimeric polypeptide of the present disclosure. Kit components can be in the same container, or in separate containers.

Any of the above-described kits can further include one or more additional reagents, where such additional reagents can be selected from: a dilution buffer; a reconstitution solution; a wash buffer; a control reagent; a control expression vector; a negative control polypeptide (e.g., a chimeric polypeptide that lacks the one or more proteolytic cleavage sites, such that, upon binding, the intracellular domain is not released); a positive control polypeptide; a reagent for in vitro production of the chimeric polypeptide, and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered as below are provided. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A chimeric polypeptide comprising, from N-terminal to C-terminal and in covalent linkage:
   a) an extracellular domain comprising a specific binding member that specifically binds to a peptide-major histocompatibility complex (peptide-MHC);
   b) a proteolytically cleavable Notch receptor polypeptide comprising one or more proteolytic cleavage sites; and
   c) an intracellular domain comprising a transcriptional activator, wherein binding of the specific binding member to the peptide-MHC induces cleavage of the Notch receptor polypeptide at the one or more proteolytic cleavage sites, thereby releasing the intracellular domain.

2. The chimeric polypeptide of Aspect 1, wherein the specific binding member comprises an antibody.

3. The chimeric polypeptide of Aspect 2, wherein the antibody is a nanobody, a diabody, a triabody, or a minibody, a F(ab')2 fragment, a Fab fragment, a single chain variable fragment (scFv) or a single domain antibody (sdAb).

4. The chimeric polypeptide of any of the preceding aspects, wherein the specific binding member specifically binds a peptide-MHC comprising an intracellular cancer antigen peptide.

5. The chimeric polypeptide of Aspect 4, wherein the intracellular cancer antigen peptide is a WT1 peptide or a NY-ESO peptide.

6. The chimeric polypeptide of any of the preceding aspects, wherein the Notch receptor polypeptide comprises, at its N-terminus, one or more epidermal growth factor (EGF) repeats.

7. The chimeric polypeptide of Aspect 6, wherein the Notch receptor polypeptide comprises, at its N-terminus, 2 to 11 EGF repeats.

8. The chimeric polypeptide of any of the preceding aspects, wherein the Notch receptor polypeptide comprises a synthetic linker.

9. The chimeric polypeptide of Aspect 8, wherein the Notch receptor polypeptide comprises a synthetic linker between the one or more EGF repeats and the one or more proteolytic cleavage sites.

10. The chimeric polypeptide of any of the preceding aspects, wherein the Notch receptor polypeptide has a length from 50 amino acids to 1000 amino acids.

11 The chimeric polypeptide of Aspect 10, wherein the Notch receptor polypeptide has a length from 300 amino acids to 400 amino acids.

12. The chimeric polypeptide of any of the preceding aspects, wherein the one or more proteolytic cleavage sites comprises an S2 proteolytic cleavage site, an S3 proteolytic cleavage site or a combination thereof.

13. The chimeric polypeptide of Aspect 12, wherein the one or more proteolytic cleavage sites comprises an S2 proteolytic cleavage site that is an ADAM-17-type protease cleavage site comprising an Ala-Val dipeptide sequence.

14. The chimeric polypeptide of any of the preceding aspects, wherein the one or more proteolytic cleavage sites comprises an S3 proteolytic cleavage site that is a gamma-secretase (γ-secretase) cleavage site comprising a Gly-Val dipeptide sequence.

15. The chimeric polypeptide of any of the preceding aspects, wherein the one or more proteolytic cleavage sites further comprises an S1 proteolytic cleavage site.

16. The chimeric polypeptide of Aspect 15, wherein the S1 proteolytic cleavage site is a furin-like protease cleavage site comprising the amino acid sequence Arg-X-(Arg/Lys)-Arg (SEQ ID NO:130), where X is any amino acid.

17. The chimeric polypeptide of any of the preceding aspects, wherein the Notch receptor polypeptide lacks an S1 proteolytic cleavage site.

18. The chimeric polypeptide of any of the preceding aspects, wherein the Notch receptor polypeptide has at least 85% amino acid sequence identity to a sequence provided in FIG. 31A-32B.

19. The chimeric polypeptide of Aspect 18, wherein the Notch receptor polypeptide has at least 85% amino acid sequence identity to the sequence provided in FIG. 31A-31B or the sequence provided in FIG. 31C-31D.

20. A nucleic acid encoding the chimeric polypeptide according to any of Aspects 1-19.

21. The nucleic acid of Aspect 20, wherein the nucleic acid further comprises a transcriptional control element responsive to the transcriptional activator operably linked to a nucleic acid sequence encoding a polypeptide of interest (POI).

22. The nucleic acid of Aspect 21, wherein the POI is a heterologous polypeptide selected from the group consisting of: a reporter protein, a chimeric antigen receptor (CAR), an antibody, a chimeric bispecific binding member, an engineered T cell receptor (TCR) and an innate-immune response inducer.

23. A recombinant expression vector comprising the nucleic acid according to any of Aspects 20-22.

24. A method of inducing expression of a heterologous polypeptide in a cell, the method comprising: contacting a cell with a peptide-major histocompatibility complex (peptide-MHC), wherein the cell expresses a chimeric polypeptide according to any of Aspects 1-19 and comprises a sequence encoding the heterologous polypeptide operably linked to a transcriptional control element responsive to the transcriptional activator of the chimeric polypeptide, thereby releasing the intracellular domain of the chimeric polypeptide and inducing expression of the heterologous polypeptide.

25. The method according to Aspect 24, wherein the heterologous polypeptide is a reporter protein, a chimeric antigen receptor (CAR), an antibody, a chimeric bispecific binding member, an engineered T cell receptor (TCR) and an innate-immune response inducer.

26. A host cell comprising:
   a) a nucleic acid encoding a chimeric polypeptide according to any of Aspects 20-22 that specifically binds to a first peptide-major histocompatibility complex (peptide-MHC); and
   b) a transcriptional control element responsive to the transcriptional activator of the chimeric polypeptide operably linked to a nucleic acid encoding a polypeptide of interest (POI).

27. The host cell of Aspect 26, wherein the host cell is genetically modified and the nucleic acid and the transcriptional control element are present within the genome of the host cell.

28. The host cell of Aspect 26, wherein the nucleic acid and the transcriptional control element are present extrachromosomally within the host cell.

29. The host cell of any of Aspects 26-28, wherein the POI is a heterologous polypeptide.

30. The host cell of Aspect 29, wherein the heterologous polypeptide is selected from the group consisting of: a reporter protein, a chimeric antigen receptor (CAR), an antibody, a chimeric bispecific binding member, an engineered T cell receptor (TCR) and an innate-immune response inducer.

31. The host cell of Aspect 30, wherein the heterologous polypeptide is a CAR that specifically binds to a second peptide-MHC.

32. The host cell of Aspect 31, wherein the specific binding member of the chimeric polypeptide specifically binds to a first peptide-MHC comprising a first intracellular cancer antigen peptide and the CAR specifically binds to a second peptide-MHC comprising a second intracellular cancer antigen peptide.

33. The host cell of Aspect 32, wherein the first intracellular cancer antigen peptide is a WT1 peptide and the second intracellular cancer antigen peptide is a NY-ESO peptide.

34. The host cell of Aspect 32, wherein the first intracellular cancer antigen peptide is a NY-ESO peptide and the second intracellular cancer antigen peptide is a WT1 peptide.

35. The host cell of Aspect 30, wherein the heterologous polypeptide is an engineered TCR that specifically binds to a second peptide-MHC.

36. The host cell of Aspect 35, wherein the specific binding member of the chimeric polypeptide specifically binds to a first peptide-MHC comprising a first intracellular cancer antigen peptide and the engineered TCR specifically binds to a second peptide-MHC comprising a second intracellular cancer antigen peptide.

37. The host cell of Aspect 36, wherein the first intracellular cancer antigen peptide is a WT1 peptide and the second intracellular cancer antigen peptide is a NY-ESO peptide.

38. The host cell of Aspect 36, wherein the first intracellular cancer antigen peptide is a NY-ESO peptide and the second intracellular cancer antigen peptide is a WT1 peptide.

39. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a cancer cell;
      ii) a proteolytically cleavable Notch receptor polypeptide comprising one or more proteolytic cleavage sites; and
      iii) an intracellular domain comprising a transcriptional activator;
   b) a nucleic acid encoding a chimeric bispecific binding member operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the chimeric bispecific binding member to be expressed.

40. The host cell according to Aspect 39, wherein the chimeric bispecific binding member comprises a binding domain specific for a cancer antigen and a binding domain specific for a protein expressed on the surface of an immune cell.

41. The host cell according to Aspect 39 or 40, wherein the chimeric bispecific binding member comprises at least one antibody derived antigen-binding domains.

42. The host cell according to Aspect 41, wherein the chimeric bispecific binding member is a bispecific antibody or a fragment thereof.

43. The host cell according to any of Aspects 39-41, wherein the chimeric bispecific binding member comprises at least one receptor or ligand binding domain of a ligand-receptor binding pair.

44. The host cell according to any of Aspects 39-43, wherein the chimeric bispecific binding member comprises at least one antibody derived antigen-binding domain and at least one receptor or ligand binding domain of a ligand-receptor binding pair.

45. The host cell according to any of Aspects 40-44, wherein the protein expressed on the surface of an immune cell is CD3.

46. The host cell according to any of Aspects 40-44, wherein the protein expressed on the surface of an immune cell is Natural Killer Group 2D (NKG2D) receptor.

47. The host cell according to any of Aspects 39-46, wherein the target molecule is a cancer antigen.

48. The host cell according to any of Aspects 39-46, wherein the target molecule is a tissue specific molecule.

49 The host cell according to any of Aspects 39-46, wherein the target molecule is an organ specific molecule.

50. The host cell according to any of Aspects 39-46, wherein the target molecule is a cell type specific molecule.

51. A method of treating a subject for a neoplasia comprising administering to the subject an effective amount of host cells according to any of Aspects 39-50, wherein the neoplasia expresses the target molecule and the cancer antigen.

52. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a cancer cell;
      ii) a proteolytically cleavable Notch receptor polypeptide comprising one or more proteolytic cleavage sites; and
      iii) an intracellular domain comprising a transcriptional activator;
   b) a nucleic acid encoding an anti-Fc chimeric antigen receptor (CAR) operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the anti-Fc CAR to be expressed.

53. The host cell of Aspect 52, wherein the target molecule is a cancer antigen.

54. The host cell of Aspect 52, wherein the target molecule is a tissue specific molecule.

55. The host cell of Aspect 52, wherein the target molecule is an organ specific molecule.

56. The host cell of Aspect 52, wherein the target molecule is a cell type specific molecule.

57. The host cell of any of Aspects 52-56, wherein the host cell further comprises a nucleic acid encoding an antibody specific for a cancer antigen present on the surface of a cancer cell and comprising an Fc region that is bound by the anti-Fc CAR.

58. The host cell of Aspect 57, wherein the nucleic acid encoding the antibody is operably linked to the transcriptional control element.

59. A method of treating a subject for a neoplasia comprising administering to the subject an effective amount of host cells according to any of Aspects 52-58, wherein the neoplasia expresses the target molecule.

60. The method of Aspect 59, wherein the method further comprises administering to the subject an antibody specific for a cancer antigen present on the surface of a cancer cell and comprising an Fc region that is bound by the anti-Fc CAR.

61. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a cancer cell;
      ii) a proteolytically cleavable Notch receptor polypeptide comprising one or more proteolytic cleavage sites; and
      iii) an intracellular domain comprising a transcriptional activator;
   b) a nucleic acid encoding an innate-immune response inducer operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the innate-immune response inducer to be expressed.

62. The method of Aspect 61, wherein the target molecule is a tissue specific molecule.

63. The method of Aspect 61, wherein the target molecule is an organ specific molecule.

64. The method of Aspect 61, wherein the target molecule is a cell type specific molecule.

65. The method of Aspect 61, wherein the target molecule is a cancer antigen.

66. The method of any of Aspects 61-65, wherein the innate-immune response inducer is bacterial protein or fragment thereof.

67. The method of any of Aspects 61-65, wherein the innate-immune response inducer is viral protein or fragment thereof.

68. The method of any of Aspects 61-65, wherein the innate-immune response inducer is fungal protein or fragment thereof.

69. The method of any of Aspects 61-68, wherein the innate-immune response inducer is a protein or fragment thereof expressed by a mammalian parasite.

70. The method of Aspect 69, wherein the mammalian parasite is a human parasite.

71. A method of inducing a local innate immune response in an area of a subject, the method comprising administering to the subject an effective amount of host cells according to any of Aspects 61-70, wherein the area expresses the target molecule.

72. The method of Aspect 71, wherein the area of the subject comprises a neoplasia.

73. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a cancer cell;
      ii) a proteolytically cleavable Notch receptor polypeptide comprising one or more proteolytic cleavage sites; and
      iii) an intracellular domain comprising a transcriptional activator;
   b) a nucleic acid encoding an immune suppression factor operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the immune suppression factor to be expressed.

74. The method of Aspect 73, wherein the target molecule is a tissue specific molecule.

75. The method of Aspect 73, wherein the target molecule is an organ specific molecule.

76. The method of Aspect 73, wherein the target molecule is a cell type specific molecule.

77. The method of Aspect 73, wherein the target molecule is an autoantigen.

78. The method of any of Aspects 73-77, wherein the immune suppression factor is an immunosuppressive cytokine.

79. The method of Aspects 78, wherein the immunosuppressive cytokine is IL-10.

80. The method of any of Aspects 73-77, wherein the immune suppression factor is a cell-to-cell signaling immunosuppressive ligand.

81. The method of Aspects 80, wherein the cell-to-cell signaling immunosuppressive ligand is PD-L1.

82. A method of suppressing an immune response in a subject, the method comprising administering to the subject an effective amount of host cells according to any of Aspects 73-81, wherein the subject expresses the target molecule.

83. The method of Aspect 82, wherein the subject has an autoimmune disease.

84. A method of killing a heterogeneous tumor, the method comprising:
   contacting a heterogeneous tumor comprising a first cell expressing a killing antigen and a second cell expressing the killing antigen and a priming antigen with an engineered immune cell comprising:
      a proteolytically cleavable chimeric polypeptide that specifically binds the priming antigen;
      a nucleic acid sequence encoding a therapeutic polypeptide that specifically binds the killing antigen; and
      a transcriptional control element operably linked to the nucleic acid that is responsive to the proteolytically cleavable chimeric polypeptide,
   wherein binding of the proteolytically cleavable chimeric polypeptide to the priming antigen activates the transcriptional control element to induce expression of the therapeutic polypeptide which, when bound to the killing antigen, kills the first and second cells of the heterogeneous tumor.

85. The method of Aspect 84, wherein the therapeutic polypeptide is a chimeric antigen receptor (CAR).

86. The method of Aspect 84, wherein the therapeutic polypeptide is a T cell Receptor (TCR).

87. The method of Aspect 84, wherein the therapeutic polypeptide is a therapeutic antibody.

88. The method of Aspect 84, wherein the therapeutic polypeptide is a chimeric bispecific binding member.

89. The method of any of Aspects 84-88, wherein at least one of the priming antigen or the killing antigen is an intracellular antigen presented in the context of MHC.

90. The method of any of Aspects 84-89, wherein both the priming antigen and the killing antigen are intracellular antigens presented in the context of MHC.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Peptide-Major Histocompatibility Complex (Peptide-MHC) Induced Signaling The ability to affect cellular signaling through recognition of a peptide-MHC by a cleavable chimeric Notch polypeptide was investigated. As diagramed in FIG. 1, chimeric polypeptides were designed that include a cleavable Notch polypeptide linked to an extracellular domain that includes a specific binding member that specifically binds to a peptide-MHC of an intracellular antigen of a "sender cell". The extracellular domain of a chimeric polypeptide expressed by a "receiver cell" binds the peptide-MHC of the "sender cell". Upon such binding, the cleavable Notch polypeptide is cleaved releasing the intracellular portion which can affect intracellular processes including e.g., the expression of a transgene (e.g., "X" in FIG. 1) operatively linked to a promoter that is responsive to the freed intracellular domain.

Figure 2:
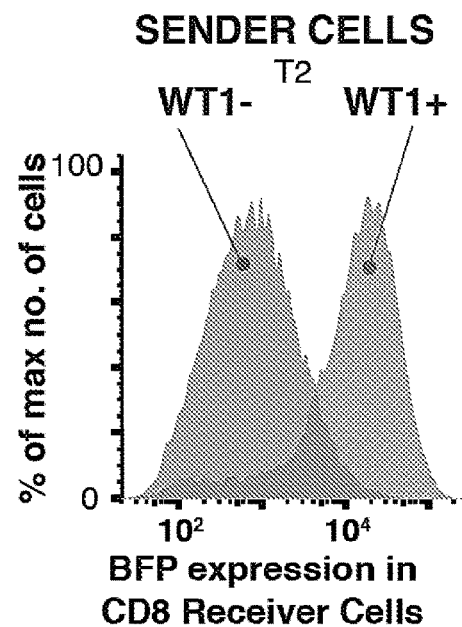
FIG. 2 demonstrates the specific expression of blue fluorescent protein (BFP) reporter in receiver cells expressing a proteolytically cleavable chimeric polypeptide according to one embodiment described herein, as generally depicted in FIG. 1, specific for MHC-presented WT1 antigen. The reporter is expressed when receiver cells were contacted with sender cells expressing the MHC-presented WT1 antigen but not when contacted with sender cells that do not express the antigen.
Figure 3:
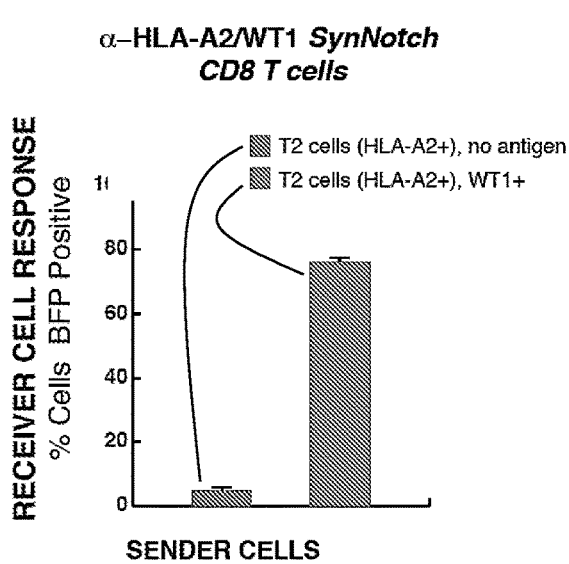
FIG. 3 provides quantification related to FIG. 2 showing WT1 intracellular antigen dependent activation of the proteolytically cleavable chimeric polypeptide.

As a representative example, a chimeric polypeptide was designed with an extracellular domain that binds to a Wilms Tumor Protein 1 (WT1) peptide-MHC and a GAL4 transcription activator intracellular domain that, when freed, binds an Upstream Activation Sequence (UAS) operatively linked to a Blue Fluorescent Protein (BFP) to serve as an activation reporter when the system is engineered into CD8 receiver cells. FIG. 2 demonstrates the relative levels of receiver cells expressing BFP reporter when contacted with either peptide-MHC negative (WT1−) or positive (WT1+) T2 sender cells. FIG. 3 provides quantification of receiver CD8 T cell response assayed in the presence of T2 cells expressing HLA-A2 with or without target WT1 intracellular antigen expression. As can be seen in FIG. 2 and FIG. 3 T cell response is highly specific to and dependent upon the presence of the presented intracellular antigen.

Figure 4:
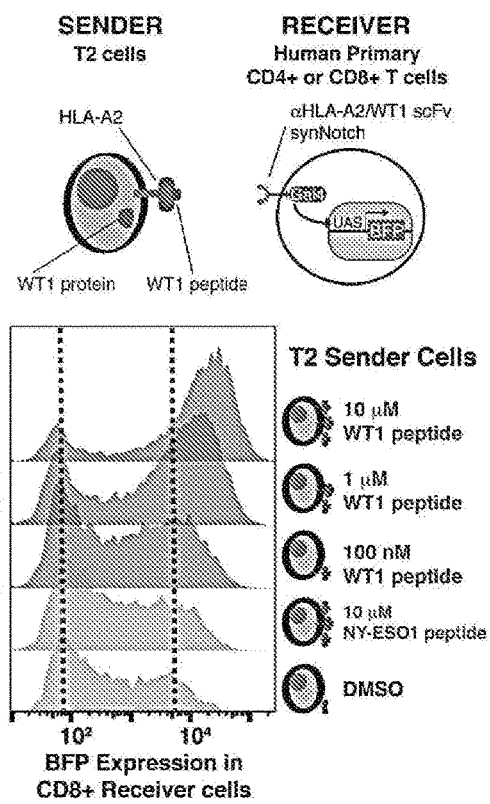
FIG. 4 demonstrates the sensitivity and antigen concentration dependent reporter activation of an anti-MHC-presented WT1 proteolytically cleavable chimeric polypeptide according to one embodiment described herein.

As demonstrated in FIG. 4, receiver cell response is also dependent on the amount of presented intracellular antigen. T2 sender cells were engineered to express different amounts of WT1 peptide-MHC (10 μM, 1 μM and 100 nM) and receiver cell response was assayed with each population. Reporter expression was seen to correlate to WT1 peptide-MHC expression level indicating dose dependent activation.

In addition, when assayed in the presence of irrelevant intracellular antigen peptide-MHC (NY-ESO1 peptide) expressing T2 cells reporter activation was similar to negative control (DMSO), further indicating that activation is antigen-specific. Across three different concentrations of either target intracellular antigen WT1 peptide-MHC or irrelevant intracellular antigen NY-ESO1 peptide-MHC, antigen concentration dependent reporter activation was seen in receiver cells in response to WT1 but not NY-ESO1 in both CD8+ T cells and CD4+ T cells (FIG. 5).

Example 2: Dual Intracellular Antigen Dependent T Cell Activation

A dual intracellular antigen AND-gate was designed such that engineered T cell activation would be dependent upon the presentation of two intracellular antigens on a target cell. Specifically, as a representative example as presented in FIG. 6, a system was designed and engineered into T cells where expression of an anti-HLA-A2/NY-ESO1 TCR is induced by the freed intracellular domain of an anti-HLA-A2/WT1 scFv synNotch. When presented with a T2 target cell expressing NY-ESO1 only, expression of the anti-HLA-A2/NY-ESO1 TCR is not induced and no T cell activation occurs. However, when presented with a T2 target cell expressing both NY-ESO1 and WT1, binding of WT1 peptide-MHC to the anti-HLA-A2/WT1 scFV synNotch induces cleavage of the Notch polypeptide, releasing a GAL4 transcription activator which binds a UAS driving expression of the anti-HLA-A2/NY-ESO1 TCR. Binding of the expressed anti-HLA-A2/NY-ESO1 TCR to the NY-ESO1 peptide-MHC on the target cell causes activation of the T cell, e.g., as detected using CD69 and/or cytotoxicity assays.

T cell activation in such a system was tested using T2 target cells expressing either antigen or both. As can be seen in FIG. 7, robust activation, as measured using CD69 expression, was seen when the engineered T cells were contacted with dual antigen (HLA-A2/NY-ESO1 and HLA-A2/WT1) T2 target cells. However, an absence of activation, similar to negative control (DMSO), was seen when the engineered T cells were contacted with T2 cells expressing only one of the two intracellular antigens (HLA-A2/NY-ESO1 or HLA-A2/WT1). Corresponding results for T2 cell killing were seen when the engineered T cells were presented with either dual- or single-antigen expressing T2 target cells (FIG. 8). These results demonstrate the functionality of dual-intracellular antigen AND-gates and the specificity of such in activating engineered T cells only in response to target cells expressing both target intracellular antigens.

Figure 9:
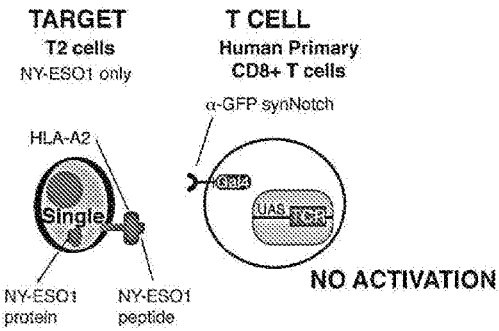
FIG. 9 schematically depicts a proteolytically cleavable chimeric polypeptide-gated circuit utilizing an anti-GFP specific chimeric polypeptide driving expression of a T cell receptor (TCR) specific for MHC-presented NY-ESO1 antigen.
Figure 10:
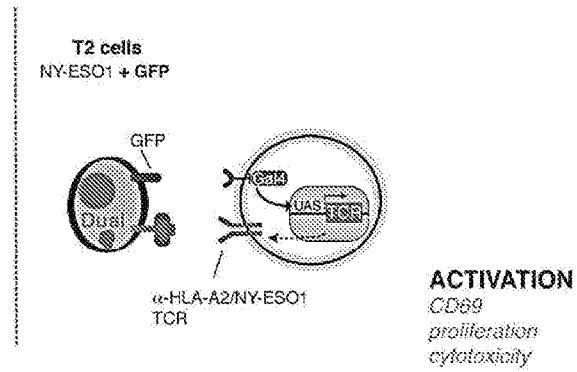
FIG. 10 schematically depicts the activation of the T cell depicted in FIG. 9 when contacted with a target expressing both surface-GFP and NY-ESO1 intracellular antigen.

To further demonstrate the versatility of this approach, an additional dual-antigen AND-gate was designed and tested targeting cells expressing both a surface target antigen and an intracellular target antigen. Specifically, as a representative example as presented in FIG. 9 and FIG. 10, a system was designed and engineered into T cells where expression of an anti-HLA-A2/NY-ESO1 TCR is induced by the freed intracellular domain of an anti-surfaced-expressed-GFP synNotch. When presented with a T2 target cell expressing NY-ESO1 only, expression of the anti-HLA-A2/NY-ESO1 TCR is not induced and no T cell activation occurs. However, when presented with a T2 target cell expressing both NY-ESO1 and GFP, binding of surface-expressed-GFP to the anti-GFP synNotch induces cleavage of the Notch polypeptide, releasing a GAL4 transcription activator which binds a UAS driving expression of the anti-HLA-A2/NY-ESO1 TCR. Binding of the expressed anti-HLA-A2/NY-ESO1 TCR to the NY-ESO1 peptide-MHC on the target cell causes activation of the T cell.

Figure 11:
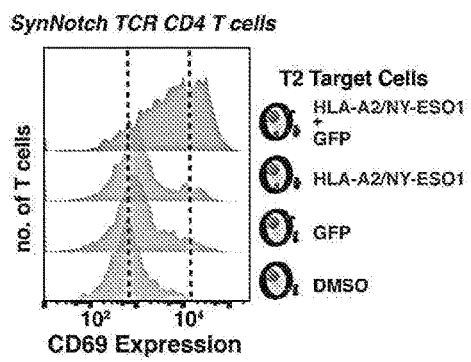
FIG. 11 depicts significant proteolytically cleavable chimeric polypeptide-gated T cell activation (as shown by CD69 activation marker expression), according to the system depicted in FIG. 9 and FIG. 10, only when contacted with target cells expressing both surface-GFP and NY-ESO1 intracellular antigens.
Figure 12:
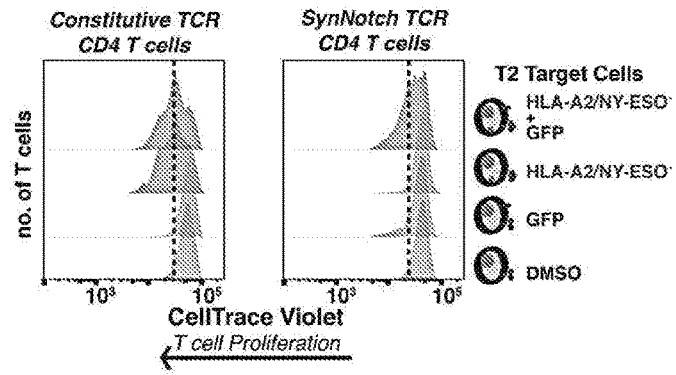
FIG. 12 depicts proteolytically cleavable chimeric polypeptide-gated T cell proliferation, according to the system depicted in FIG. 9 and FIG. 10, when contacted with target cells expressing both surface-GFP and NY-ESO1 intracellular antigens.
Figure 13:
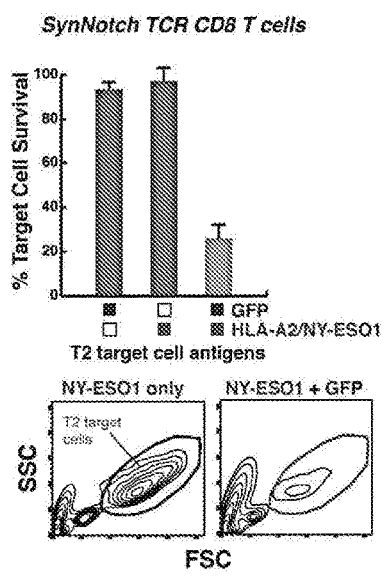
FIG. 13 depicts significant proteolytically cleavable chimeric polypeptide-gated T2 target cell killing, according to the system depicted in FIG. 9 and FIG. 10, only when contacted with target cells expressing both surface-GFP and NY-ESO1 intracellular antigens.
Figure 14:
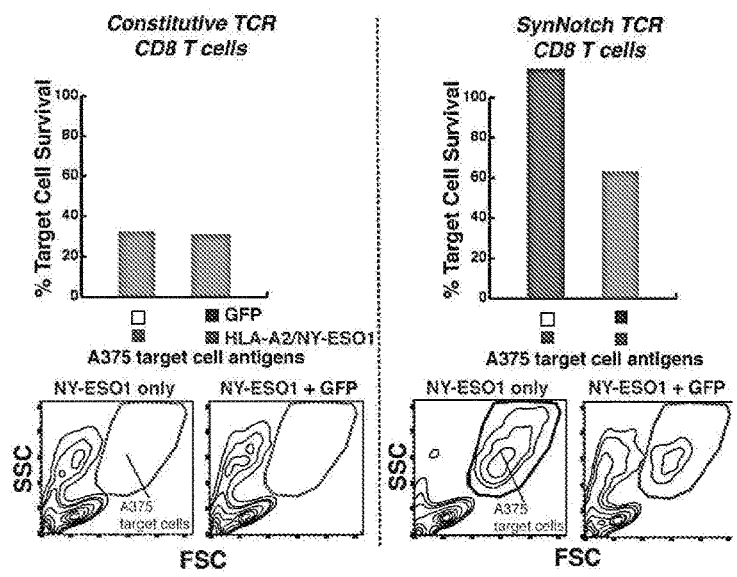
FIG. 14 depicts significant proteolytically cleavable chimeric polypeptide-gated A375 target cell killing, according to the system depicted in FIG. 9 and FIG. 10, only when contacted with target cells expressing both surface-GFP and NY-ESO1 intracellular antigens. Comparison with target cell killing by CD8 T cells constitutively expressing an ant-NY-ESO1 TCR is shown to demonstrate enhanced specificity with gated TCR expression.
Figure 15:
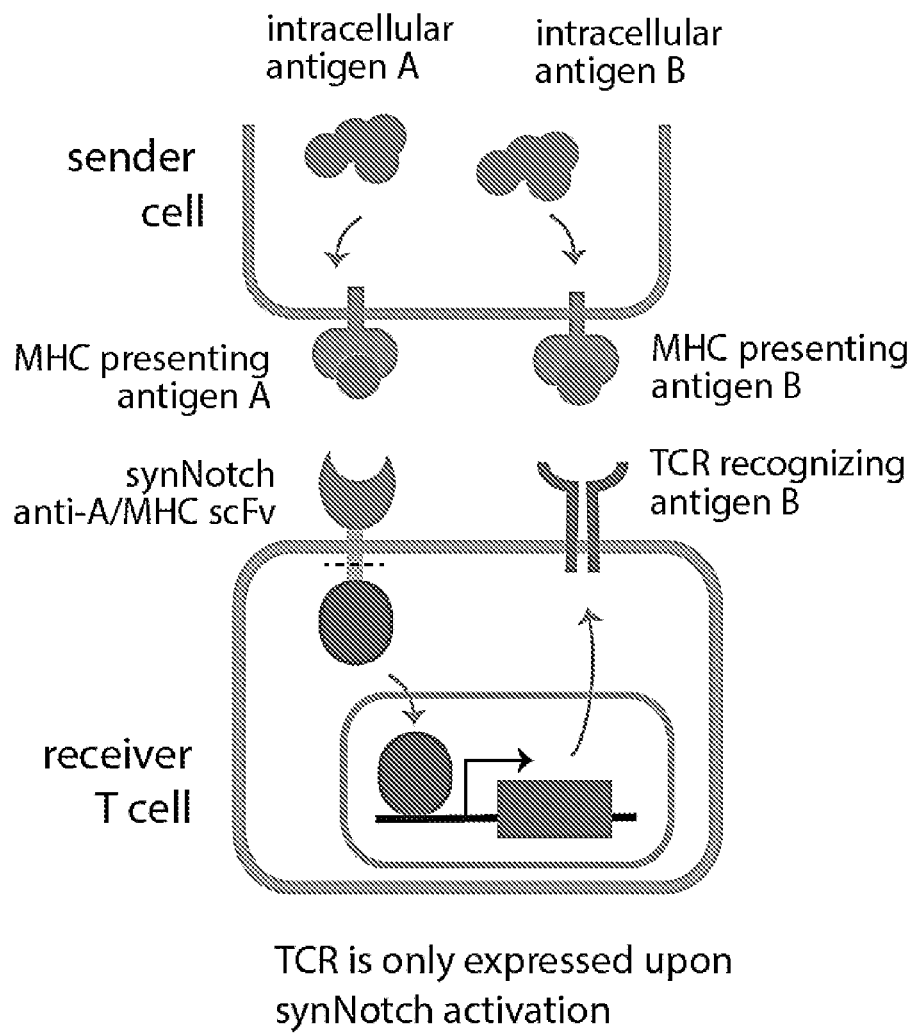
FIG. 15 provides a general schematic depiction of a dual-intracellular-antigen circuit utilizing an embodiment of a proteolytically cleavable chimeric polypeptide (synNotch) specific for a first intracellular antigen ("antigen A") to drive expression of a TCR specific for a second intracellular antigen ("antigen B").

Activation of engineered CD4+ and CD8+ T cells expressing the dual-antigen circuit was assayed using CD69 expression (FIG. 11), T cell proliferation (FIG. 12), T2 target cell killing (FIG. 13) and A375 target cell killing (FIG. 14). In each assay T cell activation and downstream effects, such as target cell killing, was dependent on expression of both target antigens by the target cells, demonstrating the robust specificity of dual-antigen synNotch AND-gates regardless of whether a combination of intracellular antigens are used (e.g., as diagramed generally in FIG. 15) or surface expressed antigen responsive components are combined with one or more intracellular antigen recognizing elements.

Figure 39:
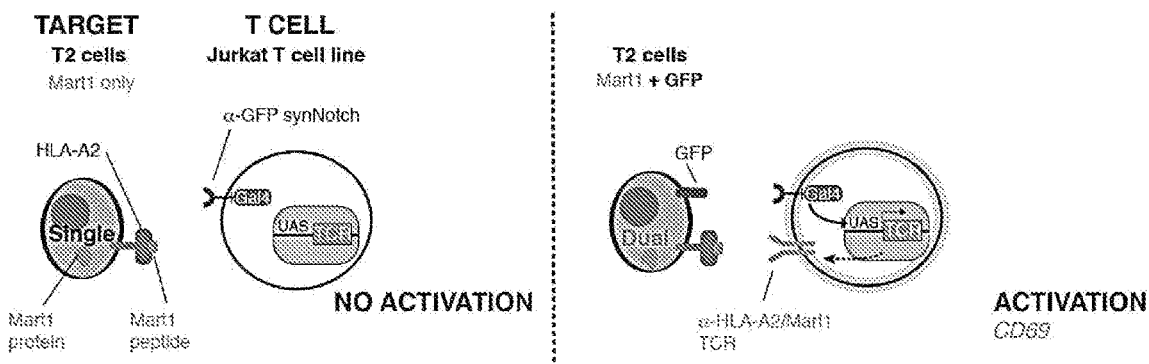
FIG. 39 schematically depicts a proteolytically cleavable chimeric polypeptide-gated circuit utilizing an anti-GFP specific chimeric polypeptide driving expression of a TCR specific for HLA-A2/Mart1.
Figure 40:
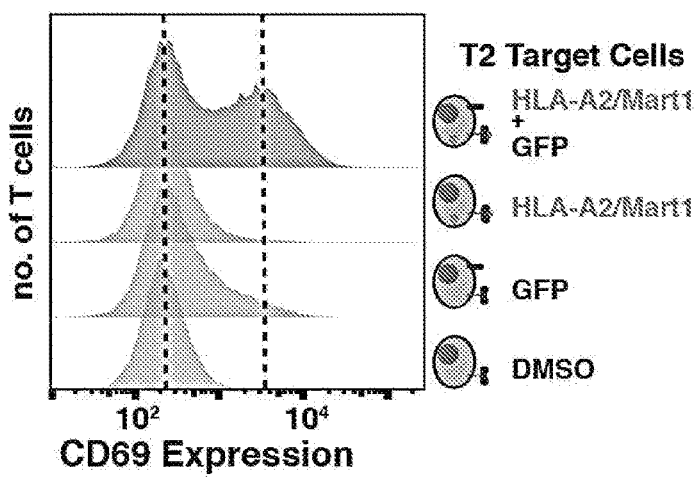
FIG. 40 depicts the specific activation of T cells expressing the circuit schematically depicted in FIG. 39 only in the presence of target cells expressing both the surface GFP and HLA-A2/Mart1 antigens.

To further demonstrate the versatility of this approach, additional dual-antigen AND-gates were designed and tested targeting cells expressing both a surface target antigen and an intracellular target antigen other than NY-ESO1. Specifically, as schematically depicted in FIG. 39, a system was designed and engineered into T cells where expression of an anti-HLA-A2/Mart1 is induced by the freed intracellular domain of an anti-surfaced-expressed-GFP synNotch. When presented with a T2 target cell expressing Mart1 only, expression of the anti-HLA-A2/Mart1 TCR is not induced and no T cell activation occurs. However, when presented with a T2 target cell expressing both Mart1 and GFP, binding of surface-expressed-GFP to the anti-GFP synNotch induces cleavage of the Notch polypeptide, releasing a GAL4 transcription activator which binds a UAS driving expression of the anti-HLA-A2/Mart1 TCR. Binding of the expressed anti-HLA-A2/Mart1 TCR to the Mart1 peptide-MHC on the target cell causes activation of the T cell. A Jurkat T cell line was engineered to express this dual-antigen circuit, and activation of the T cells was assayed using CD69 expression. As provided in FIG. 40, the results of the assay showed that T cell activation, as measured by CD69 upregulation, was dependent on the expression of both target antigens by the target cells, thus further demonstrating the robust specificity of dual-antigen synNotch AND-gates targeting pMHC antigens.

Example 3: Specific Local Delivery of Chimeric Bispecific Binding Members

Figure 16:
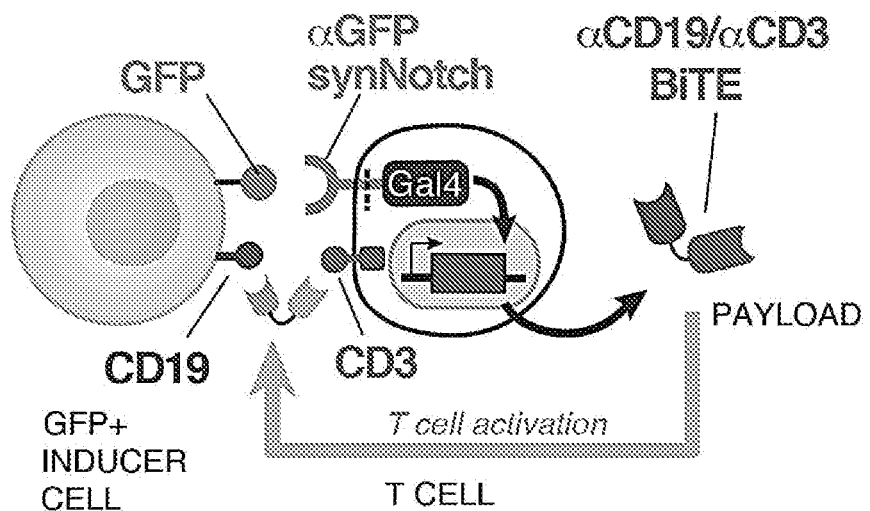
FIG. 16 depicts CD4+ T cells engineered with an α-GFP synNotch receptor controlling the expression of Blinatumomab, an α-CD19/CD3 bi-specific antibody that retargets T cells to CD19+ tumors.

The use of synNotch to induce specific local expression of chimeric bispecific binding members was assayed using a representative two component system. Specifically, as depicted in FIG. 16, an anti-GFP synNotch was used to drive expression of an anti-CD19/anti-CD3 bispecific T cell engager (BiTE) (Blinatumomab) in an engineered T cell. Upon binding GFP expressed on the surface of an inducer target cell, the anti-GFP synNotch releases a GAL4 transcriptional activator which binds a UAS operably linked to sequence encoding the anti-CD19/anti-CD3 BiTE. Expression of the BiTE results in dual-binding of target cell expressed CD19 and T cell expressed CD3 and T cell activation.

Figure 17:
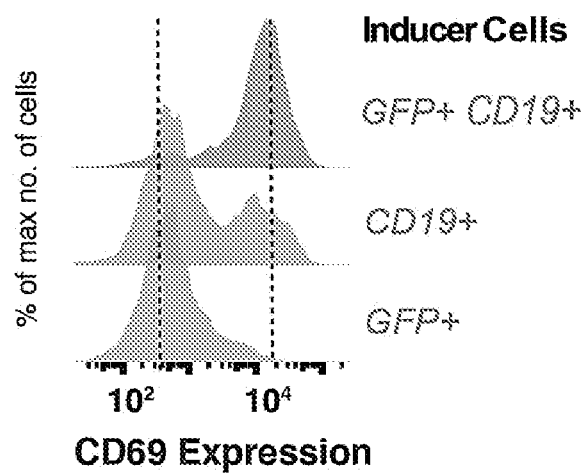
FIG. 17 provides histogram data, related to FIG. 16, showing CD69 (activation marker) expression on the synNotch T cells after co-culture with surface GFP+ only, CD19+ only, or surface GFP/CD19+ K562s. The T cells strongly activate in the presence of the surface GFP/CD19 K562s and a small percentage of the T cells activate when incubated with CD19+ only K562s due to low levels of basal leakage of Blinatumomab expression.

CD4+ T cell activation was assayed using CD69 expression. CD4+ T cells expressing an anti-GFP-GAL4 synNotch and having sequence encoding an anti-CD19/anti-CD3 BiTE operably linked to a GAL4 responsive UAS were contacted with inducer cells expressing CD19 only, GFP only or both CD19 and GFP. Significant T cell activation was seen only when inducer cells expressing both CD19 and GFP were used (FIG. 17). These in vitro results demonstrate that a chimeric bispecific binding member payload can be effectively and specifically expressed using a synNotch gated circuit and used to control cellular responses such as, e.g., T cell activation.

Figure 18:
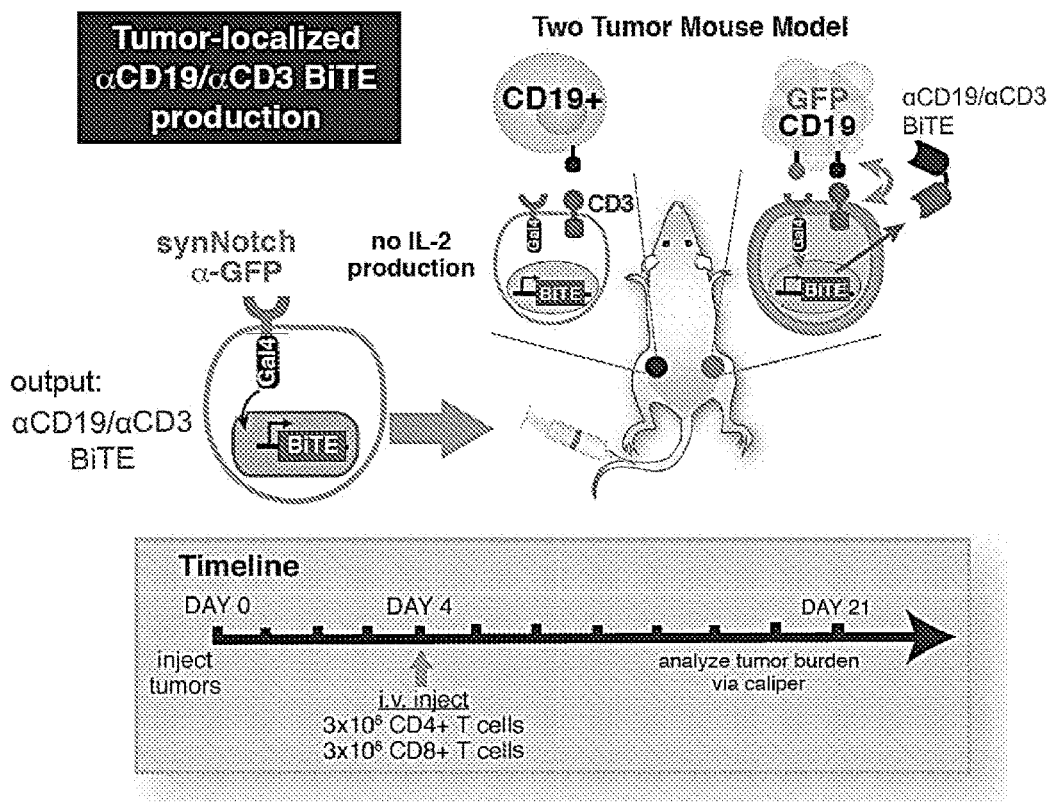
FIG. 18 depicts NSG mice subcutaneously injected with CD19− non-target K562s and target CD19+ in the left and right flank, respectively. α-GFP synNotch T cells in control of Blinatumomab (α-CD19/CD3 BiTE) expression were injected i.v. into the mice 4 days after tumor implantation. The tumors were measured by caliper over for 25 days.

The use of synNotch gated expression of a chimeric bispecific binding member was further investigated in vivo, using, as a representative example, a model of tumor-localized α-CD19/α-CD3 BiTE production (FIG. 18). Mice were subcutaneously injected with priming antigen negative (GFP−) target antigen positive (CD19+) tumor cells in the left flank and dual positive (GFP+/CD19+) tumor cells in the right flank. α-GFP synNotch T cells (CD4+ and CD8+) in control of α-CD19/α-CD3 bispecific T cell engager (BiTE) expression were injected into the mice after tumors were established. Tumors were harvested at the indicated timepoints to analyze tumor burden by caliper measurement.

Figure 19:
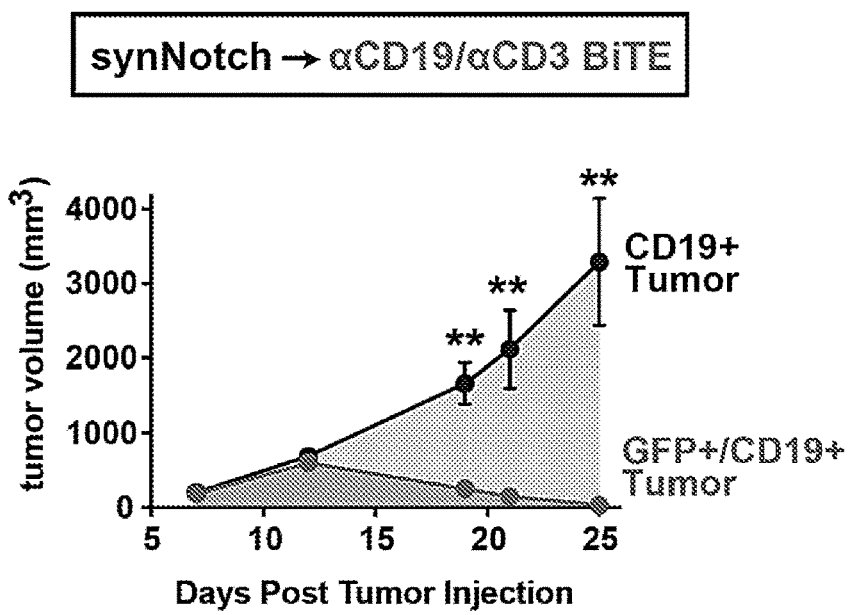
FIG. 19 provides the bilateral CD19+ and GFP/CD19+ K562 tumor growth curves in mice treated with CD4+ and CD8+ T cells engineered with the α-GFP synNotch receptor controlling Blinatumomab (α-CD19/CD3 BiTE) expression (as depicted in FIG. 18). The dual antigen GFP/CD19+ tumor is selectively cleared (n=5 mice, error=SEM, significance determined by Student's t-test ** p≤0.01).

In the described model tumor-localized production of α-CD19/α-CD3 BiTE was seen to effectively reduce tumor burden in a priming antigen-dependent manner (FIG. 19). Tumor volume was measured for left flank and right flank tumors as described above in relation to FIG. 18. Over the course of treatment tumor volume was reduced in tumors expressing both the priming antigen (GFP) and the BiTE targeted antigen (CD19) (GFP+/CD19+ Tumor). In comparison, tumor volume was not reduced in the right flank tumor expressing the BiTE targeted antigen but not the priming antigen (CD19+ Tumor). These results demonstrate the effective use of a two antigen T cell AND-gate to drive spatial specific targeting of a BiTE payload to effectively reduce tumor volume in vivo. The α-GFP synNotch could be replaced with any other SynNotch targeting effectively any other antigen, endogenously or heterologously expressed, for tissue specific, organ specific or cell type specific T cell priming.

Example 4: Specific Induction of Innate Immune Response

Figure 20:
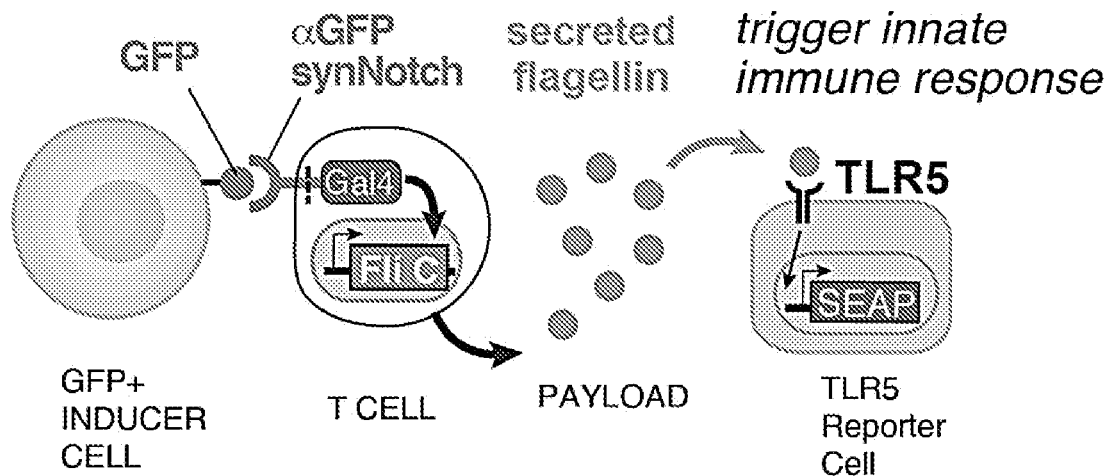
FIG. 20 depicts CD4+ T cells engineered with the α-GFP synNotch receptor controlling the expression of Flagellin. In the reporter assay, supernatant was harvested from the T cells after co-culture with surface GFP+ or GFP− K562s and added to hTLR5 HEK-blue secreted alkaline phosphatase (SEAP) reporter cells. After 24 hrs. SEAP activity was monitored and the level of Flagellin in the supernatant was measured.

The use of synNotch to specifically and/or locally induce innate immune response was investigated using a representative model system. Specifically, as depicted in FIG. 20, a system was devised using a synNotch specific for surface expressed GFP to drive expression of a reporter operably linked to nucleic acid sequence encoding flagellin (FliC) in an engineered T cell. Secretion of the flagellin payload from the T cell is dependent on synNotch binding GFP present on the surface of an inducer cell. To detect and measure innate immune response induction a Secreted Alkaline Phosphatase (SEAP) reporter was used where binding of flagellin to Toll-like receptor 5 (TLR5) on the surface of a TLR5 reporter cell drives expression of SEAP allowing quantification of innate immune response activity.

Figure 21:
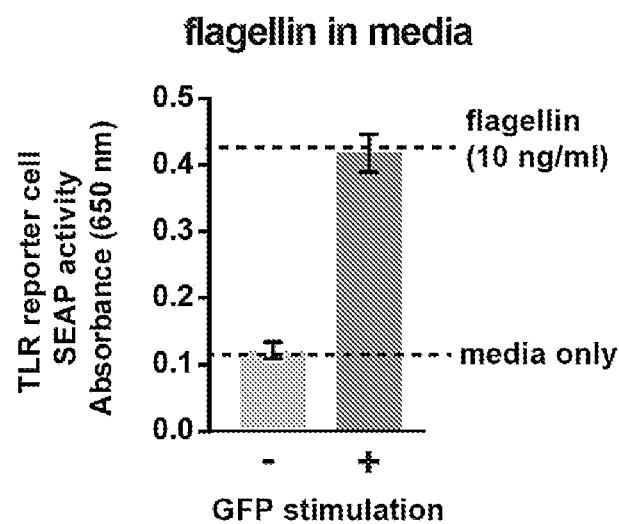
FIG. 21 provides quantification of the induced innate immune mediator reporter assay depicted in FIG. 20.

T cells engineered with the above described system were cultured in the presence of TLR5 reporter cells. TLR reporter cell SEAP activity was measured by absorbance at 650 nm with or without GFP stimulation using surface-expressing GFP+ inducer cells. The results of this assay, presented in FIG. 21, showed that the innate immune response was specifically activated in a GFP dependent manner. This example demonstrates that synNotch can be used to specifically and/or locally induce an innate immune response by driving the expression of an innate immune response inducing polypeptide using an antigen dependent synNotch polypeptide.

Example 5: Treating Heterogeneous Tumors

A multi-component strategy was developed, as depicted in FIG. 22, to program a T cell to recognize a heterogeneous tumor. The T cell is programed to (1) recognize priming cells present in the heterogeneous tumor using a tumor specific antigen that is specific to the tumor but not present in all tumor cells and (2) kill nearby cells of the heterogeneous tumor using a tumor associated antigen that is present in all tumor cells but is not tumor specific.

The use of a synNotch system to treat a heterogeneous tumor was investigated using a representative model system. Specifically, as depicted in FIG. 23, a T cells was engineered to produce a "priming" synNotch receptor specific for a GFP priming antigen and a "killing" CAR specific for CD19. The system was designed such that when the synNotch priming receptor binds the GFP priming antigen the freed intracellular domain of the synNotch drives expression of the CD19-specific killing CAR, resulting in cell killing when CD19 is present.

As depicted in FIG. 24, when a population of target cells expressing CD19 but not the GFP priming antigen were treated with the engineered T cells no killing of the target cells was observed. When a heterogeneous population of cells that included dual-expressing CD19+/GFP+ target cells as well as CD19+/GFP− target cells was treated with the engineered T cells, killing of the both the CD19+/GFP+ target cells and the CD19+/GFP− target cells was observed. This result demonstrated that the presence of the GFP antigen in the heterogeneous population primed the engineered T cells for CD19-specific killing generally and that cell killing by the engineered T cells was not limited to those cells expressing the priming antigen.

Figure 25:
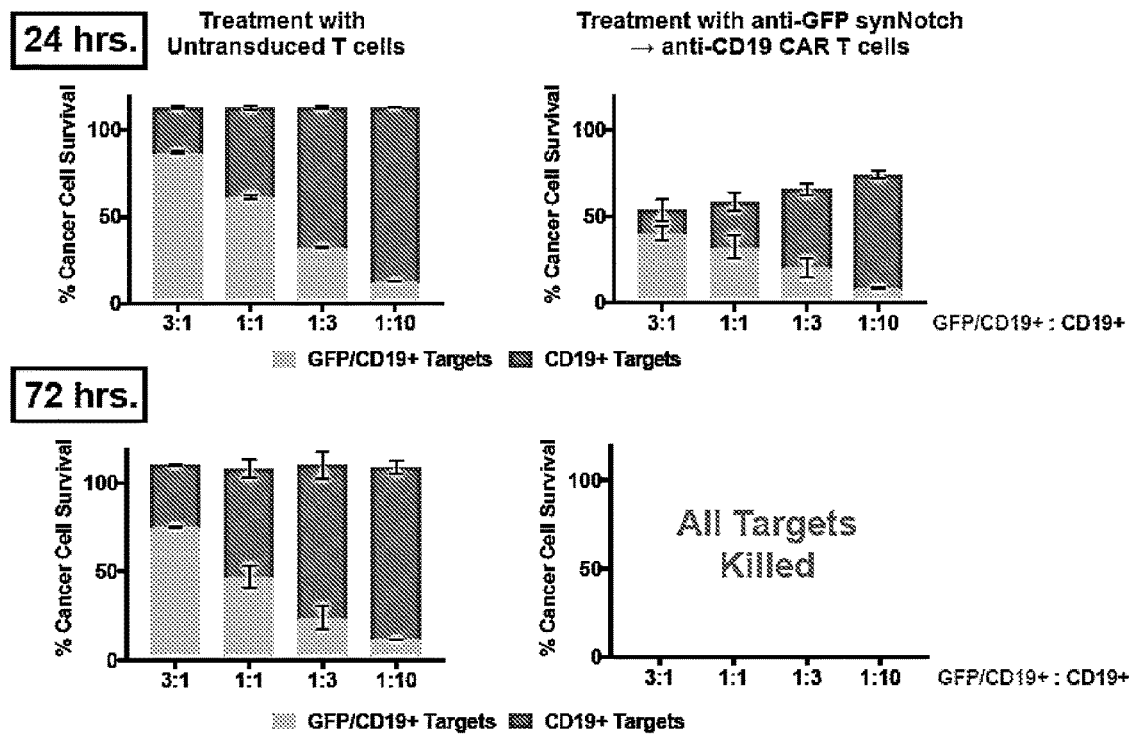
FIG. 25 provides further quantification of the model of heterogeneous tumor killing depicted in FIG. 23 using model tumors of various ratios of priming antigen-expressing cells and killing antigen-expressing cells. The "CD19+ target" bars are on top and "GFP/CD19+ target" bars are on bottom.

This effect of heterogeneous tumor cell killing was further quantified using populations with various ratios of GFP/CD19+ target cells to CD19+ only target cells. The heterogeneous population was treated with either anti-GFP synNotch→anti-CD19 CAR T cells or untransduced negative control T cells and time points were taken at 24 hours and 72 hours (FIG. 25). No cell killing was observed in any of the populations when treated with the untransduced cells. However, at 24 hours substantial cell killing was observed in all populations following treatment with the anti-GFP synNotch→anti-CD19 CAR T cells and by 72 hours all target cells were eliminated.

These results demonstrate that, regardless of the degree of tumor heterogeneity or the relative abundance/scarcity of the priming antigen, specific and effective tumor cells killing of heterogeneous tumors is achieved using such a priming→killing synNotch gated system. Put another way, the described system is effective and specific whether the heterogeneous tumor contains a high or a low percentage of priming antigen expressing cells.

Figure 26:
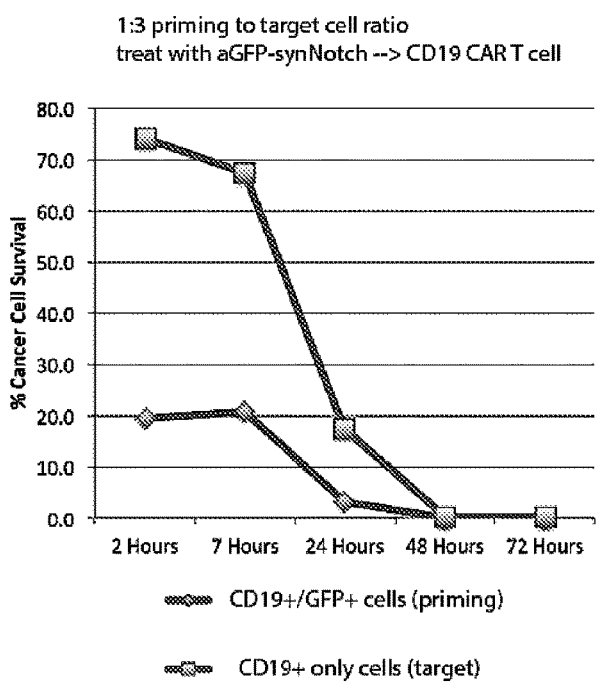
FIG. 26 provides a time-course of heterogeneous tumor killing according to the model system depicted in FIG. 23 for a tumor having a 1:3 ratio of priming antigen-expressing cells to killing antigen-expressing cells.

Higher temporal resolution of the killing effects of the system on the priming and non-priming ("target") populations in a 1:3 priming to target heterogeneous mix is provided in FIG. 26. As described above, all cells of both populations are eliminated by 72 hours post treatment.

Figure 27:
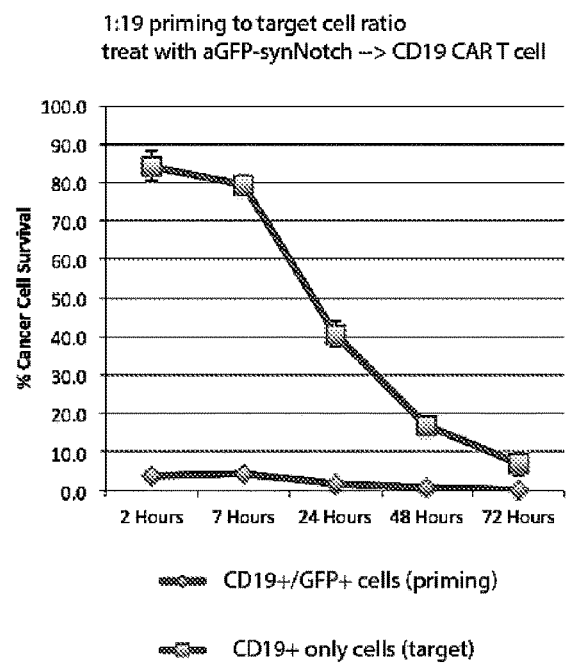
FIG. 27 provides a time-course of heterogeneous tumor killing according to the model system depicted in FIG. 23 for a tumor having a 1:19 ratio of priming antigen-expressing cells to killing antigen-expressing cells.

As can be seen in FIG. 27, even when the ratio of priming cells to non-priming target cells is as low as 1:19, the CD19+ non-priming antigen target cells are effectively killed with similar temporal dynamics to that seen in FIG. 26. By 72 hours less than 10% of the original population of target cells remained. Collectively, these results demonstrate that synNotch gated tumor cell killing systems are effective at specifically treating heterologous tumors regardless of the relative representation of cells expressing the synNotch priming antigen within the tumor.

Example 6: Controlled Expression of Immuno Suppressive Agents

Figure 28:
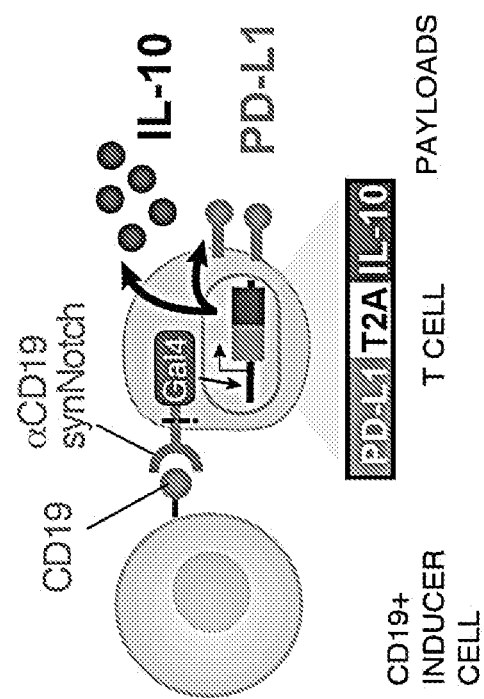
FIG. 28 schematically depicts CD4+ T cells engineered with an α-CD19 synNotch receptor controlling the expression of immunosuppressive agents PD-L1 and IL-10.

In addition to driving immune responses in cancer immunotherapy, the proteolytically cleavable chimeric polypeptides were also investigated for useful functions outside of cancer therapy. One application that was investigated using an exemplary synNotch was immunosuppression, e.g., in an autoimmune setting. SynNotch T cells were engineered that drive the simultaneous production of paracrine inhibitory signals such as the cytokine, IL-10, and the T cell inhibitory ligand, PD-L1, which drives cell-to-contact inhibition (FIG. 28).

Figure 29:
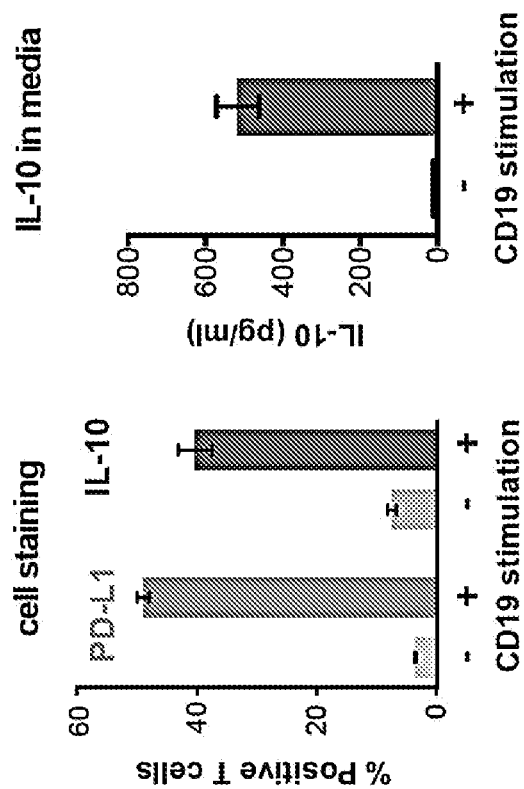
FIG. 29 provides quantification of the percentage of synNotch T cells that express PD-L1 and intracellular IL-10 after co-culture with CD19+ or CD19− K562s for 24 hrs as depicted in FIG. 28. The amount of IL-10 in the supernatant was also determined by ELISA.

As assayed using CD19 stimulation, the anti-CD19 synNotch receptor was able to drive both suppressive agents (PD-L1 and IL-10) in response to stimulation with CD19+ K562s (FIG. 29). This example, as well as other examples of synNotch receptor T cells controlling non-native synthetic T cell responses, highlight the widely diverse applications of synNotch engineered cells to produce a spectrum of therapeutic agents that can enhance the effectiveness of the therapeutic cells or reprogram a tissue or disease environment to restore homeostasis and natural function.

Figure 33:
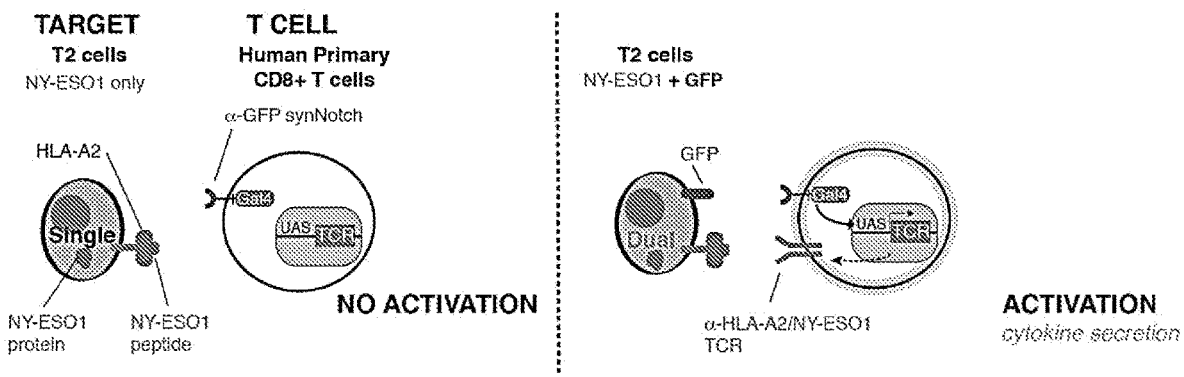
FIG. 33 schematically depicts a proteolytically cleavable chimeric polypeptide-gated circuit driving expression of either a wild-type affinity or an enhanced affinity TCR.

Example 7: Dual-Antigen Gated Cytokine Secretion Using Wild-Type Affinity and Enhanced Affinity TCRs An additional dual-antigen AND-gate was designed for surface antigen gated TCR expression to test CD8 T cell cytokine secretion in response to targeting cells expressing both the target surface antigen (surface-expressed GFP) and an intracellular target antigen (NY-ESO). Specifically, as schematically presented in FIG. 33, CD8 T cells were engineered with an anti-GFP synNotch controlling the expression of an anti-HLA-A2/NY-ESO1 TCR such that release the cytokine interferon gamma occurs in response to T2 target cells expressing both surface-expressed-GFP and HLA-A2/NY-ESO1. The system was tested with both wild-type affinity and affinity enhanced anti-HLA-A2/NY-ESO1 TCR.

Figure 34:
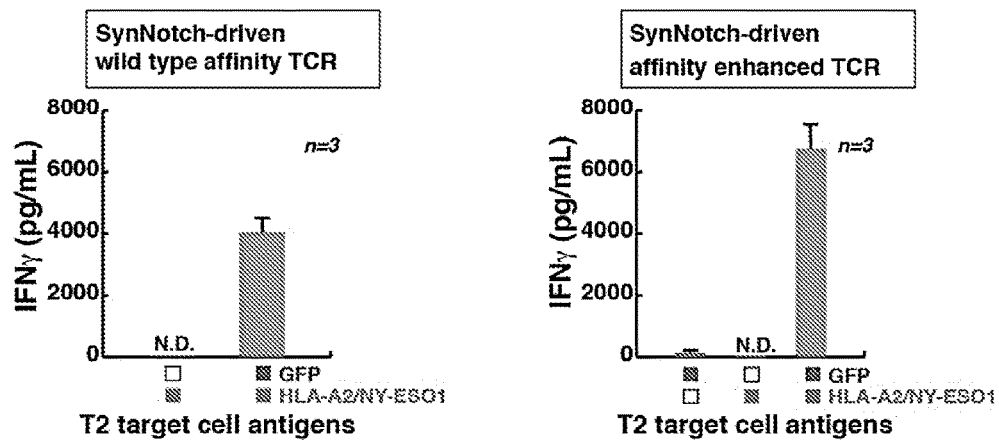
FIG. 34 depicts dual-antigen gated cytokine secretion according to the system depicted in FIG. 33.

As shown in FIG. 34, CD8 T cells having anti-GFP synNotch gated expression of either TCR were activated and secreted IFNγ only in the presence of dual-antigen GFP+/HLA-A2/NY-ESO1+ T2 target cells. Furthermore, the level of CD8 T cell activation (as measured by IFNγ release) was dependent on the affinity of the TCR for its target antigen, as the affinity enhanced TCR cells produced nearly twice as much IFNγ, as compared to the wild-type affinity TCR cells, upon target cell engagement.

These results demonstrate dual-antigen (surface antigen and intracellular antigen) gated cytokine secretion using wild-type affinity and enhanced affinity TCRs. The data also show that the level of T cell activation and cytokine secretion may be modulated through the gated expression of TCRs having different affinities to their target antigen.

Example 8: Dual-Antigen Gated CD4 T Cell Cytokine Secretion

Figure 35:
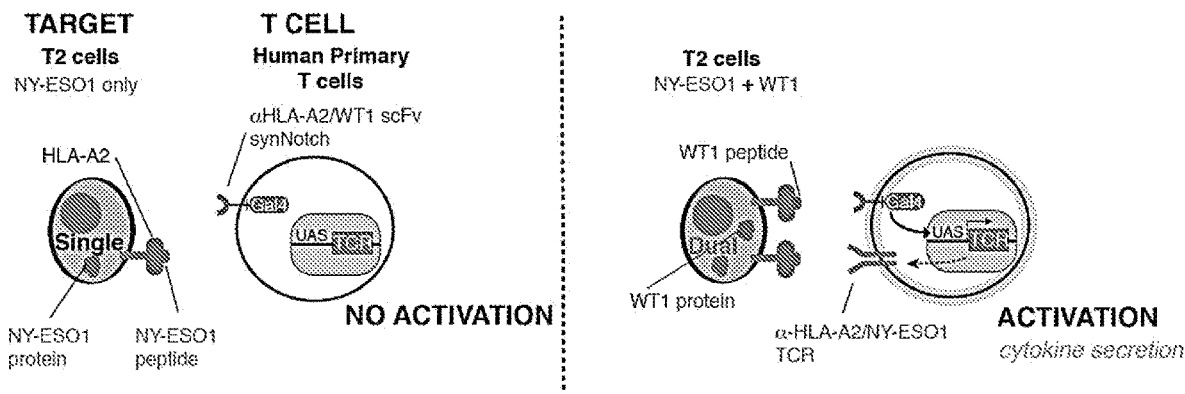
FIG. 35 schematically depicts a proteolytically cleavable chimeric polypeptide-gated circuit driving expression of a TCR in an engineered CD4 T cell.
Figure 36:
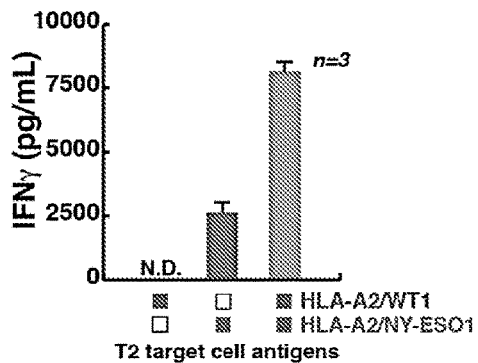
FIG. 36 depicts high level cytokine secretion in response to target cells expressing the targeted dual-antigens according to the system depicted in FIG. 35.

CD4 T cell activation and cytokine secretion was tested in CD4 T cells engineered with an anti-HLA-A2/WT1 synNotch controlling an anti-HLA-A2/NY-ESO1 TCR (as schematized in FIG. 35). As shown by the data provided in FIG. 36, the anti-HLA-A2/WT1 synNotch and anti-HLA-A2/NY-ESO1 TCR expressing cells release high levels of IFNγ specifically in response to T2 target cells expressing both HLA-A2/WT1 and HLA-A2/NY-ESO1 antigens. Some low level of cytokine secretion was seen in response to T2 target cells expressing only HLA-A2/NY-ESO1 due to partial recognition of HLA-A2 alone by the anti-HLA-A2/WT1 synNotch. Testing of multiple different anti-HLA-A2/WT1 scFvs in synNotch receptors has revealed low level measureable recognition of anti-HLA-A2 alone regardless of the specific WT1 peptide targeted. However, the high level increase of cellular activation and cytokine release in response to target cells expressing both antigens indicates that such background HLA-A2 partial recognition does not appreciably impact dual-antigen targeting and specificity.

Example 9: Clinically Relevant Dual-Antigen Targeting

Figure 37:
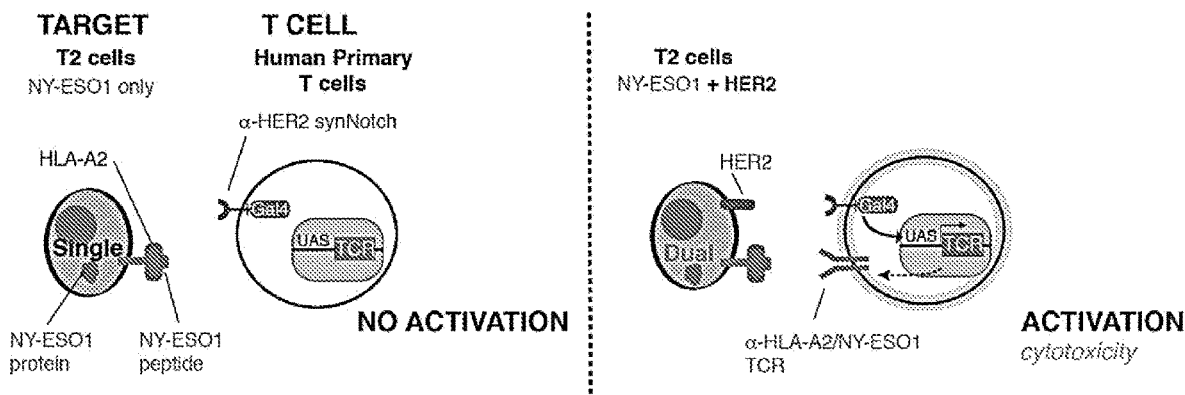
FIG. 37 schematically depicts a proteolytically cleavable chimeric polypeptide-gated circuit targeting a clinically relevant antigen pair using engineered CD4 or CD8 T cells.

To further demonstrate the versatility of the described surface antigen/pMHC antigen AND-gating strategy using a clinically relevant antigen pair, both CD8 and CD4 T cells were engineered with an anti-HER2 synNotch controlling an anti-HLA-A2/NY-ESO1 TCR. Her2 and HLA-A2/NY-ESO1 are found co-expressed in various cancers, including breast cancer and glioma. A schematic depicting this gating/targeting strategy is provided in FIG. 37.

Figure 38:
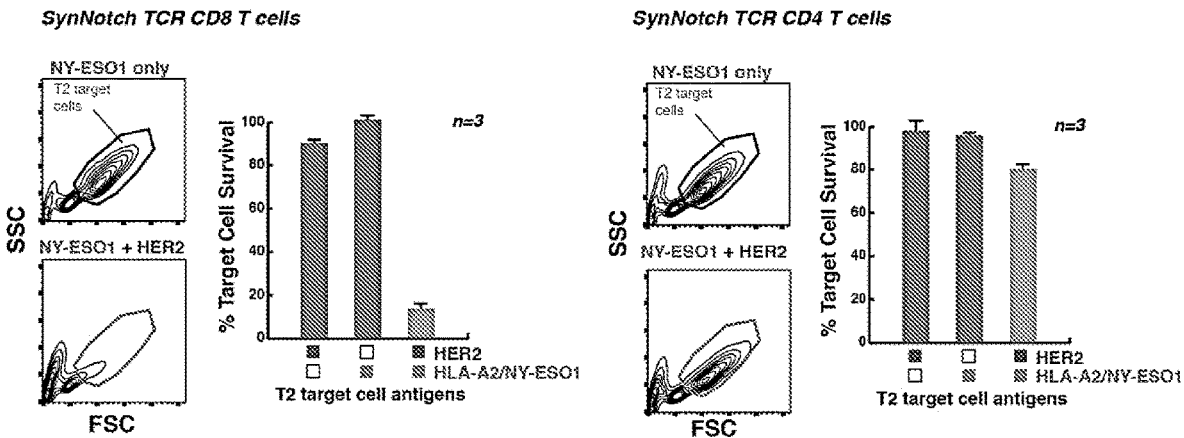
FIG. 38 depicts specific killing of target cells expressing the clinically relevant antigen pair by both engineered CD8 and CD4 T cells according to the system depicted in FIG. 37.

As shown in the results provided in FIG. 38, both the engineered CD8 and CD4 T cells specifically killed target T2 cells expressing both target antigens (HER2 and HLA-A2/NY-ESO1). Control cells expressing only one of the two antigens were not affected. Notably, the specific killing of dual-antigen target cells by the engineered CD4 cells demonstrated that surface antigen/pMHC antigen recognition circuits can induce target killing in a CD8-independent manner.

Collectively, the results of this example demonstrate that cells expressing clinically relevant antigen pairs, including those targeting at least one intracellular antigen, can be effectively targeted and killed using engineered dual-antigen gated CD8 T cells and/or dual-antigen gated CD4 T cells.

Figure 41:
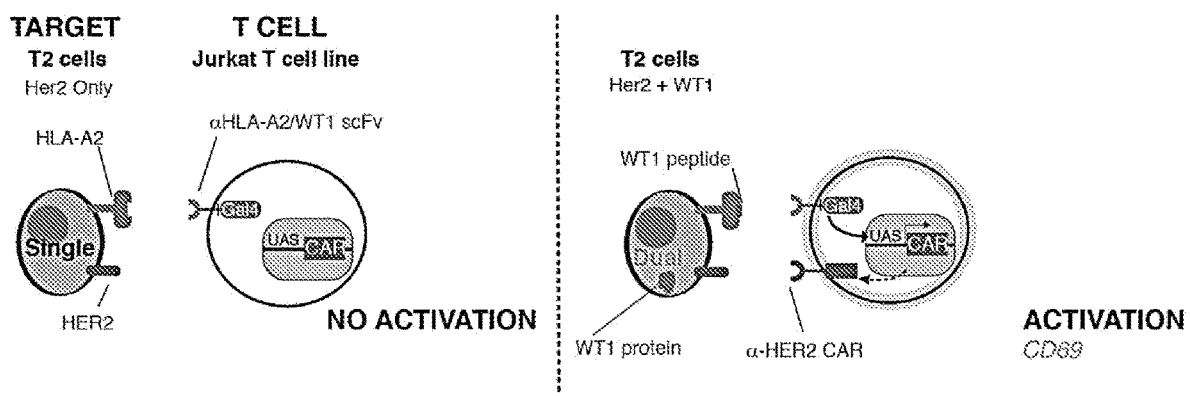
FIG. 41 schematically depicts an inside-outside proteolytically cleavable chimeric polypeptide-gated circuit utilizing an anti-HLA-A2/WT1 specific chimeric polypeptide driving expression of an anti-HER2 CAR.
Figure 42:
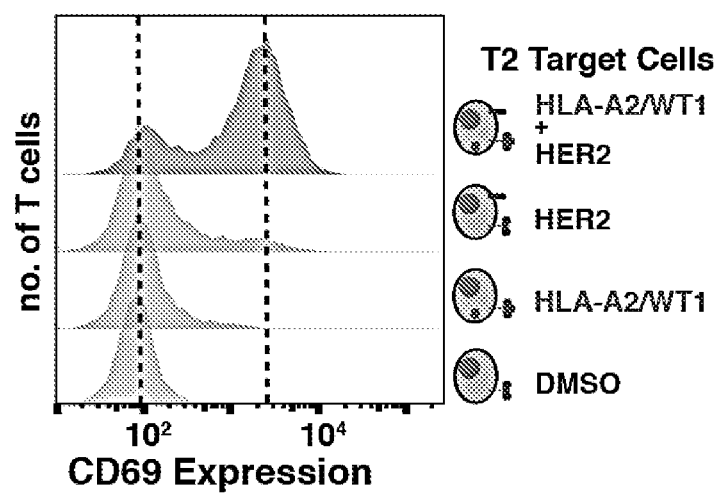
FIG. 42 depicts the specific activation of T cells expressing the circuit schematically depicted in FIG. 41 only in the presence of target cells expressing both the inside antigen (HLA-A2/WT1) and the outside antigen (HER2).

Example 10: Dual-Antigen Targeting with pMHC-Sensing synNotch Controlling CAR Expression To further demonstrate the versatility of this approach, additional dual-antigen AND-gates containing a CAR were designed and tested targeting cells expressing both a surface target antigen and an intracellular target antigen. An exemplary system is depicted in FIG. 41, where, as designed and engineered into T cells, expression of an anti-Her2 CAR is induced by the freed intracellular domain of an anti-HLA-A2/WT1 synNotch. This circuit serves as an example of a pMHC-specific synNotch receptor controlling expression of a surface antigen-specific CAR. When presented with a T2 target cell expressing Her2 only, expression of the anti-Her2 CAR is not induced and no T cell activation occurs. However, when presented with a T2 target cell expressing both WT1 and Her2, binding of surface-HLA-A2/WT1 to the anti-HLA-A2/WT1 synNotch induces cleavage of the Notch polypeptide, releasing a GAL4 transcription activator which binds a UAS driving expression of the anti-Her2 CAR. Binding of the expressed anti-Her2 CAR to Her2 on the target cell causes activation of the T cell. The resulting activation, as measured using CD69 expression, of a Jurkat T cell line engineered to express this dual-antigen circuit is provided in FIG. 42. The results of this assay showed that T cell activation (i.e. CD69 upregulation) was dependent on expression of both target antigens by the target cells, again demonstrating the robust specificity of dual-antigen syn-Notch AND-gates. This example, with a pMHC-specific synNotch receptor controlling expression of a surface antigen-specific CAR, also shows the wide diversity of antigen combinations that may be employed in dual-antigen syn-Notch AND-gates.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 134

<210> SEQ ID NO 1
<211> LENGTH: 2555
<212> TYPE: PRT
<213> ORGANISM: Homo sapiens

<400> SEQUENCE: 1

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110
```

```
Asn Gly Gly Thr Cys Asp Leu Leu Thr Leu Thr Glu Tyr Lys Cys Arg
            115                 120                 125
Cys Pro Pro Gly Trp Ser Gly Lys Ser Cys Gln Gln Ala Asp Pro Cys
        130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
            180                 185                 190
Gly Thr Cys His Asn Glu Val Gly Ser Tyr Arg Cys Val Cys Arg Ala
        195                 200                 205
Thr His Thr Gly Pro Asn Cys Glu Arg Pro Tyr Val Pro Cys Ser Pro
    210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
```

```
               530                 535                 540
Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                    565                 570                 575

Tyr Gly Ser Cys Lys Asp Gly Val Ala Thr Phe Thr Cys Leu Cys Arg
                580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
        610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                    645                 650                 655

Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                    725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
        770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                    805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
        850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                    885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Arg Gly Thr Phe Cys Glu Glu
        930                 935                 940

Asp Ile Asn Glu Cys Ala Ser Asp Pro Cys Arg Asn Gly Ala Asn Cys
945                 950                 955                 960
```

```
Thr Asp Cys Val Asp Ser Tyr Thr Cys Thr Cys Pro Ala Gly Phe Ser
            965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
            995                 1000                1005

Cys Pro Pro Gly Phe Thr Gly Ser Tyr Cys Gln His Asp Val Asn
            1010            1015            1020

Glu Cys Asp Ser Gln Pro Cys Leu His Gly Thr Cys Gln Asp
            1025            1030            1035

Gly Cys Gly Ser Tyr Arg Cys Thr Cys Pro Gln Gly Tyr Thr Gly
            1040            1045            1050

Pro Asn Cys Gln Asn Leu Val His Trp Cys Asp Ser Ser Pro Cys
            1055            1060            1065

Lys Asn Gly Gly Lys Cys Trp Gln Thr His Thr Gln Tyr Arg Cys
            1070            1075            1080

Glu Cys Pro Ser Gly Trp Thr Gly Leu Tyr Cys Asp Val Pro Ser
            1085            1090            1095

Val Ser Cys Glu Val Ala Ala Gln Arg Gln Gly Val Asp Val Ala
            1100            1105            1110

Arg Leu Cys Gln His Gly Gly Leu Cys Val Asp Ala Gly Asn Thr
            1115            1120            1125

His His Cys Arg Cys Gln Ala Gly Tyr Thr Gly Ser Tyr Cys Glu
            1130            1135            1140

Asp Leu Val Asp Glu Cys Ser Pro Ser Pro Cys Gln Asn Gly Ala
            1145            1150            1155

Thr Cys Thr Asp Tyr Leu Gly Gly Tyr Ser Cys Lys Cys Val Ala
            1160            1165            1170

Gly Tyr His Gly Val Asn Cys Ser Glu Glu Ile Asp Glu Cys Leu
            1175            1180            1185

Ser His Pro Cys Gln Asn Gly Gly Thr Cys Leu Asp Leu Pro Asn
            1190            1195            1200

Thr Tyr Lys Cys Ser Cys Pro Arg Gly Thr Gln Gly Val His Cys
            1205            1210            1215

Glu Ile Asn Val Asp Asp Cys Asn Pro Pro Val Asp Pro Val Ser
            1220            1225            1230

Arg Ser Pro Lys Cys Phe Asn Asn Gly Thr Cys Val Asp Gln Val
            1235            1240            1245

Gly Gly Tyr Ser Cys Thr Cys Pro Pro Gly Phe Val Gly Glu Arg
            1250            1255            1260

Cys Glu Gly Asp Val Asn Glu Cys Leu Ser Asn Pro Cys Asp Ala
            1265            1270            1275

Arg Gly Thr Gln Asn Cys Val Gln Arg Val Asn Asp Phe His Cys
            1280            1285            1290

Glu Cys Arg Ala Gly His Thr Gly Arg Arg Cys Glu Ser Val Ile
            1295            1300            1305

Asn Gly Cys Lys Gly Lys Pro Cys Lys Asn Gly Gly Thr Cys Ala
            1310            1315            1320

Val Ala Ser Asn Thr Ala Arg Gly Phe Ile Cys Lys Cys Pro Ala
            1325            1330            1335

Gly Phe Glu Gly Ala Thr Cys Glu Asn Asp Ala Arg Thr Cys Gly
            1340            1345            1350
```

-continued

```
Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
```

```
              1745                1750                1755

Lys Arg  Arg Arg Gln His  Gly Gln Leu Trp  Phe Pro Glu Gly  Phe
         1760             1765             1770

Lys Val  Ser Glu Ala Ser  Lys Lys Arg Arg  Glu Pro Leu Gly
1775                      1780             1785

Glu Asp  Ser Val Gly Leu  Lys Pro Leu Lys  Asn Ala Ser Asp  Gly
         1790             1795             1800

Ala Leu  Met Asp Asp Asn  Gln Asn Glu Trp  Gly Asp Glu Asp  Leu
1805                      1810             1815

Glu Thr  Lys Lys Phe Arg  Phe Glu Glu Pro  Val Val Leu Pro  Asp
         1820             1825             1830

Leu Asp  Asp Gln Thr Asp  His Arg Gln Trp  Thr Gln Gln His  Leu
1835                      1840             1845

Asp Ala  Ala Asp Leu Arg  Met Ser Ala Met  Ala Pro Thr Pro  Pro
         1850             1855             1860

Gln Gly  Glu Val Asp Ala  Asp Cys Met Asp  Val Asn Val Arg  Gly
1865                      1870             1875

Pro Asp  Gly Phe Thr Pro  Leu Met Ile Ala  Ser Cys Ser Gly  Gly
         1880             1885             1890

Gly Leu  Glu Thr Gly Asn  Ser Glu Glu Glu  Glu Asp Ala Pro  Ala
1895                      1900             1905

Val Ile  Ser Asp Phe Ile  Tyr Gln Gly Ala  Ser Leu His Asn  Gln
         1910             1915             1920

Thr Asp  Arg Thr Gly Glu  Thr Ala Leu His  Leu Ala Ala Arg  Tyr
1925                      1930             1935

Ser Arg  Ser Asp Ala Ala  Lys Arg Leu Leu  Glu Ala Ser Ala  Asp
         1940             1945             1950

Ala Asn  Ile Gln Asp Asn  Met Gly Arg Thr  Pro Leu His Ala  Ala
1955                      1960             1965

Val Ser  Ala Asp Ala Gln  Gly Val Phe Gln  Ile Leu Ile Arg  Asn
         1970             1975             1980

Arg Ala  Thr Asp Leu Asp  Ala Arg Met His  Asp Gly Thr Thr  Pro
1985                      1990             1995

Leu Ile  Leu Ala Ala Arg  Leu Ala Val Glu  Gly Met Leu Glu  Asp
         2000             2005             2010

Leu Ile  Asn Ser His Ala  Asp Val Asn Ala  Val Asp Asp Leu  Gly
2015                      2020             2025

Lys Ser  Ala Leu His Trp  Ala Ala Ala Val  Asn Asn Val Asp  Ala
         2030             2035             2040

Ala Val  Val Leu Leu Lys  Asn Gly Ala Asn  Lys Asp Met Gln  Asn
2045                      2050             2055

Asn Arg  Glu Glu Thr Pro  Leu Phe Leu Ala  Ala Arg Glu Gly  Ser
         2060             2065             2070

Tyr Glu  Thr Ala Lys Val  Leu Leu Asp His  Phe Ala Asn Arg  Asp
2075                      2080             2085

Ile Thr  Asp His Met Asp  Arg Leu Pro Arg  Asp Ile Ala Gln  Glu
         2090             2095             2100

Arg Met  His His Asp Ile  Val Arg Leu Leu  Asp Glu Tyr Asn  Leu
2105                      2110             2115

Val Arg  Ser Pro Gln Leu  His Gly Ala Pro  Leu Gly Gly Thr  Pro
         2120             2125             2130

Thr Leu  Ser Pro Pro Leu  Cys Ser Pro Asn  Gly Tyr Leu Gly  Ser
2135                      2140             2145
```

```
Leu Lys Pro Gly Val Gln Gly Lys Lys Val Arg Lys Pro Ser Ser
    2150                2155                2160

Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235

Asp Thr His Leu Gly Ile Gly His Leu Asn Val Ala Ala Lys Pro
    2240                2245                2250

Glu Met Ala Ala Leu Gly Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535
```

```
Pro Pro Thr Ser Met Gln Ser Gln Ile Ala Arg Ile Pro Glu Ala
    2540                2545                2550

Phe Lys
    2555

<210> SEQ ID NO 2
<211> LENGTH: 2531
<212> TYPE: PRT
<213> ORGANISM: Mus musculus

<400> SEQUENCE: 2

Met Pro Arg Leu Leu Thr Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
            20                  25                  30

Asn Gly Gly Arg Cys Glu Val Ala Asn Gly Thr Glu Ala Cys Val Cys
        35                  40                  45

Ser Gly Ala Phe Val Gly Gln Arg Cys Gln Asp Ser Asn Pro Cys Leu
    50                  55                  60

Ser Thr Pro Cys Lys Asn Ala Gly Thr Cys His Val Val Asp His Gly
65              70                  75                  80

Gly Thr Val Asp Tyr Ala Cys Ser Cys Pro Leu Gly Phe Ser Gly Pro
                85                  90                  95

Leu Cys Leu Thr Pro Leu Asp Asn Ala Cys Leu Ala Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ser
145                 150                 155                 160

Ser Tyr Ile Cys Arg Cys Pro Pro Gly Phe His Gly Pro Thr Cys Arg
                165                 170                 175

Gln Asp Val Asn Glu Cys Ser Gln Asn Pro Gly Leu Cys Arg His Gly
            180                 185                 190

Gly Thr Cys His Asn Glu Ile Gly Ser Tyr Arg Cys Ala Cys Arg Ala
        195                 200                 205

Thr His Thr Gly Pro His Cys Glu Leu Pro Tyr Val Pro Cys Ser Pro
    210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255

Asn Val Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe Gln Gly Ala Thr Cys His Asp
            340                 345                 350
```

```
Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
        370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Ile Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
                485                 490                 495

Ser Pro Cys Leu His Asn Gly His Cys Met Asp Lys Ile Asn Glu Phe
            500                 505                 510

Gln Cys Gln Cys Pro Lys Gly Phe Asn Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
        595                 600                 605

Ser Gln Pro Cys Arg His Gly Gly Thr Cys Gln Asp Arg Asp Asn Ser
    610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765
```

```
Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
                820                 825                 830

Cys Ala Thr Ser Pro Cys Lys Asn Ser Gly Val Cys Lys Glu Ser Glu
                835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
                900                 905                 910

Pro Asn Pro Cys His Asn Gly Gly Ser Cys Thr Asp Gly Ile Asn Thr
                915                 920                 925

Ala Phe Cys Asp Cys Leu Pro Gly Phe Gln Gly Ala Phe Cys Glu Glu
930                 935                 940

Asp Ile Asn Glu Cys Ala Ser Asn Pro Cys Gln Asn Gly Ala Asn Cys
945                 950                 955                 960

Thr Asp Cys Val Asp Ser Tyr Thr Cys Thr Cys Pro Val Gly Phe Asn
                965                 970                 975

Gly Ile His Cys Glu Asn Asn Thr Pro Asp Cys Thr Glu Ser Ser Cys
                980                 985                 990

Phe Asn Gly Gly Thr Cys Val Asp Gly Ile Asn Ser Phe Thr Cys Leu
                995                 1000                1005

Cys Pro Pro Gly Phe Thr Gly Ser Tyr Cys Gln Tyr Asp Val Asn
1010                1015                1020

Glu Cys Asp Ser Arg Pro Cys Leu His Gly Gly Thr Cys Gln Asp
1025                1030                1035

Ser Tyr Gly Thr Tyr Lys Cys Thr Cys Pro Gln Gly Tyr Thr Gly
1040                1045                1050

Leu Asn Cys Gln Asn Leu Val Arg Trp Cys Asp Ser Ala Pro Cys
1055                1060                1065

Lys Asn Gly Gly Arg Cys Trp Gln Thr Asn Thr Gln Tyr His Cys
1070                1075                1080

Glu Cys Arg Ser Gly Trp Thr Gly Val Asn Cys Asp Val Leu Ser
1085                1090                1095

Val Ser Cys Glu Val Ala Ala Gln Lys Arg Gly Ile Asp Val Thr
1100                1105                1110

Leu Leu Cys Gln His Gly Gly Leu Cys Val Asp Glu Gly Asp Lys
1115                1120                1125

His Tyr Cys His Cys Gln Ala Gly Tyr Thr Gly Ser Tyr Cys Glu
1130                1135                1140

Asp Glu Val Asp Glu Cys Ser Pro Asn Pro Cys Gln Asn Gly Ala
1145                1150                1155

Thr Cys Thr Asp Tyr Leu Gly Gly Phe Ser Cys Lys Cys Val Ala
1160                1165                1170

Gly Tyr His Gly Ser Asn Cys Ser Glu Glu Ile Asn Glu Cys Leu
```

```
                1175               1180                1185

Ser Gln Pro Cys Gln Asn Gly Gly Thr Cys Ile Asp Leu Thr Asn
    1190                1195                1200

Ser Tyr Lys Cys Ser Cys Pro Arg Gly Thr Gln Gly Val His Cys
    1205                1210                1215

Glu Ile Asn Val Asp Asp Cys His Pro Pro Leu Asp Pro Ala Ser
    1220                1225                1230

Arg Ser Pro Lys Cys Phe Asn Asn Gly Thr Cys Val Asp Gln Val
    1235                1240                1245

Gly Gly Tyr Thr Cys Thr Cys Pro Pro Gly Phe Val Gly Glu Arg
    1250                1255                1260

Cys Glu Gly Asp Val Asn Glu Cys Leu Ser Asn Pro Cys Asp Pro
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Arg Gly Lys Pro Cys Lys Asn Gly Gly Val Cys Ala
    1310                1315                1320

Val Ala Ser Asn Thr Ala Arg Gly Phe Ile Cys Arg Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Ser Phe Thr Gly Pro Glu Cys
    1370                1375                1380

Gln Phe Pro Ala Ser Ser Pro Cys Val Gly Ser Asn Pro Cys Tyr
    1385                1390                1395

Asn Gln Gly Thr Cys Glu Pro Thr Ser Glu Asn Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Thr Gly Gly Ala Gly Arg Asp Ile Pro Pro Pro
    1430                1435                1440

Gln Ile Glu Glu Ala Cys Glu Leu Pro Glu Cys Gln Val Asp Ala
    1445                1450                1455

Gly Asn Lys Val Cys Asn Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Leu Thr Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Leu Val Val
    1565                1570                1575
```

```
Leu Leu Pro Pro Asp Gln Leu Arg Asn Asn Ser Phe His Phe Leu
1580            1585                1590

Arg Glu Leu Ser His Val Leu His Thr Asn Val Val Phe Lys Arg
1595            1600                1605

Asp Ala Gln Gly Gln Gln Met Ile Phe Pro Tyr Tyr Gly His Glu
1610            1615                1620

Glu Glu Leu Arg Lys His Pro Ile Lys Arg Ser Thr Val Gly Trp
1625            1630                1635

Ala Thr Ser Ser Leu Leu Pro Gly Thr Ser Gly Gly Arg Gln Arg
1640            1645                1650

Arg Glu Leu Asp Pro Met Asp Ile Arg Gly Ser Ile Val Tyr Leu
1655            1660                1665

Glu Ile Asp Asn Arg Gln Cys Val Gln Ser Ser Gln Cys Phe
1670            1675                1680

Gln Ser Ala Thr Asp Val Ala Ala Phe Leu Gly Ala Leu Ala Ser
1685            1690                1695

Leu Gly Ser Leu Asn Ile Pro Tyr Lys Ile Glu Ala Val Lys Ser
1700            1705                1710

Glu Pro Val Glu Pro Pro Leu Pro Ser Gln Leu His Leu Met Tyr
1715            1720                1725

Val Ala Ala Ala Ala Phe Val Leu Leu Phe Phe Val Gly Cys Gly
1730            1735                1740

Val Leu Leu Ser Arg Lys Arg Arg Arg Gln His Gly Gln Leu Trp
1745            1750                1755

Phe Pro Glu Gly Phe Lys Val Ser Glu Ala Ser Lys Lys Lys Arg
1760            1765                1770

Arg Glu Pro Leu Gly Glu Asp Ser Val Gly Leu Lys Pro Leu Lys
1775            1780                1785

Asn Ala Ser Asp Gly Ala Leu Met Asp Asp Asn Gln Asn Glu Trp
1790            1795                1800

Gly Asp Glu Asp Leu Glu Thr Lys Lys Phe Arg Phe Glu Glu Pro
1805            1810                1815

Val Val Leu Pro Asp Leu Ser Asp Gln Thr Asp His Arg Gln Trp
1820            1825                1830

Thr Gln Gln His Leu Asp Ala Ala Asp Leu Arg Met Ser Ala Met
1835            1840                1845

Ala Pro Thr Pro Pro Gln Gly Glu Val Asp Ala Asp Cys Met Asp
1850            1855                1860

Val Asn Val Arg Gly Pro Asp Gly Phe Thr Pro Leu Met Ile Ala
1865            1870                1875

Ser Cys Ser Gly Gly Gly Leu Glu Thr Gly Asn Ser Glu Glu Glu
1880            1885                1890

Glu Asp Ala Pro Ala Val Ile Ser Asp Phe Ile Tyr Gln Gly Ala
1895            1900                1905

Ser Leu His Asn Gln Thr Asp Arg Thr Gly Glu Thr Ala Leu His
1910            1915                1920

Leu Ala Ala Arg Tyr Ser Arg Ser Asp Ala Ala Lys Arg Leu Leu
1925            1930                1935

Glu Ala Ser Ala Asp Ala Asn Ile Gln Asp Asn Met Gly Arg Thr
1940            1945                1950

Pro Leu His Ala Ala Val Ser Ala Asp Ala Gln Gly Val Phe Gln
1955            1960                1965
```

```
Ile Leu Leu Arg Asn Arg Ala Thr Asp Leu Asp Ala Arg Met His
    1970                1975                1980

Asp Gly Thr Thr Pro Leu Ile Leu Ala Ala Arg Leu Ala Val Glu
    1985                1990                1995

Gly Met Leu Glu Asp Leu Ile Asn Ser His Ala Asp Val Asn Ala
    2000                2005                2010

Val Asp Asp Leu Gly Lys Ser Ala Leu His Trp Ala Ala Ala Val
    2015                2020                2025

Asn Asn Val Asp Ala Ala Val Val Leu Leu Lys Asn Gly Ala Asn
    2030                2035                2040

Lys Asp Met Gln Asn Asn Lys Glu Glu Thr Pro Leu Phe Leu Ala
    2045                2050                2055

Ala Arg Glu Gly Ser Tyr Glu Thr Ala Lys Val Leu Leu Asp His
    2060                2065                2070

Phe Ala Asn Arg Asp Ile Thr Asp His Met Asp Arg Leu Pro Arg
    2075                2080                2085

Asp Ile Ala Gln Glu Arg Met His His Asp Ile Val Arg Leu Leu
    2090                2095                2100

Asp Glu Tyr Asn Leu Val Arg Ser Pro Gln Leu His Gly Thr Ala
    2105                2110                2115

Leu Gly Gly Thr Pro Thr Leu Ser Pro Thr Leu Cys Ser Pro Asn
    2120                2125                2130

Gly Tyr Leu Gly Asn Leu Lys Ser Ala Thr Gln Gly Lys Lys Ala
    2135                2140                2145

Arg Lys Pro Ser Thr Lys Gly Leu Ala Cys Gly Ser Lys Glu Ala
    2150                2155                2160

Lys Asp Leu Lys Ala Arg Arg Lys Lys Ser Gln Asp Gly Lys Gly
    2165                2170                2175

Cys Leu Leu Asp Ser Ser Ser Met Leu Ser Pro Val Asp Ser Leu
    2180                2185                2190

Glu Ser Pro His Gly Tyr Leu Ser Asp Val Ala Ser Pro Pro Leu
    2195                2200                2205

Leu Pro Ser Pro Phe Gln Gln Ser Pro Ser Met Pro Leu Ser His
    2210                2215                2220

Leu Pro Gly Met Pro Asp Thr His Leu Gly Ile Ser His Leu Asn
    2225                2230                2235

Val Ala Ala Lys Pro Glu Met Ala Ala Leu Ala Gly Gly Ser Arg
    2240                2245                2250

Leu Ala Phe Glu Pro Pro Pro Arg Leu Ser His Leu Pro Val
    2255                2260                2265

Ala Ser Ser Ala Ser Thr Val Leu Ser Thr Asn Gly Thr Gly Ala
    2270                2275                2280

Met Asn Phe Thr Val Gly Ala Pro Ala Ser Leu Asn Gly Gln Cys
    2285                2290                2295

Glu Trp Leu Pro Arg Leu Gln Asn Gly Met Val Pro Ser Gln Tyr
    2300                2305                2310

Asn Pro Leu Arg Pro Gly Val Thr Pro Gly Thr Leu Ser Thr Gln
    2315                2320                2325

Ala Ala Gly Leu Gln His Ser Met Met Gly Pro Leu His Ser Ser
    2330                2335                2340

Leu Ser Thr Asn Thr Leu Ser Pro Ile Ile Tyr Gln Gly Leu Pro
    2345                2350                2355

Asn Thr Arg Leu Ala Thr Gln Pro His Leu Val Gln Thr Gln Gln
```

```
                2360                2365                2370

Val Gln Pro Gln Asn Leu Gln Leu Gln Pro Gln Asn Leu Gln Pro
    2375                2380                2385

Pro Ser Gln Pro His Leu Ser Val Ser Ser Ala Ala Asn Gly His
    2390                2395                2400

Leu Gly Arg Ser Phe Leu Ser Gly Glu Pro Ser Gln Ala Asp Val
    2405                2410                2415

Gln Pro Leu Gly Pro Ser Ser Leu Pro Val His Thr Ile Leu Pro
    2420                2425                2430

Gln Glu Ser Gln Ala Leu Pro Thr Ser Leu Pro Ser Ser Met Val
    2435                2440                2445

Pro Pro Met Thr Thr Thr Gln Phe Leu Thr Pro Pro Ser Gln His
    2450                2455                2460

Ser Tyr Ser Ser Ser Pro Val Asp Asn Thr Pro Ser His Gln Leu
    2465                2470                2475

Gln Val Pro Glu His Pro Phe Leu Thr Pro Ser Pro Glu Ser Pro
    2480                2485                2490

Asp Gln Trp Ser Ser Ser Ser Pro His Ser Asn Ile Ser Asp Trp
    2495                2500                2505

Ser Glu Gly Ile Ser Ser Pro Pro Thr Thr Met Pro Ser Gln Ile
    2510                2515                2520

Thr His Ile Pro Glu Ala Phe Lys
    2525                2530

<210> SEQ ID NO 3
<211> LENGTH: 1429
<212> TYPE: PRT
<213> ORGANISM: Caenorhabditis elegans

<400> SEQUENCE: 3

Met Arg Ile Pro Thr Ile Cys Phe Leu Phe Leu Leu Ile Ser Leu Ser
1               5                   10                  15

Lys Ser Leu His Ile Gly Ser Cys Leu Gly Leu Ile Cys Gly Arg Asn
            20                  25                  30

Gly His Cys His Ala Gly Pro Val Asn Gly Thr Gln Thr Ser Tyr Trp
        35                  40                  45

Cys Arg Cys Asp Glu Gly Phe Gly Gly Glu Tyr Cys Glu Gln Gln Cys
    50                  55                  60

Asp Val Ser Lys Cys Gly Ala Asp Glu Lys Cys Val Phe Asp Lys Asp
65                  70                  75                  80

Tyr Arg Met Glu Thr Cys Val Cys Lys Asp Cys Asp Ile Asn Gly Asn
                85                  90                  95

Ser Leu Leu Lys Pro Ser Cys Pro Ser Gly Tyr Gly Asp Asp Cys
            100                 105                 110

Lys Thr Gln Gly Trp Cys Tyr Pro Ser Val Cys Met Asn Gly Gly Gln
        115                 120                 125

Cys Ile Gly Ala Gly Asn Arg Ala Lys Cys Ala Cys Pro Asp Gly Phe
    130                 135                 140

Lys Gly Glu Arg Cys Glu Leu Asp Val Asn Glu Cys Glu Glu Asn Lys
145                 150                 155                 160

Asn Ala Cys Gly Asn Arg Ser Thr Cys Met Asn Thr Leu Gly Thr Tyr
                165                 170                 175

Ile Cys Val Cys Pro Gln Gly Phe Leu Pro Pro Asp Cys Leu Lys Pro
            180                 185                 190
```

-continued

Gly Asn Thr Ser Thr Val Glu Phe Lys Gln Pro Val Cys Phe Leu Glu
         195                 200                 205

Ile Ser Ala Asp His Pro Asp Gly Arg Ser Met Tyr Cys Gln Asn Gly
    210                 215                 220

Gly Phe Cys Asp Lys Ala Ser Ser Lys Cys Gln Cys Pro Pro Gly Tyr
225                 230                 235                 240

His Gly Ser Thr Cys Glu Leu Leu Glu Lys Glu Asp Ser Cys Ala Ser
                245                 250                 255

Asn Pro Cys Ser His Gly Val Cys Ile Ser Phe Ser Gly Gly Phe Gln
            260                 265                 270

Cys Ile Cys Asp Asp Gly Tyr Ser Gly Ser Tyr Cys Gln Glu Gly Lys
    275                 280                 285

Asp Asn Cys Val Asn Asn Lys Cys Glu Ala Gly Ser Lys Cys Ile Asn
    290                 295                 300

Gly Val Asn Ser Tyr Phe Cys Asp Cys Pro Glu Arg Thr Gly Pro
305                 310                 315                 320

Tyr Cys Glu Lys Met Asp Cys Ser Ala Ile Pro Asp Ile Cys Asn His
                325                 330                 335

Gly Thr Cys Ile Asp Ser Pro Leu Ser Glu Lys Ala Phe Glu Cys Gln
            340                 345                 350

Cys Glu Pro Gly Tyr Glu Gly Ile Leu Cys Glu Gln Asp Lys Asn Glu
        355                 360                 365

Cys Leu Ser Glu Asn Met Cys Leu Asn Asn Gly Thr Cys Val Asn Leu
370                 375                 380

Pro Gly Ser Phe Arg Cys Asp Cys Ala Arg Gly Phe Gly Gly Lys Trp
385                 390                 395                 400

Cys Asp Glu Pro Leu Asn Met Cys Gln Asp Phe His Cys Glu Asn Asp
                405                 410                 415

Gly Thr Cys Met His Thr Ser Asp His Ser Pro Val Cys Gln Cys Lys
            420                 425                 430

Asn Gly Phe Ile Gly Lys Arg Cys Glu Lys Glu Cys Pro Ile Gly Phe
        435                 440                 445

Gly Gly Val Arg Cys Asp Leu Arg Leu Glu Ile Gly Ile Cys Ser Arg
450                 455                 460

Gln Gly Gly Lys Cys Phe Asn Gly Gly Lys Cys Leu Ser Gly Phe Cys
465                 470                 475                 480

Val Cys Pro Pro Asp Phe Thr Gly Asn Gln Cys Glu Val Asn Arg Lys
                485                 490                 495

Asn Gly Lys Ser Ser Leu Ser Glu Asn Leu Cys Leu Ser Asp Pro Cys
            500                 505                 510

Met Asn Asn Ala Thr Cys Ile Asp Val Asp Ala His Ile Gly Tyr Ala
        515                 520                 525

Cys Ile Cys Lys Gln Gly Phe Glu Gly Asp Ile Cys Glu Arg His Lys
    530                 535                 540

Asp Leu Cys Leu Glu Asn Pro Cys Ser Asn Gly Gly Val Cys His Gln
545                 550                 555                 560

His Arg Glu Ser Phe Ser Cys Asp Cys Pro Pro Gly Phe Tyr Gly Asn
                565                 570                 575

Gly Cys Glu Gln Glu Lys Met Phe Arg Cys Leu Lys Ser Thr Cys Gln
            580                 585                 590

Asn Gly Gly Val Cys Ile Asn Glu Glu Lys Gly Arg Lys Cys Glu
        595                 600                 605

Cys Ser Tyr Gly Phe Ser Gly Ala Arg Cys Glu Glu Lys Ile Asn Leu

-continued

```
            610                 615                 620
Thr Gly Phe Thr Glu Lys Asp Ser Leu Leu Arg Ser Val Cys Glu Lys
625                 630                 635                 640

Arg Lys Cys Ser Glu Arg Ala Asn Asp Gly Asn Cys Asp Ala Asp Cys
                    645                 650                 655

Asn Tyr Ala Ala Cys Lys Phe Asp Gly Gly Asp Cys Ser Gly Lys Arg
                660                 665                 670

Glu Pro Phe Ser Lys Cys Arg Tyr Gly Asn Met Cys Ala Asp Phe Phe
            675                 680                 685

Ala Asn Gly Val Cys Asn Gln Ala Cys Asn Asn Glu Glu Cys Leu Tyr
690                 695                 700

Asp Gly Met Asp Cys Leu Pro Ala Val Val Arg Cys Pro Val Lys Ile
705                 710                 715                 720

Arg Glu His Cys Ala Ser Arg Phe Ala Asn Gly Ile Cys Asp Pro Glu
                    725                 730                 735

Cys Asn Thr Asn Gly Cys Gly Phe Asp Gly Gly Asp Cys Asp Asn Glu
                740                 745                 750

Thr Asn Ala Thr Ile Ile Thr Asn Ile Arg Ile Thr Val Gln Met Asp
            755                 760                 765

Pro Lys Glu Phe Gln Val Thr Gly Gly Gln Ser Leu Met Glu Ile Ser
770                 775                 780

Ser Ala Leu Arg Val Thr Val Arg Ile Gln Arg Asp Glu Glu Gly Pro
785                 790                 795                 800

Leu Val Phe Gln Trp Asn Gly Glu Ser Glu Met Asp Arg Val Lys Met
                    805                 810                 815

Asn Glu Arg Gln Leu Thr Glu Gln His Val Leu Ser Thr Ser Ile Ser
                820                 825                 830

Arg Lys Ile Lys Arg Ser Ala Thr Asn Ile Gly Val Val Tyr Leu
            835                 840                 845

Glu Val Gln Glu Asn Cys Asp Thr Gly Lys Cys Leu Tyr Lys Asp Ala
850                 855                 860

Gln Ser Val Val Asp Ser Ile Ser Ala Arg Leu Ala Lys Lys Gly Ile
865                 870                 875                 880

Asp Ser Phe Gly Ile Pro Ile Ser Glu Ala Leu Val Ala Glu Pro Arg
                    885                 890                 895

Lys Ser Gly Asn Asn Thr Gly Phe Leu Ser Trp Asn Ala Leu Leu Leu
                900                 905                 910

Ile Gly Ala Gly Cys Leu Ile Val Met Val Val Leu Met Leu Gly Ala
            915                 920                 925

Leu Pro Gly Asn Arg Thr Arg Lys Arg Arg Met Ile Asn Ala Ser Val
930                 935                 940

Trp Met Pro Pro Met Glu Asn Glu Glu Lys Arg Lys Asn His Gln
945                 950                 955                 960

Ser Ile Thr Ser Ser Gln His Ser Leu Leu Glu Ala Ser Tyr Asp Gly
                    965                 970                 975

Tyr Ile Lys Arg Gln Arg Asn Glu Leu Gln His Tyr Ser Leu Tyr Pro
                980                 985                 990

Asn Pro Gln Gly Tyr Gly Asn Gly Asn Asp Phe Leu Gly Asp Phe Asn
            995                 1000                1005

His Thr Asn Leu Gln Ile Pro Thr Glu Pro Glu Pro Glu Ser Pro
            1010                1015                1020

Ile Lys Leu His Thr Glu Ala Ala Gly Ser Tyr Ala Ile Thr Glu
            1025                1030                1035
```

```
Pro Ile Thr Arg Glu Ser Val Asn Ile Ile Asp Pro Arg His Asn
    1040                1045                1050

Arg Thr Val Leu His Trp Ile Ala Ser Asn Ser Ser Ala Glu Lys
    1055                1060                1065

Ser Glu Asp Leu Ile Val His Glu Ala Lys Glu Cys Ile Ala Ala
    1070                1075                1080

Gly Ala Asp Val Asn Ala Met Asp Cys Asp Glu Asn Thr Pro Leu
    1085                1090                1095

Met Leu Ala Val Leu Ala Arg Arg Arg Arg Leu Val Ala Tyr Leu
    1100                1105                1110

Met Lys Ala Gly Ala Asp Pro Thr Ile Tyr Asn Lys Ser Glu Arg
    1115                1120                1125

Ser Ala Leu His Gln Ala Ala Ala Asn Arg Asp Phe Gly Met Met
    1130                1135                1140

Val Tyr Met Leu Asn Ser Thr Lys Leu Lys Gly Asp Ile Glu Glu
    1145                1150                1155

Leu Asp Arg Asn Gly Met Thr Ala Leu Met Ile Val Ala His Asn
    1160                1165                1170

Glu Gly Arg Asp Gln Val Ala Ser Ala Lys Leu Leu Val Glu Lys
    1175                1180                1185

Gly Ala Lys Val Asp Tyr Asp Gly Ala Ala Arg Lys Asp Ser Glu
    1190                1195                1200

Lys Tyr Lys Gly Arg Thr Ala Leu His Tyr Ala Ala Gln Val Ser
    1205                1210                1215

Asn Met Pro Ile Val Lys Tyr Leu Val Gly Glu Lys Gly Ser Asn
    1220                1225                1230

Lys Asp Lys Gln Asp Glu Asp Gly Lys Thr Pro Ile Met Leu Ala
    1235                1240                1245

Ala Gln Glu Gly Arg Ile Glu Val Val Met Tyr Leu Ile Gln Gln
    1250                1255                1260

Gly Ala Ser Val Glu Ala Val Asp Ala Thr Asp His Thr Ala Arg
    1265                1270                1275

Gln Leu Ala Gln Ala Asn Asn His His Asn Ile Val Asp Ile Phe
    1280                1285                1290

Asp Arg Cys Arg Pro Glu Arg Glu Tyr Ser Met Asp Leu His Ile
    1295                1300                1305

Gln His Thr His Gln Pro Gln Pro Ser Arg Lys Val Thr Arg Ala
    1310                1315                1320

Pro Lys Lys Gln Thr Ser Arg Ser Lys Lys Glu Ser Ala Ser Asn
    1325                1330                1335

Ser Arg Asp Ser Thr His Leu Thr Pro Pro Ser Asp Gly Ser
    1340                1345                1350

Thr Ser Thr Pro Ser Pro Gln His Phe Met Asn Thr Thr His Thr
    1355                1360                1365

Thr Pro Thr Ser Leu Asn Tyr Leu Ser Pro Glu Tyr Gln Thr Glu
    1370                1375                1380

Ala Gly Ser Ser Glu Ala Phe Gln Pro Gln Cys Gly Ala Phe Gly
    1385                1390                1395

Asn Gly Glu Met Trp Tyr Thr Arg Ala Ser Thr Ser Tyr Thr Gln
    1400                1405                1410

Met Gln Asn Glu Pro Met Thr Arg Tyr Ser Glu Pro Ala His Tyr
    1415                1420                1425
```

Phe

```
<210> SEQ ID NO 4
<211> LENGTH: 2703
<212> TYPE: PRT
<213> ORGANISM: Drosophila melanogaster

<400> SEQUENCE: 4
```

| | | | | | | | | | | | | | | |
|---|---|---|---|---|---|---|---|---|---|---|---|---|---|---|
| Met | Gln | Ser | Gln | Arg | Ser | Arg | Arg | Ser | Arg | Ala | Pro | Asn | Thr | Trp |
| 1 | | | | 5 | | | | | 10 | | | | | 15 |
| Ile | Cys | Phe | Trp | Ile | Asn | Lys | Met | His | Ala | Val | Ala | Ser | Leu | Pro | Ala |
| | | | 20 | | | | | 25 | | | | | 30 | | |
| Ser | Leu | Pro | Leu | Leu | Leu | Leu | Thr | Leu | Ala | Phe | Ala | Asn | Leu | Pro | Asn |
| | | 35 | | | | | 40 | | | | | 45 | | | |
| Thr | Val | Arg | Gly | Thr | Asp | Thr | Ala | Leu | Val | Ala | Ala | Ser | Cys | Thr | Ser |
| | 50 | | | | | 55 | | | | | 60 | | | | |
| Val | Gly | Cys | Gln | Asn | Gly | Gly | Thr | Cys | Val | Thr | Gln | Leu | Asn | Gly | Lys |
| 65 | | | | | 70 | | | | | 75 | | | | | 80 |
| Thr | Tyr | Cys | Ala | Cys | Asp | Ser | His | Tyr | Val | Gly | Asp | Tyr | Cys | Glu | His |
| | | | | 85 | | | | | 90 | | | | | 95 | |
| Arg | Asn | Pro | Cys | Asn | Ser | Met | Arg | Cys | Gln | Asn | Gly | Gly | Thr | Cys | Gln |
| | | | 100 | | | | | 105 | | | | | 110 | | |
| Val | Thr | Phe | Arg | Asn | Gly | Arg | Pro | Gly | Ile | Ser | Cys | Lys | Cys | Pro | Leu |
| | | 115 | | | | | 120 | | | | | 125 | | | |
| Gly | Phe | Asp | Glu | Ser | Leu | Cys | Glu | Ile | Ala | Val | Pro | Asn | Ala | Cys | Asp |
| 130 | | | | | 135 | | | | | 140 | | | | | |
| His | Val | Thr | Cys | Leu | Asn | Gly | Gly | Thr | Cys | Gln | Leu | Lys | Thr | Leu | Glu |
| 145 | | | | | 150 | | | | | 155 | | | | | 160 |
| Glu | Tyr | Thr | Cys | Ala | Cys | Ala | Asn | Gly | Tyr | Thr | Gly | Glu | Arg | Cys | Glu |
| | | | | 165 | | | | | 170 | | | | | 175 | |
| Thr | Lys | Asn | Leu | Cys | Ala | Ser | Ser | Pro | Cys | Arg | Asn | Gly | Ala | Thr | Cys |
| | | | 180 | | | | | 185 | | | | | 190 | | |
| Thr | Ala | Leu | Ala | Gly | Ser | Ser | Ser | Phe | Thr | Cys | Ser | Cys | Pro | Pro | Gly |
| | | 195 | | | | | 200 | | | | | 205 | | | |
| Phe | Thr | Gly | Asp | Thr | Cys | Ser | Tyr | Asp | Ile | Glu | Glu | Cys | Gln | Ser | Asn |
| 210 | | | | | 215 | | | | | 220 | | | | | |
| Pro | Cys | Lys | Tyr | Gly | Gly | Thr | Cys | Val | Asn | Thr | His | Gly | Ser | Tyr | Gln |
| 225 | | | | | 230 | | | | | 235 | | | | | 240 |
| Cys | Met | Cys | Pro | Thr | Gly | Tyr | Thr | Gly | Lys | Asp | Cys | Asp | Thr | Lys | Tyr |
| | | | | 245 | | | | | 250 | | | | | 255 | |
| Lys | Pro | Cys | Ser | Pro | Ser | Pro | Cys | Gln | Asn | Gly | Gly | Ile | Cys | Arg | Ser |
| | | | 260 | | | | | 265 | | | | | 270 | | |
| Asn | Gly | Leu | Ser | Tyr | Glu | Cys | Lys | Cys | Pro | Lys | Gly | Phe | Glu | Gly | Lys |
| | | 275 | | | | | 280 | | | | | 285 | | | |
| Asn | Cys | Glu | Gln | Asn | Tyr | Asp | Asp | Cys | Leu | Gly | His | Leu | Cys | Gln | Asn |
| 290 | | | | | 295 | | | | | 300 | | | | | |
| Gly | Gly | Thr | Cys | Ile | Asp | Gly | Ile | Ser | Asp | Tyr | Thr | Cys | Arg | Cys | Pro |
| 305 | | | | | 310 | | | | | 315 | | | | | 320 |
| Pro | Asn | Phe | Thr | Gly | Arg | Phe | Cys | Gln | Asp | Asp | Val | Asp | Glu | Cys | Ala |
| | | | | 325 | | | | | 330 | | | | | 335 | |
| Gln | Arg | Asp | His | Pro | Val | Cys | Gln | Asn | Gly | Ala | Thr | Cys | Thr | Asn | Thr |
| | | | 340 | | | | | 345 | | | | | 350 | | |
| His | Gly | Ser | Tyr | Ser | Cys | Ile | Cys | Val | Asn | Gly | Trp | Ala | Gly | Leu | Asp |
| | | 355 | | | | | 360 | | | | | 365 | | | |

```
Cys Ser Asn Asn Thr Asp Asp Cys Lys Gln Ala Ala Cys Phe Tyr Gly
370                 375                 380
Ala Thr Cys Ile Asp Gly Val Gly Ser Phe Tyr Cys Gln Cys Thr Lys
385                 390                 395                 400
Gly Lys Thr Gly Leu Leu Cys His Leu Asp Asp Ala Cys Thr Ser Asn
                405                 410                 415
Pro Cys His Ala Asp Ala Ile Cys Asp Thr Ser Pro Ile Asn Gly Ser
            420                 425                 430
Tyr Ala Cys Ser Cys Ala Thr Gly Tyr Lys Gly Val Asp Cys Ser Glu
                435                 440                 445
Asp Ile Asp Glu Cys Asp Gln Gly Ser Pro Cys Glu His Asn Gly Ile
450                 455                 460
Cys Val Asn Thr Pro Gly Ser Tyr Arg Cys Asn Cys Ser Gln Gly Phe
465                 470                 475                 480
Thr Gly Pro Arg Cys Glu Thr Asn Ile Asn Glu Cys Glu Ser His Pro
                485                 490                 495
Cys Gln Asn Glu Gly Ser Cys Leu Asp Asp Pro Gly Thr Phe Arg Cys
                500                 505                 510
Val Cys Met Pro Gly Phe Thr Gly Thr Gln Cys Glu Ile Asp Ile Asp
            515                 520                 525
Glu Cys Gln Ser Asn Pro Cys Leu Asn Asp Gly Thr Cys His Asp Lys
530                 535                 540
Ile Asn Gly Phe Lys Cys Ser Cys Ala Leu Gly Phe Thr Gly Ala Arg
545                 550                 555                 560
Cys Gln Ile Asn Ile Asp Asp Cys Gln Ser Gln Pro Cys Arg Asn Arg
                565                 570                 575
Gly Ile Cys His Asp Ser Ile Ala Gly Tyr Ser Cys Glu Cys Pro Pro
            580                 585                 590
Gly Tyr Thr Gly Thr Ser Cys Glu Ile Asn Ile Asn Asp Cys Asp Ser
                595                 600                 605
Asn Pro Cys His Arg Gly Lys Cys Ile Asp Asp Val Asn Ser Phe Lys
610                 615                 620
Cys Leu Cys Asp Pro Gly Tyr Thr Gly Tyr Ile Cys Gln Lys Gln Ile
625                 630                 635                 640
Asn Glu Cys Glu Ser Asn Pro Cys Gln Phe Asp Gly His Cys Gln Asp
                645                 650                 655
Arg Val Gly Ser Tyr Tyr Cys Gln Cys Gln Ala Gly Thr Ser Gly Lys
            660                 665                 670
Asn Cys Glu Val Asn Val Asn Glu Cys His Ser Asn Pro Cys Asn Asn
                675                 680                 685
Gly Ala Thr Cys Ile Asp Gly Ile Asn Ser Tyr Lys Cys Gln Cys Val
690                 695                 700
Pro Gly Phe Thr Gly Gln His Cys Glu Lys Asn Val Asp Glu Cys Ile
705                 710                 715                 720
Ser Ser Pro Cys Ala Asn Asn Gly Val Cys Ile Asp Gln Val Asn Gly
                725                 730                 735
Tyr Lys Cys Glu Cys Pro Arg Gly Phe Tyr Asp Ala His Cys Leu Ser
            740                 745                 750
Asp Val Asp Glu Cys Ala Ser Asn Pro Cys Val Asn Gly Arg Cys
                755                 760                 765
Glu Asp Gly Ile Asn Glu Phe Ile Cys His Cys Pro Pro Gly Tyr Thr
770                 775                 780
Gly Lys Arg Cys Glu Leu Asp Ile Asp Glu Cys Ser Ser Asn Pro Cys
```

-continued

```
            785                 790                 795                 800
        Gln His Gly Gly Thr Cys Tyr Asp Lys Leu Asn Ala Phe Ser Cys Gln
                        805                 810                 815
        Cys Met Pro Gly Tyr Thr Gly Gln Lys Cys Glu Thr Asn Ile Asp Asp
                        820                 825                 830
        Cys Val Thr Asn Pro Cys Gly Asn Gly Thr Cys Ile Asp Lys Val
                        835                 840                 845
        Asn Gly Tyr Lys Cys Val Cys Lys Val Pro Phe Thr Gly Arg Asp Cys
        850                 855                 860
        Glu Ser Lys Met Asp Pro Cys Ala Ser Asn Arg Cys Lys Asn Glu Ala
        865                 870                 875                 880
        Lys Cys Thr Pro Ser Ser Asn Phe Leu Asp Phe Ser Cys Thr Cys Lys
                        885                 890                 895
        Leu Gly Tyr Thr Gly Arg Tyr Cys Asp Glu Ile Asp Glu Cys Ser
                        900                 905                 910
        Leu Ser Ser Pro Cys Arg Asn Gly Ala Ser Cys Leu Asn Val Pro Gly
                        915                 920                 925
        Ser Tyr Arg Cys Leu Cys Thr Lys Gly Tyr Glu Gly Arg Asp Cys Ala
        930                 935                 940
        Ile Asn Thr Asp Asp Cys Ala Ser Phe Pro Cys Gln Asn Gly Gly Thr
        945                 950                 955                 960
        Cys Leu Asp Gly Ile Gly Asp Tyr Ser Cys Leu Cys Val Asp Gly Phe
                        965                 970                 975
        Asp Gly Lys His Cys Glu Thr Asp Ile Asn Glu Cys Leu Ser Gln Pro
                        980                 985                 990
        Cys Gln Asn Gly Ala Thr Cys Ser  Gln Tyr Val Asn Ser  Tyr Thr Cys
                995                 1000                1005
        Thr Cys  Pro Leu Gly Phe Ser  Gly Ile Asn Cys Gln  Thr Asn Asp
                1010                1015                1020
        Glu Asp  Cys Thr Glu Ser Ser  Cys Leu Asn Gly Gly  Ser Cys Ile
                1025                1030                1035
        Asp Gly  Ile Asn Gly Tyr Asn  Cys Ser Cys Leu Ala  Gly Tyr Ser
                1040                1045                1050
        Gly Ala  Asn Cys Gln Tyr Lys  Leu Asn Lys Cys Asp  Ser Asn Pro
                1055                1060                1065
        Cys Leu  Asn Gly Ala Thr Cys  His Glu Gln Asn  Glu Tyr Thr
                1070                1075                1080
        Cys His  Cys Pro Ser Gly Phe  Thr Gly Lys Gln Cys  Ser Glu Tyr
                1085                1090                1095
        Val Asp  Trp Cys Gly Gln Ser  Pro Cys Glu Asn Gly  Ala Thr Cys
                1100                1105                1110
        Ser Gln  Met Lys His Gln Phe  Ser Cys Lys Cys Ser  Ala Gly Trp
                1115                1120                1125
        Thr Gly  Lys Leu Cys Asp Val  Gln Thr Ile Ser Cys  Gln Asp Ala
                1130                1135                1140
        Ala Asp  Arg Lys Gly Leu Ser  Leu Arg Gln Leu Cys  Asn Asn Gly
                1145                1150                1155
        Thr Cys  Lys Asp Tyr Gly Asn  Ser His Val Cys Tyr  Cys Ser Gln
                1160                1165                1170
        Gly Tyr  Ala Gly Ser Tyr Cys  Gln Lys Glu Ile Asp  Glu Cys Gln
                1175                1180                1185
        Ser Gln  Pro Cys Gln Asn Gly  Gly Thr Cys Arg Asp  Leu Ile Gly
                1190                1195                1200
```

-continued

```
Ala Tyr Glu Cys Gln Cys Arg Gln Gly Phe Gln Gly Gln Asn Cys
    1205                1210                1215

Glu Leu Asn Ile Asp Asp Cys Ala Pro Asn Pro Cys Gln Asn Gly
    1220                1225                1230

Gly Thr Cys His Asp Arg Val Met Asn Phe Ser Cys Ser Cys Pro
    1235                1240                1245

Pro Gly Thr Met Gly Ile Ile Cys Glu Ile Asn Lys Asp Asp Cys
    1250                1255                1260

Lys Pro Gly Ala Cys His Asn Asn Gly Ser Cys Ile Asp Arg Val
    1265                1270                1275

Gly Gly Phe Glu Cys Val Cys Gln Pro Gly Phe Val Gly Ala Arg
    1280                1285                1290

Cys Glu Gly Asp Ile Asn Glu Cys Leu Ser Asn Pro Cys Ser Asn
    1295                1300                1305

Ala Gly Thr Leu Asp Cys Val Gln Leu Val Asn Asn Tyr His Cys
    1310                1315                1320

Asn Cys Arg Pro Gly His Met Gly Arg His Cys Glu His Lys Val
    1325                1330                1335

Asp Phe Cys Ala Gln Ser Pro Cys Gln Asn Gly Gly Asn Cys Asn
    1340                1345                1350

Ile Arg Gln Ser Gly His His Cys Ile Cys Asn Asn Gly Phe Tyr
    1355                1360                1365

Gly Lys Asn Cys Glu Leu Ser Gly Gln Asp Cys Asp Ser Asn Pro
    1370                1375                1380

Cys Arg Val Gly Asn Cys Val Val Ala Asp Glu Gly Phe Gly Tyr
    1385                1390                1395

Arg Cys Glu Cys Pro Arg Gly Thr Leu Gly Glu His Cys Glu Ile
    1400                1405                1410

Asp Thr Leu Asp Glu Cys Ser Pro Asn Pro Cys Ala Gln Gly Ala
    1415                1420                1425

Ala Cys Glu Asp Leu Leu Gly Asp Tyr Glu Cys Leu Cys Pro Ser
    1430                1435                1440

Lys Trp Lys Gly Lys Arg Cys Asp Ile Tyr Asp Ala Asn Tyr Pro
    1445                1450                1455

Gly Trp Asn Gly Gly Ser Gly Ser Gly Asn Asp Arg Tyr Ala Ala
    1460                1465                1470

Asp Leu Glu Gln Gln Arg Ala Met Cys Asp Lys Arg Gly Cys Thr
    1475                1480                1485

Glu Lys Gln Gly Asn Gly Ile Cys Asp Ser Asp Cys Asn Thr Tyr
    1490                1495                1500

Ala Cys Asn Phe Asp Gly Asn Asp Cys Ser Leu Gly Ile Asn Pro
    1505                1510                1515

Trp Ala Asn Cys Thr Ala Asn Glu Cys Trp Asn Lys Phe Lys Asn
    1520                1525                1530

Gly Lys Cys Asn Glu Glu Cys Asn Asn Ala Ala Cys His Tyr Asp
    1535                1540                1545

Gly His Asp Cys Glu Arg Lys Leu Lys Ser Cys Asp Ser Leu Phe
    1550                1555                1560

Asp Ala Tyr Cys Gln Lys His Tyr Gly Asp Gly Phe Cys Asp Tyr
    1565                1570                1575

Gly Cys Asn Asn Ala Glu Cys Ser Trp Asp Gly Leu Asp Cys Glu
    1580                1585                1590
```

```
Asn Lys Thr Gln Ser Pro Val Leu Ala Glu Gly Ala Met Ser Val
1595                1600                1605

Val Met Leu Met Asn Val Glu Ala Phe Arg Glu Ile Gln Ala Gln
1610                1615                1620

Phe Leu Arg Asn Met Ser His Met Leu Arg Thr Thr Val Arg Leu
1625                1630                1635

Lys Lys Asp Ala Leu Gly His Asp Ile Ile Asn Trp Lys Asp
1640                1645                1650

Asn Val Arg Val Pro Glu Ile Glu Asp Thr Asp Phe Ala Arg Lys
1655                1660                1665

Asn Lys Ile Leu Tyr Thr Gln Gln Val His Gln Thr Gly Ile Gln
1670                1675                1680

Ile Tyr Leu Glu Ile Asp Asn Arg Lys Cys Thr Glu Cys Phe Thr
1685                1690                1695

His Ala Val Glu Ala Ala Glu Phe Leu Ala Ala Thr Ala Ala Lys
1700                1705                1710

His Gln Leu Arg Asn Asp Phe Gln Ile His Ser Val Arg Gly Ile
1715                1720                1725

Lys Asn Pro Gly Asp Glu Asp Asn Gly Glu Pro Pro Ala Asn Val
1730                1735                1740

Lys Tyr Val Ile Thr Gly Ile Ile Leu Val Ile Ile Ala Leu Ala
1745                1750                1755

Phe Phe Gly Met Val Leu Ser Thr Gln Arg Lys Arg Ala His Gly
1760                1765                1770

Val Thr Trp Phe Pro Glu Gly Phe Arg Ala Pro Ala Ala Val Met
1775                1780                1785

Ser Arg Arg Arg Arg Asp Pro His Gly Gln Glu Met Arg Asn Leu
1790                1795                1800

Asn Lys Gln Val Ala Met Gln Ser Gln Gly Val Gly Gln Pro Gly
1805                1810                1815

Ala His Trp Ser Asp Asp Glu Ser Asp Met Pro Leu Pro Lys Arg
1820                1825                1830

Gln Arg Ser Asp Pro Val Ser Gly Val Gly Leu Gly Asn Asn Gly
1835                1840                1845

Gly Tyr Ala Ser Asp His Thr Met Val Ser Glu Tyr Glu Glu Ala
1850                1855                1860

Asp Gln Arg Val Trp Ser Gln Ala His Leu Asp Val Val Asp Val
1865                1870                1875

Arg Ala Ile Met Thr Pro Pro Ala His Gln Asp Gly Gly Lys His
1880                1885                1890

Asp Val Asp Ala Arg Gly Pro Cys Gly Leu Thr Pro Leu Met Ile
1895                1900                1905

Ala Ala Val Arg Gly Gly Gly Leu Asp Thr Gly Glu Asp Ile Glu
1910                1915                1920

Asn Asn Glu Asp Ser Thr Ala Gln Val Ile Ser Asp Leu Leu Ala
1925                1930                1935

Gln Gly Ala Glu Leu Asn Ala Thr Met Asp Lys Thr Gly Glu Thr
1940                1945                1950

Ser Leu His Leu Ala Ala Arg Phe Ala Arg Ala Asp Ala Ala Lys
1955                1960                1965

Arg Leu Leu Asp Ala Gly Ala Asp Ala Asn Cys Gln Asp Asn Thr
1970                1975                1980

Gly Arg Thr Pro Leu His Ala Ala Val Ala Ala Asp Ala Met Gly
```

-continued

```
               1985                1990                1995
Val Phe Gln Ile Leu Leu Arg Asn Arg Ala Thr Asn Leu Asn Ala
    2000                2005                2010

Arg Met His Asp Gly Thr Thr Pro Leu Ile Leu Ala Ala Arg Leu
    2015                2020                2025

Ala Ile Glu Gly Met Val Glu Asp Leu Ile Thr Ala Asp Ala Asp
    2030                2035                2040

Ile Asn Ala Ala Asp Asn Ser Gly Lys Thr Ala Leu His Trp Ala
    2045                2050                2055

Ala Ala Val Asn Asn Thr Glu Ala Val Asn Ile Leu Leu Met His
    2060                2065                2070

His Ala Asn Arg Asp Ala Gln Asp Asp Lys Asp Glu Thr Pro Leu
    2075                2080                2085

Phe Leu Ala Ala Arg Glu Gly Ser Tyr Glu Ala Cys Lys Ala Leu
    2090                2095                2100

Leu Asp Asn Phe Ala Asn Arg Glu Ile Thr Asp His Met Asp Arg
    2105                2110                2115

Leu Pro Arg Asp Val Ala Ser Glu Arg Leu His His Asp Ile Val
    2120                2125                2130

Arg Leu Leu Asp Glu His Val Pro Arg Ser Pro Gln Met Leu Ser
    2135                2140                2145

Met Thr Pro Gln Ala Met Ile Gly Ser Pro Pro Gly Gln Gln
    2150                2155                2160

Gln Pro Gln Leu Ile Thr Gln Pro Thr Val Ile Ser Ala Gly Asn
    2165                2170                2175

Gly Gly Asn Asn Gly Asn Gly Asn Ala Ser Gly Lys Gln Ser Asn
    2180                2185                2190

Gln Thr Ala Lys Gln Lys Ala Ala Lys Lys Ala Lys Leu Ile Glu
    2195                2200                2205

Gly Ser Pro Asp Asn Gly Leu Asp Ala Thr Gly Ser Leu Arg Arg
    2210                2215                2220

Lys Ala Ser Ser Lys Lys Thr Ser Ala Ala Ser Lys Lys Ala Ala
    2225                2230                2235

Asn Leu Asn Gly Leu Asn Pro Gly Gln Leu Thr Gly Gly Val Ser
    2240                2245                2250

Gly Val Pro Gly Val Pro Pro Thr Asn Ser Ala Ala Gln Ala Ala
    2255                2260                2265

Ala Ala Ala Ala Ala Ala Val Ala Ala Met Ser His Glu Leu Glu
    2270                2275                2280

Gly Ser Pro Val Gly Val Gly Met Gly Gly Asn Leu Pro Ser Pro
    2285                2290                2295

Tyr Asp Thr Ser Ser Met Tyr Ser Asn Ala Met Ala Ala Pro Leu
    2300                2305                2310

Ala Asn Gly Asn Pro Asn Thr Gly Ala Lys Gln Pro Pro Ser Tyr
    2315                2320                2325

Glu Asp Cys Ile Lys Asn Ala Gln Ser Met Gln Ser Leu Gln Gly
    2330                2335                2340

Asn Gly Leu Asp Met Ile Lys Leu Asp Asn Tyr Ala Tyr Ser Met
    2345                2350                2355

Gly Ser Pro Phe Gln Gln Glu Leu Leu Asn Gly Gln Gly Leu Gly
    2360                2365                2370

Met Asn Gly Asn Gly Gln Arg Asn Gly Val Gly Pro Gly Val Leu
    2375                2380                2385
```

Pro Gly Gly Leu Cys Gly Met Gly Gly Leu Ser Gly Ala Gly Asn
    2390                2395                2400

Gly Asn Ser His Glu Gln Gly Leu Ser Pro Pro Tyr Ser Asn Gln
    2405                2410                2415

Ser Pro Pro His Ser Val Gln Ser Ser Leu Ala Leu Ser Pro His
    2420                2425                2430

Ala Tyr Leu Gly Ser Pro Ser Pro Ala Lys Ser Arg Pro Ser Leu
    2435                2440                2445

Pro Thr Ser Pro Thr His Ile Gln Ala Met Arg His Ala Thr Gln
    2450                2455                2460

Gln Lys Gln Phe Gly Gly Ser Asn Leu Asn Ser Leu Leu Gly Gly
    2465                2470                2475

Ala Asn Gly Gly Gly Val Val Gly Gly Gly Gly Gly Gly Gly Gly
    2480                2485                2490

Gly Val Gly Gln Gly Pro Gln Asn Ser Pro Val Ser Leu Gly Ile
    2495                2500                2505

Ile Ser Pro Thr Gly Ser Asp Met Gly Ile Met Leu Ala Pro Pro
    2510                2515                2520

Gln Ser Ser Lys Asn Ser Ala Ile Met Gln Thr Ile Ser Pro Gln
    2525                2530                2535

Gln Gln Gln Gln Gln Gln Gln Gln Gln Gln Gln His Gln Gln
    2540                2545                2550

Gln Gln Gln Gln Gln Gln Gln Gln Gln Gln Gln Gln Gln Gln Gln
    2555                2560                2565

Leu Gly Gly Leu Glu Phe Gly Ser Ala Gly Leu Asp Leu Asn Gly
    2570                2575                2580

Phe Cys Gly Ser Pro Asp Ser Phe His Ser Gly Gln Met Asn Pro
    2585                2590                2595

Pro Ser Ile Gln Ser Ser Met Ser Gly Ser Ser Pro Ser Thr Asn
    2600                2605                2610

Met Leu Ser Pro Ser Ser Gln His Asn Gln Gln Ala Phe Tyr Gln
    2615                2620                2625

Tyr Leu Thr Pro Ser Ser Gln His Ser Gly Gly His Thr Pro Gln
    2630                2635                2640

His Leu Val Gln Thr Leu Asp Ser Tyr Pro Thr Pro Ser Pro Glu
    2645                2650                2655

Ser Pro Gly His Trp Ser Ser Ser Pro Arg Ser Asn Ser Asp
    2660                2665                2670

Trp Ser Glu Gly Val Gln Ser Pro Ala Ala Asn Asn Leu Tyr Ile
    2675                2680                2685

Ser Gly Gly His Gln Ala Asn Lys Gly Ser Glu Ala Ile Tyr Ile
    2690                2695                2700

<210> SEQ ID NO 5
<211> LENGTH: 2900
<212> TYPE: PRT
<213> ORGANISM: Bos taurus

<400> SEQUENCE: 5

Met Thr Pro Val Cys Thr Pro Thr Arg Pro Gly Pro Cys Ala His Pro
1               5                   10                  15

Ala Leu Pro Arg Ser Thr Pro His Ser Ile Thr Asp Ser Ser Arg Ala
            20                  25                  30

Glu Pro Ile Glu Ser Phe Leu Val Leu Ser Pro Ala Leu Glu Leu Arg

-continued

```
                 35                  40                  45
Leu Leu Leu Ala Val Val Gly Gln Asp Thr Pro Leu Gly Asp Val Trp
 50                  55                  60
Ala Gly Gly Lys Ala Ser Gly Gly Asp Thr Glu Gly Pro Leu Ser
 65                  70                  75                  80
Glu Gly Ser Lys Glu Gly Glu Ala Ala Thr Gly Pro Gln Ala Pro Gly
                 85                  90                  95
Ala Glu Trp His Ala Pro Pro Arg Ser Thr Cys Leu Ser Ser Thr Pro
                100                 105                 110
Arg Pro Glu Ala Val Pro Pro Ser Leu Pro Cys Arg Ser Pro Gly Trp
                115                 120                 125
Gly Ala Cys Gly Gly Arg Arg Pro Gly Pro Ala Leu Glu Pro Ala His
                130                 135                 140
Met Gly Ser Val Pro Ser Gln Gln Arg Pro Pro Gly Leu Asp Arg Ser
145                 150                 155                 160
Arg Glu Asp Asn Gly Pro Pro Gln Pro Leu Pro Ser Pro His Gly Gly
                165                 170                 175
Ala Ser Leu Ala Pro Ala Pro Pro Ala Cys Arg Gly Trp Gln Pro
                180                 185                 190
Pro Leu Arg Trp Pro Gly Ala Ala Ala Arg Val Pro Gly His Arg
                195                 200                 205
Arg Thr Cys Ser Pro Ala Ala Leu Cys Pro Cys Cys Arg Cys Leu Ile
                210                 215                 220
Tyr Trp Ala Arg Phe Ser Ser His Cys Asn Ser Arg Ser Leu Pro Gly
225                 230                 235                 240
Gln Asp Ala Leu Gly Pro Gly Leu Trp Val Pro Ser Ala Thr Gln Ala
                245                 250                 255
Gly Thr Arg Gln Pro Val Thr Gly Ser Thr Leu Ser Gly Gly His Ala
                260                 265                 270
Thr Phe Pro Arg Leu Gln Gly Met Ala Leu Pro Glu Pro Glu Gly Glu
                275                 280                 285
Gly Pro Pro Thr Thr Ser Ala Gln Gly Cys Gly Pro Ser Val Arg Ala
                290                 295                 300
Ala Phe Pro Gly Arg Cys Gln Leu Gly Ala Val Gly Ala Phe His Pro
305                 310                 315                 320
Arg Gly Ser Ala Ala Gly Lys Arg Glu Ala Trp Leu Val Pro Glu Pro
                325                 330                 335
Leu Leu Gly Phe Pro Ser Ser Ser Arg Leu Arg Gly Asp Pro Gly Gly
                340                 345                 350
His Val Pro Pro Arg Leu Lys Lys Pro Arg Gln Gln Val Ala Lys Gly
                355                 360                 365
Gly Pro Gly Ala Gly Val Ala Gly Ala Glu Pro Phe Pro Val Gly Ser
                370                 375                 380
Ala Gly Asp Gln Ala Trp Gly Trp Ala Gly Gly Lys Ala Pro Pro Thr
385                 390                 395                 400
Pro Gly Ser Pro Ala Thr Val Ala Ala Arg Glu Pro Ala Gln Gly Leu
                405                 410                 415
Pro Asp Cys Gly Gly Ala Phe Ala Gly Gln Gln Cys Gln Ala Pro Asn
                420                 425                 430
Pro Cys Leu Ser Ala Pro Cys Lys Asn Gly Gly Thr Cys His Thr Thr
                435                 440                 445
Glu Arg Glu Gly Leu Val Asp Tyr Val Cys Gly Cys Arg Leu Gly Phe
450                 455                 460
```

```
Ser Gly Pro Leu Cys Leu Thr Pro Arg Asp His Ala Cys Leu Ala Ser
465                 470                 475                 480

Pro Cys Leu Asn Gly Thr Cys Asp Leu Leu Thr Leu Thr Glu Tyr
            485                 490                 495

Lys Cys Leu Cys Thr Pro Gly Trp Ser Gly Lys Thr Cys Gln Gln Ala
            500                 505                 510

Asp Pro Cys Ala Ser Asn Pro Cys Ala Asn Gly Gly Gln Cys Leu Pro
            515                 520                 525

Phe Glu Ala Ser Tyr Ile Cys His Cys Pro Gly Phe His Gly Pro
530                 535                 540

Thr Cys Arg Gln Asp Val Asn Glu Cys Ser Gln Ser Pro Gly Leu Cys
545                 550                 555                 560

His His Gly Gly Thr Cys Leu Asn Glu Val Gly Ser Tyr Arg Cys Val
                565                 570                 575

Cys Arg Pro Thr His Thr Gly Pro His Cys Glu Leu Pro Tyr Val Pro
            580                 585                 590

Cys Ser Pro Ser Pro Cys Gln Asn Gly Gly Thr Cys Arg Pro Thr Gly
            595                 600                 605

Asp Thr Thr His Glu Cys Ala Cys Leu Pro Gly Phe Thr Gly Gln Asn
    610                 615                 620

Cys Glu Glu Asn Ile Asp Asp Cys Pro Gly Asn Ser Cys Lys Asn Gly
625                 630                 635                 640

Gly Ala Cys Val Asp Gly Val Asn Thr Tyr Asn Cys Arg Cys Pro Pro
                645                 650                 655

Glu Trp Thr Gly Gln Tyr Cys Thr Glu Asp Val Asp Glu Cys Gln Leu
            660                 665                 670

Met Pro Asn Ala Cys Gln Asn Gly Gly Thr Cys His Asn Thr His Gly
            675                 680                 685

Gly Tyr Asn Cys Val Cys Val Asn Gly Trp Thr Gly Glu Asp Cys Ser
            690                 695                 700

Glu Asn Ile Asp Asp Cys Ala Ser Ala Ser Cys Phe Gln Gly Ala Thr
705                 710                 715                 720

Cys His Asp Arg Val Ala Ser Phe Tyr Cys Glu Cys Pro His Gly Arg
                725                 730                 735

Thr Gly Leu Leu Cys His Leu Asn Asp Ala Cys Ile Ser Asn Pro Cys
            740                 745                 750

Asn Glu Gly Ser Asn Cys Asp Thr Asn Pro Val Asn Gly Lys Ala Ile
            755                 760                 765

Cys Thr Cys Pro Ser Gly Tyr Thr Gly Pro Ala Cys Ser Gln Asp Val
            770                 775                 780

Asp Glu Cys Ser Leu Gly Ala Asn Pro Cys Glu His Ala Gly Lys Cys
785                 790                 795                 800

Ile Asn Thr Leu Gly Ser Phe Glu Cys Gln Cys Leu Gln Gly Tyr Thr
                805                 810                 815

Gly Pro Arg Cys Glu Ile Asp Val Asn Glu Cys Val Ser Asn Pro Cys
            820                 825                 830

Gln Asn Asp Ala Thr Cys Leu Asp Gln Ile Gly Glu Phe Gln Cys Ile
            835                 840                 845

Cys Met Pro Gly Tyr Glu Gly Leu His Cys Glu Val Asn Thr Asp Glu
            850                 855                 860

Cys Ala Ser Ser Pro Cys Leu Gln Asn Gly Arg Cys Leu Asp Lys Ile
865                 870                 875                 880
```

```
Asn Glu Phe Val Cys Glu Cys Pro Thr Gly Phe Thr Gly His Leu Cys
            885                 890                 895
Gln Tyr Asp Val Asp Glu Cys Ala Ser Thr Pro Cys Lys Asn Gly Ala
        900                 905                 910
Lys Cys Leu Asp Gly Pro Asn Thr Tyr Thr Cys Val Cys Thr Glu Gly
        915                 920                 925
Tyr Thr Gly Pro His Cys Glu Val Asp Ile Asp Glu Cys Asp Pro Asp
    930                 935                 940
Pro Cys His Tyr Gly Ser Cys Lys Asp Gly Val Ala Thr Phe Thr Cys
945                 950                 955                 960
Leu Cys Gln Pro Gly Tyr Thr Gly His His Cys Glu Ser Asn Ile Asn
            965                 970                 975
Glu Cys His Ser Gln Pro Cys Arg His Gly Gly Thr Cys Gln Asp Arg
        980                 985                 990
Asp Asn Ala Tyr Leu Cys Phe Cys  Leu Lys Gly Thr Thr Gly Pro Asn
            995                 1000                1005
Cys Glu  Ile Asn Leu Asp Asp  Cys Ala Ser Asn Pro  Cys Asp Ser
    1010                1015                 1020
Gly Thr  Cys Leu Asp Lys Ile  Asp Gly Tyr Glu Cys  Ala Cys Glu
    1025                1030                 1035
Pro Gly  Tyr Thr Gly Ser Met  Cys Asn Ile Asn Ile  Asp Glu Cys
    1040                1045                 1050
Ala Asp  Ser Pro Cys His Asn  Gly Gly Thr Cys Glu  Asp Gly Ile
    1055                1060                 1065
Asn Gly  Phe Thr Cys Arg Cys  Pro Glu Gly Tyr His  Asp Pro Thr
    1070                1075                 1080
Cys Leu  Ser Glu Val Asn Glu  Cys Ser Ser Asn Pro  Cys Ile His
    1085                1090                 1095
Gly Ala  Cys Arg Asp Ser Leu  Asn Gly Tyr Lys Cys  Asp Cys Asp
    1100                1105                 1110
Pro Gly  Trp Ser Gly Ala Asn  Cys Asp Val Asn Asn  Asp Glu Cys
    1115                1120                 1125
Glu Ser  Asn Pro Cys Ile Asn  Gly Gly Thr Cys Lys  Asp Met Thr
    1130                1135                 1140
Ser Gly  Tyr Val Cys Ala Cys  Arg Glu Gly Phe Ser  Gly Pro Asn
    1145                1150                 1155
Cys Gln  Thr Asn Ile Asn Glu  Cys Ala Ser Asn Pro  Cys Leu Asn
    1160                1165                 1170
Gln Gly  Thr Cys Ile Asp Asp  Val Ala Gly Tyr Lys  Cys Asn Cys
    1175                1180                 1185
Leu Leu  Pro Tyr Thr Gly Ala  Thr Cys Glu Val Val  Leu Ala Pro
    1190                1195                 1200
Cys Ala  Pro Gly Pro Cys Arg  Asn Gly Gly Glu Cys  Arg Glu Ser
    1205                1210                 1215
Glu Asp  Tyr Glu Ser Phe Ser  Cys Ala Cys Pro Ala  Gly Trp Gln
    1220                1225                 1230
Gly Gln  Thr Cys Glu Ile Asp  Ile Asn Glu Cys Val  Lys Ser Pro
    1235                1240                 1245
Cys Arg  Ala Gly Ala Ser Cys  Gln Asn Thr Asn Gly  Ser Tyr Arg
    1250                1255                 1260
Cys His  Cys Gln Ala Gly Tyr  Thr Gly Arg Asn Cys  Glu Thr Asp
    1265                1270                 1275
Ile Asp  Asp Cys Arg Pro Asn  Pro Cys His Asn Gly  Gly Ser Cys
```

```
                1280                1285                1290

Thr Asp Gly Ile Asn Thr Ala Phe Cys Asp Cys Leu Pro Gly Phe
    1295                1300                1305

Gln Gly Ala Phe Cys Glu Glu Asp Ile Asn Glu Cys Ala Ser Ser
    1310                1315                1320

Pro Cys Arg Asn Gly Ala Asn Cys Thr Asp Cys Val Asp Ser Tyr
    1325                1330                1335

Thr Cys Thr Cys Pro Thr Gly Phe Ser Gly Ile His Cys Glu Asn
    1340                1345                1350

Asn Thr Pro Asp Cys Thr Glu Ser Ser Cys Phe Asn Gly Gly Thr
    1355                1360                1365

Cys Val Asp Gly Ile Asn Ser Phe Thr Cys Leu Cys Pro Pro Gly
    1370                1375                1380

Phe Thr Gly Ser Tyr Cys Gln His Asp Val Asn Glu Cys Asp Ser
    1385                1390                1395

Arg Pro Cys Leu His Gly Gly Thr Cys His Asp Ser Tyr Gly Thr
    1400                1405                1410

Tyr Thr Cys Thr Cys Pro Gln Gly Tyr Thr Gly Leu Asn Cys Gln
    1415                1420                1425

Thr Leu Val Arg Trp Cys Asp Ser Ser Pro Cys Lys Asn Asp Gly
    1430                1435                1440

Arg Cys Trp Gln Thr Asn Ala Leu Tyr Arg Cys Glu Cys His Ser
    1445                1450                1455

Gly Trp Thr Gly Leu Tyr Cys Asp Val Pro Ser Val Ser Cys Glu
    1460                1465                1470

Val Ala Ala Arg Gln Gln Gly Val Asn Val Thr His Leu Cys Arg
    1475                1480                1485

Asn Gly Gly Leu Cys Met Asn Ala Gly Asn Thr His Arg Cys His
    1490                1495                1500

Cys Gln Ala Gly Tyr Thr Gly Ser Tyr Cys Glu Glu Gln Val Asp
    1505                1510                1515

Glu Cys Ser Pro Ser Pro Cys Gln Asn Gly Ala Thr Cys Thr Asp
    1520                1525                1530

Tyr Pro Gly Gly Tyr Ser Cys Glu Cys Val Ala Gly Tyr His Gly
    1535                1540                1545

Val Asn Cys Ser Glu Glu Val Asn Glu Cys Leu Ser Gln Pro Cys
    1550                1555                1560

Arg Asn Gly Gly Thr Cys Ile Asp Leu Thr Asn Thr Tyr Lys Cys
    1565                1570                1575

Ser Cys Pro Arg Gly Thr Gln Gly Val His Cys Glu Ile Asn Val
    1580                1585                1590

Asp Asp Cys Asn Pro Pro Ile Asp Pro Val Ser Arg Gly Pro Lys
    1595                1600                1605

Cys Phe Asn Asn Gly Thr Cys Val Asp Gln Val Gly Gly Tyr Ser
    1610                1615                1620

Cys Ser Cys Pro Pro Gly Phe Val Gly Glu Arg Cys Glu Gly Asp
    1625                1630                1635

Val Asn Glu Cys Leu Ser Asn Pro Cys Asp Ala Arg Gly Thr Gln
    1640                1645                1650

Asn Cys Val Gln His Val Asn Ala Phe His Cys Glu Cys Arg Ala
    1655                1660                1665

Gly His Thr Gly Arg Arg Cys Glu Ser Val Ile Asn Gly Cys Lys
    1670                1675                1680
```

```
Asp Arg Pro Cys Lys Asn Gly Gly Ser Cys Ala Val Ala Ser Asn
1685                1690                1695

Thr Ala Arg Gly Phe Ile Cys Lys Cys Pro Ala Gly Phe Glu Gly
1700                1705                1710

Ala Thr Cys Glu Asn Asp Ala Arg Ser Cys Gly Ser Leu Arg Cys
1715                1720                1725

Leu Asn Gly Gly Thr Cys Ile Ala Gly Pro Arg Ser Pro Thr Cys
1730                1735                1740

Leu Cys Leu Gly Pro Phe Thr Gly Pro Glu Cys Gln Phe Pro Ala
1745                1750                1755

Ser Ser Pro Cys Val Gly Gly Asn Pro Cys Tyr Asn Gln Gly Val
1760                1765                1770

Cys Glu Pro Thr Ala Glu Ser Pro Phe Tyr Arg Cys Arg Cys Pro
1775                1780                1785

Ala Lys Phe Asn Gly Leu Leu Cys His Ile Leu Asp Tyr Ser Phe
1790                1795                1800

Gly Gly Gly Val Gly Leu Asp Ile Pro Pro Gln Ile Glu Glu
1805                1810                1815

Thr Cys Glu Leu Pro Gly Cys Arg Glu Glu Ala Gly Asn Lys Val
1820                1825                1830

Cys Ser Leu Gln Cys Asn Ser His Ala Cys Gly Trp Asp Gly Gly
1835                1840                1845

Asp Cys Ser Leu Asp Phe Asp Asp Pro Trp Gln Asn Cys Thr Gln
1850                1855                1860

Ser Leu Gln Cys Trp Lys Tyr Phe Ser Asn Gly Arg Cys Asp Ser
1865                1870                1875

Gln Cys Asn Ser Ala Gly Cys Leu Phe Asp Gly Phe Asp Cys Gln
1880                1885                1890

Arg Ala Glu Gly Gln Cys Asn Pro Leu Tyr Asp Gln Tyr Cys Lys
1895                1900                1905

Asp His Phe Arg Asp Gly His Cys Asp Gln Gly Cys Asn Ser Ala
1910                1915                1920

Glu Cys Glu Trp Asp Gly Leu Asp Cys Ala Glu His Val Pro Glu
1925                1930                1935

Arg Leu Ala Ala Gly Thr Leu Val Leu Val Val Leu Met Pro Pro
1940                1945                1950

Glu Gln Leu Arg Asn Arg Ser Leu His Phe Leu Arg Glu Leu Ser
1955                1960                1965

Arg Leu Leu His Thr Asn Val Val Phe Lys Arg Asp Ala Ser Gly
1970                1975                1980

Gln Gln Met Ile Phe Pro Tyr Tyr Gly Arg Ala Pro Leu Pro Ala
1985                1990                1995

Gly Glu Arg Ser Glu Glu Cys Arg Cys Glu His His Ala Cys Pro
2000                2005                2010

Ala Gly Ala Gly Gln Gly Glu Pro Ser Gly Pro Leu Cys Thr Ser
2015                2020                2025

Arg Ser Ile Val Tyr Leu Glu Ile Asp Asn Arg Gln Cys Val Gln
2030                2035                2040

Ser Ser Ser Gln Cys Phe Gln Ser Ala Thr Asp Val Ala Ala Phe
2045                2050                2055

Leu Gly Ala Leu Ala Ser Leu Gly Ser Leu Asn Ile Pro Tyr Lys
2060                2065                2070
```

-continued

```
Ile Glu Ala Val Gln Ser Glu Thr Val Glu Pro Pro Pro Pro Pro
2075                2080                2085

Pro Leu His Phe Met Tyr Val Ala Val Val Ala Phe Val Leu Leu
    2090                2095                2100

Phe Phe Val Gly Cys Gly Val Leu Leu Ser Arg Lys Arg Arg Arg
    2105                2110                2115

Gln His Gly Gln Leu Trp Phe Pro Glu Gly Phe Lys Val Ser Glu
    2120                2125                2130

Ala Ser Lys Lys Lys Arg Arg Glu Pro Leu Gly Glu Asp Ser Val
    2135                2140                2145

Gly Leu Lys Pro Leu Lys Asn Ser Ser Asp Gly Ala Leu Met Asp
    2150                2155                2160

Asp Asn Gln Asn Glu Trp Gly Asp Glu Gly Leu Glu Ala Lys Lys
    2165                2170                2175

Phe Arg Phe Glu Glu Pro Val Val Leu Pro Asp Leu Asp Asp Gln
    2180                2185                2190

Thr Asp His Arg Gln Trp Thr Gln Gln His Leu Asp Ala Ala Asp
    2195                2200                2205

Leu Arg Val Ser Ala Met Ala Pro Thr Pro Pro Gln Gly Glu Ala
    2210                2215                2220

Asp Ala Asp Cys Met Asp Val Asn Val Arg Gly Pro Asp Gly Phe
    2225                2230                2235

Thr Pro Leu Met Ile Ala Ser Cys Ser Gly Gly Gly Leu Glu Thr
    2240                2245                2250

Gly Asn Ser Glu Glu Glu Glu Asp Ala Pro Ala Val Ile Ser Asp
    2255                2260                2265

Phe Ile Tyr Gln Gly Ala Ser Leu His Asn Gln Thr Asp Arg Thr
    2270                2275                2280

Gly Glu Thr Ala Leu His Leu Ala Ala Arg Tyr Ser Arg Ser Asp
    2285                2290                2295

Ala Ala Lys Arg Leu Leu Glu Ala Ser Ala Asp Ala Asn Ile Gln
    2300                2305                2310

Asp Asn Met Gly Arg Thr Pro Leu His Ala Ala Val Ser Ala Asp
    2315                2320                2325

Ala Gln Gly Val Phe Gln Ile Leu Ile Arg Asn Arg Ala Thr Asp
    2330                2335                2340

Leu Asp Ala Arg Met His Asp Gly Thr Thr Pro Leu Ile Leu Ala
    2345                2350                2355

Ala Arg Leu Ala Val Glu Gly Met Leu Glu Asp Leu Ile Asn Ser
    2360                2365                2370

His Ala Asp Val Asn Ala Val Asp Asp Leu Gly Lys Ser Ala Leu
    2375                2380                2385

His Trp Ala Ala Ala Val Asn Asn Val Glu Ala Ala Val Val Leu
    2390                2395                2400

Leu Lys Asn Gly Ala Asn Lys Asp Met Gln Asn Asn Lys Glu Glu
    2405                2410                2415

Thr Pro Leu Phe Leu Ala Ala Arg Glu Gly Ser Tyr Glu Thr Ala
    2420                2425                2430

Lys Val Leu Leu Asp His Phe Ala Asn Arg Asp Ile Thr Asp His
    2435                2440                2445

Met Asp Arg Leu Pro Arg Asp Ile Ala Gln Glu Arg Met His His
    2450                2455                2460

Asp Ile Val Arg Leu Leu Asp Glu Tyr Ser Leu Val Arg Ser Pro
```

```
                2465                    2470                    2475
Pro Leu His Gly Ala Thr Leu Gly Gly Thr Pro Thr Leu Ser Pro
    2480                    2485                    2490
Pro Leu Cys Ser Pro Asn Gly Tyr Leu Gly Asn Leu Lys Pro Pro
    2495                    2500                    2505
Met Gln Gly Lys Lys Ala Arg Lys Pro Ser Thr Lys Gly Leu Ala
    2510                    2515                    2520
Cys Gly Gly Lys Glu Pro Lys Asp Leu Lys Ala Arg Arg Lys Lys
    2525                    2530                    2535
Ser Gln Asp Gly Lys Gly Cys Leu Leu Asp Ser Gly Ser Val Met
    2540                    2545                    2550
Ser Pro Val Asp Ser Leu Glu Ser Pro His Gly Tyr Leu Ser Asp
    2555                    2560                    2565
Val Ala Ser Pro Pro Leu Leu Pro Ser Pro Phe Gln Pro Ser Pro
    2570                    2575                    2580
Ser Val Pro Leu Asn His Leu Pro Gly Met Pro Glu Thr His Leu
    2585                    2590                    2595
Gly Val Ser His Leu Ser Val Ala Ala Lys Pro Glu Met Ala Val
    2600                    2605                    2610
Leu Ser Gly Gly Ser Arg Leu Ala Phe Glu Ala Gly Pro Pro Arg
    2615                    2620                    2625
Leu Ser His Leu Pro Val Ala Ser Ser Thr Ser Thr Ile Leu Gly
    2630                    2635                    2640
Ser Gly Gly Ser Gly Gly Ser Gly Ala Val Asn Phe Thr Val Gly
    2645                    2650                    2655
Gly Ala Ala Gly Leu Asn Gly Gln Cys Glu Trp Leu Ser Arg Leu
    2660                    2665                    2670
Gln Asn Gly Leu Val Pro Asn Gln Tyr Asn Pro Leu Arg Gly Gly
    2675                    2680                    2685
Val Thr Pro Gly Thr Leu Ser Thr Gln Ala Ala Gly Leu Gln His
    2690                    2695                    2700
Gly Thr Val Gly Pro Leu His Ala Pro Ala Leu Ser Gln Val Met
    2705                    2710                    2715
Thr Tyr Gln Ala Leu Pro Ser Thr Arg Leu Ala Ser Gln Pro His
    2720                    2725                    2730
Leu Val Gln Pro Gln Gln Asn Leu Gln Met Gln Pro Pro Ser Met
    2735                    2740                    2745
Pro Pro Gln Pro Asn Leu Gln Pro His Leu Gly Val Ser Ser Ala
    2750                    2755                    2760
Ala Ser Gly His Leu Gly Arg Ser Phe Leu Gly Gly Glu Leu Ser
    2765                    2770                    2775
Gln Ala Asp Met Gln Pro Leu Gly Pro Gly Asn Leu Ala Ala His
    2780                    2785                    2790
Thr Val Leu Pro Gln Asp Gly Gln Val Leu Pro Thr Ser Leu Pro
    2795                    2800                    2805
Ser Thr Leu Ala Pro Pro Thr Met Ala Pro Met Thr Thr Ala
    2810                    2815                    2820
Gln Phe Leu Thr Pro Pro Ser Gln His Ser Tyr Ser Ser Pro
    2825                    2830                    2835
Val Asp Asn Thr Pro Ser His Gln Leu Gln Val Pro Glu His Pro
    2840                    2845                    2850
Phe Leu Thr Pro Ser Pro Glu Ser Pro Asp Gln Trp Ser Ser Ser
    2855                    2860                    2865
```

```
Ser Pro His Ser Asn Ile Ser Asp Trp Ser Glu Gly Ile Ser Ser
    2870                2875                2880

Pro Pro Thr Ser Val Pro Ser Gln Ile Ala His Val Pro Glu Ala
    2885                2890                2895

Phe Lys
    2900

<210> SEQ ID NO 6
<211> LENGTH: 2561
<212> TYPE: PRT
<213> ORGANISM: Gallus gallus

<400> SEQUENCE: 6

Met Gly Arg Cys Ser Ala Ala His Pro Arg Gly Gly Val His Cys Pro
1               5                   10                  15

Gly Leu Cys Ala Val Pro Asp Ala Leu Leu Phe Pro Gly Val Arg
                20                  25                  30

Cys Thr Gln Leu Ala Glu Ser Cys Leu Asn Gly Gly Lys Cys Glu Thr
                35                  40                  45

Phe Leu Asn Gly Thr Glu Val Cys Gln Cys Ser Ser Ala His Met Gly
    50                  55                  60

Glu Arg Cys Gln Leu Pro Asn Pro Cys Leu Ser Ser Pro Cys Lys Asn
65                  70                  75                  80

Ala Gly Thr Cys Ile Pro Leu Leu Arg Gly Ser Thr Ala Asp Tyr Thr
                85                  90                  95

Cys Val Cys Arg Leu Gly Phe Thr Asp Glu Leu Cys Leu Thr Pro Leu
                100                 105                 110

Asp Asn Ala Cys Leu Asn Asn Pro Cys Arg Asn Gly Gly Thr Cys Asp
            115                 120                 125

Leu Val Thr Leu Ser Glu Tyr Lys Cys Arg Cys Pro Pro Gly Trp Ser
    130                 135                 140

Gly Lys Thr Cys Gln Gln Ala Asp Pro Cys Ala Ser Asn Pro Cys Ala
145                 150                 155                 160

Asn Gly Gly Gln Cys Val Pro Phe Glu Ala His Tyr Ile Cys Arg Cys
                165                 170                 175

Thr Ala Gly Phe His Gly Ala Asn Cys Lys Gln Asp Val Asn Glu Cys
                180                 185                 190

Asn Ile Ser Pro Pro Val Cys Lys Asn Gly Gly Ser Cys Thr Asn Glu
            195                 200                 205

Val Gly Thr Tyr Gln Cys Ser Cys Lys Pro Ala Tyr Thr Gly Gln Asn
    210                 215                 220

Cys Glu His Leu Tyr Val Pro Cys Asn Pro Ser Pro Cys Gln Asn Gly
225                 230                 235                 240

Gly Thr Cys Arg Gln Thr Gly Asp Thr Thr Tyr Asp Cys Thr Cys Leu
                245                 250                 255

Pro Gly Phe Thr Gly Gln Asn Cys Glu Glu Asn Ile Asp Asp Cys Pro
                260                 265                 270

Gly Asn Asn Cys Arg Asn Gly Gly Thr Cys Val Asp Gly Val Asn Thr
            275                 280                 285

Tyr Asn Cys Gln Cys Pro Pro Glu Trp Thr Gly Gln Tyr Cys Thr Glu
    290                 295                 300

Asp Val Asp Glu Cys Gln Leu Met Pro Asn Ala Cys Gln Asn Gly Gly
305                 310                 315                 320

Thr Cys His Asn Asn His Gly Gly Tyr Asn Cys Val Cys Val Asn Gly
```

```
                    325                 330                 335
Trp Thr Gly Glu Asp Cys Ser Glu Asn Ile Asp Asp Cys Ala Met Ala
                340                 345                 350

Ala Cys Phe Gln Gly Ala Thr Cys His Asp Arg Val Ala Ser Phe Tyr
                355                 360                 365

Cys Glu Cys Pro His Gly Arg Thr Gly Leu Leu Cys His Leu Asp Asp
                370                 375                 380

Ala Cys Ile Ser Asn Pro Cys Asn Glu Gly Ser Asn Cys Asp Thr Asn
385                 390                 395                 400

Pro Val Asn Gly Lys Ala Ile Cys Thr Cys Pro Ser Gly Tyr Met Gly
                405                 410                 415

Pro Ala Cys Asn Gln Asp Val Asp Glu Cys Ser Leu Gly Ala Asn Pro
                420                 425                 430

Cys Glu His Ala Gly Lys Cys Ile Asn Thr Gln Gly Ser Phe Gln Cys
                435                 440                 445

Gln Cys Leu Gln Gly Tyr Ser Gly Pro Arg Cys Glu Ile Asp Val Asn
                450                 455                 460

Glu Cys Leu Ser Asn Pro Cys Gln Asn Asp Ala Thr Cys Leu Asp Gln
465                 470                 475                 480

Ile Gly Glu Phe Gln Cys Ile Cys Met Pro Gly Tyr Glu Gly Val Tyr
                485                 490                 495

Cys Glu Ile Asn Thr Asp Glu Cys Ala Ser Ser Pro Cys Leu His Asn
                500                 505                 510

Gly Asn Cys Leu Asp Lys Ile Asn Glu Phe His Cys Glu Cys Pro Thr
                515                 520                 525

Gly Phe Asn Gly His Leu Cys Gln Phe Asp Ile Asp Glu Cys Ala Ser
                530                 535                 540

Thr Pro Cys Lys Asn Gly Ala Lys Cys Val Asp Gly Pro Asn Thr Tyr
545                 550                 555                 560

Ser Cys Glu Cys Thr Glu Gly Phe Ser Gly Val His Cys Glu Ile Asp
                565                 570                 575

Ile Asp Glu Cys Asn Pro Asp Pro Cys His Tyr Gly Thr Cys Lys Asp
                580                 585                 590

Ser Ile Ala Ala Phe Thr Cys Leu Cys Gln Pro Gly Tyr Thr Gly His
                595                 600                 605

Arg Cys Asp Ile Asn Ile Asn Glu Cys Gln Ser Gln Pro Cys Arg Asn
610                 615                 620

Gly Gly Thr Cys Gln Asp Arg Asp Asn Ala Tyr Asn Cys Leu Cys Leu
625                 630                 635                 640

Lys Gly Thr Thr Gly Pro Asn Cys Glu Ile Asn Leu Asp Asp Cys Ala
                645                 650                 655

Ser Asn Pro Cys Asp Tyr Gly Lys Cys Ile Asp Lys Ile Asn Gly Tyr
                660                 665                 670

Glu Cys Thr Cys Glu Pro Gly Tyr Thr Gly Arg Met Cys Asn Ile Asn
                675                 680                 685

Ile Asp Glu Cys Ala Ser Asn Pro Cys His Asn Gly Gly Thr Cys Lys
                690                 695                 700

Asp Gly Ile Asn Gly Phe Thr Cys Leu Cys Pro Glu Gly Phe His Asp
705                 710                 715                 720

Pro Lys Cys Leu Ser Glu Val Asn Glu Cys Asn Ser Asn Pro Cys Ile
                725                 730                 735

His Gly Arg Cys His Asp Gly Leu Asn Gly Tyr Arg Cys Asp Cys Asp
                740                 745                 750
```

```
Pro Gly Trp Ser Gly Thr Asn Cys Asp Ile Asn Asn Glu Cys Glu
        755                 760                 765

Ser Asn Pro Cys Met Asn Gly Gly Thr Cys Lys Asp Met Thr Ser Gly
    770                 775                 780

Tyr Ile Cys Thr Cys Arg Glu Gly Phe Ser Gly Pro Asn Cys Gln Thr
785                 790                 795                 800

Asn Ile Asn Glu Cys Ala Ser Asn Pro Cys Leu Asn Gln Gly Thr Cys
                805                 810                 815

Ile Asp Asp Val Ala Gly Tyr Thr Cys Asn Cys Leu Leu Pro Tyr Thr
                820                 825                 830

Gly Ala Thr Cys Glu Asp Val Leu Ala Pro Cys Ala Gly Gly Pro Cys
                835                 840                 845

Lys Asn Gly Gly Glu Cys Arg Glu Ser Glu Asp Tyr Lys Arg Phe Ser
    850                 855                 860

Cys Ser Cys Pro Pro Gly Trp Gln Gly Gln Thr Cys Glu Ile Asp Ile
865                 870                 875                 880

Asn Glu Cys Val Lys Ser Pro Cys Arg Asn Gly Ala Thr Cys Gln Asn
                885                 890                 895

Thr Asn Gly Ser Tyr Arg Cys Leu Cys Arg Val Gly Phe Ala Gly Arg
        900                 905                 910

Asn Cys Asp Thr Asp Ile Asp Asp Cys Gln Pro Asn Pro Cys His Asn
        915                 920                 925

Gly Gly Ser Cys Ser Asp Gly Ile Gly Thr Phe Phe Cys Glu Cys Leu
        930                 935                 940

Ala Gly Phe Arg Gly Leu Lys Cys Glu Glu Asp Ile Asn Glu Cys Ala
945                 950                 955                 960

Ser Asn Pro Cys Lys Asn Gly Ala Asn Cys Thr Asp Cys Val Asn Ser
                965                 970                 975

Tyr Thr Cys Thr Cys Pro Ser Gly Phe Ser Gly Ile His Cys Glu Asn
                980                 985                 990

Asn Thr Pro Asp Cys Thr Glu Ser Ser Cys Phe Asn Gly Gly Thr Cys
        995                 1000                1005

Val Asp Gly Ile Asn Thr Phe Thr Cys Leu Cys Pro Ser Gly Phe
    1010                1015                1020

Thr Gly Ser Tyr Cys Glu His Asn Ile Asn Glu Cys Asp Ser Lys
    1025                1030                1035

Pro Cys Leu Asn Gly Gly Thr Cys Gln Asp Ser Tyr Gly Thr Tyr
    1040                1045                1050

Lys Cys Thr Cys Pro Gln Gly Tyr Thr Gly Leu Asn Cys Gln Asn
    1055                1060                1065

Leu Val Arg Trp Cys Asp Ser Ser Pro Cys Lys Asn Gly Gly Lys
    1070                1075                1080

Cys Trp Gln Thr Asn Asn Leu Tyr Arg Cys Glu Cys Asn Ser Gly
    1085                1090                1095

Trp Thr Gly Leu Tyr Cys Asp Val Pro Ser Val Ser Cys Glu Val
    1100                1105                1110

Ala Ala Lys Gln Gln Gly Ile Asp Val Ala His Leu Cys Arg Asn
    1115                1120                1125

Ser Gly Leu Cys Val Asp Ser Gly Asn Thr His Phe Cys Arg Cys
    1130                1135                1140

Gln Ala Gly Tyr Thr Gly Ser Tyr Cys Glu Glu Gln Val Asp Glu
    1145                1150                1155
```

-continued

Cys Ser Pro Asn Pro Cys Gln Asn Gly Ala Thr Cys Thr Asp Tyr
1160            1165            1170

Leu Gly Gly Tyr Ser Cys Glu Cys Val Ala Gly Tyr His Gly Val
1175            1180            1185

Asn Cys Ser Glu Glu Ile Asn Glu Cys Leu Ser His Pro Cys Gln
1190            1195            1200

Asn Gly Gly Thr Cys Ile Asp Leu Ile Asn Thr Tyr Lys Cys Ser
1205            1210            1215

Cys Pro Arg Gly Thr Gln Gly Val His Cys Glu Ile Asn Val Asp
1220            1225            1230

Asp Cys Ser Pro Phe Phe Asp Pro Val Thr Leu Gly Pro Lys Cys
1235            1240            1245

Phe Asn Asn Gly Lys Cys Thr Asp Arg Val Gly Tyr Ser Cys
1250            1255            1260

Ile Cys Pro Pro Gly Phe Val Gly Glu Arg Cys Glu Gly Asp Val
1265            1270            1275

Asn Glu Cys Leu Ser Asn Pro Cys Asp Ala Arg Gly Thr Gln Asn
1280            1285            1290

Cys Val Gln Arg Val Asn Asp Tyr Lys Cys Glu Cys Arg Pro Gly
1295            1300            1305

Tyr Ala Gly Arg Arg Cys Asp Thr Val Val Asp Gly Cys Lys Gly
1310            1315            1320

Lys Pro Cys Arg Asn Gly Gly Thr Cys Ala Val Ala Ser Asn Thr
1325            1330            1335

Gly Arg Gly Phe Ile Cys Lys Cys Pro Pro Gly Phe Val Gly Ala
1340            1345            1350

Thr Cys Glu Asn Asp Ser His Thr Cys Gly Thr Leu His Cys Leu
1355            1360            1365

Asn Gly Gly Thr Cys Ile Ser Met His Lys Ser Ser Lys Cys Val
1370            1375            1380

Cys Ala Ala Ala Phe Thr Gly Pro Glu Cys Gln Tyr Pro Ala Ser
1385            1390            1395

Ser Pro Cys Ile Ser Asn Pro Cys Tyr Asn Gly Gly Thr Cys Glu
1400            1405            1410

Phe Leu Ser Asp Ala Ser Pro Tyr Tyr His Cys Asn Cys Pro Ala
1415            1420            1425

Asn Phe Asn Gly Leu Asn Cys His Ile Leu Asp Phe Asp Phe Gln
1430            1435            1440

Gly Gly Phe Gly Gln Asp Ile Ile Pro Pro Lys Ile Glu Glu Lys
1445            1450            1455

Cys Glu Ile Ala Val Cys Ala Ser Tyr Ala Gly Asn Lys Ile Cys
1460            1465            1470

Asp Gly Lys Cys Asn Asn His Ala Cys Gly Trp Asp Gly Gly Asp
1475            1480            1485

Cys Ser Leu Asn Phe Asn Asp Pro Trp Lys Asn Cys Ser Gln Ser
1490            1495            1500

Leu Gln Cys Trp Lys Tyr Phe Asn Asp Gly Lys Cys Asp Ser Gln
1505            1510            1515

Cys Asn Asn Ala Gly Cys Leu Tyr Asp Gly Phe Asp Cys Gln Lys
1520            1525            1530

Tyr Glu Gly Gln Cys Asn Pro Leu Tyr Asp Gln Tyr Cys Lys Asp
1535            1540            1545

His Phe Ser Asp Gly His Cys Asp Gln Gly Cys Asn Asn Phe Glu

|  |  |  |
|---|---|---|
| 1550 | 1555 | 1560 |

Cys Glu Trp Asp Gly Leu Asp Cys Ala Asn Asn Met Pro Glu Lys
1565                 1570                1575

Leu Ala Asp Gly Thr Leu Val Val Val Leu Ile Thr Pro Glu
1580                 1585                1590

Asn Leu Lys Asn Asn Ser Phe Asn Phe Leu Arg Glu Leu Ser Arg
1595                 1600                1605

Val Leu His Thr Asn Val Val Phe Lys Lys Asn Ala Lys Gly Glu
1610                 1615                1620

Tyr Met Ile Phe Pro Tyr Tyr Gly Asn Glu Glu Leu Lys Lys
1625                 1630                1635

His Tyr Ile Lys Arg Ser Thr Glu Asp Trp Ala Asp Met Ser Ser
1640                 1645                1650

Ala Val Ile Asn Lys Val Lys Ser Ser Leu Tyr Ser Arg Ala Gly
1655                 1660                1665

Arg Arg Gln Lys Arg Glu Leu Asp Gln Met Asp Ile Arg Gly Ser
1670                 1675                1680

Ile Val Tyr Leu Glu Ile Asp Asn Arg Gln Cys Ile Gln Ser Ser
1685                 1690                1695

Ser Gln Cys Phe Gln Ser Ala Thr Asp Val Ala Ala Phe Leu Gly
1700                 1705                1710

Ala Leu Ala Ser Leu Gly Asn Leu Asn Ile Pro Tyr Lys Ile Glu
1715                 1720                1725

Ala Val Lys Ser Glu Thr Ala Glu Pro Ala Arg Asn Ser Gln Leu
1730                 1735                1740

Tyr Pro Met Tyr Val Val Ala Ala Leu Val Leu Leu Ala Phe
1745                 1750                1755

Ile Gly Val Gly Val Leu Val Ser Arg Lys Arg Arg Arg Glu His
1760                 1765                1770

Gly Gln Leu Trp Phe Pro Glu Gly Phe Lys Val Thr Glu Ser Ser
1775                 1780                1785

Lys Lys Lys Arg Arg Glu Pro Leu Gly Glu Asp Ser Val Gly Leu
1790                 1795                1800

Lys Pro Leu Lys Asn Ala Ser Asp Gly Thr Leu Met Asp Asp Asn
1805                 1810                1815

Gln Asn Glu Trp Gly Asp Glu Glu Thr Leu Asp Thr Lys Lys Phe
1820                 1825                1830

Arg Phe Glu Glu Gln Ala Met Leu Pro Asp Thr Asp Asp Gln Thr
1835                 1840                1845

Asp His Arg Gln Trp Thr Gln Gln His Leu Asp Ala Ala Asp Leu
1850                 1855                1860

Arg Ile Ser Ser Met Ala Pro Thr Pro Pro Gln Gly Glu Ile Asp
1865                 1870                1875

Ala Asp Cys Met Asp Val Asn Val Arg Gly Pro Asp Gly Phe Thr
1880                 1885                1890

Pro Leu Met Ile Ala Ser Cys Ser Gly Gly Gly Leu Glu Thr Gly
1895                 1900                1905

Asn Ser Glu Glu Glu Asp Asp Ala Pro Ala Val Ile Ser Asp Phe
1910                 1915                1920

Ile Tyr Gln Gly Ala Ser Leu His Asn Gln Thr Asp Arg Thr Gly
1925                 1930                1935

Glu Thr Ala Leu His Leu Ala Ala Arg Tyr Ser Arg Ser Asp Ala
1940                 1945                1950

-continued

```
Ala Lys Arg Leu Leu Glu Ala Ser Ala Asp Ala Asn Ile Gln Asp
    1955                1960                1965

Asn Met Gly Arg Thr Pro Leu His Ala Ala Val Ser Ala Asp Ala
    1970                1975                1980

Gln Gly Val Phe Gln Ile Leu Ile Arg Asn Arg Ala Thr Asp Leu
    1985                1990                1995

Asp Ala Arg Met His Asp Gly Thr Thr Pro Leu Ile Leu Ala Ala
    2000                2005                2010

Arg Leu Ala Val Glu Gly Met Leu Glu Asp Leu Ile Asn Cys His
    2015                2020                2025

Ala Asp Val Asn Ala Val Asp Leu Gly Lys Ser Ala Leu His
    2030                2035                2040

Trp Ala Ala Val Asn Asn Val Glu Ala Ala Val Val Leu Leu
    2045                2050                2055

Lys Asn Gly Ala Asn Lys Asp Met Gln Asn Asn Lys Glu Glu Thr
    2060                2065                2070

Pro Leu Phe Leu Ala Ala Arg Glu Gly Ser Tyr Glu Thr Ala Lys
    2075                2080                2085

Val Leu Leu Asp His Phe Ala Asn Arg Asp Ile Thr Asp His Met
    2090                2095                2100

Asp Arg Leu Pro Arg Asp Ile Ala Gln Glu Arg Met His His Asp
    2105                2110                2115

Ile Val Arg Leu Leu Asp Glu Tyr Asn Leu Val Arg Ser Pro Pro
    2120                2125                2130

Leu His Ser Gly Pro Leu Gly Ala Pro Thr Leu Ser Pro Pro Leu
    2135                2140                2145

Cys Ser Pro Ser Ser Tyr Ile Gly Asn Leu Lys Pro Ala Val Gln
    2150                2155                2160

Gly Lys Lys Ala Arg Lys Pro Ser Thr Lys Gly Leu Ser Cys Asn
    2165                2170                2175

Gly Lys Asp Ser Lys Asp Leu Lys Ala Arg Arg Lys Lys Ser Gln
    2180                2185                2190

Asp Gly Lys Gly Cys Leu Leu Asp Asn Ser Ser Val Leu Ser Pro
    2195                2200                2205

Val Asp Ser Leu Glu Ser Pro His Gly Tyr Leu Ser Asp Val Ala
    2210                2215                2220

Ser Pro Pro Leu Met Thr Ser Pro Phe Gln Gln Ser Pro Ser Met
    2225                2230                2235

Pro Leu Asn His Leu Pro Gly Met Pro Asp Ala His Met Ser Ile
    2240                2245                2250

Asn His Leu Asn Met Ala Gly Lys Gln Glu Met Ala Leu Gly Gly
    2255                2260                2265

Ser Gly Arg Met Ala Phe Glu Ala Val Pro Pro Arg Leu Ser His
    2270                2275                2280

Leu Pro Val Ser Ser Pro Ser Thr Ala Met Ser Asn Ala Pro Met
    2285                2290                2295

Asn Phe Ser Val Gly Gly Ala Ala Gly Leu Ser Gly Gln Cys Asp
    2300                2305                2310

Trp Leu Ser Arg Leu Gln Ser Gly Met Val Gln Asn Gln Tyr Gly
    2315                2320                2325

Ala Met Arg Gly Gly Met Gln Pro Gly Thr His Gln Gln Ala Gln
    2330                2335                2340
```

Asn Leu Gln His Gly Met Met Ser Ser Leu His Asn Gly Leu Pro
2345                2350                2355

Ser Thr Ser Leu Ser Gln Met Met Ser Tyr Gln Ala Met Pro Ser
2360                2365                2370

Thr Arg Leu Ala Ser Gln Pro His Leu Leu Gln Asn Gln Gln Met
2375                2380                2385

Gln Gln Met Gln Gln Pro Gly Met Gln Pro Gln Gly Met Gln
2390                2395                2400

Pro Gln Pro Gly Met Gln Gln Pro Gln Gln Gln Pro Gln Gln Gln
2405                2410                2415

Pro Gln Pro Gln Gln His His Asn Pro Gly Ser Asn Ala Ser Gly
2420                2425                2430

His Met Gly Gln Asn Phe Leu Gly Thr Glu Leu Ser Gln Pro Asp
2435                2440                2445

Met Gln Pro Val Ser Ser Ser Ala Met Ala Val His Thr Ile Leu
2450                2455                2460

Pro Gln Asp Ser Gln Leu Leu Pro Thr Ser Leu Pro Ser Ser Leu
2465                2470                2475

Ala Gln Pro Met Thr Thr Thr Gln Phe Leu Thr Pro Pro Ser Gln
2480                2485                2490

His Ser Tyr Ser Ser Pro Leu Asp Asn Thr Pro Ser His Gln Leu
2495                2500                2505

Gln Val Pro Asp His Pro Phe Leu Thr Pro Ser Pro Glu Ser Pro
2510                2515                2520

Asp Gln Trp Ser Ser Ser Ser Pro His Ser Asn Val Ser Asp Trp
2525                2530                2535

Ser Glu Gly Ile Ser Ser Pro Pro Thr Ser Met Gln Ser Gln Met
2540                2545                2550

Gly His Ile Pro Glu Ala Phe Lys
2555                2560

<210> SEQ ID NO 7
<211> LENGTH: 2531
<212> TYPE: PRT
<213> ORGANISM: Rattus rattus

<400> SEQUENCE: 7

Met Pro Arg Leu Leu Ala Pro Leu Leu Cys Leu Thr Leu Pro Ala
1               5                   10                  15

Leu Ala Ala Arg Gly Leu Arg Cys Ser Gln Pro Ser Gly Thr Cys Leu
                20                  25                  30

Asn Gly Gly Arg Cys Glu Val Ala Asn Gly Thr Glu Ala Cys Val Cys
            35                  40                  45

Ser Gly Ala Phe Val Gly Gln Arg Cys Gln Asp Pro Ser Pro Cys Leu
        50                  55                  60

Ser Thr Pro Cys Lys Asn Ala Gly Thr Cys Tyr Val Val Asp His Gly
65                  70                  75                  80

Gly Ile Val Asp Tyr Ala Cys Ser Cys Pro Leu Gly Phe Ser Gly Pro
                85                  90                  95

Leu Cys Leu Thr Pro Leu Ala Asn Ala Cys Leu Ala Asn Pro Cys Arg
                100                 105                 110

Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
        130                 135                 140

```
Ala Ser Asn Pro Cys Ala Asn Gly Gly Gln Cys Leu Pro Phe Glu Ser
145                 150                 155                 160

Ser Tyr Ile Cys Gly Cys Pro Gly Phe His Gly Pro Thr Cys Arg
            165                 170                 175

Gln Asp Val Asn Glu Cys Ser Gln Asn Pro Gly Leu Cys Arg His Gly
                180                 185                 190

Gly Thr Cys His Asn Glu Ile Gly Ser Tyr Arg Cys Ala Cys Arg Ala
            195                 200                 205

Thr His Thr Gly Pro His Cys Glu Leu Pro Tyr Val Pro Cys Ser Pro
            210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255

Asn Val Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
290                 295                 300

Ala Cys Gln Asn Ala Gly Thr Cys His Asn Ser His Gly Gly Tyr Asn
305                 310                 315                 320

Cys Val Cys Val Asn Gly Trp Thr Gly Glu Asp Cys Ser Asp Asn Ile
            325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Arg Gly Tyr Thr Gly Pro Ala Cys Ser Gln Asp Val Asp Glu Cys
            405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
    435                 440                 445

Cys Glu Ile Asp Val Asn Glu Cys Ile Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
            485                 490                 495

Ser Pro Cys Leu His Asn Gly Arg Cys Val Asp Lys Ile Asn Glu Phe
        500                 505                 510

Leu Cys Gln Cys Pro Lys Gly Phe Ser Gly His Leu Cys Gln Tyr Asp
    515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560
```

```
Thr His Cys Glu Val Asp Ile Asp Glu Cys Asp Pro Asp Pro Cys His
            565                 570                 575
Ile Gly Leu Cys Lys Asp Gly Val Ala Thr Phe Thr Cys Leu Cys Gln
            580                 585                 590
Pro Gly Tyr Thr Gly His His Cys Glu Thr Asn Ile Asn Glu Cys His
            595                 600                 605
Ser Gln Pro Cys Arg His Gly Thr Cys Gln Asp Arg Asp Asn Tyr
            610                 615                 620
Tyr Leu Cys Leu Cys Leu Lys Gly Thr Thr Gly Pro Asn Cys Glu Ile
625                 630                 635                 640
Asn Leu Asp Asp Cys Ala Ser Asn Pro Cys Asp Ser Gly Thr Cys Leu
            645                 650                 655
Asp Lys Ile Asp Gly Tyr Glu Cys Ala Cys Glu Pro Gly Tyr Thr Gly
            660                 665                 670
Ser Met Cys Asn Val Asn Ile Asp Glu Cys Ala Gly Ser Pro Cys His
            675                 680                 685
Asn Gly Gly Thr Cys Glu Asp Gly Ile Ala Gly Phe Thr Cys Arg Cys
            690                 695                 700
Pro Glu Gly Tyr His Asp Pro Thr Cys Leu Ser Glu Val Asn Glu Cys
705                 710                 715                 720
Asn Ser Asn Pro Cys Ile His Gly Ala Cys Arg Asp Gly Leu Asn Gly
            725                 730                 735
Tyr Lys Cys Asp Cys Ala Pro Gly Trp Ser Gly Thr Asn Cys Asp Ile
            740                 745                 750
Asn Asn Asn Glu Cys Glu Ser Asn Pro Cys Val Asn Gly Gly Thr Cys
            755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
            805                 810                 815
Cys Pro Leu Pro Tyr Thr Gly Ala Thr Cys Glu Val Val Leu Ala Pro
            820                 825                 830
Cys Ala Thr Ser Pro Cys Lys Asn Ser Gly Val Cys Lys Glu Ser Glu
            835                 840                 845
Asp Tyr Glu Ser Phe Ser Cys Val Cys Pro Thr Gly Trp Gln Gly Gln
            850                 855                 860
Thr Cys Glu Ile Asp Ile Asn Glu Cys Val Lys Ser Pro Cys Arg His
865                 870                 875                 880
Gly Ala Ser Cys Gln Asn Thr Asn Gly Ser Tyr Arg Cys Leu Cys Gln
            885                 890                 895
Ala Gly Tyr Thr Gly Arg Asn Cys Glu Ser Asp Ile Asp Asp Cys Arg
            900                 905                 910
Pro Asn Pro Cys His Asn Gly Gly Ser Cys Thr Asp Gly Val Asn Ala
            915                 920                 925
Ala Phe Cys Asp Cys Leu Pro Gly Phe Gln Gly Ala Phe Cys Glu Glu
            930                 935                 940
Asp Ile Asn Glu Cys Ala Thr Asn Pro Cys Gln Asn Gly Ala Asn Cys
945                 950                 955                 960
Thr Asp Cys Val Asp Ser Tyr Thr Cys Thr Cys Pro Thr Gly Phe Asn
            965                 970                 975
Gly Ile His Cys Glu Asn Asn Thr Pro Asp Cys Thr Glu Ser Ser Cys
```

```
            980             985             990
Phe Asn Gly Gly Thr Cys Val Asp Gly Ile Asn Ser Phe Thr Cys Leu
            995             1000            1005

Cys Pro Pro Gly Phe Thr Gly Ser Tyr Cys Gln Tyr Asp Val Asn
    1010            1015            1020

Glu Cys Asp Ser Arg Pro Cys Leu His Gly Gly Thr Cys Gln Asp
    1025            1030            1035

Ser Tyr Gly Thr Tyr Lys Cys Thr Cys Pro Gln Gly Tyr Thr Gly
    1040            1045            1050

Leu Asn Cys Gln Asn Leu Val Arg Trp Cys Asp Ser Ala Pro Cys
    1055            1060            1065

Lys Asn Gly Gly Lys Cys Trp Gln Thr Asn Thr Gln Tyr His Cys
    1070            1075            1080

Glu Cys Arg Ser Gly Trp Thr Gly Phe Asn Cys Asp Val Leu Ser
    1085            1090            1095

Val Ser Cys Glu Val Ala Ala Gln Lys Arg Gly Ile Asp Val Thr
    1100            1105            1110

Leu Leu Cys Gln His Gly Gly Leu Cys Val Asp Glu Glu Asp Lys
    1115            1120            1125

His Tyr Cys His Cys Gln Ala Gly Tyr Thr Gly Ser Tyr Cys Glu
    1130            1135            1140

Asp Glu Val Asp Glu Cys Ser Pro Asn Pro Cys Gln Asn Gly Ala
    1145            1150            1155

Thr Cys Thr Asp Tyr Leu Gly Gly Phe Ser Cys Lys Cys Val Ala
    1160            1165            1170

Gly Tyr His Gly Ser Asn Cys Ser Glu Glu Ile Asn Glu Cys Leu
    1175            1180            1185

Ser Gln Pro Cys Gln Asn Gly Gly Thr Cys Ile Asp Leu Thr Asn
    1190            1195            1200

Thr Tyr Lys Cys Ser Cys Pro Arg Gly Thr Gln Gly Val His Cys
    1205            1210            1215

Glu Ile Asn Val Asp Asp Cys His Pro Pro Leu Asp Pro Ala Ser
    1220            1225            1230

Arg Ser Pro Lys Cys Phe Asn Asn Gly Thr Cys Val Asp Gln Val
    1235            1240            1245

Gly Gly Tyr Thr Cys Thr Cys Pro Pro Gly Phe Val Gly Glu Arg
    1250            1255            1260

Cys Glu Gly Asp Val Asn Glu Cys Leu Ser Asn Pro Cys Asp Pro
    1265            1270            1275

Arg Gly Thr Gln Asn Cys Val Gln Arg Val Asn Asp Phe His Cys
    1280            1285            1290

Glu Cys Arg Ala Gly His Thr Gly Arg Arg Cys Glu Ser Val Ile
    1295            1300            1305

Asn Gly Cys Arg Gly Lys Pro Cys Arg Asn Gly Gly Val Cys Ala
    1310            1315            1320

Val Ala Ser Asn Thr Ala Arg Gly Phe Ile Cys Arg Cys Pro Ala
    1325            1330            1335

Arg Phe Glu Gly Ala Thr Cys Glu Asn Asp Ala Arg Thr Cys Gly
    1340            1345            1350

Ser Leu Arg Cys Leu Asn Gly Gly Thr Cys Ile Ser Gly Pro Arg
    1355            1360            1365

Ser Pro Thr Cys Leu Cys Leu Gly Ser Phe Thr Gly Pro Glu Cys
    1370            1375            1380
```

```
Gln Phe Pro Ala Ser Ser Pro Cys Val Gly Ser Asn Pro Cys Tyr
    1385            1390                1395

Asn Gln Gly Thr Cys Glu Pro Thr Ser Glu Ser Pro Phe Tyr Arg
    1400            1405                1410

Cys Leu Cys Pro Ala Lys Phe Asn Gly Leu Leu Cys His Ile Leu
    1415            1420                1425

Asp Tyr Ser Phe Thr Gly Ala Ala Gly Arg Asp Ile Pro Pro Pro
    1430            1435                1440

Gln Ile Glu Glu Ala Cys Glu Leu Pro Glu Cys Gln Glu Asp Ala
    1445            1450                1455

Gly Asn Lys Val Cys Asn Leu Gln Cys Asn Asn His Ala Cys Gly
    1460            1465                1470

Trp Asp Gly Gly Asp Cys Ser Leu Asn Phe Asn Asp Pro Trp Lys
    1475            1480                1485

Asn Cys Thr Gln Ser Leu Gln Cys Trp Lys Tyr Phe Ser Asp Gly
    1490            1495                1500

His Cys Asp Ser Gln Cys Asn Ser Ala Gly Cys Leu Phe Asp Gly
    1505            1510                1515

Phe Asp Cys Gln Leu Thr Glu Gly Gln Cys Asn Pro Leu Tyr Asp
    1520            1525                1530

Gln Tyr Cys Lys Asp His Phe Ser Asp Gly His Cys Asp Gln Gly
    1535            1540                1545

Cys Asn Ser Ala Glu Cys Glu Trp Asp Gly Leu Asp Cys Ala Glu
    1550            1555                1560

His Val Pro Glu Arg Leu Ala Ala Gly Thr Leu Val Leu Val Val
    1565            1570                1575

Leu Leu Pro Pro Asp Gln Leu Arg Asn Asn Ser Phe His Phe Leu
    1580            1585                1590

Arg Asp Val Ser His Val Leu His Thr Asn Val Val Phe Lys Arg
    1595            1600                1605

Asp Ala Gln Gly Gln Gln Met Ile Phe Pro Tyr Tyr Gly Arg Glu
    1610            1615                1620

Glu Glu Leu Arg Lys His Pro Ile Lys Arg Ser Ala Val Gly Trp
    1625            1630                1635

Ala Thr Thr Ser Leu Leu Pro Gly Thr Asn Gly Gly Arg Gln Arg
    1640            1645                1650

Arg Glu Leu Asp Pro Met Asp Ile His Gly Ser Ile Val Tyr Leu
    1655            1660                1665

Glu Ile Asp Asn Arg Gln Cys Val Gln Ser Ser Gln Cys Phe
    1670            1675                1680

Gln Ser Ala Thr Asp Val Ala Ala Phe Leu Gly Ala Leu Ala Ser
    1685            1690                1695

Leu Gly Ser Leu Asn Ile Pro Tyr Lys Ile Glu Ala Val Lys Ser
    1700            1705                1710

Glu Thr Val Glu Pro Pro Leu Pro Ser Gln Leu His Leu Met Tyr
    1715            1720                1725

Val Ala Ala Ala Ala Phe Val Leu Leu Phe Phe Val Gly Cys Gly
    1730            1735                1740

Val Leu Leu Ser Arg Lys Arg Arg Arg Gln His Gly Gln Leu Trp
    1745            1750                1755

Phe Pro Glu Gly Phe Lys Val Ser Glu Ala Ser Lys Lys Lys Arg
    1760            1765                1770
```

```
Arg Glu Pro Leu Gly Glu Asp Ser Val Gly Leu Lys Pro Leu Lys
    1775                1780                1785

Asn Ala Ser Asp Gly Ala Leu Met Asp Asp Asn Gln Asn Glu Trp
    1790                1795                1800

Gly Asp Glu Asp Leu Glu Thr Lys Lys Phe Arg Phe Glu Glu Pro
    1805                1810                1815

Val Val Leu Pro Asp Leu Asp Asp Gln Thr Asp His Arg Gln Trp
    1820                1825                1830

Thr Gln Gln His Leu Asp Ala Ala Asp Leu Arg Val Ser Ala Met
    1835                1840                1845

Ala Pro Thr Pro Pro Gln Gly Glu Val Asp Ala Asp Cys Met Asp
    1850                1855                1860

Val Asn Val Arg Gly Pro Asp Gly Phe Thr Pro Leu Met Ile Ala
    1865                1870                1875

Ser Cys Ser Gly Gly Gly Leu Glu Thr Gly Asn Ser Glu Glu Glu
    1880                1885                1890

Glu Asp Ala Pro Ala Val Ile Ser Asp Phe Ile Tyr Gln Gly Ala
    1895                1900                1905

Ser Leu His Asn Gln Thr Asp Arg Thr Gly Glu Thr Ala Leu His
    1910                1915                1920

Leu Ala Ala Arg Tyr Ser Arg Ser Asp Ala Ala Lys Arg Leu Leu
    1925                1930                1935

Glu Ala Ser Ala Asp Ala Asn Ile Gln Asp Asn Met Gly Arg Thr
    1940                1945                1950

Pro Leu His Ala Ala Val Ser Ala Asp Ala Gln Gly Val Phe Gln
    1955                1960                1965

Ile Leu Leu Arg Asn Arg Ala Thr Asp Leu Asp Ala Arg Met His
    1970                1975                1980

Asp Gly Thr Thr Pro Leu Ile Leu Ala Ala Arg Leu Ala Val Glu
    1985                1990                1995

Gly Met Leu Glu Asp Leu Ile Asn Ser His Ala Asp Val Asn Ala
    2000                2005                2010

Val Asp Asp Leu Gly Lys Ser Ala Leu His Trp Ala Ala Ala Val
    2015                2020                2025

Asn Asn Val Asp Ala Ala Val Val Leu Leu Lys Asn Gly Ala Asn
    2030                2035                2040

Lys Asp Met Gln Asn Asn Lys Glu Glu Thr Pro Leu Phe Leu Ala
    2045                2050                2055

Ala Arg Glu Gly Ser Tyr Glu Thr Ala Lys Val Leu Leu Asp His
    2060                2065                2070

Phe Ala Asn Arg Asp Ile Thr Asp His Met Asp Arg Leu Pro Arg
    2075                2080                2085

Asp Ile Ala Gln Glu Arg Met His His Asp Ile Val Arg Leu Leu
    2090                2095                2100

Asp Glu Tyr Asn Leu Val Arg Ser Pro Gln Leu His Gly Thr Ala
    2105                2110                2115

Leu Gly Gly Thr Pro Thr Leu Ser Pro Thr Leu Cys Ser Pro Asn
    2120                2125                2130

Gly Tyr Leu Gly Asn Leu Lys Ser Ala Thr Gln Gly Lys Lys Ala
    2135                2140                2145

Arg Lys Pro Ser Thr Lys Gly Leu Ala Cys Ser Ser Lys Glu Ala
    2150                2155                2160

Lys Asp Leu Lys Ala Arg Arg Lys Lys Ser Gln Asp Gly Lys Gly
```

```
                2165                2170                2175

Cys Leu Leu Asp Ser Ser Met Leu Ser Pro Val Asp Ser Leu
    2180                2185                2190

Glu Ser Pro His Gly Tyr Leu Ser Asp Val Ala Ser Pro Pro Leu
    2195                2200                2205

Leu Pro Ser Pro Phe Gln Gln Ser Pro Ser Met Pro Leu Ser His
    2210                2215                2220

Leu Pro Gly Met Pro Asp Thr His Leu Gly Ile Ser His Leu Asn
    2225                2230                2235

Val Ala Ala Lys Pro Glu Met Ala Ala Leu Ala Gly Gly Ser Arg
    2240                2245                2250

Leu Ala Phe Glu Pro Pro Pro Arg Leu Ser His Leu Pro Val
    2255                2260                2265

Ala Ser Ser Ala Ser Thr Val Leu Ser Thr Asn Gly Thr Gly Ala
    2270                2275                2280

Met Asn Phe Thr Val Gly Ala Pro Ala Ser Leu Asn Gly Gln Cys
    2285                2290                2295

Glu Trp Leu Pro Arg Leu Gln Asn Gly Met Val Pro Ser Gln Tyr
    2300                2305                2310

Asn Pro Leu Arg Pro Gly Val Thr Pro Gly Thr Leu Ser Thr Gln
    2315                2320                2325

Ala Ala Gly Leu Gln His Gly Met Met Gly Pro Ile His Ser Ser
    2330                2335                2340

Leu Ser Thr Asn Thr Leu Ser Pro Ile Ile Tyr Gln Gly Leu Pro
    2345                2350                2355

Asn Thr Arg Leu Ala Thr Gln Pro His Leu Val Gln Thr Gln Gln
    2360                2365                2370

Val Gln Pro Gln Asn Leu Gln Ile Gln Pro Gln Asn Leu Gln Pro
    2375                2380                2385

Pro Ser Gln Pro His Leu Ser Val Ser Ser Ala Ala Asn Gly His
    2390                2395                2400

Leu Gly Arg Ser Phe Leu Ser Gly Glu Pro Ser Gln Ala Asp Val
    2405                2410                2415

Gln Pro Leu Gly Pro Ser Ser Leu Pro Val His Thr Ile Leu Pro
    2420                2425                2430

Gln Glu Ser Gln Ala Leu Pro Thr Ser Leu Pro Ser Ser Met Val
    2435                2440                2445

Pro Pro Met Thr Thr Thr Gln Phe Leu Thr Pro Ser Gln His
    2450                2455                2460

Ser Tyr Ser Ser Ser Pro Val Asp Asn Thr Pro Ser His Gln Leu
    2465                2470                2475

Gln Val Pro Glu His Pro Phe Leu Thr Pro Ser Pro Glu Ser Pro
    2480                2485                2490

Asp Gln Trp Ser Ser Ser Arg His Ser Asn Ile Ser Asp Trp
    2495                2500                2505

Ser Glu Gly Ile Ser Ser Pro Pro Thr Ser Met Pro Ser Gln Ile
    2510                2515                2520

Thr His Ile Pro Glu Ala Phe Lys
    2525                2530

<210> SEQ ID NO 8
<211> LENGTH: 2471
<212> TYPE: PRT
<213> ORGANISM: Homo sapiens
```

```
<400> SEQUENCE: 8

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
```

-continued

```
                405                 410                 415
Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
            435                 440                 445

Ala Gly Pro Arg Cys Glu Met Asp Ile Asn Glu Cys His Ser Asp Pro
            450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
            485                 490                 495

Glu Cys Gln Ser Asn Pro Cys Val Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
            530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
            565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
            595                 600                 605

Asp Glu Cys Tyr Ser Ser Pro Cys Leu Asn Asp Gly Arg Cys Ile Asp
            610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
            645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
            675                 680                 685

Asn Pro Cys Arg Lys Gly Ala Thr Cys Ile Asn Gly Val Asn Gly Phe
            690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
            725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
            755                 760                 765

Gly Gly Thr Cys Asp Asn Leu Val Asn Gly Tyr Arg Cys Thr Cys Lys
            770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
            805                 810                 815

Tyr Thr Cys His Cys Val Leu Pro Tyr Thr Gly Lys Asn Cys Gln Thr
            820                 825                 830
```

```
Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
            885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
        995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Leu Leu Cys Glu Glu Asn Ile Asp Asp Cys Ala Arg Gly Pro
    1220                1225                1230
```

-continued

His Cys Leu Asn Gly Gly Gln Cys Met Asp Arg Ile Gly Gly Tyr
1235              1240              1245

Ser Cys Arg Cys Leu Pro Gly Phe Ala Gly Glu Arg Cys Glu Gly
1250              1255              1260

Asp Ile Asn Glu Cys Leu Ser Asn Pro Cys Ser Ser Glu Gly Ser
1265              1270              1275

Leu Asp Cys Ile Gln Leu Thr Asn Asp Tyr Leu Cys Val Cys Arg
1280              1285              1290

Ser Ala Phe Thr Gly Arg His Cys Glu Thr Phe Val Asp Val Cys
1295              1300              1305

Pro Gln Met Pro Cys Leu Asn Gly Gly Thr Cys Ala Val Ala Ser
1310              1315              1320

Asn Met Pro Asp Gly Phe Ile Cys Arg Cys Pro Pro Gly Phe Ser
1325              1330              1335

Gly Ala Arg Cys Gln Ser Ser Cys Gly Gln Val Lys Cys Arg Lys
1340              1345              1350

Gly Glu Gln Cys Val His Thr Ala Ser Gly Pro Arg Cys Phe Cys
1355              1360              1365

Pro Ser Pro Arg Asp Cys Glu Ser Gly Cys Ala Ser Ser Pro Cys
1370              1375              1380

Gln His Gly Gly Ser Cys His Pro Gln Arg Gln Pro Pro Tyr Tyr
1385              1390              1395

Ser Cys Gln Cys Ala Pro Pro Phe Ser Gly Ser Arg Cys Glu Leu
1400              1405              1410

Tyr Thr Ala Pro Pro Ser Thr Pro Pro Ala Thr Cys Leu Ser Gln
1415              1420              1425

Tyr Cys Ala Asp Lys Ala Arg Asp Gly Val Cys Asp Glu Ala Cys
1430              1435              1440

Asn Ser His Ala Cys Gln Trp Asp Gly Gly Asp Cys Ser Leu Thr
1445              1450              1455

Met Glu Asn Pro Trp Ala Asn Cys Ser Ser Pro Leu Pro Cys Trp
1460              1465              1470

Asp Tyr Ile Asn Asn Gln Cys Asp Glu Leu Cys Asn Thr Val Glu
1475              1480              1485

Cys Leu Phe Asp Asn Phe Glu Cys Gln Gly Asn Ser Lys Thr Cys
1490              1495              1500

Lys Tyr Asp Lys Tyr Cys Ala Asp His Phe Lys Asp Asn His Cys
1505              1510              1515

Asp Gln Gly Cys Asn Ser Glu Glu Cys Gly Trp Asp Gly Leu Asp
1520              1525              1530

Cys Ala Ala Asp Gln Pro Glu Asn Leu Ala Glu Gly Thr Leu Val
1535              1540              1545

Ile Val Val Leu Met Pro Pro Glu Gln Leu Leu Gln Asp Ala Arg
1550              1555              1560

Ser Phe Leu Arg Ala Leu Gly Thr Leu Leu His Thr Asn Leu Arg
1565              1570              1575

Ile Lys Arg Asp Ser Gln Gly Glu Leu Met Val Tyr Pro Tyr Tyr
1580              1585              1590

Gly Glu Lys Ser Ala Ala Met Lys Lys Gln Arg Met Thr Arg Arg
1595              1600              1605

Ser Leu Pro Gly Glu Gln Glu Gln Glu Val Ala Gly Ser Lys Val
1610              1615              1620

Phe Leu Glu Ile Asp Asn Arg Gln Cys Val Gln Asp Ser Asp His

```
            1625                1630                1635

Cys Phe Lys Asn Thr Asp Ala Ala Ala Leu Leu Ala Ser His
        1640                1645                1650

Ala Ile Gln Gly Thr Leu Ser Tyr Pro Leu Val Ser Val Val Ser
        1655                1660                1665

Glu Ser Leu Thr Pro Glu Arg Thr Gln Leu Leu Tyr Leu Leu Ala
        1670                1675                1680

Val Ala Val Val Ile Ile Leu Phe Ile Ile Leu Leu Gly Val Ile
        1685                1690                1695

Met Ala Lys Arg Lys Arg Lys His Gly Ser Leu Trp Leu Pro Glu
        1700                1705                1710

Gly Phe Thr Leu Arg Arg Asp Ala Ser Asn His Lys Arg Arg Glu
        1715                1720                1725

Pro Val Gly Gln Asp Ala Val Gly Leu Lys Asn Leu Ser Val Gln
        1730                1735                1740

Val Ser Glu Ala Asn Leu Ile Gly Thr Gly Thr Ser Glu His Trp
        1745                1750                1755

Val Asp Asp Glu Gly Pro Gln Pro Lys Lys Val Lys Ala Glu Asp
        1760                1765                1770

Glu Ala Leu Leu Ser Glu Glu Asp Asp Pro Ile Asp Arg Arg Pro
        1775                1780                1785

Trp Thr Gln Gln His Leu Glu Ala Ala Asp Ile Arg Arg Thr Pro
        1790                1795                1800

Ser Leu Ala Leu Thr Pro Pro Gln Ala Glu Gln Glu Val Asp Val
        1805                1810                1815

Leu Asp Val Asn Val Arg Gly Pro Asp Gly Cys Thr Pro Leu Met
        1820                1825                1830

Leu Ala Ser Leu Arg Gly Gly Ser Ser Asp Leu Ser Asp Glu Asp
        1835                1840                1845

Glu Asp Ala Glu Asp Ser Ser Ala Asn Ile Ile Thr Asp Leu Val
        1850                1855                1860

Tyr Gln Gly Ala Ser Leu Gln Ala Gln Thr Asp Arg Thr Gly Glu
        1865                1870                1875

Met Ala Leu His Leu Ala Ala Arg Tyr Ser Arg Ala Asp Ala Ala
        1880                1885                1890

Lys Arg Leu Leu Asp Ala Gly Ala Asp Ala Asn Ala Gln Asp Asn
        1895                1900                1905

Met Gly Arg Cys Pro Leu His Ala Ala Val Ala Ala Asp Ala Gln
        1910                1915                1920

Gly Val Phe Gln Ile Leu Ile Arg Asn Arg Val Thr Asp Leu Asp
        1925                1930                1935

Ala Arg Met Asn Asp Gly Thr Thr Pro Leu Ile Leu Ala Ala Arg
        1940                1945                1950

Leu Ala Val Glu Gly Met Val Ala Glu Leu Ile Asn Cys Gln Ala
        1955                1960                1965

Asp Val Asn Ala Val Asp Asp His Gly Lys Ser Ala Leu His Trp
        1970                1975                1980

Ala Ala Ala Val Asn Asn Val Glu Ala Thr Leu Leu Leu Leu Lys
        1985                1990                1995

Asn Gly Ala Asn Arg Asp Met Gln Asp Asn Lys Glu Glu Thr Pro
        2000                2005                2010

Leu Phe Leu Ala Ala Arg Glu Gly Ser Tyr Glu Ala Ala Lys Ile
        2015                2020                2025
```

```
Leu Leu Asp His Phe Ala Asn Arg Asp Ile Thr Asp His Met Asp
    2030            2035            2040

Arg Leu Pro Arg Asp Val Ala Arg Asp Arg Met His His Asp Ile
    2045            2050            2055

Val Arg Leu Leu Asp Glu Tyr Asn Val Thr Pro Ser Pro Pro Gly
    2060            2065            2070

Thr Val Leu Thr Ser Ala Leu Ser Pro Val Ile Cys Gly Pro Asn
    2075            2080            2085

Arg Ser Phe Leu Ser Leu Lys His Thr Pro Met Gly Lys Lys Ser
    2090            2095            2100

Arg Arg Pro Ser Ala Lys Ser Thr Met Pro Thr Ser Leu Pro Asn
    2105            2110            2115

Leu Ala Lys Glu Ala Lys Asp Ala Lys Gly Ser Arg Arg Lys Lys
    2120            2125            2130

Ser Leu Ser Glu Lys Val Gln Leu Ser Glu Ser Ser Val Thr Leu
    2135            2140            2145

Ser Pro Val Asp Ser Leu Glu Ser Pro His Thr Tyr Val Ser Asp
    2150            2155            2160

Thr Thr Ser Ser Pro Met Ile Thr Ser Pro Gly Ile Leu Gln Ala
    2165            2170            2175

Ser Pro Asn Pro Met Leu Ala Thr Ala Ala Pro Ala Pro Val
    2180            2185            2190

His Ala Gln His Ala Leu Ser Phe Ser Asn Leu His Glu Met Gln
    2195            2200            2205

Pro Leu Ala His Gly Ala Ser Thr Val Leu Pro Ser Val Ser Gln
    2210            2215            2220

Leu Leu Ser His His His Ile Val Ser Pro Gly Ser Gly Ser Ala
    2225            2230            2235

Gly Ser Leu Ser Arg Leu His Pro Val Pro Val Pro Ala Asp Trp
    2240            2245            2250

Met Asn Arg Met Glu Val Asn Glu Thr Gln Tyr Asn Glu Met Phe
    2255            2260            2265

Gly Met Val Leu Ala Pro Ala Glu Gly Thr His Pro Gly Ile Ala
    2270            2275            2280

Pro Gln Ser Arg Pro Pro Glu Gly Lys His Ile Thr Thr Pro Arg
    2285            2290            2295

Glu Pro Leu Pro Pro Ile Val Thr Phe Gln Leu Ile Pro Lys Gly
    2300            2305            2310

Ser Ile Ala Gln Pro Ala Gly Ala Pro Gln Pro Gln Ser Thr Cys
    2315            2320            2325

Pro Pro Ala Val Ala Gly Pro Leu Pro Thr Met Tyr Gln Ile Pro
    2330            2335            2340

Glu Met Ala Arg Leu Pro Ser Val Ala Phe Pro Thr Ala Met Met
    2345            2350            2355

Pro Gln Gln Asp Gly Gln Val Ala Gln Thr Ile Leu Pro Ala Tyr
    2360            2365            2370

His Pro Phe Pro Ala Ser Val Gly Lys Tyr Pro Thr Pro Pro Ser
    2375            2380            2385

Gln His Ser Tyr Ala Ser Ser Asn Ala Ala Glu Arg Thr Pro Ser
    2390            2395            2400

His Ser Gly His Leu Gln Gly Glu His Pro Tyr Leu Thr Pro Ser
    2405            2410            2415
```

-continued

Pro Glu Ser Pro Asp Gln Trp Ser Ser Ser Pro His Ser Ala
    2420            2425                2430

Ser Asp Trp Ser Asp Val Thr Thr Ser Pro Thr Pro Gly Gly Ala
    2435            2440                2445

Gly Gly Gly Gln Arg Gly Pro Gly Thr His Met Ser Glu Pro Pro
    2450            2455                2460

His Asn Asn Met Gln Val Tyr Ala
    2465            2470

<210> SEQ ID NO 9
<211> LENGTH: 2321
<212> TYPE: PRT
<213> ORGANISM: Homo sapiens

<400> SEQUENCE: 9

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
    195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

```
Ala Val Cys Phe His Gly Ala Thr Cys His Asp Arg Val Ala Ser Phe
            325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Pro Gly Phe Thr
        370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
            405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
        450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
            485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
            565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
            645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
            725                 730                 735
```

-continued

Ala Cys Glu Ser Gln Pro Cys Arg Ala Gly Gly Thr Cys Ser Ser Asp
                    740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
        770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Asp Val Asp Glu Cys Ala Gly
                805                 810                 815

Pro Ala Pro Cys Gly Pro His Gly Ile Cys Thr Asn Leu Ala Gly Ser
                820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
        850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
                900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
        995                 1000                1005

Cys Gln Asn Gly Gly Arg Cys Val Gln Thr Gly Ala Tyr Cys Leu
    1010                1015                1020

Cys Pro Pro Gly Trp Ser Gly Arg Leu Cys Asp Ile Arg Ser Leu
    1025                1030                1035

Pro Cys Arg Glu Ala Ala Gln Ile Gly Val Arg Leu Glu Gln
    1040                1045                1050

Leu Cys Gln Ala Gly Gly Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Asp Val Asp Glu Cys Ala Ser
    1115                1120                1125

Gln Pro Cys Gln His Gly Gly Ser Cys Ile Asp Leu Val Ala Arg
    1130                1135                1140

Tyr Leu Cys Ser Cys Pro Pro Gly Thr Leu Gly Val Leu Cys Glu

```
       1145                1150                1155

Ile  Asn  Glu  Asp  Cys  Gly  Pro  Gly  Pro  Leu  Asp  Ser  Gly
       1160                1165                1170

Pro  Arg  Cys  Leu  His  Asn  Gly  Thr  Cys  Val  Asp  Leu  Val  Gly  Gly
       1175                1180                1185

Phe  Arg  Cys  Thr  Cys  Pro  Pro  Gly  Tyr  Thr  Gly  Leu  Arg  Cys  Glu
       1190                1195                1200

Ala  Asp  Ile  Asn  Glu  Cys  Arg  Ser  Gly  Ala  Cys  His  Ala  Ala  His
       1205                1210                1215

Thr  Arg  Asp  Cys  Leu  Gln  Asp  Pro  Gly  Gly  Gly  Phe  Arg  Cys  Leu
       1220                1225                1230

Cys  His  Ala  Gly  Phe  Ser  Gly  Pro  Arg  Cys  Gln  Thr  Val  Leu  Ser
       1235                1240                1245

Pro  Cys  Glu  Ser  Gln  Pro  Cys  Gln  His  Gly  Gly  Gln  Cys  Arg  Pro
       1250                1255                1260

Ser  Pro  Gly  Pro  Gly  Gly  Leu  Thr  Phe  Thr  Cys  His  Cys  Ala
       1265                1270                1275

Gln  Pro  Phe  Trp  Gly  Pro  Arg  Cys  Glu  Arg  Val  Ala  Arg  Ser  Cys
       1280                1285                1290

Arg  Glu  Leu  Gln  Cys  Pro  Val  Gly  Val  Pro  Cys  Gln  Gln  Thr  Pro
       1295                1300                1305

Arg  Gly  Pro  Arg  Cys  Ala  Cys  Pro  Pro  Gly  Leu  Ser  Gly  Pro  Ser
       1310                1315                1320

Cys  Arg  Ser  Phe  Pro  Gly  Ser  Pro  Pro  Gly  Ala  Ser  Asn  Ala  Ser
       1325                1330                1335

Cys  Ala  Ala  Ala  Pro  Cys  Leu  His  Gly  Gly  Ser  Cys  Arg  Pro  Ala
       1340                1345                1350

Pro  Leu  Ala  Pro  Phe  Phe  Arg  Cys  Ala  Cys  Ala  Gln  Gly  Trp  Thr
       1355                1360                1365

Gly  Pro  Arg  Cys  Glu  Ala  Pro  Ala  Ala  Ala  Pro  Glu  Val  Ser  Glu
       1370                1375                1380

Glu  Pro  Arg  Cys  Pro  Arg  Ala  Ala  Cys  Gln  Ala  Lys  Arg  Gly  Asp
       1385                1390                1395

Gln  Arg  Cys  Asp  Arg  Glu  Cys  Asn  Ser  Pro  Gly  Cys  Gly  Trp  Asp
       1400                1405                1410

Gly  Gly  Asp  Cys  Ser  Leu  Ser  Val  Gly  Asp  Pro  Trp  Arg  Gln  Cys
       1415                1420                1425

Glu  Ala  Leu  Gln  Cys  Trp  Arg  Leu  Phe  Asn  Asn  Ser  Arg  Cys  Asp
       1430                1435                1440

Pro  Ala  Cys  Ser  Ser  Pro  Ala  Cys  Leu  Tyr  Asp  Asn  Phe  Asp  Cys
       1445                1450                1455

His  Ala  Gly  Gly  Arg  Glu  Arg  Thr  Cys  Asn  Pro  Val  Tyr  Glu  Lys
       1460                1465                1470

Tyr  Cys  Ala  Asp  His  Phe  Ala  Asp  Gly  Arg  Cys  Asp  Gln  Gly  Cys
       1475                1480                1485

Asn  Thr  Glu  Glu  Cys  Gly  Trp  Asp  Gly  Leu  Asp  Cys  Ala  Ser  Glu
       1490                1495                1500

Val  Pro  Ala  Leu  Leu  Ala  Arg  Gly  Val  Leu  Val  Leu  Thr  Val  Leu
       1505                1510                1515

Leu  Pro  Pro  Glu  Glu  Leu  Leu  Arg  Ser  Ser  Ala  Asp  Phe  Leu  Gln
       1520                1525                1530

Arg  Leu  Ser  Ala  Ile  Leu  Arg  Thr  Ser  Leu  Arg  Phe  Arg  Leu  Asp
       1535                1540                1545
```

```
Ala His Gly Gln Ala Met Val Phe Pro Tyr His Arg Pro Ser Pro
    1550            1555                1560

Gly Ser Glu Pro Arg Ala Arg Arg Glu Leu Ala Pro Glu Val Ile
    1565            1570                1575

Gly Ser Val Val Met Leu Glu Ile Asp Asn Arg Leu Cys Leu Gln
    1580            1585                1590

Ser Pro Glu Asn Asp His Cys Phe Pro Asp Ala Gln Ser Ala Ala
    1595            1600                1605

Asp Tyr Leu Gly Ala Leu Ser Ala Val Glu Arg Leu Asp Phe Pro
    1610            1615                1620

Tyr Pro Leu Arg Asp Val Arg Gly Glu Pro Leu Glu Pro Pro Glu
    1625            1630                1635

Pro Ser Val Pro Leu Leu Pro Leu Leu Val Ala Gly Ala Val Leu
    1640            1645                1650

Leu Leu Val Ile Leu Val Leu Gly Val Met Val Ala Arg Arg Lys
    1655            1660                1665

Arg Glu His Ser Thr Leu Trp Phe Pro Glu Gly Phe Ser Leu His
    1670            1675                1680

Lys Asp Val Ala Ser Gly His Lys Gly Arg Arg Glu Pro Val Gly
    1685            1690                1695

Gln Asp Ala Leu Gly Met Lys Asn Met Ala Lys Gly Glu Ser Leu
    1700            1705                1710

Met Gly Glu Val Ala Thr Asp Trp Met Asp Thr Glu Cys Pro Glu
    1715            1720                1725

Ala Lys Arg Leu Lys Val Glu Glu Pro Gly Met Gly Ala Glu Glu
    1730            1735                1740

Ala Val Asp Cys Arg Gln Trp Thr Gln His His Leu Val Ala Ala
    1745            1750                1755

Asp Ile Arg Val Ala Pro Ala Met Ala Leu Thr Pro Pro Gln Gly
    1760            1765                1770

Asp Ala Asp Ala Asp Gly Met Asp Val Asn Val Arg Gly Pro Asp
    1775            1780                1785

Gly Phe Thr Pro Leu Met Leu Ala Ser Phe Cys Gly Gly Ala Leu
    1790            1795                1800

Glu Pro Met Pro Thr Glu Glu Asp Glu Ala Asp Asp Thr Ser Ala
    1805            1810                1815

Ser Ile Ile Ser Asp Leu Ile Cys Gln Gly Ala Gln Leu Gly Ala
    1820            1825                1830

Arg Thr Asp Arg Thr Gly Glu Thr Ala Leu His Leu Ala Ala Arg
    1835            1840                1845

Tyr Ala Arg Ala Asp Ala Ala Lys Arg Leu Leu Asp Ala Gly Ala
    1850            1855                1860

Asp Thr Asn Ala Gln Asp His Ser Gly Arg Thr Pro Leu His Thr
    1865            1870                1875

Ala Val Thr Ala Asp Ala Gln Gly Val Phe Gln Ile Leu Ile Arg
    1880            1885                1890

Asn Arg Ser Thr Asp Leu Asp Ala Arg Met Ala Asp Gly Ser Thr
    1895            1900                1905

Ala Leu Ile Leu Ala Ala Arg Leu Ala Val Glu Gly Met Val Glu
    1910            1915                1920

Glu Leu Ile Ala Ser His Ala Asp Val Asn Ala Val Asp Glu Leu
    1925            1930                1935
```

```
Gly Lys Ser Ala Leu His Trp Ala Ala Ala Val Asn Asn Val Glu
    1940            1945                1950
Ala Thr Leu Ala Leu Leu Lys Asn Gly Ala Asn Lys Asp Met Gln
    1955            1960                1965
Asp Ser Lys Glu Glu Thr Pro Leu Phe Leu Ala Ala Arg Glu Gly
    1970            1975                1980
Ser Tyr Glu Ala Ala Lys Leu Leu Leu Asp His Phe Ala Asn Arg
    1985            1990                1995
Glu Ile Thr Asp His Leu Asp Arg Leu Pro Arg Asp Val Ala Gln
    2000            2005                2010
Glu Arg Leu His Gln Asp Ile Val Arg Leu Leu Asp Gln Pro Ser
    2015            2020                2025
Gly Pro Arg Ser Pro Pro Gly Pro His Gly Leu Gly Pro Leu Leu
    2030            2035                2040
Cys Pro Pro Gly Ala Phe Leu Pro Gly Leu Lys Ala Ala Gln Ser
    2045            2050                2055
Gly Ser Lys Lys Ser Arg Arg Pro Pro Gly Lys Ala Gly Leu Gly
    2060            2065                2070
Pro Gln Gly Pro Arg Gly Arg Gly Lys Lys Leu Thr Leu Ala Cys
    2075            2080                2085
Pro Gly Pro Leu Ala Asp Ser Ser Val Thr Leu Ser Pro Val Asp
    2090            2095                2100
Ser Leu Asp Ser Pro Arg Pro Phe Gly Gly Pro Pro Ala Ser Pro
    2105            2110                2115
Gly Gly Phe Pro Leu Glu Gly Pro Tyr Ala Ala Ala Thr Ala Thr
    2120            2125                2130
Ala Val Ser Leu Ala Gln Leu Gly Gly Pro Gly Arg Ala Gly Leu
    2135            2140                2145
Gly Arg Gln Pro Pro Gly Gly Cys Val Leu Ser Leu Gly Leu Leu
    2150            2155                2160
Asn Pro Val Ala Val Pro Leu Asp Trp Ala Arg Leu Pro Pro Pro
    2165            2170                2175
Ala Pro Pro Gly Pro Ser Phe Leu Leu Pro Leu Ala Pro Gly Pro
    2180            2185                2190
Gln Leu Leu Asn Pro Gly Thr Pro Val Ser Pro Gln Glu Arg Pro
    2195            2200                2205
Pro Pro Tyr Leu Ala Val Pro Gly His Gly Glu Glu Tyr Pro Ala
    2210            2215                2220
Ala Gly Ala His Ser Ser Pro Pro Lys Ala Arg Phe Leu Arg Val
    2225            2230                2235
Pro Ser Glu His Pro Tyr Leu Thr Pro Ser Pro Glu Ser Pro Glu
    2240            2245                2250
His Trp Ala Ser Pro Ser Pro Pro Ser Leu Ser Asp Trp Ser Glu
    2255            2260                2265
Ser Thr Pro Ser Pro Ala Thr Ala Thr Gly Ala Met Ala Thr Thr
    2270            2275                2280
Thr Gly Ala Leu Pro Ala Gln Pro Leu Pro Leu Ser Val Pro Ser
    2285            2290                2295
Ser Leu Ala Gln Ala Gln Thr Gln Leu Gly Pro Gln Pro Glu Val
    2300            2305                2310
Thr Pro Lys Arg Gln Val Leu Ala
    2315            2320
```

<210> SEQ ID NO 10
<211> LENGTH: 2003
<212> TYPE: PRT
<213> ORGANISM: Homo sapiens

<400> SEQUENCE: 10

```
Met Gln Pro Pro Ser Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380
```

```
Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
            405                 410                 415

Leu Cys Leu Cys Gln Pro Gly Tyr Ser Gly Pro Thr Cys His Gln Asp
        420                 425                 430

Leu Asp Glu Cys Leu Met Ala Gln Gln Gly Pro Ser Pro Cys Glu His
            435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
            515                 520                 525

His Asp Leu Leu Asn Gly Phe Gln Cys Ile Cys Leu Pro Gly Phe Ser
    530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
            595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
                675                 680                 685

Glu Ala Glu Leu Gly Gly Cys Ile Ser Ala Pro Cys Ala His Gly Gly
            690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
            755                 760                 765

Asp Tyr Cys Val Ser Ala Pro Cys Phe Asn Gly Gly Thr Cys Val Asn
            770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
```

```
                805                 810                 815
Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
            835                 840                 845

Ala Gln Lys Pro Cys Pro Arg Asn Ser His Cys Leu Gln Thr Gly Pro
    850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
            900                 905                 910

Ser Tyr Phe Cys His Cys Pro Pro Gly Phe Gln Gly Ser Leu Cys Gln
            915                 920                 925

Asp His Val Asn Pro Cys Glu Ser Arg Pro Cys Gln Asn Gly Ala Thr
    930                 935                 940

Cys Met Ala Gln Pro Ser Gly Tyr Leu Cys Gln Cys Ala Pro Gly Tyr
945                 950                 955                 960

Asp Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His Cys
            980                 985                 990

Ala Cys Pro Pro Gly Phe Val Gly Leu Arg Cys Glu Gly Asp Val Asp
            995                 1000                1005

Glu Cys Leu Asp Gln Pro Cys His Pro Thr Gly Thr Ala Ala Cys
    1010                1015                1020

His Ser Leu Ala Asn Ala Phe Tyr Cys Gln Cys Leu Pro Gly His
    1025                1030                1035

Thr Gly Gln Trp Cys Glu Val Glu Ile Asp Pro Cys His Ser Gln
    1040                1045                1050

Pro Cys Phe His Gly Gly Thr Cys Glu Ala Thr Ala Gly Ser Pro
    1055                1060                1065

Leu Gly Phe Ile Cys His Cys Pro Lys Gly Phe Glu Gly Pro Thr
    1070                1075                1080

Cys Ser His Arg Ala Pro Ser Cys Gly Phe His His Cys His His
    1085                1090                1095

Gly Gly Leu Cys Leu Pro Ser Pro Lys Pro Gly Phe Pro Pro Arg
    1100                1105                1110

Cys Ala Cys Leu Ser Gly Tyr Gly Gly Pro Asp Cys Leu Thr Pro
    1115                1120                1125

Pro Ala Pro Lys Gly Cys Gly Pro Pro Ser Pro Cys Leu Tyr Asn
    1130                1135                1140

Gly Ser Cys Ser Glu Thr Thr Gly Leu Gly Gly Pro Gly Phe Arg
    1145                1150                1155

Cys Ser Cys Pro His Ser Ser Pro Gly Pro Arg Cys Gln Lys Pro
    1160                1165                1170

Gly Ala Lys Gly Cys Glu Gly Arg Ser Gly Asp Gly Ala Cys Asp
    1175                1180                1185

Ala Gly Cys Ser Gly Pro Gly Gly Asn Trp Asp Gly Gly Asp Cys
    1190                1195                1200

Ser Leu Gly Val Pro Asp Pro Trp Lys Gly Cys Pro Ser His Ser
    1205                1210                1215
```

Arg Cys Trp Leu Leu Phe Arg Asp Gly Gln Cys His Pro Gln Cys
1220                1225                1230

Asp Ser Glu Glu Cys Leu Phe Asp Gly Tyr Asp Cys Glu Thr Pro
1235                1240                1245

Pro Ala Cys Thr Pro Ala Tyr Asp Gln Tyr Cys His Asp His Phe
1250                1255                1260

His Asn Gly His Cys Glu Lys Gly Cys Asn Thr Ala Glu Cys Gly
1265                1270                1275

Trp Asp Gly Gly Asp Cys Arg Pro Glu Asp Gly Asp Pro Glu Trp
1280                1285                1290

Gly Pro Ser Leu Ala Leu Leu Val Val Leu Ser Pro Pro Ala Leu
1295                1300                1305

Asp Gln Gln Leu Phe Ala Leu Ala Arg Val Leu Ser Leu Thr Leu
1310                1315                1320

Arg Val Gly Leu Trp Val Arg Lys Asp Arg Asp Gly Arg Asp Met
1325                1330                1335

Val Tyr Pro Tyr Pro Gly Ala Arg Ala Glu Glu Lys Leu Gly Gly
1340                1345                1350

Thr Arg Asp Pro Thr Tyr Gln Glu Arg Ala Ala Pro Gln Thr Gln
1355                1360                1365

Pro Leu Gly Lys Glu Thr Asp Ser Leu Ser Ala Gly Phe Val Val
1370                1375                1380

Val Met Gly Val Asp Leu Ser Arg Cys Gly Pro Asp His Pro Ala
1385                1390                1395

Ser Arg Cys Pro Trp Asp Pro Gly Leu Leu Leu Arg Phe Leu Ala
1400                1405                1410

Ala Met Ala Ala Val Gly Ala Leu Glu Pro Leu Leu Pro Gly Pro
1415                1420                1425

Leu Leu Ala Val His Pro His Ala Gly Thr Ala Pro Pro Ala Asn
1430                1435                1440

Gln Leu Pro Trp Pro Val Leu Cys Ser Pro Val Ala Gly Val Ile
1445                1450                1455

Leu Leu Ala Leu Gly Ala Leu Leu Val Leu Gln Leu Ile Arg Arg
1460                1465                1470

Arg Arg Arg Glu His Gly Ala Leu Trp Leu Pro Pro Gly Phe Thr
1475                1480                1485

Arg Arg Pro Arg Thr Gln Ser Ala Pro His Arg Arg Arg Pro Pro
1490                1495                1500

Leu Gly Glu Asp Ser Ile Gly Leu Lys Ala Leu Lys Pro Lys Ala
1505                1510                1515

Glu Val Asp Glu Asp Gly Val Val Met Cys Ser Gly Pro Glu Glu
1520                1525                1530

Gly Glu Glu Val Gly Gln Ala Glu Glu Thr Gly Pro Pro Ser Thr
1535                1540                1545

Cys Gln Leu Trp Ser Leu Ser Gly Gly Cys Gly Ala Leu Pro Gln
1550                1555                1560

Ala Ala Met Leu Thr Pro Pro Gln Glu Ser Glu Met Glu Ala Pro
1565                1570                1575

Asp Leu Asp Thr Arg Gly Pro Asp Gly Val Thr Pro Leu Met Ser
1580                1585                1590

Ala Val Cys Cys Gly Glu Val Gln Ser Gly Thr Phe Gln Gly Ala
1595                1600                1605

```
Trp Leu Gly Cys Pro Glu Pro Trp Glu Pro Leu Leu Asp Gly Gly
    1610            1615            1620

Ala Cys Pro Gln Ala His Thr Val Gly Thr Gly Glu Thr Pro Leu
    1625            1630            1635

His Leu Ala Ala Arg Phe Ser Arg Pro Thr Ala Ala Arg Arg Leu
    1640            1645            1650

Leu Glu Ala Gly Ala Asn Pro Asn Gln Pro Asp Arg Ala Gly Arg
    1655            1660            1665

Thr Pro Leu His Ala Ala Val Ala Ala Asp Ala Arg Glu Val Cys
    1670            1675            1680

Gln Leu Leu Leu Arg Ser Arg Gln Thr Ala Val Asp Ala Arg Thr
    1685            1690            1695

Glu Asp Gly Thr Thr Pro Leu Met Leu Ala Ala Arg Leu Ala Val
    1700            1705            1710

Glu Asp Leu Val Glu Glu Leu Ile Ala Ala Gln Ala Asp Val Gly
    1715            1720            1725

Ala Arg Asp Lys Trp Gly Lys Thr Ala Leu His Trp Ala Ala Ala
    1730            1735            1740

Val Asn Asn Ala Arg Ala Ala Arg Ser Leu Leu Gln Ala Gly Ala
    1745            1750            1755

Asp Lys Asp Ala Gln Asp Asn Arg Glu Gln Thr Pro Leu Phe Leu
    1760            1765            1770

Ala Ala Arg Glu Gly Ala Val Glu Val Ala Gln Leu Leu Leu Gly
    1775            1780            1785

Leu Gly Ala Ala Arg Glu Leu Arg Asp Gln Ala Gly Leu Ala Pro
    1790            1795            1800

Ala Asp Val Ala His Gln Arg Asn His Trp Asp Leu Leu Thr Leu
    1805            1810            1815

Leu Glu Gly Ala Gly Pro Pro Glu Ala Arg His Lys Ala Thr Pro
    1820            1825            1830

Gly Arg Glu Ala Gly Pro Phe Pro Arg Ala Arg Thr Val Ser Val
    1835            1840            1845

Ser Val Pro Pro His Gly Gly Gly Ala Leu Pro Arg Cys Arg Thr
    1850            1855            1860

Leu Ser Ala Gly Ala Gly Pro Arg Gly Gly Ala Cys Leu Gln
    1865            1870            1875

Ala Arg Thr Trp Ser Val Asp Leu Ala Ala Arg Gly Gly Gly Ala
    1880            1885            1890

Tyr Ser His Cys Arg Ser Leu Ser Gly Val Gly Ala Gly Gly Gly
    1895            1900            1905

Pro Thr Pro Arg Gly Arg Arg Phe Ser Ala Gly Met Arg Gly Pro
    1910            1915            1920

Arg Pro Asn Pro Ala Ile Met Arg Gly Arg Tyr Gly Val Ala Ala
    1925            1930            1935

Gly Arg Gly Gly Arg Val Ser Thr Asp Asp Trp Pro Cys Asp Trp
    1940            1945            1950

Val Ala Leu Gly Ala Cys Gly Ser Ala Ser Asn Ile Pro Ile Pro
    1955            1960            1965

Pro Pro Cys Leu Thr Pro Ser Pro Glu Arg Gly Ser Pro Gln Leu
    1970            1975            1980

Asp Cys Gly Pro Pro Ala Leu Gln Glu Met Pro Ile Asn Gln Gly
    1985            1990            1995

Gly Glu Gly Lys Lys
```

-continued

```
                                        2000
```

<210> SEQ ID NO 11
<211> LENGTH: 2470
<212> TYPE: PRT
<213> ORGANISM: Mus musculus

<400> SEQUENCE: 11

Met Pro Asp Leu Arg Pro Ala Ala Leu Arg Ala Leu Leu Trp Leu Trp
1               5                   10                  15

Leu Cys Gly Ala Gly Pro Ala His Ala Leu Gln Cys Arg Gly Gly Gln
            20                  25                  30

Glu Pro Cys Val Asn Glu Gly Thr Cys Val Thr Tyr His Asn Gly Thr
        35                  40                  45

Gly Phe Cys Arg Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Pro Gln Gly Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Arg Asp Thr
        115                 120                 125

Tyr Glu Cys Thr Cys Gln Val Gly Phe Thr Gly Lys Gln Cys Gln Trp
    130                 135                 140

Thr Asp Ala Cys Leu Ser His Pro Cys Glu Asn Gly Ser Thr Cys Thr
145                 150                 155                 160

Ser Val Ala Ser Gln Phe Ser Cys Lys Cys Pro Ala Gly Leu Thr Gly
                165                 170                 175

Gln Lys Cys Glu Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205

Cys Gly Gln Gly Phe Thr Gly Gln His Cys Asp Ser Pro Tyr Val Arg
    210                 215                 220

Gly Leu Pro Cys Val Asn Gly Gly Thr Cys Arg Gln Thr Gly Asp Phe
225                 230                 235                 240

Thr Leu Glu Cys Asn Cys Leu Pro Gly Phe Glu Gly Ser Thr Cys Glu
                245                 250                 255

Arg Asn Ile Asp Asp Cys Pro Asn His Lys Cys Gln Asn Gly Gly Val
            260                 265                 270

Cys Val Asp Gly Val Asn Thr Tyr Asn Cys Arg Cys Pro Pro Gln Trp
        275                 280                 285

Thr Gly Gln Phe Cys Thr Glu Asp Val Asp Glu Cys Leu Leu Gln Pro
    290                 295                 300

Asn Ala Cys Gln Asn Gly Gly Thr Cys Thr Asn Arg Asn Gly Gly Tyr
305                 310                 315                 320

Gly Cys Val Cys Val Asn Gly Trp Ser Gly Asp Asp Cys Ser Glu Asn
                325                 330                 335

Ile Asp Asp Cys Ala Tyr Ala Ser Cys Thr Pro Gly Ser Thr Cys Ile
            340                 345                 350

Asp Arg Val Ala Ser Phe Ser Cys Leu Cys Pro Glu Gly Lys Ala Gly
        355                 360                 365

```
Leu Leu Cys His Leu Asp Asp Ala Cys Ile Ser Asn Pro Cys His Lys
    370                 375                 380

Gly Ala Leu Cys Asp Thr Asn Pro Leu Asn Gly Gln Tyr Ile Cys Thr
385                 390                 395                 400

Cys Pro Gln Gly Tyr Lys Gly Ala Asp Cys Thr Glu Asp Val Asp Glu
                405                 410                 415

Cys Ala Met Ala Asn Ser Asn Pro Cys Glu His Ala Gly Lys Cys Val
            420                 425                 430

Asn Thr Asp Gly Ala Phe His Cys Glu Cys Leu Lys Gly Tyr Ala Gly
            435                 440                 445

Pro Arg Cys Glu Met Asp Ile Asn Glu Cys His Ser Asp Pro Cys Gln
450                 455                 460

Asn Asp Ala Thr Cys Leu Asp Lys Ile Gly Gly Phe Thr Cys Leu Cys
465                 470                 475                 480

Met Pro Gly Phe Lys Gly Val His Cys Glu Leu Glu Val Asn Glu Cys
                485                 490                 495

Gln Ser Asn Pro Cys Val Asn Asn Gly Gln Cys Val Asp Lys Val Asn
                500                 505                 510

Arg Phe Gln Cys Leu Cys Pro Pro Gly Phe Thr Gly Pro Val Cys Gln
                515                 520                 525

Ile Asp Ile Asp Asp Cys Ser Ser Thr Pro Cys Leu Asn Gly Ala Lys
530                 535                 540

Cys Ile Asp His Pro Asn Gly Tyr Glu Cys Gln Cys Ala Thr Gly Phe
545                 550                 555                 560

Thr Gly Ile Leu Cys Asp Glu Asn Ile Asp Asn Cys Asp Pro Asp Pro
                565                 570                 575

Cys His His Gly Gln Cys Gln Asp Gly Ile Asp Ser Tyr Thr Cys Ile
            580                 585                 590

Cys Asn Pro Gly Tyr Met Gly Ala Ile Cys Ser Asp Gln Ile Asp Glu
            595                 600                 605

Cys Tyr Ser Ser Pro Cys Leu Asn Asp Gly Arg Cys Ile Asp Leu Val
    610                 615                 620

Asn Gly Tyr Gln Cys Asn Cys Gln Pro Gly Thr Ser Gly Leu Asn Cys
625                 630                 635                 640

Glu Ile Asn Phe Asp Asp Cys Ala Ser Asn Pro Cys Met His Gly Val
                645                 650                 655

Cys Val Asp Gly Ile Asn Arg Tyr Ser Cys Val Cys Ser Pro Gly Phe
                660                 665                 670

Thr Gly Gln Arg Cys Asn Ile Asp Ile Asp Glu Cys Ala Ser Asn Pro
            675                 680                 685

Cys Arg Lys Gly Ala Thr Cys Ile Asn Asp Val Asn Gly Phe Arg Cys
    690                 695                 700

Ile Cys Pro Glu Gly Pro His His Pro Ser Cys Tyr Ser Gln Val Asn
705                 710                 715                 720

Glu Cys Leu Ser Asn Pro Cys Ile His Gly Asn Cys Thr Gly Gly Leu
                725                 730                 735

Ser Gly Tyr Lys Cys Leu Cys Asp Ala Gly Trp Val Gly Val Asn Cys
                740                 745                 750

Glu Val Asp Lys Asn Glu Cys Leu Ser Asn Pro Cys Gln Asn Gly Gly
                755                 760                 765

Thr Cys Asn Asn Leu Val Asn Gly Tyr Arg Cys Thr Cys Lys Lys Gly
770                 775                 780

Phe Lys Gly Tyr Asn Cys Gln Val Asn Ile Asp Glu Cys Ala Ser Asn
```

```
                785                 790                795                800
       Pro Cys Leu Asn Gln Gly Thr Cys Phe Asp Asp Val Ser Gly Tyr Thr
                           805                 810                815

Cys His Cys Met Leu Pro Tyr Thr Gly Lys Asn Cys Gln Thr Val Leu
                           820                 825                830

Ala Pro Cys Ser Pro Asn Pro Cys Glu Asn Ala Ala Val Cys Lys Glu
                           835                 840                845

Ala Pro Asn Phe Glu Ser Phe Ser Cys Leu Cys Ala Pro Gly Trp Gln
       850                         855                 860

Gly Lys Arg Cys Thr Val Asp Val Asp Glu Cys Ile Ser Lys Pro Cys
       865                         870                 875                880

Met Asn Asn Gly Val Cys His Asn Thr Gln Gly Ser Tyr Val Cys Glu
                           885                 890                895

Cys Pro Pro Gly Phe Ser Gly Met Asp Cys Glu Glu Asp Ile Asn Asp
                           900                 905                910

Cys Leu Ala Asn Pro Cys Gln Asn Gly Gly Ser Cys Val Asp His Val
                           915                 920                925

Asn Thr Phe Ser Cys Gln Cys His Pro Gly Phe Ile Gly Asp Lys Cys
                930                 935                940

Gln Thr Asp Met Asn Glu Cys Leu Ser Glu Pro Cys Lys Asn Gly Gly
       945                         950                 955                960

Thr Cys Ser Asp Tyr Val Asn Ser Tyr Thr Cys Thr Cys Pro Ala Gly
                           965                 970                975

Phe His Gly Val His Cys Glu Asn Asn Ile Asp Glu Cys Thr Glu Ser
                           980                 985                990

Ser Cys Phe Asn Gly Gly Thr Cys Val Asp Gly Ile Asn Ser Phe Ser
                           995                 1000               1005

Cys Leu Cys Pro Val Gly Phe Thr Gly Pro Phe Cys Leu His Asp
                1010                1015                1020

Ile Asn Glu Cys Ser Ser Asn Pro Cys Leu Asn Ala Gly Thr Cys
                1025                1030                1035

Val Asp Gly Leu Gly Thr Tyr Arg Cys Ile Cys Pro Leu Gly Tyr
                1040                1045                1050

Thr Gly Lys Asn Cys Gln Thr Leu Val Asn Leu Cys Ser Arg Ser
                1055                1060                1065

Pro Cys Lys Asn Lys Gly Thr Cys Val Gln Glu Lys Ala Arg Pro
                1070                1075                1080

His Cys Leu Cys Pro Pro Gly Trp Asp Gly Ala Tyr Cys Asp Val
                1085                1090                1095

Leu Asn Val Ser Cys Lys Ala Ala Ala Leu Gln Lys Gly Val Pro
                1100                1105                1110

Val Glu His Leu Cys Gln His Ser Gly Ile Cys Ile Asn Ala Gly
                1115                1120                1125

Asn Thr His His Cys Gln Cys Pro Leu Gly Tyr Thr Gly Ser Tyr
                1130                1135                1140

Cys Glu Glu Gln Leu Asp Glu Cys Ala Ser Asn Pro Cys Gln His
                1145                1150                1155

Gly Ala Thr Cys Asn Asp Phe Ile Gly Gly Tyr Arg Cys Glu Cys
                1160                1165                1170

Val Pro Gly Tyr Gln Gly Val Asn Cys Glu Tyr Glu Val Asp Glu
                1175                1180                1185

Cys Gln Asn Gln Pro Cys Gln Asn Gly Gly Thr Cys Ile Asp Leu
                1190                1195                1200
```

```
Val Asn His Phe Lys Cys Ser Cys Pro Pro Gly Thr Arg Gly Leu
1205                 1210                1215

Leu Cys Glu Glu Asn Ile Asp Glu Cys Ala Gly Gly Pro His Cys
1220                 1225                1230

Leu Asn Gly Gly Gln Cys Val Asp Arg Ile Gly Gly Tyr Thr Cys
1235                 1240                1245

Arg Cys Leu Pro Gly Phe Ala Gly Glu Arg Cys Glu Gly Asp Ile
1250                 1255                1260

Asn Glu Cys Leu Ser Asn Pro Cys Ser Ser Glu Gly Ser Leu Asp
1265                 1270                1275

Cys Val Gln Leu Lys Asn Asn Tyr Asn Cys Ile Cys Arg Ser Ala
1280                 1285                1290

Phe Thr Gly Arg His Cys Glu Thr Phe Leu Asp Val Cys Pro Gln
1295                 1300                1305

Lys Pro Cys Leu Asn Gly Gly Thr Cys Ala Val Ala Ser Asn Met
1310                 1315                1320

Pro Asp Gly Phe Ile Cys Arg Cys Pro Pro Gly Phe Ser Gly Ala
1325                 1330                1335

Arg Leu Gln Ser Ser Cys Gly Gln Val Lys Cys Arg Arg Gly Glu
1340                 1345                1350

Gln Cys Ile His Thr Asp Ser Gly Pro Arg Cys Phe Cys Leu Asn
1355                 1360                1365

Pro Lys Asp Cys Glu Ser Gly Cys Ala Ser Asn Pro Cys Gln His
1370                 1375                1380

Gly Gly Thr Cys Tyr Pro Gln Arg Gln Pro Pro His Tyr Ser Cys
1385                 1390                1395

Arg Cys Pro Pro Ser Phe Gly Gly Ser His Cys Glu Leu Tyr Thr
1400                 1405                1410

Ala Pro Thr Ser Thr Pro Pro Ala Thr Cys Gln Ser Gln Tyr Cys
1415                 1420                1425

Ala Asp Lys Ala Arg Asp Gly Ile Cys Asp Glu Ala Cys Asn Ser
1430                 1435                1440

His Ala Cys Gln Trp Asp Gly Gly Asp Cys Ser Leu Thr Met Glu
1445                 1450                1455

Asp Pro Trp Ala Asn Cys Thr Ser Thr Leu Arg Cys Trp Glu Tyr
1460                 1465                1470

Ile Asn Asn Gln Cys Asp Glu Gln Cys Asn Thr Ala Glu Cys Leu
1475                 1480                1485

Phe Asp Asn Phe Glu Cys Gln Arg Asn Ser Lys Thr Cys Lys Tyr
1490                 1495                1500

Asp Lys Tyr Cys Ala Asp His Phe Lys Asp Asn His Cys Asp Gln
1505                 1510                1515

Gly Cys Asn Ser Glu Glu Cys Gly Trp Asp Gly Leu Asp Cys Ala
1520                 1525                1530

Ser Asp Gln Pro Glu Asn Leu Ala Glu Gly Thr Leu Ile Ile Val
1535                 1540                1545

Val Leu Leu Pro Pro Glu Gln Leu Leu Gln Asp Ser Arg Ser Phe
1550                 1555                1560

Leu Arg Ala Leu Gly Thr Leu Leu His Thr Asn Leu Arg Ile Lys
1565                 1570                1575

Gln Asp Ser Gln Gly Ala Leu Met Val Tyr Pro Tyr Phe Gly Glu
1580                 1585                1590
```

```
Lys Ser Ala Ala Met Lys Lys Gln Lys Met Thr Arg Arg Ser Leu
1595                1600                1605

Pro Glu Glu Gln Glu Gln Glu Glu Val Ile Gly Ser Lys Ile
1610                1615                1620

Phe Leu Glu Ile Asp Asn Arg Gln Cys Val Gln Asp Ser Asp Gln
1625                1630                1635

Cys Phe Lys Asn Thr Asp Ala Ala Ala Leu Leu Ala Ser His
1640                1645                1650

Ala Ile Gln Gly Thr Leu Ser Tyr Pro Leu Val Ser Val Phe Ser
1655                1660                1665

Glu Leu Glu Ser Pro Arg Asn Ala Gln Leu Leu Tyr Leu Leu Ala
1670                1675                1680

Val Ala Val Val Ile Ile Leu Phe Phe Ile Leu Leu Gly Val Ile
1685                1690                1695

Met Ala Lys Arg Lys Gln Ala Trp Leu Pro Leu Ala Ala Gly Arg
1700                1705                1710

Phe Thr Leu Arg Arg Asp Ser Ser Asn His Lys Arg Arg Glu Pro
1715                1720                1725

Val Gly Gln Asp Ala Val Gly Leu Lys Asn Leu Ser Val Gln Val
1730                1735                1740

Ser Glu Ala Asn Leu Ile Gly Ser Gly Thr Ser Glu His Trp Val
1745                1750                1755

Asp Asp Glu Gly Pro Gln Pro Lys Lys Ala Lys Ala Glu Asp Glu
1760                1765                1770

Ala Leu Leu Ser Glu Asp Asp Pro Ile Asp Arg Arg Pro Trp Thr
1775                1780                1785

Gln Gln His Leu Glu Ala Ala Asp Ile Ser His Thr Pro Ser Leu
1790                1795                1800

Ala Leu Thr Pro Pro Gln Ala Glu Gln Glu Val Asp Val Leu Asp
1805                1810                1815

Val Asn Val Arg Gly Pro Asp Gly Cys Thr Pro Leu Met Leu Ala
1820                1825                1830

Ser Leu Arg Gly Gly Ser Ser Asp Leu Ser Asp Glu Asp Glu Asp
1835                1840                1845

Ala Glu Asp Ser Ser Ala Asn Ile Ile Thr Asp Leu Val Tyr Gln
1850                1855                1860

Gly Ala Ser Leu Gln Ala Gln Thr Asp Arg Thr Gly Glu Met Ala
1865                1870                1875

Leu His Leu Ala Ala Arg Tyr Ser Arg Ala Asp Ala Ala Lys Arg
1880                1885                1890

Leu Leu Asp Ala Gly Ala Asp Arg Asn Ala Gln Asp Asn Met Gly
1895                1900                1905

Arg Cys Pro Leu His Ala Ala Val Ala Gly Asp Ala Gln Gly Val
1910                1915                1920

Phe Gln Ile Leu Ile Arg Asn Arg Val Thr Asp Leu Asp Ala Arg
1925                1930                1935

Met Asn Asp Gly Thr Thr Pro Leu Ile Leu Ala Ala Arg Leu Ala
1940                1945                1950

Val Glu Gly Met Val Ala Glu Leu Ile Asn Cys Gln Ala Asp Val
1955                1960                1965

Asn Ala Val Asp Asp His Gly Lys Ser Ala Leu His Trp Ala Ala
1970                1975                1980

Ala Val Asn Asn Val Glu Ala Thr Leu Leu Leu Leu Lys Asn Gly
```

```
              1985                1990                1995
Ala  Asn  Arg  Asp  Met  Gln  Asp  Asn  Lys  Glu  Thr  Pro  Leu  Phe
              2000                2005                2010

Leu  Ala  Ala  Arg  Glu  Gly  Ser  Tyr  Glu  Ala  Ala  Lys  Ile  Leu  Leu
              2015                2020                2025

Asp  His  Phe  Ala  Asn  Arg  Asp  Ile  Thr  Asp  His  Met  Asp  Arg  Leu
              2030                2035                2040

Pro  Arg  Asp  Val  Ala  Arg  Asp  Arg  Met  His  His  Asp  Ile  Val  Arg
              2045                2050                2055

Leu  Leu  Asp  Glu  Tyr  Asn  Val  Thr  Pro  Ser  Pro  Pro  Gly  Thr  Val
              2060                2065                2070

Leu  Thr  Ser  Ala  Leu  Ser  Pro  Val  Leu  Cys  Gly  Pro  Asn  Arg  Ser
              2075                2080                2085

Phe  Leu  Ser  Leu  Lys  His  Thr  Pro  Met  Gly  Lys  Lys  Ala  Arg  Arg
              2090                2095                2100

Pro  Asn  Thr  Lys  Ser  Thr  Met  Pro  Thr  Ser  Leu  Pro  Asn  Leu  Ala
              2105                2110                2115

Lys  Glu  Ala  Lys  Asp  Ala  Lys  Gly  Ser  Arg  Arg  Lys  Lys  Cys  Leu
              2120                2125                2130

Asn  Glu  Lys  Val  Gln  Leu  Ser  Glu  Ser  Ser  Val  Thr  Leu  Ser  Pro
              2135                2140                2145

Val  Asp  Ser  Leu  Glu  Ser  Pro  His  Thr  Tyr  Val  Ser  Asp  Ala  Thr
              2150                2155                2160

Ser  Ser  Pro  Met  Ile  Thr  Ser  Pro  Gly  Ile  Leu  Gln  Ala  Ser  Pro
              2165                2170                2175

Thr  Pro  Leu  Leu  Ala  Ala  Ala  Pro  Ala  Ala  Pro  Val  His  Thr
              2180                2185                2190

Gln  His  Ala  Leu  Ser  Phe  Ser  Asn  Leu  His  Asp  Met  Gln  Pro  Leu
              2195                2200                2205

Ala  Pro  Gly  Ala  Ser  Thr  Val  Leu  Pro  Ser  Val  Ser  Gln  Leu  Leu
              2210                2215                2220

Ser  His  His  His  Ile  Ala  Pro  Pro  Gly  Ser  Ser  Ser  Ala  Gly  Ser
              2225                2230                2235

Leu  Gly  Arg  Leu  His  Pro  Val  Pro  Val  Pro  Ala  Asp  Trp  Met  Asn
              2240                2245                2250

Arg  Val  Glu  Met  Asn  Glu  Thr  Gln  Tyr  Ser  Glu  Met  Phe  Gly  Met
              2255                2260                2265

Val  Leu  Ala  Pro  Ala  Glu  Gly  Ala  His  Pro  Gly  Ile  Ala  Ala  Pro
              2270                2275                2280

Gln  Ser  Arg  Pro  Pro  Glu  Gly  Lys  His  Met  Ser  Thr  Gln  Arg  Glu
              2285                2290                2295

Pro  Leu  Pro  Pro  Ile  Val  Thr  Phe  Gln  Leu  Ile  Pro  Lys  Arg  Ser
              2300                2305                2310

Ile  Ala  Gln  Ala  Ala  Gly  Ala  Pro  Gln  Thr  Gln  Ser  Ser  Cys  Pro
              2315                2320                2325

Pro  Ala  Val  Ala  Gly  Pro  Leu  Pro  Ser  Met  Tyr  Gln  Ile  Pro  Glu
              2330                2335                2340

Met  Pro  Arg  Leu  Pro  Ser  Val  Ala  Phe  Pro  Pro  Thr  Met  Met  Pro
              2345                2350                2355

Gln  Gln  Glu  Gly  Gln  Val  Ala  Gln  Thr  Ile  Val  Pro  Thr  Tyr  His
              2360                2365                2370

Pro  Phe  Pro  Ala  Ser  Val  Gly  Lys  Tyr  Pro  Thr  Pro  Pro  Ser  Gln
              2375                2380                2385
```

His Ser Tyr Ala Ser Ser Asn Ala Ala Glu Arg Thr Pro Ser His
    2390            2395                2400

Gly Gly His Leu Gln Gly Glu His Pro Tyr Leu Thr Pro Ser Pro
    2405            2410                2415

Glu Ser Pro Asp Gln Trp Ser Ser Ser Pro His Ser Ala Ser
    2420            2425                2430

Asp Trp Ser Asp Val Thr Thr Ser Pro Thr Pro Gly Gly Gly
    2435            2440                2445

Gly Gly Gln Arg Gly Pro Gly Thr His Met Ser Glu Pro Pro His
    2450            2455                2460

Ser Asn Met Gln Val Tyr Ala
    2465            2470

<210> SEQ ID NO 12
<211> LENGTH: 1964
<212> TYPE: PRT
<213> ORGANISM: Mus musculus

<400> SEQUENCE: 12

Met Gln Pro Gln Leu Leu Leu Leu Leu Leu Pro Leu Asn Phe Pro
1               5                   10                  15

Val Ile Leu Thr Arg Glu Leu Leu Cys Gly Gly Ser Pro Glu Pro Cys
            20                  25                  30

Ala Asn Gly Gly Thr Cys Leu Arg Leu Ser Gln Gly Gln Gly Ile Cys
        35                  40                  45

Gln Cys Ala Pro Gly Phe Leu Gly Glu Thr Cys Gln Phe Pro Asp Pro
50                  55                  60

Cys Arg Asp Thr Gln Leu Cys Lys Asn Gly Gly Ser Cys Gln Ala Leu
65                  70                  75                  80

Leu Pro Thr Pro Pro Ser Ser Arg Ser Pro Thr Ser Pro Leu Thr Pro
                85                  90                  95

His Phe Ser Cys Thr Cys Pro Ser Gly Phe Thr Gly Asp Arg Cys Gln
            100                 105                 110

Thr His Leu Glu Glu Leu Cys Pro Pro Ser Phe Cys Ser Asn Gly Gly
        115                 120                 125

His Cys Tyr Val Gln Ala Ser Gly Arg Pro Gln Cys Ser Cys Glu Pro
    130                 135                 140

Gly Trp Thr Gly Glu Gln Cys Gln Leu Arg Asp Phe Cys Ser Ala Asn
145                 150                 155                 160

Pro Cys Ala Asn Gly Gly Val Cys Leu Ala Thr Tyr Pro Gln Ile Gln
                165                 170                 175

Cys Arg Cys Pro Pro Gly Phe Glu Gly His Thr Cys Glu Arg Asp Ile
            180                 185                 190

Asn Glu Cys Phe Leu Glu Pro Gly Pro Cys Pro Gln Gly Thr Ser Cys
        195                 200                 205

His Asn Thr Leu Gly Ser Tyr Gln Cys Leu Cys Pro Val Gly Gln Glu
    210                 215                 220

Gly Pro Gln Cys Lys Leu Arg Lys Gly Ala Cys Pro Pro Gly Ser Cys
225                 230                 235                 240

Leu Asn Gly Gly Thr Cys Gln Leu Val Pro Glu Gly His Ser Thr Phe
                245                 250                 255

His Leu Cys Leu Cys Pro Pro Gly Phe Thr Gly Leu Asp Cys Glu Met
            260                 265                 270

Asn Pro Asp Asp Cys Val Arg His Gln Cys Gln Asn Gly Ala Thr Cys

```
                275                 280                 285
Leu Asp Gly Leu Asp Thr Tyr Thr Cys Leu Cys Pro Lys Thr Trp Lys
290                 295                 300

Gly Trp Asp Cys Ser Glu Asp Ile Asp Glu Cys Glu Ala Arg Gly Pro
305                 310                 315                 320

Pro Arg Cys Arg Asn Gly Gly Thr Cys Gln Asn Thr Ala Gly Ser Phe
                325                 330                 335

His Cys Val Cys Val Ser Gly Trp Gly Gly Ala Gly Cys Glu Glu Asn
                340                 345                 350

Leu Asp Asp Cys Ala Ala Ala Thr Cys Ala Pro Gly Ser Thr Cys Ile
                355                 360                 365

Asp Arg Val Gly Ser Phe Ser Cys Leu Cys Pro Pro Gly Arg Thr Gly
                370                 375                 380

Leu Leu Cys His Leu Glu Asp Met Cys Leu Ser Gln Pro Cys His Val
385                 390                 395                 400

Asn Ala Gln Cys Ser Thr Asn Pro Leu Thr Gly Ser Thr Leu Cys Ile
                405                 410                 415

Cys Gln Pro Gly Tyr Ser Gly Ser Thr Cys His Gln Asp Leu Asp Glu
                420                 425                 430

Cys Gln Met Ala Gln Gln Pro Ser Pro Cys Glu His Gly Gly Ser
                435                 440                 445

Cys Ile Asn Thr Pro Gly Ser Phe Asn Cys Leu Cys Leu Pro Gly Tyr
                450                 455                 460

Thr Gly Ser Arg Cys Glu Ala Asp His Asn Glu Cys Leu Ser Gln Pro
465                 470                 475                 480

Cys His Pro Gly Ser Thr Cys Leu Asp Leu Leu Ala Thr Phe His Cys
                485                 490                 495

Leu Cys Pro Pro Gly Leu Glu Gly Arg Leu Cys Glu Val Glu Val Asn
                500                 505                 510

Glu Cys Thr Ser Asn Pro Cys Leu Asn Gln Ala Ala Cys His Asp Leu
                515                 520                 525

Leu Asn Gly Phe Gln Cys Leu Cys Leu Pro Gly Phe Thr Gly Ala Arg
                530                 535                 540

Cys Glu Lys Asp Met Asp Glu Cys Ser Ser Thr Pro Cys Ala Asn Gly
545                 550                 555                 560

Gly Arg Cys Arg Asp Gln Pro Gly Ala Phe Tyr Cys Glu Cys Leu Pro
                565                 570                 575

Gly Phe Glu Gly Pro His Cys Glu Lys Glu Val Asp Glu Cys Leu Ser
                580                 585                 590

Asp Pro Cys Pro Val Gly Ala Ser Cys Leu Asp Leu Pro Gly Ala Phe
                595                 600                 605

Phe Cys Leu Cys Arg Pro Gly Phe Thr Gly Gln Leu Cys Glu Val Pro
                610                 615                 620

Leu Cys Thr Pro Asn Met Cys Gln Pro Gly Gln Gln Cys Gln Gly Gln
625                 630                 635                 640

Glu His Arg Ala Pro Cys Leu Cys Pro Asp Gly Ser Pro Gly Cys Val
                645                 650                 655

Pro Ala Glu Asp Asn Cys Pro Cys His His Gly His Cys Gln Arg Ser
                660                 665                 670

Leu Cys Val Cys Asp Glu Gly Trp Thr Gly Pro Glu Cys Glu Thr Glu
                675                 680                 685

Leu Gly Gly Cys Ile Ser Thr Pro Cys Ala His Gly Gly Thr Cys His
690                 695                 700
```

-continued

```
Pro Gln Pro Ser Gly Tyr Asn Cys Thr Cys Pro Ala Gly Tyr Met Gly
705                 710                 715                 720

Leu Thr Cys Ser Glu Glu Val Thr Ala Cys His Ser Gly Pro Cys Leu
            725                 730                 735

Asn Gly Gly Ser Cys Ser Ile Arg Pro Glu Gly Tyr Ser Cys Thr Cys
            740                 745                 750

Leu Pro Ser His Thr Gly Arg His Cys Gln Thr Ala Val Asp His Cys
        755                 760                 765

Val Ser Ala Ser Cys Leu Asn Gly Gly Thr Cys Val Asn Lys Pro Gly
770                 775                 780

Thr Phe Phe Cys Leu Cys Ala Thr Gly Phe Gln Gly Leu His Cys Glu
785                 790                 795                 800

Glu Lys Thr Asn Pro Ser Cys Ala Asp Ser Pro Cys Arg Asn Lys Ala
            805                 810                 815

Thr Cys Gln Asp Thr Pro Arg Gly Ala Arg Cys Leu Cys Ser Pro Gly
            820                 825                 830

Tyr Thr Gly Ser Ser Cys Gln Thr Leu Ile Asp Leu Cys Ala Arg Lys
        835                 840                 845

Pro Cys Pro His Thr Ala Arg Cys Leu Gln Ser Gly Pro Ser Phe Gln
    850                 855                 860

Cys Leu Cys Leu Gln Gly Trp Thr Gly Ala Leu Cys Asp Phe Pro Leu
865                 870                 875                 880

Ser Cys Gln Met Ala Ala Met Ser Gln Gly Ile Glu Ile Ser Gly Leu
            885                 890                 895

Cys Gln Asn Gly Gly Leu Cys Ile Asp Thr Gly Ser Ser Tyr Phe Cys
            900                 905                 910

Arg Cys Pro Pro Gly Phe Gln Gly Lys Leu Cys Gln Asp Asn Met Asn
        915                 920                 925

Pro Cys Glu Pro Asn Pro Cys His His Gly Ser Thr Cys Val Pro Gln
    930                 935                 940

Pro Ser Gly Tyr Val Cys Gln Cys Ala Pro Gly Tyr Glu Gly Gln Asn
945                 950                 955                 960

Cys Ser Lys Val Leu Glu Ala Cys Gln Ser Gln Pro Cys His Asn His
            965                 970                 975

Gly Thr Cys Thr Ser Arg Pro Gly Gly Phe His Cys Ala Cys Pro Pro
            980                 985                 990

Gly Phe Val Gly Leu Arg Cys Glu  Gly Asp Val Asp Glu  Cys Leu Asp
        995                 1000                1005

Arg Pro Cys His Pro Ser Gly  Thr Ala Ala Cys His  Ser Leu Ala
    1010                1015                1020

Asn Ala Phe Tyr Cys Gln Cys  Leu Pro Gly His Thr  Gly Gln Arg
    1025                1030                1035

Cys Glu Val Glu Met Asp Leu  Cys Gln Ser Gln Pro  Cys Ser Asn
    1040                1045                1050

Gly Gly Ser Cys Glu Ile Thr  Thr Gly Pro Pro Pro  Gly Phe Thr
    1055                1060                1065

Cys His Cys Pro Lys Gly Phe  Glu Gly Pro Thr Cys  Ser His Lys
    1070                1075                1080

Ala Leu Ser Cys Gly Ile His  His Cys His Asn Gly  Gly Leu Cys
    1085                1090                1095

Leu Pro Ser Pro Lys Pro Gly  Ser Pro Pro Leu Cys  Ala Cys Leu
    1100                1105                1110
```

```
Ser Gly Phe Gly Gly Pro Asp Cys Leu Thr Pro Pro Ala Pro Pro
1115                1120                1125

Gly Cys Gly Pro Pro Ser Pro Cys Leu His Asn Gly Thr Cys Thr
1130                1135                1140

Glu Thr Pro Gly Leu Gly Asn Pro Gly Phe Gln Cys Thr Cys Pro
1145                1150                1155

Pro Asp Ser Pro Gly Pro Arg Cys Gln Arg Pro Gly Ala Ser Gly
1160                1165                1170

Cys Glu Gly Arg Gly Gly Asp Gly Thr Cys Asp Ala Gly Cys Ser
1175                1180                1185

Gly Pro Gly Gly Asp Trp Asp Gly Gly Asp Cys Ser Leu Gly Val
1190                1195                1200

Pro Asp Pro Trp Lys Gly Cys Pro Pro His Ser Gln Cys Trp Leu
1205                1210                1215

Leu Phe Arg Asp Gly Arg Cys His Pro Gln Cys Asp Ser Glu Glu
1220                1225                1230

Cys Leu Phe Asp Gly Tyr Asp Cys Glu Ile Pro Leu Thr Cys Ile
1235                1240                1245

Pro Ala Tyr Asp Gln Tyr Cys Arg Asp His Phe His Asn Gly His
1250                1255                1260

Cys Glu Lys Gly Cys Asn Asn Ala Glu Cys Gly Trp Asp Gly Gly
1265                1270                1275

Asp Cys Arg Pro Glu Gly Glu Asp Ser Glu Gly Arg Pro Ser Leu
1280                1285                1290

Ala Leu Leu Val Val Leu Arg Pro Pro Ala Leu Asp Gln Gln Leu
1295                1300                1305

Leu Ala Leu Ala Arg Val Leu Ser Leu Thr Leu Arg Val Gly Leu
1310                1315                1320

Trp Val Arg Lys Asp Ser Glu Gly Arg Asn Met Val Phe Pro Tyr
1325                1330                1335

Pro Gly Thr Arg Ala Lys Glu Glu Leu Ser Gly Ala Arg Asp Ser
1340                1345                1350

Ser Ser Trp Glu Arg Gln Ala Pro Pro Thr Gln Pro Leu Gly Lys
1355                1360                1365

Glu Thr Glu Ser Leu Gly Ala Gly Phe Val Val Val Met Gly Val
1370                1375                1380

Asp Leu Ser Arg Cys Gly Pro Glu His Pro Ala Ser Arg Cys Pro
1385                1390                1395

Trp Asp Ser Gly Leu Leu Leu Arg Phe Leu Ala Ala Met Ala Ala
1400                1405                1410

Val Gly Ala Leu Glu Pro Leu Leu Pro Gly Pro Leu Leu Ala Ala
1415                1420                1425

His Pro Gln Ala Gly Thr Arg Pro Pro Ala Asn Gln Leu Pro Trp
1430                1435                1440

Pro Ile Leu Cys Ser Pro Val Val Gly Val Leu Leu Ala Leu
1445                1450                1455

Gly Ala Leu Leu Val Leu Gln Leu Ile Arg Arg Arg Arg Glu
1460                1465                1470

His Gly Ala Leu Trp Leu Pro Pro Gly Phe Ile Arg Arg Pro Gln
1475                1480                1485

Ala Gln Gln Ala Pro His Arg Arg Arg Pro Pro Leu Gly Glu Asp
1490                1495                1500

Asn Ile Gly Leu Lys Ala Leu Lys Pro Glu Ala Glu Val Asp Glu
```

-continued

```
                1505                1510                1515

Asp Gly Val Ala Met Cys Ser Gly Pro Glu Gly Glu Ala Glu
    1520                1525                1530

Glu Thr Ala Ser Ala Ser Arg Cys Gln Leu Trp Pro Leu Asn Ser
    1535                1540                1545

Ser Cys Gly Glu Leu Pro Gln Ala Ala Met Leu Thr Pro Pro Gln
    1550                1555                1560

Glu Cys Glu Ser Glu Val Leu Asp Val Asp Thr Cys Gly Pro Asp
    1565                1570                1575

Gly Val Thr Pro Leu Met Ser Ala Val Phe Cys Gly Gly Val Gln
    1580                1585                1590

Ser Thr Thr Gly Ala Ser Pro Gln Arg Leu Gly Leu Gly Asn Leu
    1595                1600                1605

Glu Pro Trp Glu Pro Leu Leu Asp Arg Gly Ala Cys Pro Gln Ala
    1610                1615                1620

His Thr Val Gly Thr Gly Glu Thr Pro Leu His Leu Ala Ala Arg
    1625                1630                1635

Phe Ser Arg Pro Thr Ala Ala Arg Arg Leu Leu Glu Ala Gly Ala
    1640                1645                1650

Asn Pro Asn Gln Pro Asp Arg Ala Gly Arg Thr Pro Leu His Thr
    1655                1660                1665

Ala Val Ala Ala Asp Ala Arg Glu Val Cys Gln Leu Leu Leu Ala
    1670                1675                1680

Ser Arg Gln Thr Ser Val Asp Ala Arg Thr Glu Asp Gly Thr Thr
    1685                1690                1695

Pro Leu Met Leu Ala Ala Arg Leu Ala Val Glu Asp Leu Val Glu
    1700                1705                1710

Glu Leu Ile Ala Ala Arg Ala Asp Val Gly Ala Arg Asp Lys Arg
    1715                1720                1725

Gly Lys Thr Ala Leu His Trp Ala Ala Ala Val Asn Asn Ala Arg
    1730                1735                1740

Ala Ala Arg Ser Leu Leu Gln Ala Gly Ala Asp Lys Asp Ala Gln
    1745                1750                1755

Asp Ser Arg Glu Gln Thr Pro Leu Phe Leu Ala Ala Arg Glu Gly
    1760                1765                1770

Ala Val Glu Val Ala Gln Leu Leu Leu Glu Leu Gly Ala Ala Arg
    1775                1780                1785

Gly Leu Arg Asp Gln Ala Gly Leu Ala Pro Gly Asp Val Ala Arg
    1790                1795                1800

Gln Arg Ser His Trp Asp Leu Leu Thr Leu Leu Glu Gly Ala Gly
    1805                1810                1815

Pro Thr Thr Gln Glu Ala Arg Ala His Ala Arg Thr Thr Pro Gly
    1820                1825                1830

Gly Gly Ala Ala Ala Arg Cys Arg Thr Leu Ser Ala Gly Ala Arg
    1835                1840                1845

Pro Arg Gly Gly Gly Ala Cys Leu Gln Ala Arg Thr Trp Ser Val
    1850                1855                1860

Asp Leu Gly Ala Arg Gly Gly Lys Val Tyr Ala Arg Cys Arg Ser
    1865                1870                1875

Arg Ser Gly Ser Cys Gly Gly Pro Thr Thr Arg Gly Arg Arg Phe
    1880                1885                1890

Ser Ala Gly Ser Arg Gly Arg Arg Gly Ala Arg Ala Ser Gln Asp
    1895                1900                1905
```

Asp Trp Pro Arg Asp Trp Val Ala Leu Glu Ala Cys Gly Ser Ala
    1910            1915                1920

Cys Ser Ala Pro Ile Pro Pro Ser Leu Thr Pro Ser Pro Glu
    1925            1930                1935

Arg Gly Ser Pro Gln Val Ala Trp Gly Leu Pro Val His Gln Glu
    1940            1945                1950

Ile Pro Leu Asn Ser Val Val Arg Asn Leu Asn
    1955            1960

<210> SEQ ID NO 13
<211> LENGTH: 2318
<212> TYPE: PRT
<213> ORGANISM: Mus musculus

<400> SEQUENCE: 13

Met Gly Leu Gly Ala Arg Gly Arg Arg Arg Arg Leu Met Ala
1               5                   10                  15

Leu Pro Pro Pro Pro Pro Met Arg Ala Leu Pro Leu Leu Leu
            20                  25                  30

Leu Ala Gly Leu Gly Ala Ala Ala Pro Pro Cys Leu Asp Gly Ser Pro
            35                  40                  45

Cys Ala Asn Gly Gly Arg Cys Thr His Gln Gln Pro Ser Leu Glu Ala
    50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
                100                 105                 110

Phe Gln Gly Pro Asp Cys Ser Gln Pro Asp Pro Cys Val Ser Arg Pro
            115                 120                 125

Cys Val His Gly Ala Pro Cys Ser Val Gly Pro Asp Gly Arg Phe Ala
    130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
                180                 185                 190

Leu Leu Cys Glu Asn Pro Val Val Pro Cys Ala Pro Ser Pro Cys Arg
            195                 200                 205

Asn Gly Gly Thr Cys Arg Gln Ser Ser Asp Val Thr Tyr Asp Cys Ala
    210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
                260                 265                 270

Thr Glu Asp Val Asp Glu Cys Gln Leu Gln Pro Asn Ala Cys His Asn
            275                 280                 285

Gly Gly Thr Cys Phe Asn Leu Leu Gly Gly His Ser Cys Val Cys Val
    290                 295                 300

Asn Gly Trp Thr Gly Glu Ser Cys Ser Gln Asn Ile Asp Asp Cys Ala

```
            305                 310                 315                 320
        Thr Ala Val Cys Phe His Gly Ala Thr Cys His Asp Arg Val Ala Ser
                        325                 330                 335
        Phe Tyr Cys Ala Cys Pro Met Gly Lys Thr Gly Leu Leu Cys His Leu
                        340                 345                 350
        Asp Asp Ala Cys Val Ser Asn Pro Cys His Glu Asp Ala Ile Cys Asp
                        355                 360                 365
        Thr Asn Pro Val Ser Gly Arg Ala Ile Cys Thr Cys Pro Pro Gly Phe
            370                 375                 380
        Thr Gly Gly Ala Cys Asp Gln Asp Val Asp Glu Cys Ser Ile Gly Ala
        385                 390                 395                 400
        Asn Pro Cys Glu His Leu Gly Arg Cys Val Asn Thr Gln Gly Ser Phe
                        405                 410                 415
        Leu Cys Gln Cys Gly Arg Gly Tyr Thr Gly Pro Arg Cys Glu Thr Asp
                        420                 425                 430
        Val Asn Glu Cys Leu Ser Gly Pro Cys Arg Asn Gln Ala Thr Cys Leu
                        435                 440                 445
        Asp Arg Ile Gly Gln Phe Thr Cys Ile Cys Met Ala Gly Phe Thr Gly
            450                 455                 460
        Thr Tyr Cys Glu Val Asp Ile Asp Glu Cys Gln Ser Ser Pro Cys Val
        465                 470                 475                 480
        Asn Gly Gly Val Cys Lys Asp Arg Val Asn Gly Phe Ser Cys Thr Cys
                        485                 490                 495
        Pro Ser Gly Phe Ser Gly Ser Met Cys Gln Leu Asp Val Asp Glu Cys
                        500                 505                 510
        Ala Ser Thr Pro Cys Arg Asn Gly Ala Lys Cys Val Asp Gln Pro Asp
                        515                 520                 525
        Gly Tyr Glu Cys Arg Cys Ala Glu Gly Phe Glu Gly Thr Leu Cys Glu
                        530                 535                 540
        Arg Asn Val Asp Asp Cys Ser Pro Asp Pro Cys His His Gly Arg Cys
        545                 550                 555                 560
        Val Asp Gly Ile Ala Ser Phe Ser Cys Ala Cys Ala Pro Gly Tyr Thr
                        565                 570                 575
        Gly Ile Arg Cys Glu Ser Gln Val Asp Glu Cys Arg Ser Gln Pro Cys
                        580                 585                 590
        Arg Tyr Gly Gly Lys Cys Leu Asp Leu Val Asp Lys Tyr Leu Cys Arg
                        595                 600                 605
        Cys Pro Pro Gly Thr Thr Gly Val Asn Cys Glu Val Asn Ile Asp Asp
            610                 615                 620
        Cys Ala Ser Asn Pro Cys Thr Phe Gly Val Cys Arg Asp Gly Ile Asn
        625                 630                 635                 640
        Arg Tyr Asp Cys Val Cys Gln Pro Gly Phe Thr Gly Pro Leu Cys Asn
                        645                 650                 655
        Val Glu Ile Asn Glu Cys Ala Ser Ser Pro Cys Gly Glu Gly Gly Ser
                        660                 665                 670
        Cys Val Asp Gly Glu Asn Gly Phe His Cys Leu Cys Pro Pro Gly Ser
                        675                 680                 685
        Leu Pro Pro Leu Cys Leu Pro Ala Asn His Pro Cys Ala His Lys Pro
            690                 695                 700
        Cys Ser His Gly Val Cys His Asp Ala Pro Gly Gly Phe Arg Cys Val
        705                 710                 715                 720
        Cys Glu Pro Gly Trp Ser Gly Pro Arg Cys Ser Gln Ser Leu Ala Pro
                        725                 730                 735
```

-continued

Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
            755                 760                 765

Gln Cys Glu Val Leu Ser Pro Cys Thr Pro Ser Leu Cys His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
            835                 840                 845

Gln Asp Ile Asp Asp Cys Asp Pro Asn Pro Cys Leu His Gly Gly Ser
        850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
            915                 920                 925

Cys Ser Pro Ser Ser Cys Phe Asn Gly Gly Thr Cys Val Asp Gly Val
        930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn Pro Val Asp Trp Cys Ser Gln Ala
            995                 1000                1005

Pro Cys Gln Asn Gly Gly Arg Cys Val Gln Thr Gly Ala Tyr Cys
    1010                1015                1020

Ile Cys Pro Pro Gly Trp Ser Gly Arg Leu Cys Asp Ile Gln Ser
    1025                1030                1035

Leu Pro Cys Thr Glu Ala Ala Ala Gln Met Gly Val Arg Leu Glu
    1040                1045                1050

Gln Leu Cys Gln Glu Gly Gly Lys Cys Ile Asp Lys Gly Arg Ser
    1055                1060                1065

His Tyr Cys Val Cys Pro Glu Gly Arg Thr Gly Ser His Cys Glu
    1070                1075                1080

His Glu Val Asp Pro Cys Thr Ala Gln Pro Cys Gln His Gly Gly
    1085                1090                1095

Thr Cys Arg Gly Tyr Met Gly Gly Tyr Val Cys Glu Cys Pro Ala
    1100                1105                1110

Gly Tyr Ala Gly Asp Ser Cys Glu Asp Asn Ile Asp Glu Cys Ala
    1115                1120                1125

Ser Gln Pro Cys Gln Asn Gly Gly Ser Cys Ile Asp Leu Val Ala
    1130                1135                1140

-continued

| | | | | | | | | | | | |
|---|---|---|---|---|---|---|---|---|---|---|---|
| Arg | Tyr | Leu | Cys | Ser | Cys | Pro | Pro | Gly | Thr | Leu | Gly | Val | Leu | Cys |
| 1145 | | | | | 1150 | | | | | 1155 | |
| Glu | Ile | Asn | Glu | Asp | Asp | Cys | Asp | Leu | Gly | Pro | Ser | Leu | Asp | Ser |
| 1160 | | | | | 1165 | | | | | 1170 | |
| Gly | Val | Gln | Cys | Leu | His | Asn | Gly | Thr | Cys | Val | Asp | Leu | Val | Gly |
| 1175 | | | | | 1180 | | | | | 1185 | |
| Gly | Phe | Arg | Cys | Asn | Cys | Pro | Pro | Gly | Tyr | Thr | Gly | Leu | His | Cys |
| 1190 | | | | | 1195 | | | | | 1200 | |
| Glu | Ala | Asp | Ile | Asn | Glu | Cys | Arg | Pro | Gly | Ala | Cys | His | Ala | Ala |
| 1205 | | | | | 1210 | | | | | 1215 | |
| His | Thr | Arg | Asp | Cys | Leu | Gln | Asp | Pro | Gly | Gly | His | Phe | Arg | Cys |
| 1220 | | | | | 1225 | | | | | 1230 | |
| Val | Cys | His | Pro | Gly | Phe | Thr | Gly | Pro | Arg | Cys | Gln | Ile | Ala | Leu |
| 1235 | | | | | 1240 | | | | | 1245 | |
| Ser | Pro | Cys | Glu | Ser | Gln | Pro | Cys | Gln | His | Gly | Gly | Gln | Cys | Arg |
| 1250 | | | | | 1255 | | | | | 1260 | |
| His | Ser | Leu | Gly | Arg | Gly | Gly | Leu | Thr | Phe | Thr | Cys | His | Cys |
| 1265 | | | | | 1270 | | | | | 1275 | |
| Val | Pro | Pro | Phe | Trp | Gly | Leu | Arg | Cys | Glu | Arg | Val | Ala | Arg | Ser |
| 1280 | | | | | 1285 | | | | | 1290 | |
| Cys | Arg | Glu | Leu | Gln | Cys | Pro | Val | Gly | Ile | Pro | Cys | Gln | Gln | Thr |
| 1295 | | | | | 1300 | | | | | 1305 | |
| Ala | Arg | Gly | Pro | Arg | Cys | Ala | Cys | Pro | Pro | Gly | Leu | Ser | Gly | Pro |
| 1310 | | | | | 1315 | | | | | 1320 | |
| Ser | Cys | Arg | Val | Ser | Arg | Ala | Ser | Pro | Ser | Gly | Ala | Thr | Asn | Ala |
| 1325 | | | | | 1330 | | | | | 1335 | |
| Ser | Cys | Ala | Ser | Ala | Pro | Cys | Leu | His | Gly | Gly | Ser | Cys | Leu | Pro |
| 1340 | | | | | 1345 | | | | | 1350 | |
| Val | Gln | Ser | Val | Pro | Phe | Phe | Arg | Cys | Val | Cys | Ala | Pro | Gly | Trp |
| 1355 | | | | | 1360 | | | | | 1365 | |
| Gly | Gly | Pro | Arg | Cys | Glu | Thr | Pro | Ser | Ala | Ala | Pro | Glu | Val | Pro |
| 1370 | | | | | 1375 | | | | | 1380 | |
| Glu | Glu | Pro | Arg | Cys | Pro | Arg | Ala | Ala | Cys | Gln | Ala | Lys | Arg | Gly |
| 1385 | | | | | 1390 | | | | | 1395 | |
| Asp | Gln | Asn | Cys | Asp | Arg | Glu | Cys | Asn | Thr | Pro | Gly | Cys | Gly | Trp |
| 1400 | | | | | 1405 | | | | | 1410 | |
| Asp | Gly | Gly | Asp | Cys | Ser | Leu | Asn | Val | Asp | Asp | Pro | Trp | Arg | Gln |
| 1415 | | | | | 1420 | | | | | 1425 | |
| Cys | Glu | Ala | Leu | Gln | Cys | Trp | Arg | Leu | Phe | Asn | Asn | Ser | Arg | Cys |
| 1430 | | | | | 1435 | | | | | 1440 | |
| Asp | Pro | Ala | Cys | Ser | Ser | Pro | Ala | Cys | Leu | Tyr | Asp | Asn | Phe | Asp |
| 1445 | | | | | 1450 | | | | | 1455 | |
| Cys | Tyr | Ser | Gly | Gly | Arg | Asp | Arg | Thr | Cys | Asn | Pro | Val | Tyr | Glu |
| 1460 | | | | | 1465 | | | | | 1470 | |
| Lys | Tyr | Cys | Ala | Asp | His | Phe | Ala | Asp | Gly | Arg | Cys | Asp | Gln | Gly |
| 1475 | | | | | 1480 | | | | | 1485 | |
| Cys | Asn | Thr | Glu | Glu | Cys | Gly | Trp | Asp | Gly | Leu | Asp | Cys | Ala | Ser |
| 1490 | | | | | 1495 | | | | | 1500 | |
| Glu | Val | Pro | Ala | Leu | Leu | Ala | Arg | Gly | Val | Leu | Val | Leu | Thr | Val |
| 1505 | | | | | 1510 | | | | | 1515 | |
| Leu | Leu | Pro | Pro | Glu | Glu | Leu | Leu | Arg | Ser | Ser | Ala | Asp | Phe | Leu |
| 1520 | | | | | 1525 | | | | | 1530 | |
| Gln | Arg | Leu | Ser | Ala | Ile | Leu | Arg | Thr | Ser | Leu | Arg | Phe | Arg | Leu |

-continued

```
            1535                1540                1545

Asp Ala Arg Gly Gln Ala Met Val Phe Pro Tyr His Arg Pro Ser
            1550                1555                1560

Pro Gly Ser Glu Ser Arg Val Arg Arg Glu Leu Gly Pro Glu Val
            1565                1570                1575

Ile Gly Ser Val Val Met Leu Glu Ile Asp Asn Arg Leu Cys Leu
            1580                1585                1590

Gln Ser Ala Glu Asn Asp His Cys Phe Pro Asp Ala Gln Ser Ala
            1595                1600                1605

Ala Asp Tyr Leu Gly Ala Leu Ser Ala Val Glu Arg Leu Asp Phe
            1610                1615                1620

Pro Tyr Pro Leu Arg Asp Val Arg Gly Glu Pro Leu Glu Ala Pro
            1625                1630                1635

Glu Gln Ser Val Pro Leu Leu Pro Leu Leu Val Ala Gly Ala Val
            1640                1645                1650

Phe Leu Leu Ile Ile Phe Ile Leu Gly Val Met Val Ala Arg Arg
            1655                1660                1665

Lys Arg Glu His Ser Thr Leu Trp Phe Pro Glu Gly Phe Ala Leu
            1670                1675                1680

His Lys Asp Ile Ala Ala Gly His Lys Gly Arg Arg Glu Pro Val
            1685                1690                1695

Gly Gln Asp Ala Leu Gly Met Lys Asn Met Ala Lys Gly Glu Ser
            1700                1705                1710

Leu Met Gly Glu Val Val Thr Asp Leu Asn Asp Ser Glu Cys Pro
            1715                1720                1725

Glu Ala Lys Arg Leu Lys Val Glu Glu Pro Gly Met Gly Ala Glu
            1730                1735                1740

Glu Pro Glu Asp Cys Arg Gln Trp Thr Gln His His Leu Val Ala
            1745                1750                1755

Ala Asp Ile Arg Val Ala Pro Ala Thr Ala Leu Thr Pro Pro Gln
            1760                1765                1770

Gly Asp Ala Asp Ala Asp Gly Val Asp Val Asn Val Arg Gly Pro
            1775                1780                1785

Asp Gly Phe Thr Pro Leu Met Leu Ala Ser Phe Cys Gly Gly Ala
            1790                1795                1800

Leu Glu Pro Met Pro Ala Glu Glu Asp Glu Ala Asp Asp Thr Ser
            1805                1810                1815

Ala Ser Ile Ile Ser Asp Leu Ile Cys Gln Gly Ala Gln Leu Gly
            1820                1825                1830

Ala Arg Thr Asp Arg Thr Gly Glu Thr Ala Leu His Leu Ala Ala
            1835                1840                1845

Arg Tyr Ala Arg Ala Asp Ala Ala Lys Arg Leu Leu Asp Ala Gly
            1850                1855                1860

Ala Asp Thr Asn Ala Gln Asp His Ser Gly Arg Thr Pro Leu His
            1865                1870                1875

Thr Ala Val Thr Ala Asp Ala Gln Gly Val Phe Gln Ile Leu Ile
            1880                1885                1890

Arg Asn Arg Ser Thr Asp Leu Asp Ala Arg Met Ala Asp Gly Ser
            1895                1900                1905

Thr Ala Leu Ile Leu Ala Ala Arg Leu Ala Val Glu Gly Met Val
            1910                1915                1920

Glu Glu Leu Ile Ala Ser His Ala Asp Val Asn Ala Val Asp Glu
            1925                1930                1935
```

-continued

```
Leu Gly Lys Ser Ala Leu His Trp Ala Ala Val Asn Asn Val
    1940            1945               1950

Glu Ala Thr Leu Ala Leu Leu Lys Asn Gly Ala Asn Lys Asp Met
    1955            1960               1965

Gln Asp Ser Lys Glu Glu Thr Pro Leu Phe Leu Ala Ala Arg Glu
    1970            1975               1980

Gly Ser Tyr Glu Ala Ala Lys Leu Leu Leu Asp His Leu Ala Asn
    1985            1990               1995

Arg Glu Ile Thr Asp His Leu Asp Arg Leu Pro Arg Asp Val Ala
    2000            2005               2010

Gln Glu Arg Leu His Gln Asp Ile Val Arg Leu Leu Asp Gln Pro
    2015            2020               2025

Ser Gly Pro Arg Ser Pro Ser Gly Pro His Gly Leu Gly Pro Leu
    2030            2035               2040

Leu Cys Pro Pro Gly Ala Phe Leu Pro Gly Leu Lys Ala Val Gln
    2045            2050               2055

Ser Gly Thr Lys Lys Ser Arg Arg Pro Pro Gly Lys Thr Gly Leu
    2060            2065               2070

Gly Pro Gln Gly Thr Arg Gly Arg Gly Lys Lys Leu Thr Leu Ala
    2075            2080               2085

Cys Pro Gly Pro Leu Ala Asp Ser Ser Val Thr Leu Ser Pro Val
    2090            2095               2100

Asp Ser Leu Asp Ser Pro Arg Pro Phe Ser Gly Pro Pro Ala Ser
    2105            2110               2115

Pro Gly Gly Phe Pro Leu Glu Gly Pro Tyr Ala Thr Thr Ala Thr
    2120            2125               2130

Ala Val Ser Leu Ala Gln Leu Gly Ala Ser Arg Ala Gly Pro Leu
    2135            2140               2145

Gly Arg Gln Pro Pro Gly Gly Cys Val Leu Ser Phe Gly Leu Leu
    2150            2155               2160

Asn Pro Val Ala Val Pro Leu Asp Trp Ala Arg Leu Pro Pro Pro
    2165            2170               2175

Ala Pro Pro Gly Pro Ser Phe Leu Leu Pro Leu Ala Pro Gly Pro
    2180            2185               2190

Gln Leu Leu Asn Pro Gly Ala Pro Val Ser Pro Gln Glu Arg Pro
    2195            2200               2205

Pro Pro Tyr Leu Ala Ala Pro Gly His Gly Glu Glu Tyr Pro Ala
    2210            2215               2220

Ala Gly Thr Arg Ser Ser Pro Thr Lys Ala Arg Phe Leu Arg Val
    2225            2230               2235

Pro Ser Glu His Pro Tyr Leu Thr Pro Ser Pro Glu Ser Pro Glu
    2240            2245               2250

His Trp Ala Ser Pro Ser Pro Pro Ser Leu Ser Asp Trp Ser Asp
    2255            2260               2265

Ser Thr Pro Ser Pro Ala Thr Ala Thr Asn Ala Thr Ala Ser Gly
    2270            2275               2280

Ala Leu Pro Ala Gln Pro His Pro Ile Ser Val Pro Ser Leu Pro
    2285            2290               2295

Gln Ser Gln Thr Gln Leu Gly Pro Gln Pro Glu Val Thr Pro Lys
    2300            2305               2310

Arg Gln Val Met Ala
    2315
```

<210> SEQ ID NO 14
<211> LENGTH: 2471
<212> TYPE: PRT
<213> ORGANISM: Rattus norvegicus

<400> SEQUENCE: 14

```
Met Pro Ala Leu Arg Pro Ala Leu Arg Ala Leu Leu Trp Leu Trp
1               5                   10                  15

Leu Cys Gly Ala Gly Pro Ala His Ala Leu Gln Cys Arg Gly Gly Gln
            20                  25                  30

Glu Pro Cys Val Asn Glu Gly Thr Cys Val Thr Tyr His Asn Gly Thr
            35                  40                  45

Gly Tyr Cys Arg Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Thr Gln Ala Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Trp Asp Thr
        115                 120                 125

Tyr Glu Cys Thr Cys Gln Val Gly Phe Thr Gly Lys Gln Cys Gln Trp
        130                 135                 140

Thr Asp Val Cys Leu Ser His Pro Cys Glu Asn Gly Ser Thr Cys Ser
145                 150                 155                 160

Ser Val Ala Asn Gln Phe Ser Cys Arg Cys Pro Ala Gly Ile Thr Gly
                165                 170                 175

Gln Lys Cys Asp Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205

Cys Pro Gln Arg Phe Thr Gly Gln His Cys Asp Ser Pro Tyr Val Pro
        210                 215                 220

Cys Ala Pro Ser Pro Cys Val Asn Gly Gly Thr Cys Arg Gln Thr Gly
225                 230                 235                 240

Asp Phe Thr Ser Glu Cys His Cys Leu Pro Gly Phe Glu Gly Ser Asn
                245                 250                 255

Cys Glu Arg Asn Ile Asp Asp Cys Pro Asn His Lys Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
        290                 295                 300

Gln Pro Asn Ala Cys Gln Asn Gly Gly Thr Cys Thr Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Leu Cys Pro Glu Gly Lys
        355                 360                 365

Ala Gly Leu Leu Cys His Leu Asp Asp Ala Cys Ile Ser Asn Pro Cys
        370                 375                 380
```

```
His Lys Gly Ala Leu Cys Asp Thr Asn Pro Leu Asn Gly Gln Tyr Ile
385                 390                 395                 400

Cys Thr Cys Pro Gln Ala Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Val Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Thr Leu Cys Asp Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Leu
625                 630                 635                 640

Asn Cys Glu Ile Asn Phe Asp Asp Cys Ala Ser Asn Pro Cys Leu His
                645                 650                 655

Gly Ala Cys Val Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Asp Ala Thr Cys Ile Asn Asp Val Asn Gly Phe
    690                 695                 700

Arg Cys Met Cys Pro Glu Gly Pro His His Pro Ser Cys Tyr Ser Gln
705                 710                 715                 720

Val Asn Glu Cys Leu Ser Ser Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asn Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800
```

```
Ser Asn Pro Cys Leu Asn Gln Gly Thr Cys Leu Asp Asp Val Ser Gly
                805                 810                 815

Tyr Thr Cys His Cys Met Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ala Pro Asn Phe Glu Ser Phe Thr Cys Leu Cys Ala Pro Gly
    850                 855                 860

Trp Gln Gly Gln Arg Cys Thr Val Asp Val Asp Glu Cys Val Ser Lys
865                 870                 875                 880

Pro Cys Met Asn Asn Gly Ile Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asn Asp Cys Leu Ala Asn Pro Cys Gln Asn Gly Gly Ser Cys Val Asp
            915                 920                 925

Lys Val Asn Thr Phe Ser Cys Leu Cys Leu Pro Gly Phe Val Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Thr Cys Pro
                965                 970                 975

Ala Gly Phe His Gly Val His Cys Glu Asn Asn Ile Asp Glu Cys Thr
            980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Pro Phe Cys Leu
    1010                1015                1020

His Asp Ile Asn Glu Cys Ser Ser Asn Pro Cys Leu Asn Ser Gly
    1025                1030                1035

Thr Cys Val Asp Gly Leu Gly Thr Tyr Arg Cys Thr Cys Pro Leu
    1040                1045                1050

Gly Tyr Thr Gly Lys Asn Cys Gln Thr Leu Val Asn Leu Cys Ser
    1055                1060                1065

Pro Ser Pro Cys Lys Asn Lys Gly Thr Cys Ala Gln Glu Lys Ala
    1070                1075                1080

Arg Pro Arg Cys Leu Cys Pro Pro Gly Trp Asp Gly Ala Tyr Cys
    1085                1090                1095

Asp Val Leu Asn Val Ser Cys Lys Ala Ala Ala Leu Gln Lys Gly
    1100                1105                1110

Val Pro Val Glu His Leu Cys Gln His Ser Gly Ile Cys Ile Asn
    1115                1120                1125

Ala Gly Asn Thr His His Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
```

-continued

```
            1205                1210                1215
Gly Leu Leu Cys Glu Glu Asn Ile Asp Asp Cys Ala Gly Ala Pro
            1220                1225                1230
His Cys Leu Asn Gly Gly Gln Cys Val Asp Arg Ile Gly Gly Tyr
            1235                1240                1245
Ser Cys Arg Cys Leu Pro Gly Phe Ala Gly Glu Arg Cys Glu Gly
            1250                1255                1260
Asp Ile Asn Glu Cys Leu Ser Asn Pro Cys Ser Ser Glu Gly Ser
            1265                1270                1275
Leu Asp Cys Ile Gln Leu Lys Asn Asn Tyr Gln Cys Val Cys Arg
            1280                1285                1290
Ser Ala Phe Thr Gly Arg His Cys Glu Thr Phe Leu Asp Val Cys
            1295                1300                1305
Pro Gln Lys Pro Cys Leu Asn Gly Gly Thr Cys Ala Val Ala Ser
            1310                1315                1320
Asn Val Pro Asp Gly Phe Ile Cys Arg Cys Pro Pro Gly Phe Ser
            1325                1330                1335
Gly Ala Arg Cys Gln Ser Ser Cys Gly Gln Val Lys Cys Arg Arg
            1340                1345                1350
Gly Glu Gln Cys Val His Thr Ala Ser Gly Pro His Cys Phe Cys
            1355                1360                1365
Pro Asn His Lys Asp Cys Glu Ser Gly Cys Ala Ser Asn Pro Cys
            1370                1375                1380
Gln His Gly Gly Thr Cys Tyr Pro Gln Arg Gln Pro Pro Tyr Tyr
            1385                1390                1395
Ser Cys Arg Cys Ser Pro Pro Phe Trp Gly Ser His Cys Glu Ser
            1400                1405                1410
Tyr Thr Ala Pro Thr Ser Thr Pro Pro Ala Thr Cys Leu Ser Gln
            1415                1420                1425
Tyr Cys Ala Asp Lys Ala Arg Asp Gly Ile Cys Asp Glu Ala Cys
            1430                1435                1440
Asn Ser His Ala Cys Gln Trp Asp Gly Gly Asp Cys Ser Leu Thr
            1445                1450                1455
Met Glu Asp Pro Trp Ala Asn Cys Thr Ser Ser Leu Arg Cys Trp
            1460                1465                1470
Glu Tyr Ile Asn Asn Gln Cys Asp Glu Leu Cys Asn Thr Ala Glu
            1475                1480                1485
Cys Leu Phe Asp Asn Phe Glu Cys Gln Arg Asn Ser Lys Thr Cys
            1490                1495                1500
Lys Tyr Asp Lys Tyr Cys Ala Asp His Phe Lys Asp Asn His Cys
            1505                1510                1515
Asp Lys Gly Cys Asn Asn Glu Glu Cys Gly Trp Asp Gly Leu Asp
            1520                1525                1530
Cys Ala Ala Asp Gln Pro Glu Asn Leu Ala Glu Gly Ile Leu Val
            1535                1540                1545
Ile Val Val Leu Leu Pro Pro Glu Gln Leu Leu Gln Asp Ser Arg
            1550                1555                1560
Ser Phe Leu Arg Ala Leu Gly Thr Leu Leu His Thr Asn Leu Arg
            1565                1570                1575
Ile Lys Gln Asp Ser Gln Gly Ala Leu Met Val Tyr Pro Tyr Tyr
            1580                1585                1590
Gly Glu Lys Ser Ala Ala Met Lys Lys Gln Lys Val Ala Arg Arg
            1595                1600                1605
```

```
Ser Leu Pro Asp Glu Gln Glu  Gln Ile Ile Gly  Ser Lys Val
    1610             1615              1620

Phe Leu Glu Ile Asp Asn Arg  Gln Cys Val Gln Asp  Ser Asp Gln
    1625             1630              1635

Cys Phe Lys Asn Thr Asp Ala  Ala Ala Ala Leu Leu  Ala Ser His
    1640             1645              1650

Ala Ile Gln Gly Thr Leu Ser  Tyr Pro Leu Val Ser  Val Val Ser
    1655             1660              1665

Glu Ser Glu Asp Pro Arg Asn  Thr Pro Leu Leu Tyr  Leu Leu Ala
    1670             1675              1680

Val Ala Val Val Ile Ile Leu  Phe Leu Ile Leu Leu  Gly Val Ile
    1685             1690              1695

Met Ala Lys Arg Lys Arg Lys  His Gly Phe Leu Trp  Leu Pro Glu
    1700             1705              1710

Gly Phe Thr Leu Arg Arg Asp  Ser Ser Asn His Lys  Arg Arg Glu
    1715             1720              1725

Pro Val Gly Gln Asp Ala Val  Gly Leu Lys Asn Leu  Ser Val Gln
    1730             1735              1740

Val Ser Glu Ala Asn Leu Ile  Gly Ser Thr Thr Ser  Glu His Trp
    1745             1750              1755

Gly Asp Asp Glu Gly Pro Gln  Pro Lys Lys Ala Lys  Ala Glu Asp
    1760             1765              1770

Asp Glu Ala Leu Leu Ser Glu  Asp Asp Pro Val Asp  Arg Arg Pro
    1775             1780              1785

Trp Thr Gln Gln His Leu Glu  Ala Ala Asp Ile Arg  Arg Thr Pro
    1790             1795              1800

Ser Leu Ala Leu Thr Pro Pro  Gln Ala Glu Gln Glu  Val Asp Val
    1805             1810              1815

Leu Asp Val Asn Val Arg Gly  Pro Asp Gly Cys Thr  Pro Leu Met
    1820             1825              1830

Leu Ala Ser Leu Arg Gly Gly  Ser Ser Asp Leu Ser  Asp Glu Asp
    1835             1840              1845

Glu Asp Ala Glu Asp Ser Ser  Ala Asn Ile Ile Thr  Asp Leu Val
    1850             1855              1860

Tyr Gln Gly Ala Ser Leu Gln  Ala Gln Thr Asp Arg  Thr Gly Glu
    1865             1870              1875

Met Ala Leu His Leu Ala Ala  Arg Tyr Ser Arg Ala  Asp Ala Ala
    1880             1885              1890

Lys Arg Leu Leu Asp Ala Gly  Ala Asp Ala Asn Ala  Gln Asp Asn
    1895             1900              1905

Met Gly Arg Cys Pro Leu His  Ala Ala Val Ala Ala  Asp Ala Gln
    1910             1915              1920

Gly Val Phe Gln Ile Leu Ile  Arg Asn Arg Val Thr  Asp Leu Asp
    1925             1930              1935

Ala Arg Met Asn Asp Gly Thr  Thr Pro Leu Ile Leu  Ala Ala Arg
    1940             1945              1950

Leu Ala Val Glu Gly Met Val  Ala Glu Leu Ile Asn  Cys Gln Ala
    1955             1960              1965

Asp Val Asn Ala Val Asp Asp  His Gly Lys Ser Ala  Leu His Trp
    1970             1975              1980

Ala Ala Ala Val Asn Asn Val  Glu Ala Thr Leu Leu  Leu Leu Lys
    1985             1990              1995
```

```
Asn Gly Ala Asn Arg Asp Met Gln Asp Asn Lys Glu Thr Pro
    2000                2005                2010

Leu Phe Leu Ala Ala Arg Glu Gly Ser Tyr Glu Ala Ala Lys Ile
    2015                2020                2025

Leu Leu Asp His Phe Ala Asn Arg Asp Ile Thr Asp His Met Asp
    2030                2035                2040

Arg Leu Pro Arg Asp Val Ala Arg Asp Arg Met His His Asp Ile
    2045                2050                2055

Val Arg Leu Leu Asp Glu Tyr Asn Val Thr Pro Ser Pro Pro Gly
    2060                2065                2070

Thr Val Leu Thr Ser Ala Leu Ser Pro Val Leu Cys Gly Pro Asn
    2075                2080                2085

Arg Ser Phe Leu Ser Leu Lys His Thr Pro Met Gly Lys Lys Ala
    2090                2095                2100

Arg Arg Pro Asn Thr Lys Ser Thr Met Pro Thr Ser Leu Pro Asn
    2105                2110                2115

Leu Ala Lys Glu Ala Lys Asp Val Lys Gly Ser Arg Arg Lys Lys
    2120                2125                2130

Cys Leu Asn Glu Lys Val Gln Leu Ser Glu Ser Ser Val Thr Leu
    2135                2140                2145

Ser Pro Val Asp Ser Leu Glu Ser Pro His Thr Tyr Val Ser Asp
    2150                2155                2160

Ala Thr Ser Ser Pro Met Ile Thr Ser Pro Gly Ile Leu Gln Ala
    2165                2170                2175

Ser Pro Thr Pro Leu Leu Ala Ala Ala Pro Ala Ala Pro Val His
    2180                2185                2190

Ala Gln His Ala Leu Ser Phe Ser Asn Leu His Glu Met Gln Pro
    2195                2200                2205

Leu Arg Pro Gly Ala Ser Thr Val Leu Pro Ser Val Ser Gln Leu
    2210                2215                2220

Leu Ser His His His Ile Val Pro Pro Gly Ser Gly Ser Ala Gly
    2225                2230                2235

Ser Leu Gly Arg Leu His Ser Val Pro Val Pro Ser Asp Trp Met
    2240                2245                2250

Asn Arg Val Glu Met Ser Glu Thr Gln Tyr Ser Glu Met Phe Gly
    2255                2260                2265

Met Val Leu Ala Pro Ala Glu Gly Thr His Pro Gly Met Ala Ala
    2270                2275                2280

Pro Gln Ser Arg Ala Pro Glu Gly Lys Pro Ile Pro Thr Gln Arg
    2285                2290                2295

Glu Pro Leu Pro Pro Ile Val Thr Phe Gln Leu Ile Pro Lys Gly
    2300                2305                2310

Ser Leu Ala Gln Ala Ala Gly Ala Pro Gln Thr Gln Ser Gly Cys
    2315                2320                2325

Pro Pro Ala Val Ala Gly Pro Leu Pro Ser Met Tyr Gln Ile Pro
    2330                2335                2340

Glu Met Ala Arg Leu Pro Ser Val Ala Phe Pro Thr Met Met
    2345                2350                2355

Pro Gln Gln Glu Gly Gln Val Ala Gln Thr Ile Val Pro Thr Tyr
    2360                2365                2370

His Pro Phe Pro Ala Ser Val Gly Lys Tyr Pro Thr Pro Pro Ser
    2375                2380                2385

Gln His Ser Tyr Ala Ser Ser Asn Ala Ala Glu Arg Thr Pro Asn
```

```
                2390                2395                2400
His Gly Gly His Leu Gln Gly Glu His Pro Tyr Leu Thr Pro Ser
        2405                2410                2415

Pro Glu Ser Pro Asp Gln Trp Ser Ser Ser Pro His Ser Ala
    2420                2425                2430

Ser Asp Trp Ser Asp Val Thr Thr Ser Pro Thr Pro Gly Gly Gly
    2435                2440                2445

Gly Gly Gly Gln Arg Gly Pro Gly Thr His Met Ser Glu Pro Pro
    2450                2455                2460

His Ser Asn Met Gln Val Tyr Ala
    2465                2470

<210> SEQ ID NO 15
<211> LENGTH: 2319
<212> TYPE: PRT
<213> ORGANISM: Rattus norvegicus

<400> SEQUENCE: 15

Met Gly Pro Gly Ala Arg Gly Arg Arg Arg Arg Leu Met Ala
1               5                   10                  15

Leu Pro Pro Pro Pro Pro Met Arg Ala Leu Pro Leu Leu Leu
            20                  25                  30

Leu Leu Ala Gly Leu Gly Ala Ala Pro Pro Cys Leu Asp Gly Ser
            35                  40                  45

Pro Cys Ala Asn Gly Gly Arg Cys Thr His Gln Gln Pro Ser Arg Glu
    50                  55                  60

Ala Ala Cys Leu Cys Leu Pro Gly Trp Val Gly Glu Arg Cys Gln Leu
65                  70                  75                  80

Glu Asp Pro Cys His Ser Gly Pro Cys Ala Gly Arg Gly Val Cys Gln
                85                  90                  95

Ser Ser Val Val Ala Gly Val Ala Arg Phe Ser Cys Arg Cys Leu Arg
                100                 105                 110

Gly Phe Arg Gly Pro Asp Cys Ser Leu Pro Asp Pro Cys Phe Ser Ser
            115                 120                 125

Pro Cys Ala His Gly Ala Pro Cys Ser Val Gly Ser Asp Gly Arg Tyr
    130                 135                 140

Ala Cys Ala Cys Pro Pro Gly Tyr Gln Gly Arg Asn Cys Arg Ser Asp
145                 150                 155                 160

Ile Asp Glu Cys Arg Ala Gly Ala Ser Cys Arg His Gly Gly Thr Cys
                165                 170                 175

Ile Asn Thr Pro Gly Ser Phe His Cys Leu Cys Pro Leu Gly Tyr Thr
            180                 185                 190

Gly Leu Leu Cys Glu Asn Pro Ile Val Pro Cys Ala Pro Ser Pro Cys
        195                 200                 205

Arg Asn Gly Gly Thr Cys Arg Gln Ser Ser Asp Val Thr Tyr Asp Cys
    210                 215                 220

Ala Cys Leu Pro Gly Phe Glu Gly Gln Asn Cys Glu Val Asn Val Asp
225                 230                 235                 240

Asp Cys Pro Gly His Arg Cys Leu Asn Gly Gly Thr Cys Val Asp Gly
                245                 250                 255

Val Asn Thr Tyr Asn Cys Gln Cys Pro Pro Glu Trp Thr Gly Gln Phe
            260                 265                 270

Cys Thr Glu Asp Val Asp Glu Cys Gln Leu Gln Pro Asn Ala Cys His
        275                 280                 285
```

-continued

```
Asn Gly Gly Thr Cys Phe Asn Leu Leu Gly Gly His Ser Cys Val Cys
    290                 295                 300
Val Asn Gly Trp Thr Gly Glu Ser Cys Ser Gln Asn Ile Asp Asp Cys
305                 310                 315                 320
Ala Thr Ala Val Cys Phe His Gly Ala Thr Cys His Asp Arg Val Ala
                325                 330                 335
Ser Phe Tyr Cys Ala Cys Pro Met Gly Lys Thr Gly Leu Leu Cys His
            340                 345                 350
Leu Asp Asp Ala Cys Val Ser Asn Pro Cys His Glu Asp Ala Ile Cys
        355                 360                 365
Asp Thr Asn Pro Val Ser Gly Arg Ala Ile Cys Thr Cys Pro Pro Gly
370                 375                 380
Phe Thr Gly Gly Ala Cys Asp Gln Asp Val Asp Glu Cys Ser Ile Gly
385                 390                 395                 400
Ala Asn Pro Cys Glu His Leu Gly Arg Cys Val Asn Thr Gln Gly Ser
                405                 410                 415
Phe Leu Cys Gln Cys Gly Arg Gly Tyr Thr Gly Pro Arg Cys Glu Thr
            420                 425                 430
Asp Val Asn Glu Cys Leu Ser Gly Pro Cys Arg Asn Gln Ala Thr Cys
        435                 440                 445
Leu Asp Arg Ile Gly Gln Phe Thr Cys Ile Cys Met Ala Gly Phe Thr
450                 455                 460
Gly Thr Phe Cys Glu Val Asp Ile Asp Glu Cys Gln Ser Ser Pro Cys
465                 470                 475                 480
Val Asn Gly Gly Val Cys Lys Asp Arg Val Asn Gly Phe Ser Cys Thr
                485                 490                 495
Cys Pro Ser Gly Phe Ser Gly Ser Thr Cys Gln Leu Asp Val Asp Glu
            500                 505                 510
Cys Ala Ser Thr Pro Cys Arg Asn Gly Ala Lys Cys Val Asp Gln Pro
        515                 520                 525
Asp Gly Tyr Glu Cys Arg Cys Ala Glu Gly Phe Glu Gly Thr Leu Cys
530                 535                 540
Glu Arg Asn Val Asp Asp Cys Ser Pro Asp Pro Cys His His Gly Arg
545                 550                 555                 560
Cys Val Asp Gly Ile Ala Ser Phe Ser Cys Ala Cys Ala Pro Gly Tyr
                565                 570                 575
Thr Gly Ile Arg Cys Glu Ser Gln Val Asp Glu Cys Arg Ser Gln Pro
            580                 585                 590
Cys Arg Tyr Gly Gly Lys Cys Leu Asp Leu Val Asp Lys Tyr Leu Cys
        595                 600                 605
Arg Cys Pro Pro Gly Thr Thr Gly Val Asn Cys Glu Val Asn Ile Asp
610                 615                 620
Asp Cys Ala Ser Asn Pro Cys Thr Phe Gly Val Cys Arg Asp Gly Ile
625                 630                 635                 640
Asn Arg Tyr Asp Cys Val Cys Gln Pro Gly Phe Thr Gly Pro Leu Cys
                645                 650                 655
Asn Val Glu Ile Asn Glu Cys Ala Ser Ser Pro Cys Gly Glu Gly Gly
            660                 665                 670
Ser Cys Val Asp Gly Glu Asn Gly Phe His Cys Leu Cys Pro Pro Gly
        675                 680                 685
Ser Leu Pro Pro Leu Cys Leu Pro Ala Asn His Pro Cys Ala His Lys
690                 695                 700
Pro Cys Ser His Gly Val Cys His Asp Ala Pro Gly Gly Phe Gln Cys
```

```
            705                 710                 715                 720
Val Cys Asp Pro Gly Trp Ser Gly Pro Arg Cys Ser Gln Ser Leu Ala
                725                 730                 735

Pro Asp Ala Cys Glu Ser Gln Pro Cys Gln Ala Gly Gly Thr Cys Thr
                740                 745                 750

Ser Asp Gly Ile Gly Phe His Cys Thr Cys Ala Pro Gly Phe Gln Gly
                755                 760                 765

His Gln Cys Glu Val Leu Ser Pro Cys Thr Pro Ser Leu Cys Glu His
        770                 775                 780

Gly Gly His Cys Glu Ser Asp Pro Asp Gln Leu Thr Val Cys Ser Cys
785                 790                 795                 800

Pro Pro Gly Trp Gln Gly Pro Arg Cys Gln Gln Asp Val Asp Glu Cys
                805                 810                 815

Ala Gly Ala Ser Pro Cys Gly Pro His Gly Thr Cys Thr Asn Leu Pro
                820                 825                 830

Gly Ser Phe Arg Cys Ile Cys His Gly Gly Tyr Thr Gly Pro Phe Cys
                835                 840                 845

Asp Gln Asp Ile Asp Asp Cys Asp Pro Asn Pro Cys Leu Asn Gly Gly
        850                 855                 860

Ser Cys Gln Asp Gly Val Gly Ser Phe Ser Cys Ser Cys Leu Ser Gly
865                 870                 875                 880

Phe Ala Gly Pro Arg Cys Ala Arg Asp Val Asp Glu Cys Leu Ser Ser
                885                 890                 895

Pro Cys Gly Pro Gly Thr Cys Thr Asp His Val Ala Ser Phe Thr Cys
                900                 905                 910

Thr Cys Pro Pro Gly Tyr Gly Gly Phe His Cys Glu Thr Asp Leu Leu
                915                 920                 925

Asp Cys Ser Pro Ser Ser Cys Phe Asn Gly Gly Thr Cys Val Asp Gly
        930                 935                 940

Val Asn Ser Phe Ser Cys Leu Cys Arg Pro Gly Tyr Thr Gly Thr His
945                 950                 955                 960

Cys Gln Tyr Lys Val Asp Pro Cys Phe Ser Arg Pro Cys Leu His Gly
                965                 970                 975

Gly Ile Cys Asn Pro Thr His Ser Gly Phe Glu Cys Thr Cys Arg Glu
                980                 985                 990

Gly Phe Thr Gly Asn Gln Cys Gln Asn Pro Val Asp Trp Cys Ser Gln
                995                 1000                1005

Ala Pro Cys Gln Asn Gly Gly Arg Cys Val Gln Thr Gly Ala Tyr
        1010                1015                1020

Cys Ile Cys Pro Pro Glu Trp Ser Gly Pro Leu Cys Asp Ile Pro
        1025                1030                1035

Ser Leu Pro Cys Thr Glu Ala Ala Ala His Met Gly Val Arg Leu
        1040                1045                1050

Glu Gln Leu Cys Gln Ala Gly Gly Gln Cys Ile Asp Lys Asp His
        1055                1060                1065

Ser His Tyr Cys Val Cys Pro Glu Gly Arg Met Gly Ser His Cys
        1070                1075                1080

Glu Gln Glu Val Asp Pro Cys Thr Ala Gln Pro Cys Gln His Gly
        1085                1090                1095

Gly Thr Cys Arg Gly Tyr Met Gly Gly Tyr Val Cys Glu Cys Pro
        1100                1105                1110

Thr Gly Tyr Ser Gly Asp Ser Cys Glu Asp Asp Val Asp Glu Cys
        1115                1120                1125
```

```
Ala Ser Gln Pro Cys Gln Asn Gly Gly Ser Cys Ile Asp Leu Val
1130             1135              1140

Ala His Tyr Leu Cys Ser Cys Pro Pro Gly Thr Leu Gly Val Leu
1145             1150              1155

Cys Glu Ile Asn Glu Asp Asp Cys Gly Pro Gly Pro Ser Leu Asp
1160             1165              1170

Ser Gly Leu Arg Cys Leu His Asn Gly Thr Cys Val Asp Leu Val
1175             1180              1185

Gly Gly Phe Arg Cys Asn Cys Pro Pro Gly Tyr Thr Gly Leu His
1190             1195              1200

Cys Glu Ala Asp Ile Asn Glu Cys Arg Pro Gly Thr Cys His Ala
1205             1210              1215

Ala His Thr Arg Asp Cys Leu Gln Asp Pro Gly Gly His Phe Arg
1220             1225              1230

Cys Ile Cys Leu Pro Gly Phe Thr Gly Pro Arg Cys Gln Thr Ala
1235             1240              1245

Leu Phe Pro Cys Glu Ser Gln Pro Cys Gln His Gly Gly Gln Cys
1250             1255              1260

Arg Pro Ser Leu Gly Arg Gly Gly Leu Thr Phe Thr Cys His
1265             1270              1275

Cys Val Gln Pro Phe Trp Gly Leu Arg Cys Glu Arg Val Ala Arg
1280             1285              1290

Ser Cys Arg Glu Leu Gln Cys Pro Val Gly Ile Pro Cys Gln Gln
1295             1300              1305

Thr Ala Arg Gly Pro Arg Cys Ala Cys Pro Pro Gly Leu Ser Gly
1310             1315              1320

Pro Ser Cys Arg Val Ser Arg Ala Ser Pro Ser Gly Ala Thr Asn
1325             1330              1335

Thr Ser Cys Ala Ala Thr Pro Cys Leu His Gly Gly Ser Cys Leu
1340             1345              1350

Pro Val Gln Ser Val Pro Phe Phe Arg Cys Val Cys Ala Pro Gly
1355             1360              1365

Trp Gly Gly Pro Arg Cys Glu Thr Pro Ser Ala Ala Pro Glu Val
1370             1375              1380

Pro Glu Glu Pro Arg Cys Pro Arg Ala Ala Cys Gln Ala Lys Arg
1385             1390              1395

Gly Asp Gln Asn Cys Asp Arg Glu Cys Asn Ser Pro Gly Cys Gly
1400             1405              1410

Trp Asp Gly Gly Asp Cys Ser Leu Asn Val Asp Asp Pro Trp Arg
1415             1420              1425

Gln Cys Glu Ala Leu Gln Cys Trp Arg Leu Phe Asn Asn Ser Arg
1430             1435              1440

Cys Asp Pro Ala Cys Ser Ser Pro Ala Cys Leu Tyr Asp Asn Phe
1445             1450              1455

Asp Cys Tyr Ser Gly Gly Arg Asp Arg Thr Cys Asn Pro Val Tyr
1460             1465              1470

Lys Lys Tyr Cys Ala Asp His Phe Ala Asp Gly Arg Cys Asp Gln
1475             1480              1485

Gly Cys Asn Thr Glu Glu Cys Gly Trp Asp Gly Leu Asp Cys Ala
1490             1495              1500

Ser Glu Val Pro Ala Leu Leu Ala Arg Gly Val Leu Val Leu Thr
1505             1510              1515
```

```
Val Leu Leu Pro Pro Glu Glu Leu Leu Arg Ser Ser Ala Asp Phe
1520                1525                1530

Leu Gln Arg Leu Ser Ala Ile Leu Arg Thr Ser Leu Arg Phe Arg
1535                1540                1545

Leu Asp Ala Arg Gly Gln Ala Met Val Phe Pro Tyr His Arg Pro
1550                1555                1560

Ser Pro Gly Ser Glu Ser Arg Val Arg Arg Glu Leu Gly Pro Glu
1565                1570                1575

Val Ile Gly Ser Val Val Met Leu Glu Ile Asp Asn Arg Leu Cys
1580                1585                1590

Leu Lys Ser Ala Glu Asn Asp His Cys Phe Pro Asp Ala Gln Ser
1595                1600                1605

Ala Ala Asp Tyr Leu Gly Ala Leu Ser Ala Val Glu Arg Leu Asp
1610                1615                1620

Phe Pro Tyr Pro Leu Arg Asp Val Arg Gly Glu Pro Leu Glu Pro
1625                1630                1635

Pro Glu Gln Ser Val Pro Leu Leu Pro Leu Leu Val Ala Gly Ala
1640                1645                1650

Val Phe Leu Leu Val Ile Phe Val Leu Gly Val Met Val Ala Arg
1655                1660                1665

Arg Lys Arg Glu His Ser Thr Leu Trp Phe Pro Glu Gly Phe Ala
1670                1675                1680

Leu His Lys Asp Ile Ala Ala Gly His Lys Gly Arg Arg Glu Pro
1685                1690                1695

Val Gly Gln Asp Ala Leu Gly Met Lys Asn Met Thr Lys Gly Glu
1700                1705                1710

Ser Leu Met Gly Glu Val Ala Thr Asp Trp Asn Asp Ser Glu Cys
1715                1720                1725

Pro Glu Ala Lys Arg Leu Lys Val Glu Glu Pro Gly Met Gly Ala
1730                1735                1740

Glu Glu Pro Val Asp Cys Arg Gln Trp Thr Gln His His Leu Val
1745                1750                1755

Ala Ala Asp Ile Arg Val Ala Pro Ala Met Ala Leu Thr Pro Pro
1760                1765                1770

Gln Gly Asp Ala Asp Ala Asp Gly Met Asp Val Asn Val Arg Gly
1775                1780                1785

Pro Asp Gly Phe Thr Pro Leu Met Leu Ala Ser Phe Cys Gly Gly
1790                1795                1800

Ala Leu Glu Pro Met Pro Ala Glu Glu Asp Glu Ala Asp Asp Thr
1805                1810                1815

Ser Ala Ser Ile Ile Ser Asp Leu Ile Cys Gln Gly Ala Gln Leu
1820                1825                1830

Gly Ala Arg Thr Asp Arg Thr Gly Glu Thr Ala Leu His Leu Ala
1835                1840                1845

Ala Arg Tyr Ala Arg Ala Asp Ala Ala Lys Arg Leu Leu Asp Ala
1850                1855                1860

Gly Ala Asp Thr Asn Ala Gln Asp His Ser Gly Arg Thr Pro Leu
1865                1870                1875

His Thr Ala Val Thr Ala Asp Ala Gln Gly Val Phe Gln Ile Leu
1880                1885                1890

Ile Arg Asn Arg Ser Thr Asp Leu Asp Ala Arg Met Ala Asp Gly
1895                1900                1905

Ser Thr Ala Leu Ile Leu Ala Ala Arg Leu Ala Val Glu Gly Met
```

|     |     |     |     |     |     |     |     |     |     |     |     |
| --- | --- | --- | --- | --- | --- | --- | --- | --- | --- | --- | --- |
|     | 1910 |     |     |     | 1915 |     |     |     | 1920 |     |     |
| Val | Glu | Glu | Leu | Ile | Ala | Ser | His | Ala | Asp | Val | Asn | Ala | Val | Asp |
|     | 1925 |     |     |     | 1930 |     |     |     | 1935 |     |     |
| Glu | Leu | Gly | Lys | Ser | Ala | Leu | His | Trp | Ala | Ala | Ala | Val | Asn | Asn |
|     | 1940 |     |     |     | 1945 |     |     |     | 1950 |     |     |
| Val | Glu | Ala | Thr | Leu | Ala | Leu | Leu | Lys | Asn | Gly | Ala | Asn | Lys | Asp |
|     | 1955 |     |     |     | 1960 |     |     |     | 1965 |     |     |
| Met | Gln | Asp | Ser | Lys | Glu | Glu | Thr | Pro | Leu | Phe | Leu | Ala | Ala | Arg |
|     | 1970 |     |     |     | 1975 |     |     |     | 1980 |     |     |
| Glu | Gly | Ser | Tyr | Glu | Ala | Ala | Lys | Leu | Leu | Leu | Asp | His | Phe | Ala |
|     | 1985 |     |     |     | 1990 |     |     |     | 1995 |     |     |
| Asn | Arg | Glu | Ile | Thr | Asp | His | Leu | Asp | Arg | Leu | Pro | Arg | Asp | Val |
|     | 2000 |     |     |     | 2005 |     |     |     | 2010 |     |     |
| Ala | Gln | Glu | Arg | Leu | His | Gln | Asp | Ile | Val | Arg | Leu | Leu | Asp | Gln |
|     | 2015 |     |     |     | 2020 |     |     |     | 2025 |     |     |
| Pro | Ser | Gly | Pro | Arg | Ser | Pro | Ser | Gly | Pro | His | Gly | Leu | Gly | Pro |
|     | 2030 |     |     |     | 2035 |     |     |     | 2040 |     |     |
| Leu | Leu | Cys | Pro | Pro | Gly | Ala | Phe | Leu | Pro | Gly | Leu | Lys | Ala | Val |
|     | 2045 |     |     |     | 2050 |     |     |     | 2055 |     |     |
| Gln | Ser | Gly | Thr | Lys | Lys | Ser | Arg | Arg | Pro | Pro | Gly | Lys | Thr | Gly |
|     | 2060 |     |     |     | 2065 |     |     |     | 2070 |     |     |
| Leu | Gly | Pro | Gln | Gly | Thr | Arg | Gly | Arg | Gly | Lys | Lys | Leu | Thr | Leu |
|     | 2075 |     |     |     | 2080 |     |     |     | 2085 |     |     |
| Ala | Cys | Pro | Gly | Pro | Leu | Ala | Asp | Ser | Ser | Val | Thr | Leu | Ser | Pro |
|     | 2090 |     |     |     | 2095 |     |     |     | 2100 |     |     |
| Val | Asp | Ser | Leu | Asp | Ser | Pro | Arg | Pro | Phe | Gly | Gly | Pro | Pro | Ala |
|     | 2105 |     |     |     | 2110 |     |     |     | 2115 |     |     |
| Ser | Pro | Gly | Gly | Phe | Pro | Leu | Glu | Gly | Pro | Tyr | Ala | Thr | Thr | Ala |
|     | 2120 |     |     |     | 2125 |     |     |     | 2130 |     |     |
| Thr | Thr | Val | Ser | Leu | Ala | Gln | Leu | Gly | Ala | Ser | Arg | Ala | Gly | Pro |
|     | 2135 |     |     |     | 2140 |     |     |     | 2145 |     |     |
| Leu | Gly | Arg | Gln | Pro | Pro | Gly | Gly | Cys | Val | Leu | Ser | Leu | Gly | Leu |
|     | 2150 |     |     |     | 2155 |     |     |     | 2160 |     |     |
| Leu | Asn | Pro | Val | Ala | Val | Pro | Leu | Asp | Trp | Ala | Arg | Leu | Pro | Pro |
|     | 2165 |     |     |     | 2170 |     |     |     | 2175 |     |     |
| Pro | Ala | Pro | Pro | Gly | Pro | Ser | Phe | Leu | Leu | Pro | Leu | Ala | Pro | Gly |
|     | 2180 |     |     |     | 2185 |     |     |     | 2190 |     |     |
| Ser | Gln | Leu | Leu | Asn | Pro | Ala | Thr | Pro | Val | Ser | Pro | His | Glu | Arg |
|     | 2195 |     |     |     | 2200 |     |     |     | 2205 |     |     |
| Pro | Pro | Pro | Tyr | Leu | Ala | Ala | Pro | Gly | His | Gly | Glu | Glu | Tyr | Pro |
|     | 2210 |     |     |     | 2215 |     |     |     | 2220 |     |     |
| Ala | Ala | Gly | Thr | His | Ser | Ser | Pro | Thr | Lys | Ala | Arg | Phe | Leu | Arg |
|     | 2225 |     |     |     | 2230 |     |     |     | 2235 |     |     |
| Val | Pro | Ser | Glu | His | Pro | Tyr | Leu | Thr | Pro | Ser | Pro | Glu | Ser | Pro |
|     | 2240 |     |     |     | 2245 |     |     |     | 2250 |     |     |
| Glu | His | Trp | Ala | Ser | Pro | Ser | Pro | Pro | Ser | Leu | Ser | Asp | Trp | Ser |
|     | 2255 |     |     |     | 2260 |     |     |     | 2265 |     |     |
| Asp | Ser | Thr | Pro | Ser | Pro | Ala | Thr | Ala | Thr | Ser | Ala | Thr | Ala | Ala |
|     | 2270 |     |     |     | 2275 |     |     |     | 2280 |     |     |
| Gly | Ala | Leu | Pro | Ala | Gln | Pro | His | Pro | Ile | Ser | Val | Pro | Ser | Leu |
|     | 2285 |     |     |     | 2290 |     |     |     | 2295 |     |     |
| Pro | Gln | Ser | Gln | Thr | Gln | Leu | Gly | Pro | Gln | Pro | Glu | Val | Thr | Pro |
|     | 2300 |     |     |     | 2305 |     |     |     | 2310 |     |     |

Lys Arg Gln Val Met Ala
     2315

<210> SEQ ID NO 16
<211> LENGTH: 333
<212> TYPE: PRT
<213> ORGANISM: Artificial sequence
<220> FEATURE:
<223> OTHER INFORMATION: synthetic amino acid sequence

<400> SEQUENCE: 16

Ile Leu Asp Tyr Ser Phe Thr Gly Gly Ala Gly Arg Asp Ile Pro Pro
1               5                   10                  15

Pro Gln Ile Glu Glu Ala Cys Glu Leu Pro Glu Cys Gln Val Asp Ala
            20                  25                  30

Gly Asn Lys Val Cys Asn Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln
                85                  90                  95

Leu Thr Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
        115                 120                 125

Glu Trp Asp Gly Leu Asp Cys Ala Glu His Val Pro Glu Arg Leu Ala
    130                 135                 140

Ala Gly Thr Leu Val Leu Val Val Leu Pro Pro Asp Gln Leu Arg
145                 150                 155                 160

Asn Asn Ser Phe His Phe Leu Arg Glu Leu Ser His Val Leu His Thr
                165                 170                 175

Asn Val Val Phe Lys Arg Asp Ala Gln Gly Gln Gln Met Ile Phe Pro
            180                 185                 190

Tyr Tyr Gly His Glu Glu Glu Leu Arg Lys His Pro Ile Lys Arg Ser
        195                 200                 205

Thr Val Gly Trp Ala Thr Ser Ser Leu Leu Pro Gly Thr Ser Gly Gly
    210                 215                 220

Arg Gln Arg Arg Glu Leu Asp Pro Met Asp Ile Arg Gly Ser Ile Val
225                 230                 235                 240

Tyr Leu Glu Ile Asp Asn Arg Gln Cys Val Gln Ser Ser Ser Gln Cys
                245                 250                 255

Phe Gln Ser Ala Thr Asp Val Ala Ala Phe Leu Gly Ala Leu Ala Ser
            260                 265                 270

Leu Gly Ser Leu Asn Ile Pro Tyr Lys Ile Glu Ala Val Lys Ser Glu
        275                 280                 285

Pro Val Glu Pro Pro Leu Pro Ser Gln Leu His Leu Met Tyr Val Ala
    290                 295                 300

Ala Ala Ala Phe Val Leu Leu Phe Phe Val Gly Cys Gly Val Leu Leu
305                 310                 315                 320

Ser Arg Lys Arg Arg Arg Gln Leu Cys Ile Gln Lys Leu
                325                 330

<210> SEQ ID NO 17

<211> LENGTH: 370
<212> TYPE: PRT
<213> ORGANISM: Artificial sequence
<220> FEATURE:
<223> OTHER INFORMATION: synthetic amino acid sequence

<400> SEQUENCE: 17

```
Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His Ile Leu Asp Tyr Ser Phe Thr Gly Gly Ala Gly
        35                  40                  45

Arg Asp Ile Pro Pro Gln Ile Glu Glu Ala Cys Glu Leu Pro Glu
    50                  55                  60

Cys Gln Val Asp Ala Gly Asn Lys Val Cys Asn Leu Gln Cys Asn Asn
65                  70                  75                  80

His Ala Cys Gly Trp Asp Gly Asp Cys Ser Leu Asn Phe Asn Asp
                85                  90                  95

Pro Trp Lys Asn Cys Thr Gln Ser Leu Gln Cys Trp Lys Tyr Phe Ser
                100                 105                 110

Asp Gly His Cys Asp Ser Gln Cys Asn Ser Ala Gly Cys Leu Phe Asp
            115                 120                 125

Gly Phe Asp Cys Gln Leu Thr Glu Gly Gln Cys Asn Pro Leu Tyr Asp
130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Leu Val Val Leu Leu Pro
            180                 185                 190

Pro Asp Gln Leu Arg Asn Asn Ser Phe His Phe Leu Arg Glu Leu Ser
        195                 200                 205

His Val Leu His Thr Asn Val Val Phe Lys Arg Asp Ala Gln Gly Gln
    210                 215                 220

Gln Met Ile Phe Pro Tyr Tyr Gly His Glu Glu Leu Arg Lys His
225                 230                 235                 240

Pro Ile Lys Arg Ser Thr Val Gly Trp Ala Thr Ser Ser Leu Leu Pro
                245                 250                 255

Gly Thr Ser Gly Gly Arg Gln Arg Glu Leu Asp Pro Met Asp Ile
            260                 265                 270

Arg Gly Ser Ile Val Tyr Leu Glu Ile Asp Asn Arg Gln Cys Val Gln
    275                 280                 285

Ser Ser Ser Gln Cys Phe Gln Ser Ala Thr Asp Val Ala Ala Phe Leu
290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Pro Leu Pro Ser Gln Leu His
                325                 330                 335

Leu Met Tyr Val Ala Ala Ala Phe Val Leu Phe Phe Val Gly
            340                 345                 350

Cys Gly Val Leu Leu Ser Arg Lys Arg Arg Gln Leu Cys Ile Gln
        355                 360                 365

Lys Leu
    370
```

```
<210> SEQ ID NO 18
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 18

Arg Met Phe Pro Asn Ala Pro Tyr Leu
1               5

<210> SEQ ID NO 19
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 19

Lys Leu Val Val Val Gly Ala Gly Gly Val
1               5                   10

<210> SEQ ID NO 20
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 20

Lys Leu Val Val Val Gly Ala Val Gly Val
1               5                   10

<210> SEQ ID NO 21
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 21

Lys Leu Val Val Val Gly Ala Cys Gly Val
1               5                   10

<210> SEQ ID NO 22
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 22

Lys Leu Val Val Val Gly Ala Asp Gly Val
1               5                   10

<210> SEQ ID NO 23
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 23

Val Val Gly Ala Val Gly Val Gly Lys
1               5
```

```
<210> SEQ ID NO 24
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 24

Val Val Gly Ala Cys Gly Val Gly Lys
1               5

<210> SEQ ID NO 25
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 25

Val Val Gly Ala Gly Gly Val Gly Lys
1               5

<210> SEQ ID NO 26
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 26

Lys Ile Thr Asp Phe Gly Leu Ala Lys
1               5

<210> SEQ ID NO 27
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 27

Lys Ile Thr Asp Phe Gly Arg Ala Lys
1               5

<210> SEQ ID NO 28
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 28

Val Leu Gln Glu Leu Asn Val Thr Val
1               5

<210> SEQ ID NO 29
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 29

Glu Ala Asp Pro Thr Gly His Ser Tyr
1               5
```

```
<210> SEQ ID NO 30
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 30

Phe Leu Trp Gly Pro Arg Ala Leu Val
1               5

<210> SEQ ID NO 31
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 31

Leu Leu Gly Arg Asn Ser Phe Glu Val
1               5

<210> SEQ ID NO 32
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 32

Ser Thr Thr Pro Pro Pro Gly Thr Arg Val
1               5                   10

<210> SEQ ID NO 33
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 33

Arg Met Pro Glu Ala Ala Pro Pro Val
1               5

<210> SEQ ID NO 34
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 34

Gly Leu Ala Pro Pro Gln His Leu Ile Arg Val
1               5                   10

<210> SEQ ID NO 35
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 35

Glu Leu Ala Gly Ile Gly Ile Leu Thr Val
1               5                   10

<210> SEQ ID NO 36
```

-continued

```
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 36

Glu Ala Ala Gly Ile Gly Ile Leu Thr Val
1               5                   10

<210> SEQ ID NO 37
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 37

Ile Met Asp Gln Val Pro Phe Ser Val
1               5

<210> SEQ ID NO 38
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 38

Lys Thr Trp Gly Gln Tyr Trp Gln Val
1               5

<210> SEQ ID NO 39
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 39

Tyr Leu Glu Pro Gly Pro Val Thr Val
1               5

<210> SEQ ID NO 40
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 40

Tyr Leu Glu Pro Gly Pro Val Thr Ala
1               5

<210> SEQ ID NO 41
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 41

Ile Thr Asp Gln Val Pro Phe Ser Val
1               5

<210> SEQ ID NO 42
<211> LENGTH: 9
```

```
<212> TYPE: PRT
<213> ORGANISM: Artificial sequence
<220> FEATURE:
<223> OTHER INFORMATION: synthetic amino acid sequence

<400> SEQUENCE: 42

Asn Leu Val Pro Met Val Ala Thr Val
1               5

<210> SEQ ID NO 43
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 43

Ala Ile Ile Arg Ile Leu Gln Gln Leu
1               5

<210> SEQ ID NO 44
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 44

Val Leu His Asp Asp Leu Leu Glu Ala
1               5

<210> SEQ ID NO 45
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 45

Val Leu Arg Asp Asp Leu Leu Glu Ala
1               5

<210> SEQ ID NO 46
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 46

Ser Leu Leu Met Trp Ile Thr Gln Val
1               5

<210> SEQ ID NO 47
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 47

Leu Leu Asp Phe Val Arg Phe Met Gly Val
1               5                   10

<210> SEQ ID NO 48
<211> LENGTH: 9
<212> TYPE: PRT
```

```
<213> ORGANISM: Artificial sequence
<220> FEATURE:
<223> OTHER INFORMATION: synthetic amino acid sequence

<400> SEQUENCE: 48

Phe Met Asn Lys Phe Ile Tyr Glu Ile
1               5

<210> SEQ ID NO 49
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 49

Lys Ile Phe Gly Ser Leu Ala Phe Leu
1               5

<210> SEQ ID NO 50
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 50

Gly Val Leu Pro Ala Leu Pro Gln Val
1               5

<210> SEQ ID NO 51
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 51

Thr Met Thr Arg Val Leu Gln Gly Val
1               5

<210> SEQ ID NO 52
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 52

Phe Leu Leu Thr Arg Ile Leu Thr Ile
1               5

<210> SEQ ID NO 53
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 53

Ile Leu Ala Lys Phe Leu His Trp Leu
1               5

<210> SEQ ID NO 54
<211> LENGTH: 9
<212> TYPE: PRT
<213> ORGANISM: Artificial sequence
```

```
<220> FEATURE:
<223> OTHER INFORMATION: synthetic amino acid sequence

<400> SEQUENCE: 54

Arg Leu Val Asp Asp Phe Leu Leu Val
1               5

<210> SEQ ID NO 55
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 55

Leu Leu Leu Thr Val Leu Thr Val Val
1               5

<210> SEQ ID NO 56
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 56

Phe Leu Arg Asn Phe Ser Leu Met Leu
1               5

<210> SEQ ID NO 57
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 57

Tyr Met Asp Gly Thr Met Ser Gln Val
1               5

<210> SEQ ID NO 58
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 58

Tyr Leu Leu Pro Ala Ile Val His Ile
1               5

<210> SEQ ID NO 59
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 59

Phe Leu Ser Glu Leu Thr Gln Gln Leu
1               5

<210> SEQ ID NO 60
<211> LENGTH: 10
<212> TYPE: PRT
<213> ORGANISM: Artificial sequence
<220> FEATURE:
```

<223> OTHER INFORMATION: synthetic amino acid sequence

<400> SEQUENCE: 60

Ala Leu Tyr Val Asp Ser Leu Phe Phe Leu
1               5                   10

<210> SEQ ID NO 61
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 61

Ser Tyr Ala Met Ser
1               5

<210> SEQ ID NO 62
<211> LENGTH: 17
<212> TYPE: PRT
<213> ORGANISM: Artificial sequence
<220> FEATURE:
<223> OTHER INFORMATION: synthetic amino acid sequence

<400> SEQUENCE: 62

Gln Ile Asp Pro Trp Gly Gln Glu Thr Leu Tyr Ala Asp Ser Val Lys
1               5                   10                  15

Gly

<210> SEQ ID NO 63
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 63

Leu Thr Gly Arg Phe Asp Tyr
1               5

<210> SEQ ID NO 64
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 64

Arg Ala Ser Gln Ser Ile Ser Ser Tyr Leu Asn
1               5                   10

<210> SEQ ID NO 65
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 65

Ser Ala Ser Gln Leu Gln Ser
1               5

<210> SEQ ID NO 66
<211> LENGTH: 9
<212> TYPE: PRT
<213> ORGANISM: Artificial sequence

```
<220> FEATURE:
<223> OTHER INFORMATION: synthetic amino acid sequence

<400> SEQUENCE: 66

Gln Gln Gly Pro Gly Thr Pro Asn Thr
1               5

<210> SEQ ID NO 67
<211> LENGTH: 241
<212> TYPE: PRT
<213> ORGANISM: Artificial sequence
<220> FEATURE:
<223> OTHER INFORMATION: synthetic amino acid sequence

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Asp Pro Trp Gly Gln Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Gln Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gly Pro
    210                 215                 220

Gly Thr Pro Asn Thr Phe Gly Gln Gly Thr Lys Val Glu Ile Lys Arg
225                 230                 235                 240

Ala

<210> SEQ ID NO 68
<211> LENGTH: 241
<212> TYPE: PRT
<213> ORGANISM: Artificial sequence
<220> FEATURE:
<223> OTHER INFORMATION: synthetic amino acid sequence

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
                20                  25                  30
Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Pro
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Asn Ile Asn Gly Ser Tyr Ile His Trp Val
145                 150                 155                 160

Arg Gln Ala Pro Gly Lys Gly Leu Glu Trp Val Ala Tyr Ile Asp Pro
                165                 170                 175

Glu Thr Gly Tyr Ser Arg Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ser Arg Asp Ser Ala
            210                 215                 220

Ser Asp Ala Met Asp Val Trp Gly Gln Gly Thr Leu Val Thr Val Ser
225                 230                 235                 240

Ser

<210> SEQ ID NO 69
<211> LENGTH: 241
<212> TYPE: PRT
<213> ORGANISM: Artificial sequence
<220> FEATURE:
<223> OTHER INFORMATION: synthetic amino acid sequence

<400> SEQUENCE: 69

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Pro
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
            130                 135                 140
```

```
Cys Ala Ala Ser Gly Phe His Ile Asn Gly Ser Tyr Ile His Trp Val
145                 150                 155                 160

Arg Gln Ala Pro Gly Lys Gly Leu Lys Trp Val Ala Tyr Ile Asp Pro
                165                 170                 175

Glu Thr Gly Tyr Ser Arg Tyr Ala Asp Ser Val Lys Gly Arg Phe Ala
            180                 185                 190

Ile Ser Ala Asp Met Ser Lys Asn Thr Ala Tyr Leu Gln Met Asn Ser
        195                 200                 205

Leu Arg Ala Glu Asp Thr Ala Val Tyr Tyr Cys Ser Arg Asp Ser Ala
    210                 215                 220

Ser Asp Ala Met Asp Val Trp Gly Gln Gly Thr Leu Val Thr Val Ser
225                 230                 235                 240

Ser
```

<210> SEQ ID NO 70
<211> LENGTH: 243
<212> TYPE: PRT
<213> ORGANISM: Artificial sequence
<220> FEATURE:
<223> OTHER INFORMATION: synthetic amino acid sequence

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Pro
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Thr Ser Ser Tyr Ile His Trp Val
145                 150                 155                 160

Arg Gln Ala Pro Gly Lys Gly Leu Glu Trp Val Ala Tyr Ile Ser Pro
                165                 170                 175

Glu Asp Gly Tyr Ala Arg His Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp Asp Thr
    210                 215                 220

Tyr Tyr Tyr Ser Ala Met Asp Val Trp Gly Gln Gly Thr Leu Val Thr
225                 230                 235                 240

Val Ser Ser
```

```
<210> SEQ ID NO 71
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 71

His Leu Ser Pro Ile Asp Cys Glu Val
1               5

<210> SEQ ID NO 72
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 72

Leu Thr Ser Met Trp Ser Pro Ala Val
1               5

<210> SEQ ID NO 73
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 73

His Leu Asp His Pro His Pro Ala Val
1               5

<210> SEQ ID NO 74
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 74

Ser Leu Ser Val Met Ser Ser Asn Val
1               5

<210> SEQ ID NO 75
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 75

Met Met Ala Trp Ser Asp Asn Lys Ile
1               5

<210> SEQ ID NO 76
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 76

Thr Gln Ile Gly Ile Glu Trp Asn Leu
1               5

<210> SEQ ID NO 77
```

```
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 77

Cys Leu Phe Glu Met Gln Asp Pro Ala
1               5

<210> SEQ ID NO 78
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 78

Tyr Leu Ser His Pro Ser Cys Asn Val
1               5

<210> SEQ ID NO 79
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 79

Gly Ile Glu Trp Asn Leu Ser Pro Val
1               5

<210> SEQ ID NO 80
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 80

Gly Leu Gly Cys Ser Pro Ala Ser Ile
1               5

<210> SEQ ID NO 81
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 81

Arg Gln Ala Phe Glu Phe Pro Gln Ile
1               5

<210> SEQ ID NO 82
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 82

Gly Met Trp Thr Asp Thr Phe Glu Phe
1               5

<210> SEQ ID NO 83
<211> LENGTH: 9
```

```
<212> TYPE: PRT
<213> ORGANISM: Artificial sequence
<220> FEATURE:
<223> OTHER INFORMATION: synthetic amino acid sequence

<400> SEQUENCE: 83

Tyr Leu Asn Trp Gln Asp Thr Ala Val
1               5

<210> SEQ ID NO 84
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 84

Val Leu Trp Gly Pro Ile Thr Gln Ile
1               5

<210> SEQ ID NO 85
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 85

Thr Leu Asp His Thr Gly Val Val Val
1               5

<210> SEQ ID NO 86
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 86

Thr Met Gly Val Trp Leu His Ile Ala
1               5

<210> SEQ ID NO 87
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 87

Lys Val Trp Val Gln Gly His Tyr Leu
1               5

<210> SEQ ID NO 88
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 88

Lys Ile Asn Cys Asn Asn Phe Arg Leu
1               5

<210> SEQ ID NO 89
<211> LENGTH: 56
<212> TYPE: PRT
```

-continued

```
<213> ORGANISM: Artificial sequence
<220> FEATURE:
<223> OTHER INFORMATION: synthetic amino acid sequence

<400> SEQUENCE: 89

Ile Pro Tyr Lys Ile Glu Ala Val Lys Ser Glu Pro Val Pro Pro
1               5                   10                  15

Leu Pro Ser Gln Leu His Leu Met Tyr Val Ala Ala Ala Phe Val
            20                  25                  30

Leu Leu Phe Phe Val Gly Cys Gly Val Leu Leu Ser Arg Lys Arg
        35                  40                  45

Arg Gln Leu Cys Ile Gln Lys Leu
    50                  55

<210> SEQ ID NO 90
<211> LENGTH: 120
<212> TYPE: PRT
<213> ORGANISM: Artificial sequence
<220> FEATURE:
<223> OTHER INFORMATION: synthetic amino acid sequence

<400> SEQUENCE: 90

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
        35                  40                  45

Cys Thr Gln Ser Leu Gln Cys Trp Lys Tyr Phe Ser Asp Gly His Cys
    50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
            100                 105                 110

Cys Glu Trp Asp Gly Leu Asp Cys
        115                 120

<210> SEQ ID NO 91
<211> LENGTH: 152
<212> TYPE: PRT
<213> ORGANISM: Artificial sequence
<220> FEATURE:
<223> OTHER INFORMATION: synthetic amino acid sequence

<400> SEQUENCE: 91

Ala Ala Gly Thr Leu Val Leu Val Val Leu Leu Pro Pro Asp Gln Leu
1               5                   10                  15

Arg Asn Asn Ser Phe His Phe Leu Arg Glu Leu Ser His Val Leu His
            20                  25                  30

Thr Asn Val Val Phe Lys Arg Asp Ala Gln Gly Gln Gln Met Ile Phe
        35                  40                  45

Pro Tyr Tyr Gly His Glu Glu Glu Leu Arg Lys His Pro Ile Lys Arg
    50                  55                  60

Ser Thr Val Gly Trp Ala Thr Ser Ser Leu Leu Pro Gly Thr Ser Gly
65                  70                  75                  80

Gly Arg Gln Arg Arg Glu Leu Asp Pro Met Asp Ile Arg Gly Ser Ile
                85                  90                  95
```

```
Val Tyr Leu Glu Ile Asp Asn Arg Gln Cys Val Gln Ser Ser Ser Gln
            100                 105                 110

Cys Phe Gln Ser Ala Thr Asp Val Ala Ala Phe Leu Gly Ala Leu Ala
            115                 120                 125

Ser Leu Gly Ser Leu Asn Ile Pro Tyr Lys Ile Glu Ala Val Lys Ser
            130                 135                 140

Glu Pro Val Glu Pro Pro Leu Pro
145                 150

<210> SEQ ID NO 92
<211> LENGTH: 23
<212> TYPE: PRT
<213> ORGANISM: Artificial sequence
<220> FEATURE:
<223> OTHER INFORMATION: synthetic amino acid sequence

<400> SEQUENCE: 92

His Leu Met Tyr Val Ala Ala Ala Phe Val Leu Leu Phe Phe Val
1               5                   10                  15

Gly Cys Gly Val Leu Leu Ser
            20

<210> SEQ ID NO 93
<211> LENGTH: 306
<212> TYPE: PRT
<213> ORGANISM: Artificial sequence
<220> FEATURE:
<223> OTHER INFORMATION: synthetic amino acid sequence

<400> SEQUENCE: 93

Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
            35                  40                  45

Cys Thr Gln Ser Leu Gln Cys Trp Lys Tyr Phe Ser Asp Gly His Cys
            50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
            100                 105                 110

Cys Glu Trp Asp Gly Leu Asp Cys Ala Glu His Val Pro Glu Arg Leu
            115                 120                 125

Ala Ala Gly Thr Leu Val Leu Val Leu Leu Pro Pro Asp Gln Leu
            130                 135                 140

Arg Asn Asn Ser Phe His Phe Leu Arg Glu Leu Ser His Val Leu His
145                 150                 155                 160

Thr Asn Val Val Phe Lys Arg Asp Ala Gln Gly Gln Gln Met Ile Phe
                165                 170                 175

Pro Tyr Tyr Gly His Glu Glu Leu Arg Lys His Pro Ile Lys Arg
            180                 185                 190

Ser Thr Val Gly Trp Ala Thr Ser Ser Leu Leu Pro Gly Thr Ser Gly
            195                 200                 205

Gly Arg Gln Arg Arg Glu Leu Asp Pro Met Asp Ile Arg Gly Ser Ile
```

```
              210                 215                 220
Val Tyr Leu Glu Ile Asp Asn Arg Gln Cys Val Gln Ser Ser Ser Gln
225                 230                 235                 240

Cys Phe Gln Ser Ala Thr Asp Val Ala Ala Phe Leu Gly Ala Leu Ala
                245                 250                 255

Ser Leu Gly Ser Leu Asn Ile Pro Tyr Lys Ile Glu Ala Val Lys Ser
                260                 265                 270

Glu Pro Val Glu Pro Pro Leu Pro Ser Gln Leu His Leu Met Tyr Val
            275                 280                 285

Ala Ala Ala Ala Phe Val Leu Leu Phe Phe Val Gly Cys Gly Val Leu
        290                 295                 300

Leu Ser
305

<210> SEQ ID NO 94
<211> LENGTH: 358
<212> TYPE: PRT
<213> ORGANISM: Artificial sequence
<220> FEATURE:
<223> OTHER INFORMATION: synthetic amino acid sequence

<400> SEQUENCE: 94

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His Ile Leu Asp Tyr Ser Phe Thr Gly Gly Ala Gly
        35                  40                  45

Arg Asp Ile Pro Pro Pro Gln Ile Glu Glu Ala Cys Glu Leu Pro Glu
    50                  55                  60

Cys Gln Val Asp Ala Gly Asn Lys Val Cys Asn Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
            100                 105                 110

Asp Gly His Cys Asp Ser Gln Cys Asn Ser Ala Gly Cys Leu Phe Asp
        115                 120                 125

Gly Phe Asp Cys Gln Leu Thr Glu Gly Gln Cys Asn Pro Leu Tyr Asp
    130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Leu Val Val Leu Leu Pro
            180                 185                 190

Pro Asp Gln Leu Arg Asn Asn Ser Phe His Phe Leu Arg Glu Leu Ser
        195                 200                 205

His Val Leu His Thr Asn Val Val Phe Lys Arg Asp Ala Gln Gly Gln
    210                 215                 220

Gln Met Ile Phe Pro Tyr Tyr Gly His Glu Glu Glu Leu Arg Lys His
225                 230                 235                 240

Pro Ile Lys Arg Ser Thr Val Gly Trp Ala Thr Ser Ser Leu Leu Pro
                245                 250                 255

Gly Thr Ser Gly Gly Arg Gln Arg Arg Glu Leu Asp Pro Met Asp Ile
```

```
                260                 265                 270
Arg Gly Ser Ile Val Tyr Leu Glu Ile Asp Asn Arg Gln Cys Val Gln
            275                 280                 285

Ser Ser Ser Gln Cys Phe Gln Ser Ala Thr Asp Val Ala Ala Phe Leu
        290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Pro Leu Pro Ser Gln Leu His
                325                 330                 335

Leu Met Tyr Val Ala Ala Ala Phe Val Leu Leu Phe Phe Val Gly
            340                 345                 350

Cys Gly Val Leu Leu Ser
        355

<210> SEQ ID NO 95
<211> LENGTH: 37
<212> TYPE: PRT
<213> ORGANISM: Artificial sequence
<220> FEATURE:
<223> OTHER INFORMATION: synthetic amino acid sequence

<400> SEQUENCE: 95

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His
        35

<210> SEQ ID NO 96
<211> LENGTH: 37
<212> TYPE: PRT
<213> ORGANISM: Artificial sequence
<220> FEATURE:
<223> OTHER INFORMATION: synthetic amino acid sequence

<400> SEQUENCE: 96

Asp Ile Asn Glu Cys Val Leu Ser Pro Cys Arg His Gly Ala Ser Cys
1               5                   10                  15

Gln Asn Thr His Gly Gly Tyr Arg Cys His Cys Gln Ala Gly Tyr Ser
            20                  25                  30

Gly Arg Asn Cys Glu
        35

<210> SEQ ID NO 97
<211> LENGTH: 37
<212> TYPE: PRT
<213> ORGANISM: Artificial sequence
<220> FEATURE:
<223> OTHER INFORMATION: synthetic amino acid sequence

<400> SEQUENCE: 97

Asp Ile Asp Asp Cys Arg Pro Asn Pro Cys His Asn Gly Gly Ser Cys
1               5                   10                  15

Thr Asp Gly Ile Asn Thr Ala Phe Cys Asp Cys Leu Pro Gly Phe Arg
            20                  25                  30

Gly Thr Phe Cys Glu
        35

<210> SEQ ID NO 98
```

```
<211> LENGTH: 37
<212> TYPE: PRT
<213> ORGANISM: Artificial sequence
<220> FEATURE:
<223> OTHER INFORMATION: synthetic amino acid sequence

<400> SEQUENCE: 98

Asp Ile Asn Glu Cys Ala Ser Asp Pro Cys Arg Asn Gly Ala Asn Cys
1               5                   10                  15

Thr Asp Cys Val Asp Ser Tyr Thr Cys Thr Cys Pro Ala Gly Phe Ser
            20                  25                  30

Gly Ile His Cys Glu
        35

<210> SEQ ID NO 99
<211> LENGTH: 32
<212> TYPE: PRT
<213> ORGANISM: Artificial sequence
<220> FEATURE:
<223> OTHER INFORMATION: synthetic amino acid sequence

<400> SEQUENCE: 99

Thr Glu Ser Ser Cys Phe Asn Gly Gly Thr Cys Val Asp Gly Ile Asn
1               5                   10                  15

Ser Phe Thr Cys Leu Cys Pro Pro Gly Phe Thr Gly Ser Tyr Cys Gln
            20                  25                  30

<210> SEQ ID NO 100
<211> LENGTH: 37
<212> TYPE: PRT
<213> ORGANISM: Artificial sequence
<220> FEATURE:
<223> OTHER INFORMATION: synthetic amino acid sequence

<400> SEQUENCE: 100

Asp Val Asn Glu Cys Asp Ser Gln Pro Cys Leu His Gly Gly Thr Cys
1               5                   10                  15

Gln Asp Gly Cys Gly Ser Tyr Arg Cys Thr Cys Pro Gln Gly Tyr Thr
            20                  25                  30

Gly Pro Asn Cys Gln
        35

<210> SEQ ID NO 101
<211> LENGTH: 27
<212> TYPE: PRT
<213> ORGANISM: Artificial sequence
<220> FEATURE:
<223> OTHER INFORMATION: synthetic amino acid sequence

<400> SEQUENCE: 101

Asp Ser Ser Pro Cys Lys Asn Gly Gly Lys Cys Trp Gln Thr His Thr
1               5                   10                  15

Gln Tyr Arg Cys Glu Cys Pro Ser Gly Trp Thr
            20                  25

<210> SEQ ID NO 102
<211> LENGTH: 36
<212> TYPE: PRT
<213> ORGANISM: Artificial sequence
<220> FEATURE:
<223> OTHER INFORMATION: synthetic amino acid sequence

<400> SEQUENCE: 102

Leu Val Asp Glu Cys Ser Pro Ser Pro Cys Gln Asn Gly Ala Thr Cys
```

-continued

```
                1               5                  10                 15
Thr Asp Tyr Leu Gly Gly Tyr Ser Cys Lys Cys Val Ala Gly Tyr His
                20                 25                 30

Gly Val Asn Cys
        35

<210> SEQ ID NO 103
<211> LENGTH: 36
<212> TYPE: PRT
<213> ORGANISM: Artificial sequence
<220> FEATURE:
<223> OTHER INFORMATION: synthetic amino acid sequence

<400> SEQUENCE: 103

Ile Asp Glu Cys Leu Ser His Pro Cys Gln Asn Gly Gly Thr Cys Leu
1               5                   10                  15

Asp Leu Pro Asn Thr Tyr Lys Cys Ser Cys Pro Arg Gly Thr Gln Gly
                20                  25                  30

Val His Cys Glu
        35

<210> SEQ ID NO 104
<211> LENGTH: 28
<212> TYPE: PRT
<213> ORGANISM: Artificial sequence
<220> FEATURE:
<223> OTHER INFORMATION: synthetic amino acid sequence

<400> SEQUENCE: 104

Cys Phe Asn Asn Gly Thr Cys Val Asp Gln Val Gly Gly Tyr Ser Cys
1               5                   10                  15

Thr Cys Pro Pro Gly Phe Val Gly Glu Arg Cys Glu
                20                  25

<210> SEQ ID NO 105
<211> LENGTH: 39
<212> TYPE: PRT
<213> ORGANISM: Artificial sequence
<220> FEATURE:
<223> OTHER INFORMATION: synthetic amino acid sequence

<400> SEQUENCE: 105

Asp Val Asn Glu Cys Leu Ser Asn Pro Cys Asp Ala Arg Gly Thr Gln
1               5                   10                  15

Asn Cys Val Gln Arg Val Asn Asp Phe His Cys Glu Cys Arg Ala Gly
                20                  25                  30

His Thr Gly Arg Arg Cys Glu
        35

<210> SEQ ID NO 106
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 106

Gly Arg Arg Arg Arg Glu Leu Asp Pro Met
1               5                   10

<210> SEQ ID NO 107
<211> LENGTH: 9
<212> TYPE: PRT
```

```
<213> ORGANISM: Artificial sequence
<220> FEATURE:
<223> OTHER INFORMATION: synthetic amino acid sequence

<400> SEQUENCE: 107

Arg Gln Arg Arg Glu Leu Asp Pro Met
1               5

<210> SEQ ID NO 108
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 108

Lys Ile Glu Ala Val Lys Ser Glu
1               5

<210> SEQ ID NO 109
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 109

Lys Ile Glu Ala Val Gln Ser Glu
1               5

<210> SEQ ID NO 110
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 110

Val Gly Cys Gly Val Leu Leu Ser
1               5

<210> SEQ ID NO 111
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 111

Gly Cys Gly Val Leu Leu Ser
1               5

<210> SEQ ID NO 112
<211> LENGTH: 248
<212> TYPE: PRT
<213> ORGANISM: Artificial sequence
<220> FEATURE:
<223> OTHER INFORMATION: synthetic amino acid sequence

<400> SEQUENCE: 112

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45
```

```
Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
                115                 120                 125

Asn Ala Leu Tyr Ala Leu Ser Ala Val Gly His Phe Thr Leu Gly Cys
            130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
            195                 200                 205

Ala Asp Ala Leu Asp Asp Phe Asp Leu Asp Met Leu Pro Ala Asp Ala
        210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245

<210> SEQ ID NO 113
<211> LENGTH: 211
<212> TYPE: PRT
<213> ORGANISM: Artificial sequence
<220> FEATURE:
<223> OTHER INFORMATION: synthetic amino acid sequence

<400> SEQUENCE: 113

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
                 20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
        130                 135                 140

Thr Val Ser Ala Ala Ala Gly Gly Ser Gly Gly Ser Gly Gly Ser Asp
145                 150                 155                 160
```

```
Ala Leu Asp Asp Phe Asp Leu Asp Met Leu Gly Ser Asp Ala Leu Asp
            165                 170                 175

Asp Phe Asp Leu Asp Met Leu Gly Ser Asp Ala Leu Asp Phe Asp
        180                 185                 190

Leu Asp Met Leu Gly Ser Asp Ala Leu Asp Phe Asp Leu Asp Met
    195                 200                 205

Leu Gly Ser
    210

<210> SEQ ID NO 114
<211> LENGTH: 115
<212> TYPE: PRT
<213> ORGANISM: Artificial sequence
<220> FEATURE:
<223> OTHER INFORMATION: synthetic amino acid sequence

<400> SEQUENCE: 114

Pro Lys Lys Lys Arg Lys Val Asp Ala Leu Asp Asp Phe Asp Leu Asp
1               5                   10                  15

Met Leu Gly Ser Asp Ala Leu Asp Asp Phe Asp Leu Asp Met Leu Gly
            20                  25                  30

Ser Asp Ala Leu Asp Asp Phe Asp Leu Asp Met Leu Gly Ser Asp Ala
        35                  40                  45

Leu Asp Asp Phe Asp Leu Asp Met Leu Gly Ser Gly Gly Ser Gly Gly
    50                  55                  60

Ser Gly Gly Ser Leu Glu Ile Glu Ala Ala Phe Leu Glu Arg Glu Asn
65                  70                  75                  80

Thr Ala Leu Glu Thr Arg Val Ala Glu Leu Arg Gln Arg Val Gln Arg
                85                  90                  95

Leu Arg Asn Arg Val Ser Gln Tyr Arg Thr Arg Tyr Gly Pro Leu Gly
            100                 105                 110

Gly Gly Lys
        115

<210> SEQ ID NO 115
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 115

Gly Gly Gly Gly Ser
1               5

<210> SEQ ID NO 116
<211> LENGTH: 282
<212> TYPE: PRT
<213> ORGANISM: Artificial sequence
<220> FEATURE:
<223> OTHER INFORMATION: synthetic amino acid sequence

<400> SEQUENCE: 116

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45
```

```
Ile Tyr Asn Leu Gln Trp Phe Arg Gln Asp Pro Gly Lys Gly Leu Thr
 50                  55                  60

Ser Leu Leu Leu Ile Gln Ser Ser Gln Arg Glu Gln Thr Ser Gly Arg
 65                  70                  75                  80

Leu Asn Ala Ser Leu Asp Lys Ser Ser Gly Arg Ser Thr Leu Tyr Ile
                 85                  90                  95

Ala Ala Ser Gln Pro Gly Asp Ser Ala Thr Tyr Leu Cys Ala Val Arg
                100                 105                 110

Pro Leu Leu Asp Gly Thr Tyr Ile Pro Thr Phe Gly Arg Gly Thr Ser
                115                 120                 125

Leu Ile Val His Pro Gly Ser Ala Asp Asp Ala Lys Lys Asp Ala Ala
            130                 135                 140

Lys Lys Asp Gly Lys Ser Met Ser Ile Gly Leu Leu Cys Cys Ala Ala
145                 150                 155                 160

Leu Ser Leu Leu Trp Ala Gly Pro Val Asn Ala Gly Val Thr Gln Thr
                165                 170                 175

Pro Lys Phe Gln Val Leu Lys Thr Gly Gln Ser Met Thr Leu Gln Cys
            180                 185                 190

Ala Gln Asp Met Asn His Glu Tyr Met Ser Trp Tyr Arg Gln Asp Pro
            195                 200                 205

Gly Met Gly Leu Arg Leu Ile His Tyr Ser Val Gly Ala Gly Thr Thr
210                 215                 220

Asp Arg Gly Glu Val Pro Asn Gly Tyr Asn Val Ser Arg Ser Thr Ile
225                 230                 235                 240

Glu Asp Phe Pro Leu Arg Leu Leu Ser Ala Ala Pro Ser Gln Thr Ser
                245                 250                 255

Val Tyr Phe Cys Ala Ser Ser Tyr Val Gly Asp Thr Gly Glu Leu Phe
            260                 265                 270

Phe Gly Glu Gly Ser Arg Leu Thr Val Leu
            275                 280

<210> SEQ ID NO 117
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 117

Tyr Pro Tyr Asp Val Pro Asp Tyr Ala
1               5

<210> SEQ ID NO 118
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 118

Asp Tyr Lys Asp Asp Asp Asp Lys
1               5

<210> SEQ ID NO 119
<211> LENGTH: 10
<212> TYPE: PRT
<213> ORGANISM: Artificial sequence
<220> FEATURE:
<223> OTHER INFORMATION: synthetic amino acid sequence
```

```
<400> SEQUENCE: 119

Glu Gln Lys Leu Ile Ser Glu Glu Asp Leu
1               5                   10

<210> SEQ ID NO 120
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 120

His His His His His
1               5

<210> SEQ ID NO 121
<211> LENGTH: 6
<212> TYPE: PRT
<213> ORGANISM: Artificial sequence
<220> FEATURE:
<223> OTHER INFORMATION: synthetic amino acid sequence

<400> SEQUENCE: 121

His His His His His His
1               5

<210> SEQ ID NO 122
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 122

Trp Ser His Pro Gln Phe Glu Lys
1               5

<210> SEQ ID NO 123
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 123

Arg Tyr Ile Arg Ser
1               5

<210> SEQ ID NO 124
<211> LENGTH: 4
<212> TYPE: PRT
<213> ORGANISM: Artificial sequence
<220> FEATURE:
<223> OTHER INFORMATION: synthetic amino acid sequence

<400> SEQUENCE: 124

Phe His His Thr
1

<210> SEQ ID NO 125
<211> LENGTH: 17
<212> TYPE: PRT
<213> ORGANISM: Artificial sequence
<220> FEATURE:
<223> OTHER INFORMATION: synthetic amino acid sequence

<400> SEQUENCE: 125
```

```
Trp Glu Ala Ala Ala Arg Glu Ala Cys Cys Arg Glu Cys Cys Ala Arg
1               5                   10                  15
Ala

<210> SEQ ID NO 126
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 126

Pro Lys Lys Lys Arg Lys Val
1               5

<210> SEQ ID NO 127
<211> LENGTH: 16
<212> TYPE: PRT
<213> ORGANISM: Artificial sequence
<220> FEATURE:
<223> OTHER INFORMATION: synthetic amino acid sequence

<400> SEQUENCE: 127

Lys Arg Pro Ala Ala Thr Lys Lys Ala Gly Gln Ala Lys Lys Lys Lys
1               5                   10                  15

<210> SEQ ID NO 128
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 128

Met Val Pro Lys Lys Lys Arg Lys
1               5

<210> SEQ ID NO 129
<211> LENGTH: 17
<212> TYPE: PRT
<213> ORGANISM: Artificial sequence
<220> FEATURE:
<223> OTHER INFORMATION: synthetic amino acid sequence

<400> SEQUENCE: 129

Met Ala Pro Lys Lys Lys Arg Lys Val Gly Ile His Gly Val Pro Ala
1               5                   10                  15
Ala

<210> SEQ ID NO 130
<211> LENGTH: 4
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(2)
<223> OTHER INFORMATION: The residue at this position may be any amino
      acid.
<220> FEATURE:
<221> NAME/KEY: MISC_FEATURE
<222> LOCATION: (3)..(3)
<223> OTHER INFORMATION: The residue at this position may be an Arg or
      Lys.

<400> SEQUENCE: 130
```

Arg Xaa Xaa Arg
1

<210> SEQ ID NO 131
<211> LENGTH: 142
<212> TYPE: PRT
<213> ORGANISM: Artificial Sequence
<220> FEATURE:
<223> OTHER INFORMATION: synthetic amino acid sequence

<400> SEQUENCE: 131

```
Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Val Tyr Ile Thr Asp Lys
        35                  40                  45

Cys Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140
```

<210> SEQ ID NO 132
<211> LENGTH: 138
<212> TYPE: PRT
<213> ORGANISM: Artificial Sequence
<220> FEATURE:
<223> OTHER INFORMATION: synthetic amino acid sequence

<400> SEQUENCE: 132

```
Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Cys Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
            100                 105                 110

Ser Val Met Gly Leu Arg Ile Leu Leu Leu Lys Val Ala Gly Phe Asn
        115                 120                 125

Leu Leu Met Thr Leu Arg Leu Trp Ser Ser
    130                 135
```

-continued

```
<210> SEQ ID NO 133
<211> LENGTH: 177
<212> TYPE: PRT
<213> ORGANISM: Artificial Sequence
<220> FEATURE:
<223> OTHER INFORMATION: synthetic amino acid sequence

<400> SEQUENCE: 133
```

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

```
<210> SEQ ID NO 134
<211> LENGTH: 173
<212> TYPE: PRT
<213> ORGANISM: Artificial Sequence
<220> FEATURE:
<223> OTHER INFORMATION: synthetic amino acid sequence

<400> SEQUENCE: 134
```

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Cys Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu

```
            130                 135                 140
Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

What is claimed is:

1. A chimeric polypeptide comprising, from N-terminal to C-terminal and in covalent linkage:
   a) an extracellular domain comprising a specific binding member that specifically binds to a peptide-major histocompatibility complex (peptide-MHC);
   b) a proteolytically cleavable Notch receptor polypeptide comprising Lin12 Notch repeats, a heterodimerization (HD) domain, a transmembrane domain and one or more proteolytic cleavage sites; and
   c) an intracellular domain comprising a transcriptional activator, wherein binding of the specific binding member to the peptide-MHC induces cleavage of the Notch receptor polypeptide at the one or more proteolytic cleavage sites, thereby releasing the intracellular domain.

2. The chimeric polypeptide of claim 1, wherein the specific binding member comprises an antibody.

3. The chimeric polypeptide of claim 2, wherein the antibody is a nanobody, a diabody, a triabody, or a minibody, a F(ab')$_2$ fragment, a Fab fragment, a single chain variable fragment (scFv) or a single domain antibody (sdAb).

4. The chimeric polypeptide of claim 1, wherein the specific binding member specifically binds a peptide-MHC comprising an intracellular cancer antigen peptide.

5. The chimeric polypeptide of claim 4, wherein the intracellular cancer antigen peptide is a WT1 peptide or a NY-ESO peptide.

6. The chimeric polypeptide of claim 1, wherein the one or more proteolytic cleavage sites comprises an S2 proteolytic cleavage site, an S3 proteolytic cleavage site or a combination thereof.

7. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a target cell;
      ii) a proteolytically cleavable Notch receptor polypeptide comprising Lin12 Notch repeats, a heterodimerization (HD) domain, a transmembrane domain and one or more proteolytic cleavage sites; and
      iii) an intracellular domain comprising a transcriptional activator;
   b) a nucleic acid encoding a chimeric bispecific binding member, an anti-Fc chimeric antigen receptor (CAR), an innate-immune response inducer, or an immune suppression factor operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the chimeric bispecific binding member, the anti-Fc CAR, the innate-immune response inducer, or the immune suppression factor to be expressed,
   wherein the chimeric bispecific binding member comprises a binding domain specific for a cancer antigen and a binding domain specific for CD3 or Natural Killer Group 2D (NKG2D) receptor.

8. The host cell according to claim 7, wherein the target molecule is a cancer antigen, a tissue specific molecule, an organ specific molecule, or a cell type specific molecule.

9. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a target cell;
      ii) a proteolytically cleavable Notch receptor polypeptide comprising Lin12 Notch repeats, a heterodimerization (HD) domain, a transmembrane domain and one or more proteolytic cleavage sites; and
      iii) an intracellular domain comprising a transcriptional activator;
   b) a nucleic acid encoding a chimeric bispecific binding member, an anti-Fc chimeric antigen receptor (CAR), an innate-immune response inducer, or an immune suppression factor operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the chimeric bispecific binding member, the anti-Fc CAR, the innate-immune response inducer, or the immune suppression factor to be expressed,
   wherein the host cell further comprises a nucleic acid encoding an antibody specific for a cancer antigen present on the surface of a cancer cell and comprising an Fc region that is bound by the anti-Fc CAR.

10. The host cell of claim 9, wherein the nucleic acid encoding the antibody is operably linked to the transcriptional control element.

11. A host cell comprising:
   a) a nucleic acid encoding a chimeric polypeptide comprising, from N-terminal to C-terminal and in covalent linkage:
      i) an extracellular domain comprising a specific binding member that specifically binds to a target molecule present on the surface of a target cell;
      ii) a proteolytically cleavable Notch receptor polypeptide comprising Lin12 Notch repeats, a heterodimerization (HD) domain, a transmembrane domain and one or more proteolytic cleavage sites; and
      iii) an intracellular domain comprising a transcriptional activator;
   b) a nucleic acid encoding a chimeric bispecific binding member, an anti-Fc chimeric antigen receptor (CAR), an innate-immune response inducer, or an immune suppression factor operably linked to a transcriptional control element responsive to the transcriptional activator, wherein binding of the specific binding member to the target molecule induces cleavage of the Notch receptor polypeptide at the one or more proteolytic cleavage sites, thereby releasing the intracellular domain, activating the transcriptional control element and causing the chimeric bispecific binding member, the anti-Fc CAR, the innate-immune response inducer, or the immune suppression factor to be expressed, wherein the innate-immune response inducer is a bacterial protein or fragment thereof, a viral protein or fragment thereof, a fungal protein or fragment thereof, or a protein or fragment thereof expressed by a mammalian parasite.

* * * * *

UNITED STATES PATENT AND TRADEMARK OFFICE
CERTIFICATE OF CORRECTION

| | | |
|---|---|---|
| PATENT NO. | : 11,401,332 B2 | Page 1 of 1 |
| APPLICATION NO. | : 16/325657 | |
| DATED | : August 2, 2022 | |
| INVENTOR(S) | : Lim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

Signed and Sealed this
Eighteenth Day of February, 2025

Coke Morgan Stewart
*Acting Director of the United States Patent and Trademark Office*